US012286656B2

(12) United States Patent
Barth

(10) Patent No.: US 12,286,656 B2
(45) Date of Patent: Apr. 29, 2025

(54) PSEUDOZYMA MICROORGANISMS AND THE PRODUCTION OF ITACONIC ACID

(71) Applicant: BASF SE, Ludwigshafen am Rhein (DE)

(72) Inventor: Gerold Barth, Dresden (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/734,905

(22) PCT Filed: May 29, 2019

(86) PCT No.: PCT/EP2019/063965
§ 371 (c)(1),
(2) Date: Dec. 3, 2020

(87) PCT Pub. No.: WO2019/233853
PCT Pub. Date: Dec. 12, 2019

(65) Prior Publication Data

US 2021/0230573 A1 Jul. 29, 2021

(30) Foreign Application Priority Data

Jun. 7, 2018 (EP) .................................... 18176542

(51) Int. Cl.

*C12N 9/00* (2006.01)
*C07K 14/39* (2006.01)
*C12N 9/90* (2006.01)
*C12N 15/81* (2006.01)
*C12P 7/46* (2006.01)

(52) U.S. Cl.

CPC ................ *C12N 9/93* (2013.01); *C07K 14/39* (2013.01); *C12N 9/90* (2013.01); *C12N 15/81* (2013.01); *C12P 7/46* (2013.01); *C12Y 503/03007* (2013.01); *C12Y 602/01001* (2013.01)

(58) Field of Classification Search

None
See application file for complete search history.

(56) References Cited

U.S. PATENT DOCUMENTS

2004/0170985 A1 9/2004 Usuda et al.
2010/0285546 A1 11/2010 Liao et al.

FOREIGN PATENT DOCUMENTS

WO 2009106627 A2 9/2009
WO 2015140314 A1 9/2015
WO 2015181312 A2 12/2015
WO 2016069849 A1 5/2016
WO 2016103140 A1 6/2016

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession M9MCU5. May 29, 2013 (Year: 2013).*
Geiser, et al., "Prospecting the biodiversity of the fungal family Ustilaginaceae for the production of value-added chemicals", Fungal Biology and Biotechnology, vol. 1, Issue 1, Article No. 2, Nov. 1, 2014, 10 pages.
International Search Report and Written Opinion for International Application No. PCT/EP2019/063965, mailed Sep. 24, 2019, 13 pages.
Geiser et al., Jul. 2018, "Evolutionary freedom in the regulation of the conserved itaconate cluster by Ria1 in related Ustilaginaceae", Fungal Biology and Biotechnology, vol. 5, No. 14, 15 Pages.
Gillissen et al., Feb. 1992, "A two-component regulatory system for self/non-self recognition in Ustilago maydis", Cell, vol. 68, No. 4, pp. 647-657.
Kilaru et al., Jun. 2015, "A gene locus for targeted ectopic gene integration in Zymoseptoria tritici", Fungal Genetics and Biology, vol. 79, pp. 118-124.
Mauersberger et al., Sep. 2001, "Insertional Mutagenesis in the n-Alkane-Assimilating Yeast Yarrowia ipolytica: Generation of Tagged Mutations in Genes Involved in Hydrophobic Substrate Utilization", Journal of Bacteriology, vol. 183, No. 17, pp. 5102-5109.
Needleman et al., Mar. 1970, "A general method applicable to the search for similarities in the amino acid sequence of two proteins", Journal of Molecular Biology, vol. 48, No. 3, pp. 443-453.
Schulz et al., Jan. 1990, "The b alleles of U. maydis, whose combinations program pathogenic development, code for polypeptides containing a homeodomain-related motif", vol. 60, No. 2, pp. 295-306.
Watanabe et al., Dec. 2015, "High-level recombinant protein production by the basidiomycetous yeast Pseudozyma antarctica under a xylose-inducible xylanase promoter", Applied Microbiology and Biotechnology, vol. 100, pp. 3207-3217.
Zambanini et al., May 2017, "Efficient itaconic acid production from glycerol with Ustilago vetiveriae TZ1", Biotechnology for Biofuels, vol. 10, No. 131, 15 pages.

* cited by examiner

*Primary Examiner* — Christian L Fronda
(74) *Attorney, Agent, or Firm* — Armstrong Teasdale LLP

(57) ABSTRACT

Described herein is the fermentative production of fine chemicals, notably itaconate or itaconic acid, including production microorganisms, fermentation compositions and media, proteins useful in the production of the products, and nucleic acids for expression of such proteins, as well as methods for the production of fine chemicals.

21 Claims, 46 Drawing Sheets

Figure 1:
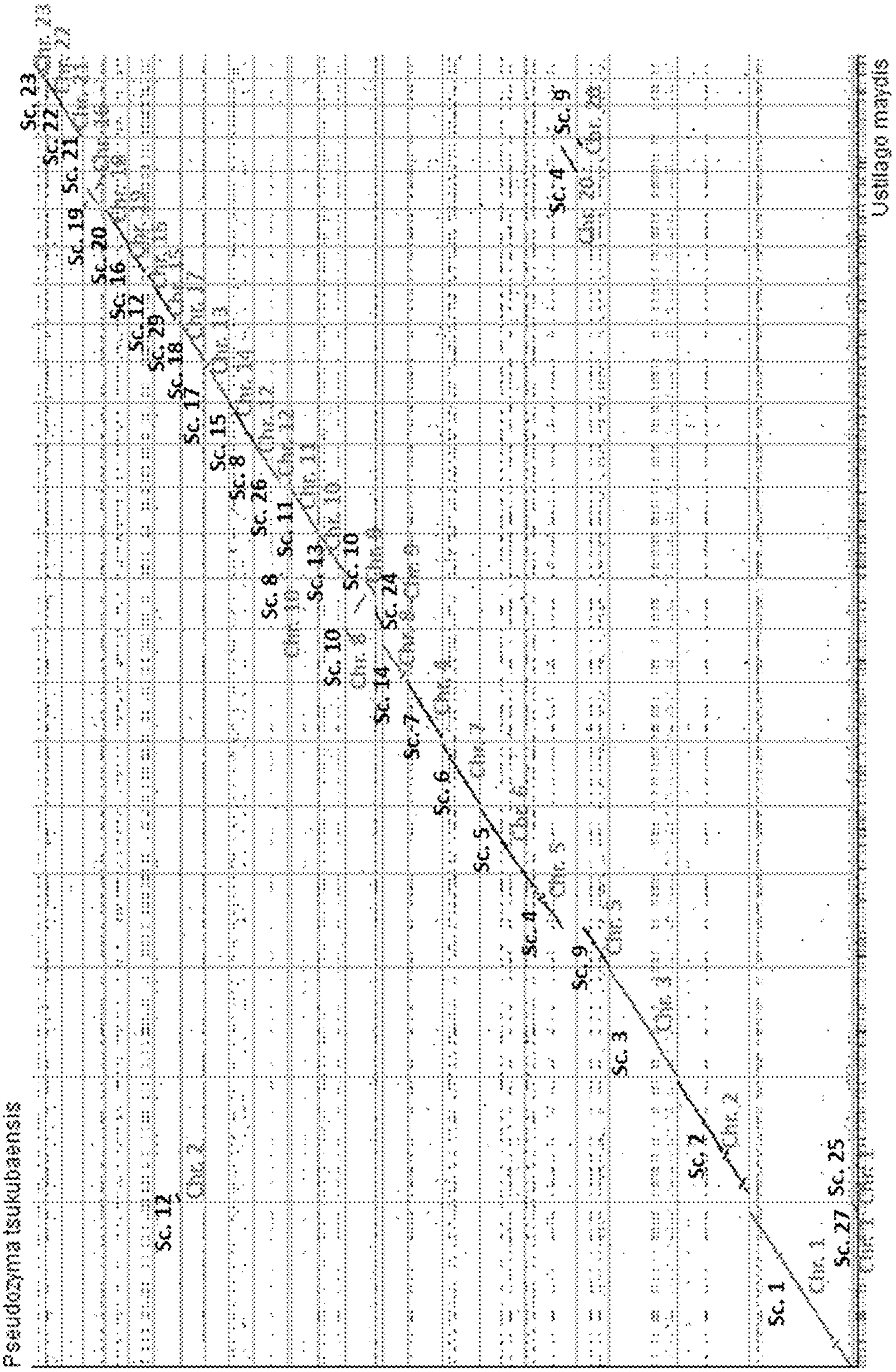

Specification includes a Sequence Listing.

FIG. 13
pPPT-pActin-RIA1
9187 bps
pPPT-pActin-ITP1
9756 bps
pPPT-pActin-TAD1
9379 bps
pPPT-pActin-MTT1
9018 bps
pPPT-pActin-ADI1
9507 bps
hsp70 promotor
hyg
hsp70 terminator'
pActin
hsp70 terminator
bla
KpnI
NsiI
RIA1
ITP1
TAD1
MTT1
ADI1
2000
4000
6000
8000

Table 1.

| glucose | | acetate | | 1 % EtOH | | 2 % EtOH | |
|---|---|---|---|---|---|---|---|
| H488 | HR12 | H488 | HR12 | H488 | HR12 | H488 | HR12 |

FIG. 37
pPTT.Cbx.oACO2
10162 bps
bla
hsp70 terminator
ACO2
pActin
Cbx
CbxR'
NsiI
BsrGI
PfI23II
KpnI
KpnI
2000
4000
6000
8000
10000
pPTT.Cbx.oACO1-EX
9400 bps
bla
hsp70 terminator
'ACO1
ACO1'
pActin
Cbx
CbxR'
NsiI
BsrGI
PfI23II
KpnI
KpnI
2000
4000
6000
8000

PSEUDOZYMA MICROORGANISMS AND THE PRODUCTION OF ITACONIC ACID

CROSS-REFERENCE TO RELATED APPLICATIONS

This application is a U.S. National Phase Application of International Patent Application No. PCT/EP2019/063965, filed May 29, 2019, which claims the benefit of priority to European Patent Application No. 18176542.1, filed Jun. 7, 2018, the entire contents of which are hereby incorporated by reference herein.

FIELD OF THE INVENTION

The present invention is concerned with the fermentative production of fine chemicals, notably itaconate or itaconic acid. The invention provides production microorganisms, fermentation compositions and media, proteins useful in the production of said products and nucleic acids for expression of such proteins, and methods for the production of fine chemicals.

BACKGROUND OF THE INVENTION

Itaconic acid, also called methylenesuccinic acid, methylene butanedioic acid, propylenedicarboxylic acid or 2-propene-1,2-dicarboxylic acid, is an essential precursor to various products, for example acrylic fibers and rubbers, or is used for example as binder and sizing agent in non-weaving fibers, paper and concrete paint. Itaconic acid esters can be used as intermediates for further commodity and specialty chemicals. The main production microorganism industrially exploited so far for the production of itaconic acid is the filamentous fungus *Aspergillus terreus* (*A. terreus*). Although high titers of itaconic acid have been achieved in *A. terreus*, the organism suffers from poor growth in media optimal for itaconic acid production and is negatively affected by shear stress, precluding fermentations in conventional stirred-tank bioreactors. Attempts to genetically optimize *A. terreus* have yielded inconclusive results at best (see for example WO2016069849).

A number of alternative microorganisms for itaconic acid production have been tested, including *Yarrowia lipolytica* (WO2016069849), *Escherichia coli* (US2010285546), Saccharomyces *cerevisiae* (WO2015181312). Geiser et al. (Fungal Biology and Biotechnology 2014, 1:2) have tested a variety of Ustilaginomycetes for itaconic acid production and found that most of the tested microorganisms also produce by-products like malate in even greater amounts, thereby diminishing expected production yields of itaconic acid. The formation of malate as a by-product is particularly disadvantageous, because the process of itaconic acid production is believed to rely on the Krebs cycle, such that a loss of malate will reduce efficiency of itaconic acid production. Other Ustilaginomycetes tested are plain plant pathogens like *Ustilago cynodontis* which require particular biosafety provisions, thereby reducing industrial applicability. Also, all productions were dependent on complex media including yeast extract, an expensive component for industrial scale fermentations. WO2009106627A2 describes a production method for production of itaconic acid using yeasts of the genera *Pseudozyma, Candida* and *Torulopsis*. However, this document reports an unacceptably low productivity (0.25 g/(l h)) and yield (37.5% w/w itaconic acid:glucose). Likewise, document WO2016103140 describes the production of inter alia itaconate by various members of the taxonomic class Ustilaginomycetes. The document reports (FIG. 13) that the obtained concentration of itaconate after nearly 7 days of cultivation was always well below 10 g/l, and for most strains tested no itaconate production could be obtained or significant by-products like malate were obtained.

Accordingly, there remains a need for an improved process of industrial scale itaconic acid production and for materials needed in such improved process, for example production microorganisms, proteins expressed by said production microorganisms and nucleic acids for such protein expression, and for fermentation compositions including media optimized for itaconic acid production and the respective itaconic acid production host.

SUMMARY OF THE INVENTION

The present invention thus provides an itaconic acid production host microorganism, wherein the microorganism comprises at least one heterologous expression cassette integrated into the genome of the microorganism outside of an ip locus, wherein the expression cassette comprises a) a heterologous RIA1 gene under the operable control of a functional promoter, and/or b) a RIA1 gene under the operable control of a heterologous functional promoter.

In a further way to describe the invention there is provided an itaconic acid production host microorganism, wherein the host is a recombinant microorganism comprising an expression cassette for expression of a RIA1 gene and/or for expression of at least two genes selected from the group consisting of ADI1, MTT1 and TAD1, wherein said expression cassette is integrated into the genome of the microorganism at an integration site, wherein the integration site a) is located between a left border gene and a right border gene, wherein the respective first nucleotides of the respective translation start codons of the left and right border genes are separated by at most 51600 nucleotides in the corresponding wild type microorganism, wherein the left border gene codes for a protein having acetyl-CoA synthetase activity and wherein the right border gene codes for a protein consisting of an amino acid sequence having at least 21% identity to SEQ ID NO. 25, and/or b) is located up to 51600 nucleotides of the nearest border of an open reading frame translating into an amino acid sequence having at least 30% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, and/or c) is located within or replaces an open reading frame translating into an amino acid sequence having at least 30% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25.

In yet a further way of describing the itaconic acid production host microorganism of the present invention the production host is a recombinant microorganism a) comprising an active itaconic acid metabolic pathway for producing itaconic acid, and b) wherein at least one gene i) coding for a protein having at least 30% sequence identity to and/or ii) the complementary strand of which hybridizes under at least low stringency conditions to a nucleic acid sequence coding for any of the protein sequences SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25 is inactivated.

In a further embodiment the invention provides integration vector comprising a RIA1 gene operably linked to a strong constitutively active promoter for integration outside of an ip locus. According to the invention is correspondingly provided a production host microorganism, wherein the microorganism is transformed with the integration vector of the present invention.

The invention further provides a method for alteration of an itaconic acid production host microorganism, comprising integrating at least one expression cassette for expression of a RIA1 gene and/or for expression of at least two genes selected from the group consisting of ADI1, MTT1 and TAD1, into the genome of a microorganism at an integration site other than an ip locus.

According to the invention there is also provided a method for obtaining a recombinant itaconic acid production host microorganism, comprising a) cultivating a parent microorganism, b) performing, in any order and/or simultaneously, if so required: one or more transformations to provide the microorganism with any heterologous ADI1, MTT1 and TAD1 gene to obtain an active itaconic acid pathway in the microorganism, at least one integration of a RIA1 gene under the control of a constitutively active promoter, wherein integration is not in an ip-locus, inactivation of at least one gene i) coding for a protein having at least 30% sequence identity to and/or ii) the complementary strand of which hybridizes under at least low stringency conditions to a nucleic acid sequence coding for any of the protein sequences SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25; and c) isolating the recombinant itaconic acid production host microorganism resulting from step b).

The invention also provides production method for itaconic acid production, the method comprising the steps a) fermenting a production host microorganism to produce itaconic acid, and b) recovering itaconic acid produced in step (a), wherein the microorganism is a microorganism according to the invention or is obtained or obtainable according to the invention.

Preferably, the production method is a batch fermentation, a fed-batch fermentation or a continuous fermentation. Also preferably the ratio of concentrations of itaconic acid to malic acid in the fermentation medium after 8 days of fed-batch fermentation is at least 15:1.

SHORT DESCRIPTION OF FIGURES

FIG. 1. Synteny plot produced by r2cat. The scaffolds of *P. tsukubaensis* H488 are mapped onto the genomic sequence of *U. maydis* 521

Figure 2:
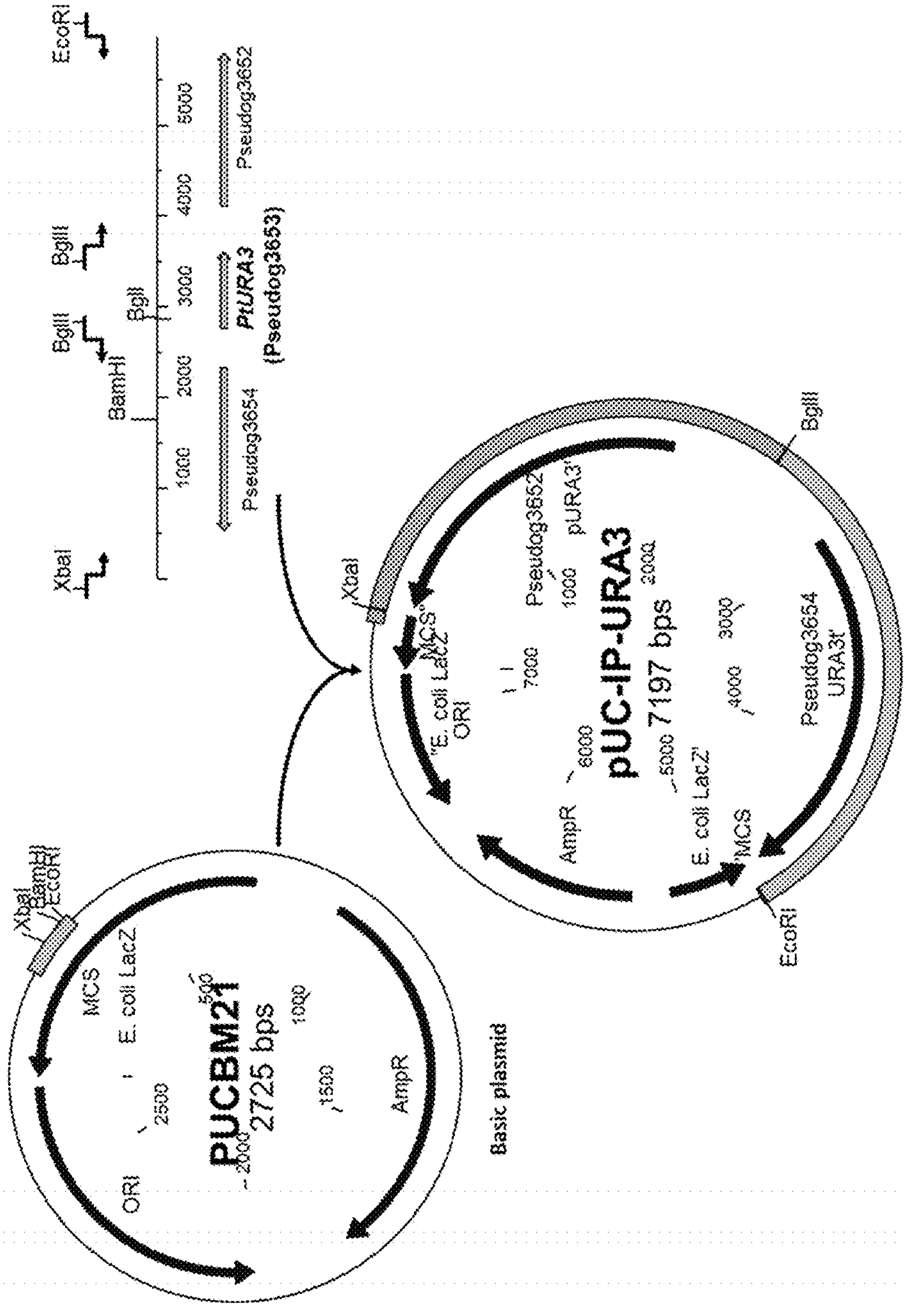

FIG. 2. Construction of pUC-IP-URA3 plasmid. Left and right flanking regions of PtURA3 were amplified with the complementation of the respective restriction sites. The XbaI & BglII and BglII & EcoRI digested fragments were ligated into a XbaI & EcoRI-cut pUCBM21 plasmid.

Figure 3:
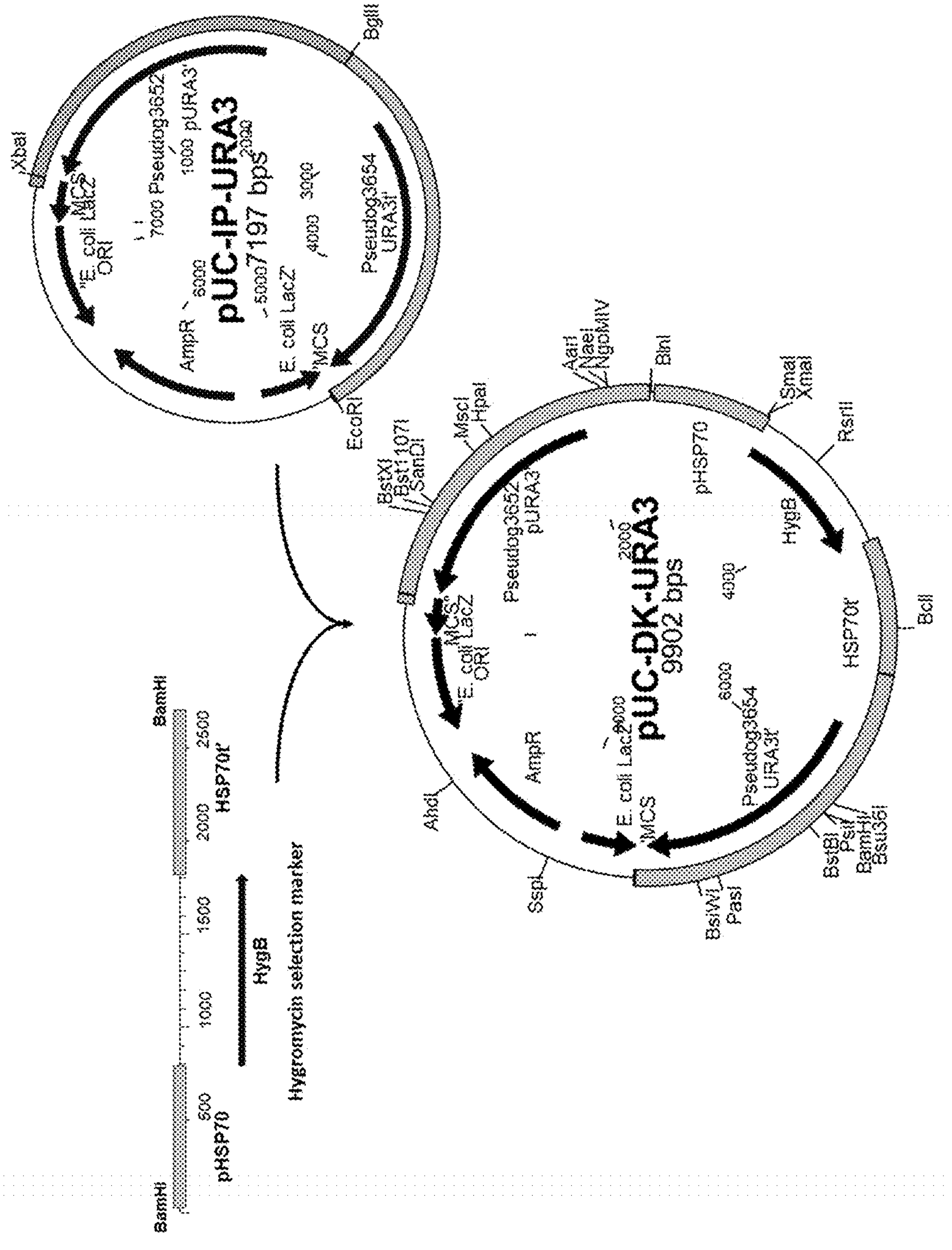
Figure 4A:
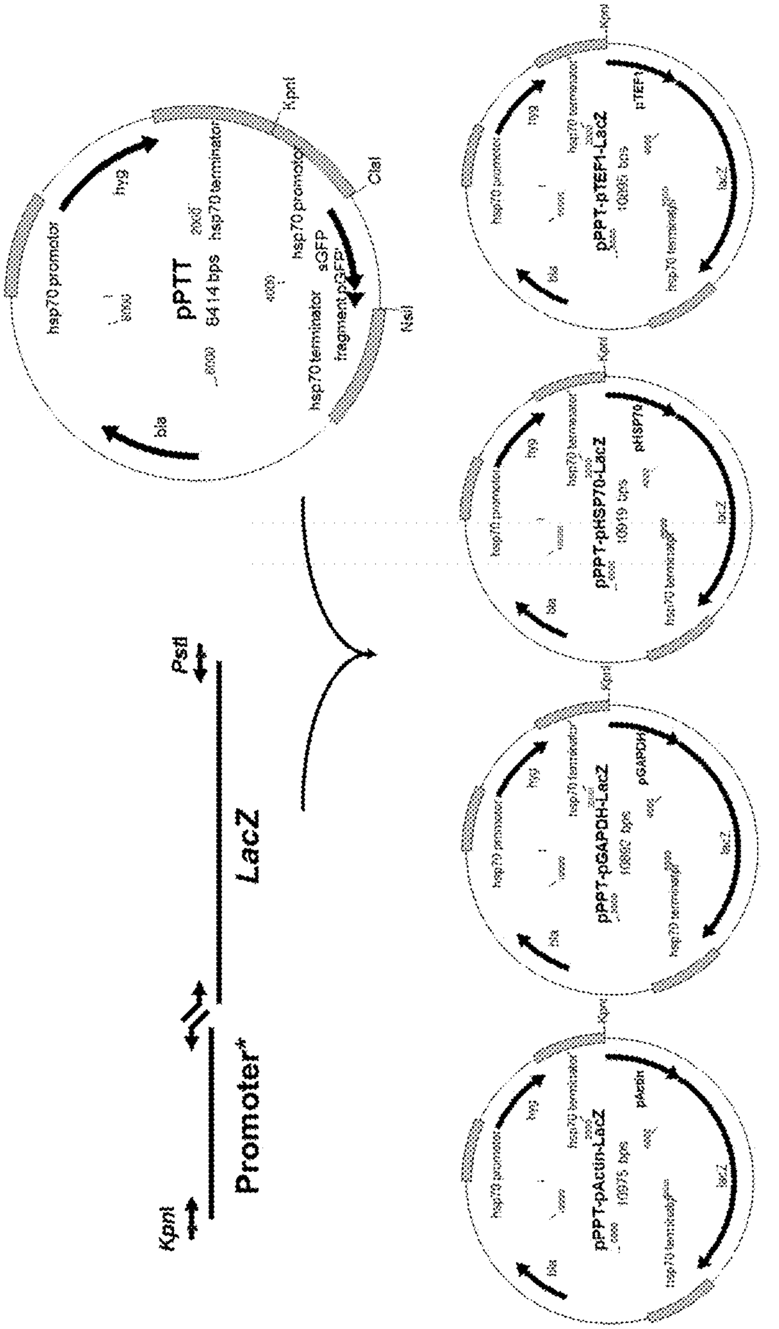
Figure 4B:
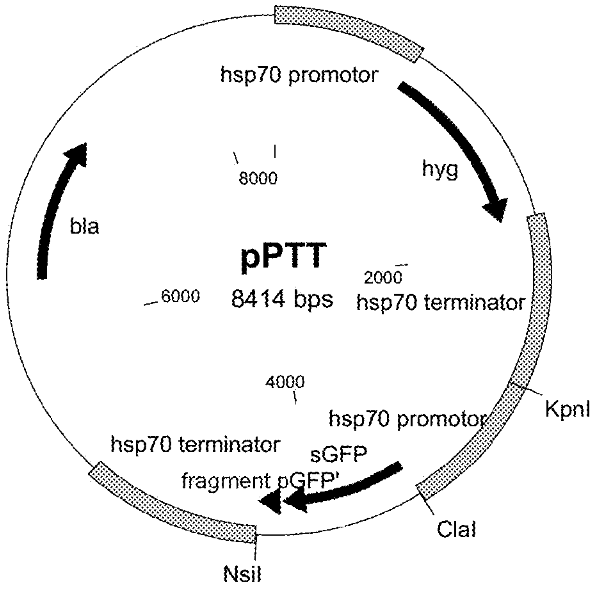
Figure 4B:
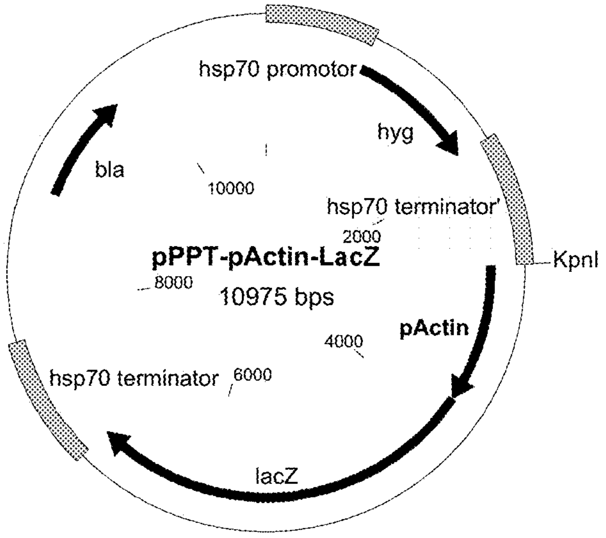
Figure 4C:
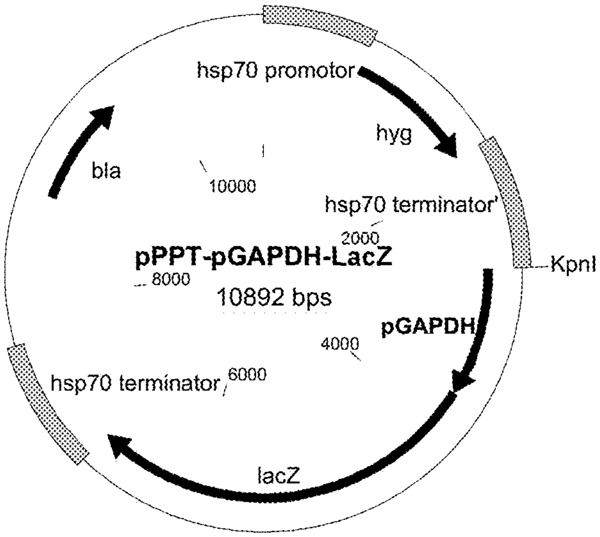
Figure 4C:
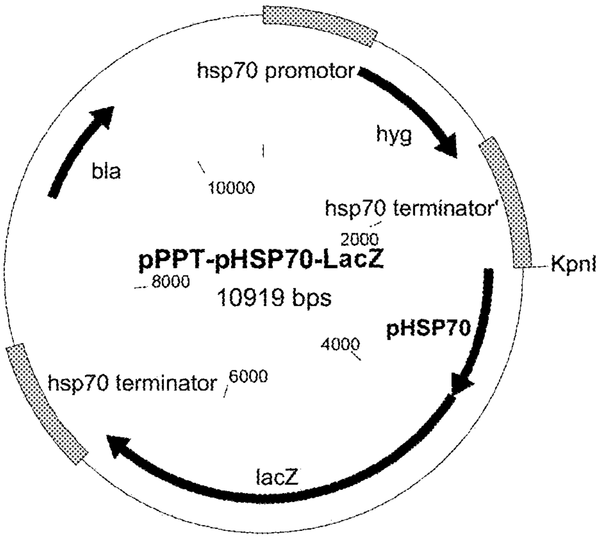
Figure 4D:
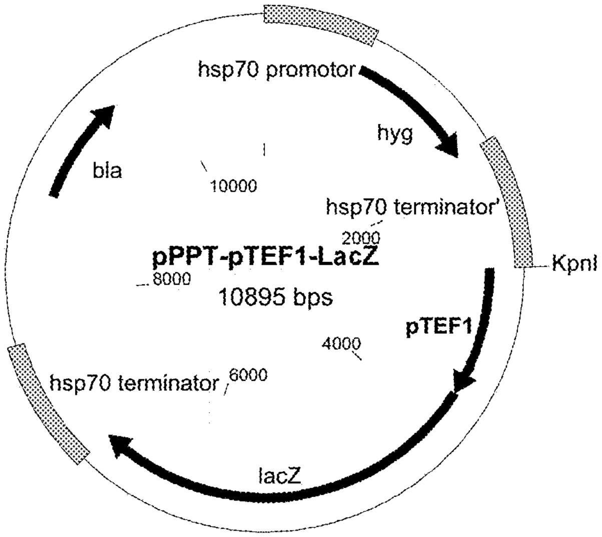

FIG. 3. Construction of the PtURA3 deletion plasmid pUC-DK-URA3. pUC-IP-URA3 was linearized using BglII. The hygromycin selection marker (consisting of the hygromycin resistance gene HygB, the HSP70 promoter and HSP70 terminator) was BamHI digested and ligated into the linearized pUC-IP-URA3 plasmid. This was possible because BamHI and BglII create compatible cohesive ends.

FIGS. 4A-4D. Cloning strategy for the construction of the LacZ-reporter gene overexpression plasmids. Respective promoter sequence (* approx. 1.050 bp long sequence of the upstream region of the respective gene) and the ORF of the LacZ reporter gene (β galactosidase) were fused together in the course of an overlap-PCR. The 5'-end was complemented with a KpnI- and the 3'-end with a PstI-restriction site. The fusion product was ligated into a KpnI & NsiI digested pPTT-plasmid due to the compatibility of the NsiI and PstI generated ends, thus creating the following LacZ overexpression plasmids: pPTT pActin LacZ; pPPT pGAPDH LacZ; pPPT pHSP70 LacZ; pPPT pTEF1 LacZ.

Figure 5:
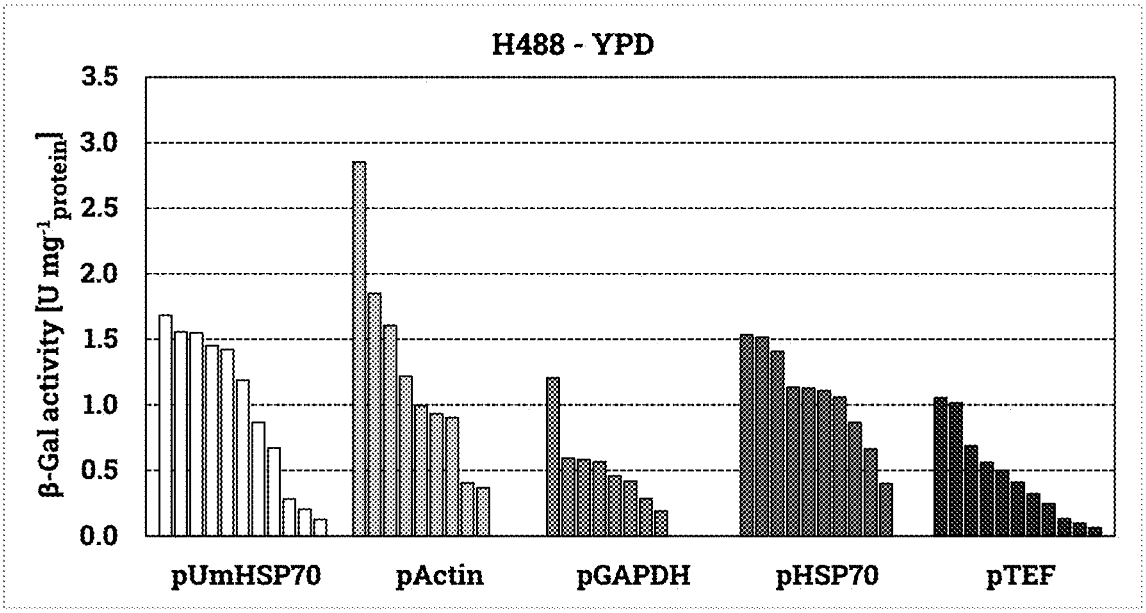

FIG. 5. β-galactosidase activity [U mg-1 total protein] of *P. tsukubaensis* H488 LacZ-transformants. The LacZ reporter gene was overexpressed under the control of either pActin, pGAPDH, pHSP70, pTEF1 or pUmHSP70 (reference) promoter respectively. The cells were cultivated for 2 d in 3 ml YPD (complete) medium.

Figure 6:
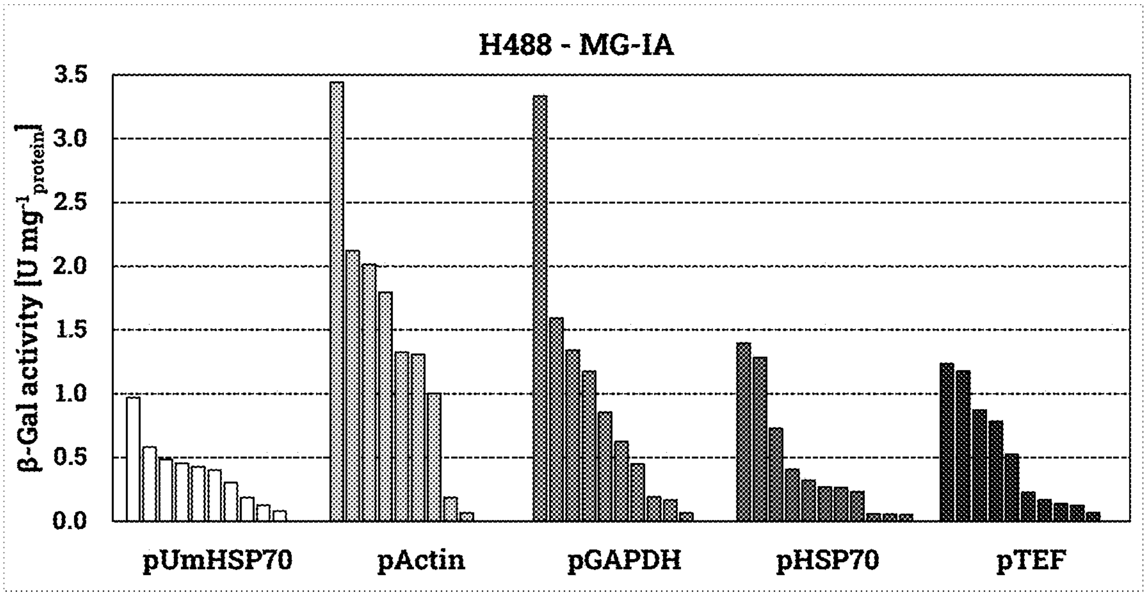

FIG. 6. β-galactosidase activity [U mg-1 total protein] of *P. tsukubaensis* H488 LacZ-transformants. The LacZ reporter gene was overexpressed under the control of either pActin, pGAPDH, pHSP70, pTEF1 or pUmHSP70 (reference) promoter respectively. The cells were cultivated for 4 d in 3 ml MG-IT minimal medium with 2 g l 1 nitrogen source and 0.2 g l-1 phosphate source.

Figure 7:
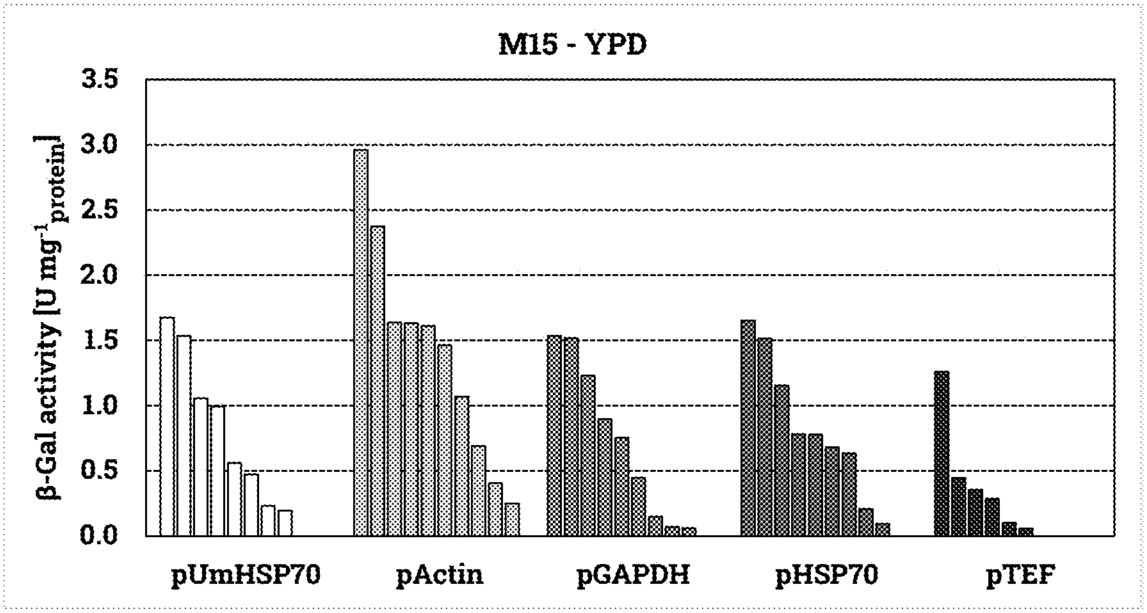

FIG. 7. β-galactosidase activity [U mg-1 total protein] of *P. tsukubaensis* M15 LacZ-transformants. The LacZ reporter gene was overexpressed under the control of either pActin, pGAPDH, pHSP70, pTEF1 or pUmHSP70 (reference) promoter respectively. The cells were cultivated for 2 d in 3 ml YPD (complete) medium.

Figure 8:
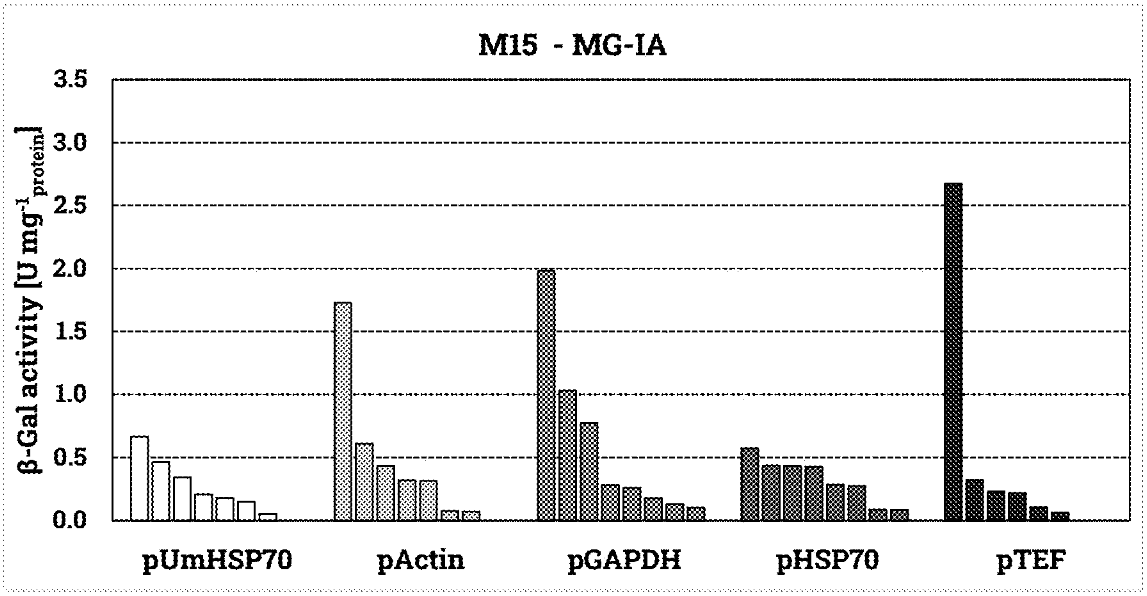

FIG. 8. β-galactosidase activity [U mg-1 total protein] of *P. tsukubaensis* M15 LacZ-transformants. The LacZ reporter gene was overexpressed under the control of either pActin, pGAPDH, pHSP70, pTEF1 or pUmHSP70 (reference) promoter respectively. The cells were cultivated for 4 d in 3 ml MG-IT minimal medium with 2 g l-1 nitrogen source and 0.2 g l-1 phosphate source.

Figure 9:
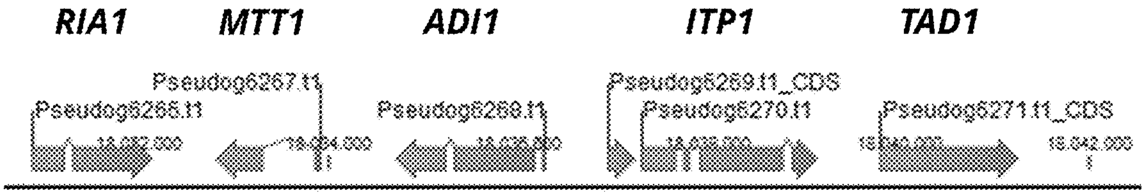

FIG. 9. Gene cluster for the production of itaconic acid in *P. tsukubaensis* H488. The cluster is located on scaffold 19 and consists of just the five genes needed for itaconic acid synthesis: RIA1 (regulator of itaconic acid), MTT1 (mitochondrial TCA transporter), ADI1 (aconitate-Δ-isomerase), ITP1 (itaconate transport protein), TAD1 (trans-aconitate decarboxylase).

Figure 10:
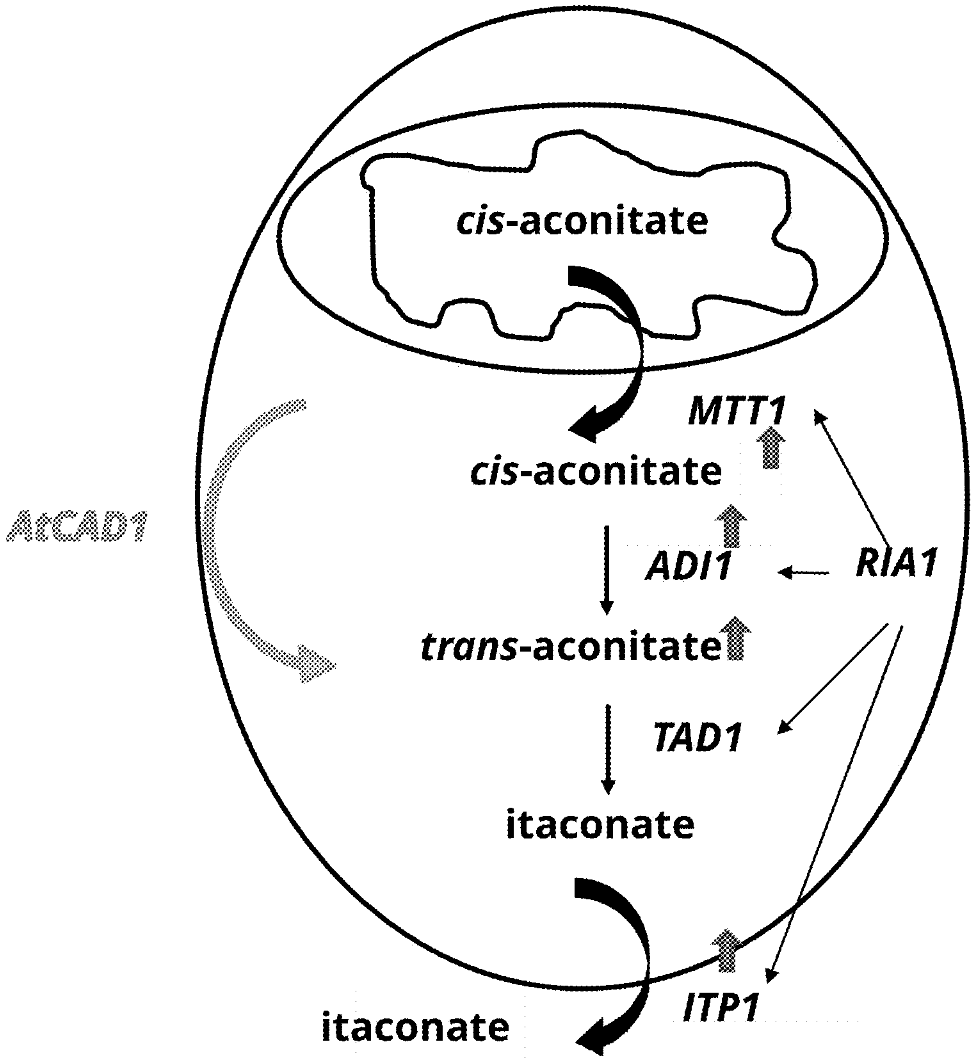

FIG. 10. Proposed pathway for itaconic acid production in *P. tsukubaensis* due to sequence similarities to *U. maydis*. cis-Aconitate is transported out of the mitochondrion by MTT1 into the cytosol where it is converted into trans-aconitate by the aconitate-Δ-isomerase (ADI1) and further decarboxylated by trans-aconitate decarboxylase (TAD1) into the final product ITA. ITA is then excreted by ITP1 into the cell surroundings. The genes ADI1, ITP1, MTT1 and TAD1 are upregulated by RIA1 activity. All genes are organized in a cluster located on scaffold 19. cis-Aconitate is directly converted by cis-aconitate decarboxylase (AtCAD1) into itaconate in the ITA producing fungus *A. terreus* (marked by grey arrow).

Figure 11:
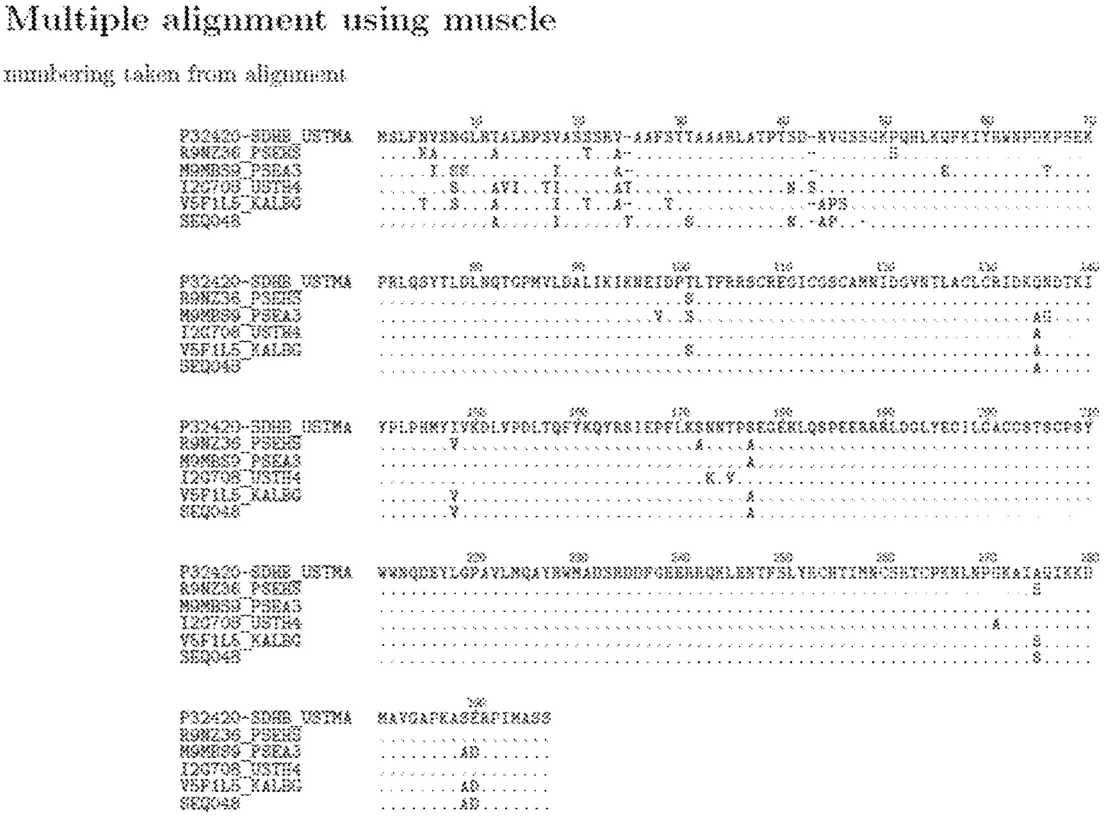

FIG. 11 is a multiple alignment of protein sequences of iron-sulphur protein subunits of succinate dehydrogenase. Only the topmost amino acid sequence is fully spelled out; for all other amino acid sequences only the amino acids differing at each respective position from the respective amino acid of the top sequence are given such that a dot indicates that at the respective position the respective amino acid of the top sequence is present. The proteins aligned are:

| legend | description | Sequence identity to SEQ ID NO. 48 |
|---|---|---|
| P32420-SDBH_USTMA | Uniprot identifier: P32420 (SDHB_USTMA); Uniprot description: Protein: Succinate dehydrogenase [ubiquinone] iron-sulfur subunit, mitochondrial Gene: SDH2 Organism: *Ustilago maydis* (strain 521/FGSC 9021) (Corn smut fungus) Status: Reviewed | 95.3% |
| R9NZ36_PSEHS | Uniprot identifier: R9NZ36 (R9NZ36_PSEHS); Uniprot description: Protein: Succinate dehydrogenase [ubiquinone] iron-sulfur subunit, mitochondrial Gene: PHSY_001500 Organism: *Pseudozyma hubeiensis* (strain SY62) (Yeast) Status: Unreviewed | 94.3% |
| M9MBS9_PSEA3 | Uniprot identifier: M9MBS9 (M9MBS9_PSEA3); Uniprot description: Protein: Succinate dehydrogenase [ubiquinone] iron-sulfur subunit, mitochondrial Gene: PANT_7c00348 Organism: *Pseudozyma antarctica* (strain T-34) (Yeast) (*Candida antarctica*) Status: Unreviewed | 93.9% |
| 12G708_USTH4 | Uniprot identifier: 12G708 (12G708_USTH4); Uniprot description: Protein: Succinate dehydrogenase [ubiquinone] iron-sulfur subunit, mitochondrial Gene: UHOR_01267 Organism: *Ustilago hordei* (strain Uh4875-4) (Barley covered smut fungus) Status: Unreviewed | 93.6% |
| V5F1L5_KALBG | Uniprot identifier: V5F1L5 (V5F1L5_KALBG); Uniprot description: Protein: Succinate dehydrogenase [ubiquinone] iron-sulfur subunit, mitochondrial Gene: PSEUBRA_SCAF1g00645 Organism: *Kalmanozyma brasiliensis* (strain GHG001) (Yeast) (*Pseudozyma brasiliensis*) Status: Unreviewed | 96.3% |

The bottom sequence "SEQ048" is the sequence according to SEQ ID NO. 48 of *Pseudozyma tsukubaensis*.

Figure 12:
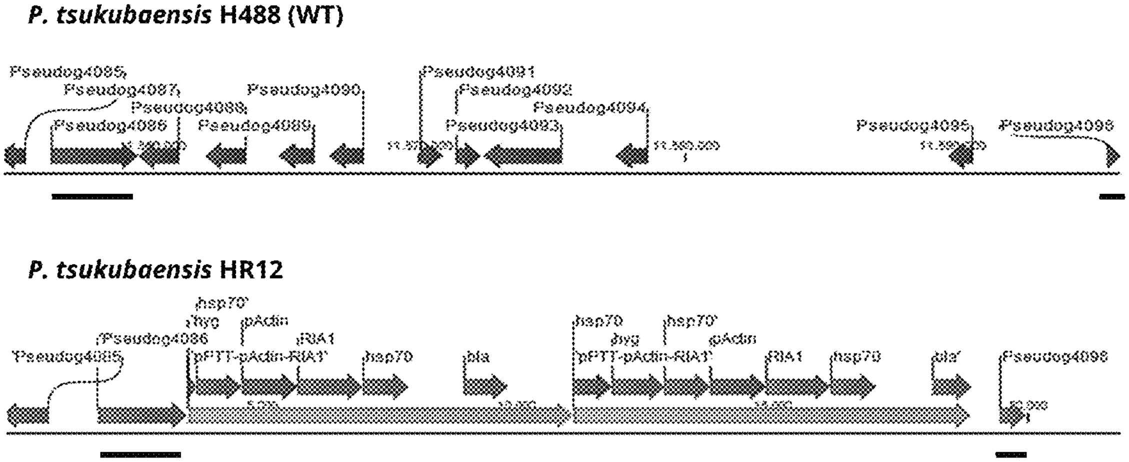

FIG. 12. Genomic locus of the integration of the RIA1-overexpression plasmid pPTT-pActin-RIA1 in the *P. tsukubaensis* strain HIR12 (bottom) compared to the affected region in the wild type strain H488 (top). Green bars mark the ORFs between which the heterologous recombination event must have taken place.

Figure 13:

FIG. 13. Plasmids created for the overexpression of native genes responsible for ITA production in *P. tsukubaensis*.

Figure 14:
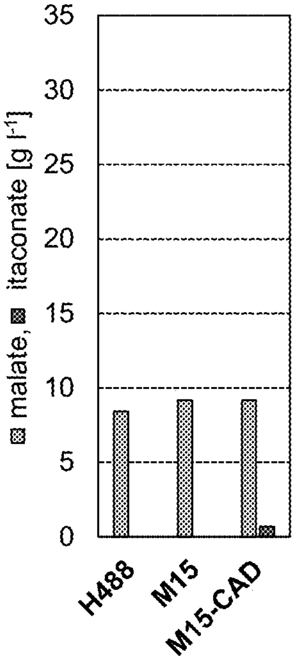

FIG. 14. *P. tsukubaensis* reference strains H488, M15 and M15-CAD

Figure 15:
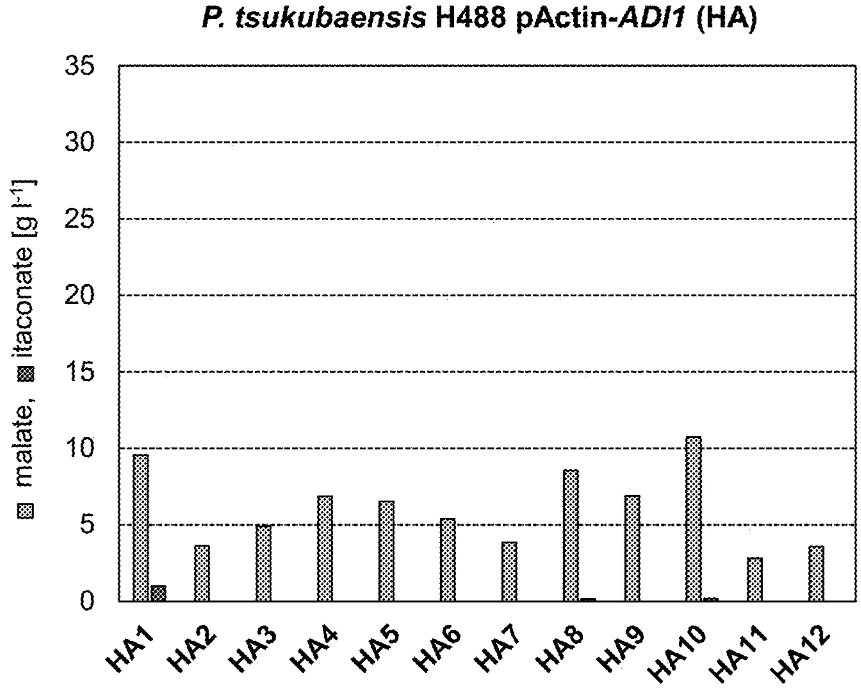

FIG. 15. Itaconic and malic acid production of *P. tsukubaensis* H488 ADI1-overexpression transformants after 10 d cultivation in 3 ml MG-IA medium.

Figure 16:
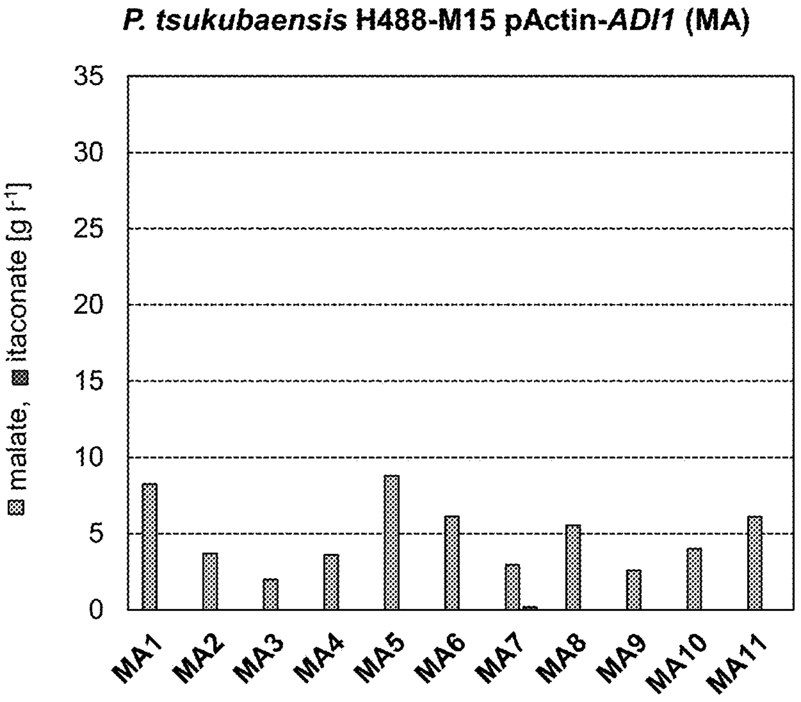

FIG. 16. Itaconic and malic acid production of *P. tsukubaensis* M15 ADI1-overexpression transformants after 10 d cultivation in 3 ml MG-IA medium.

Figure 17:
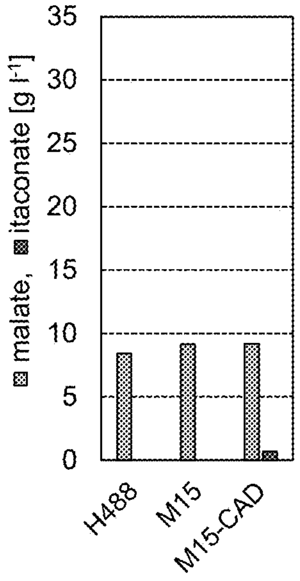

FIG. 17. *P. tsukubaensis* reference strains H488, M15 and M15-CAD.

Figure 18:
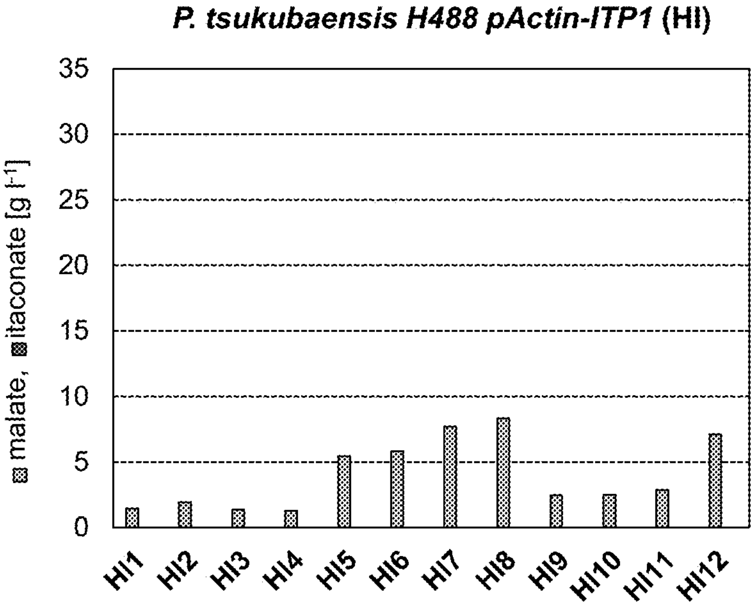

FIG. 18. Itaconic and malic acid production of *P. tsukubaensis* H488 ITP1-overexpression transformants after 10 d cultivation in 3 ml MG-IA medium.

Figure 19:
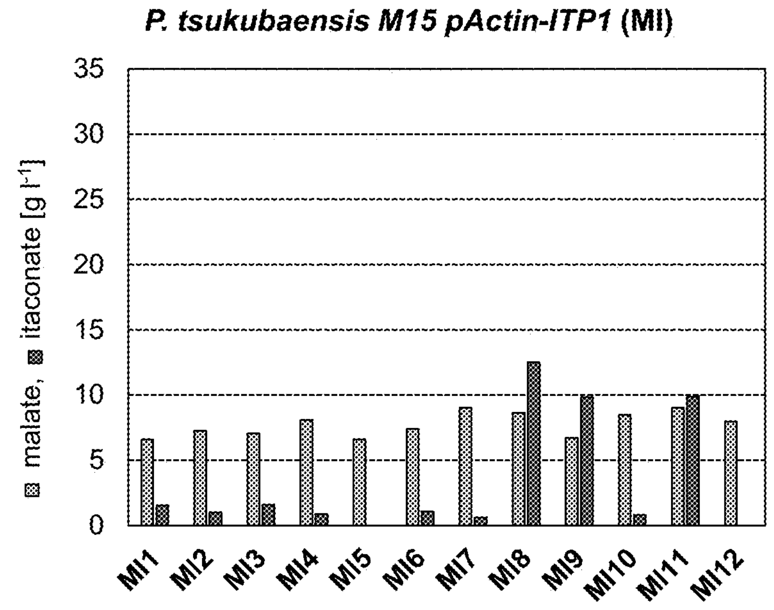

FIG. 19. Itaconic and malic acid production of *P. tsukubaensis* M15 ITP1-overexpression transformants after 10 d cultivation in 3 ml MG-IA medium.

Figure 20:
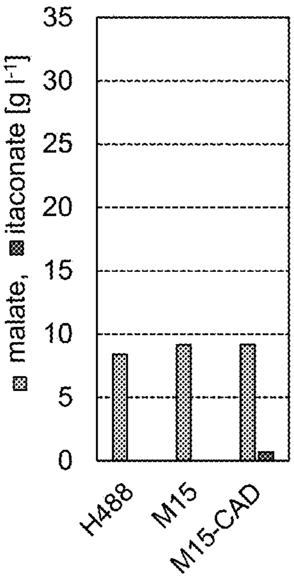

FIG. 20. *P. tsukubaensis* reference strains H488, M15 and M15-CAD.

Figure 21:
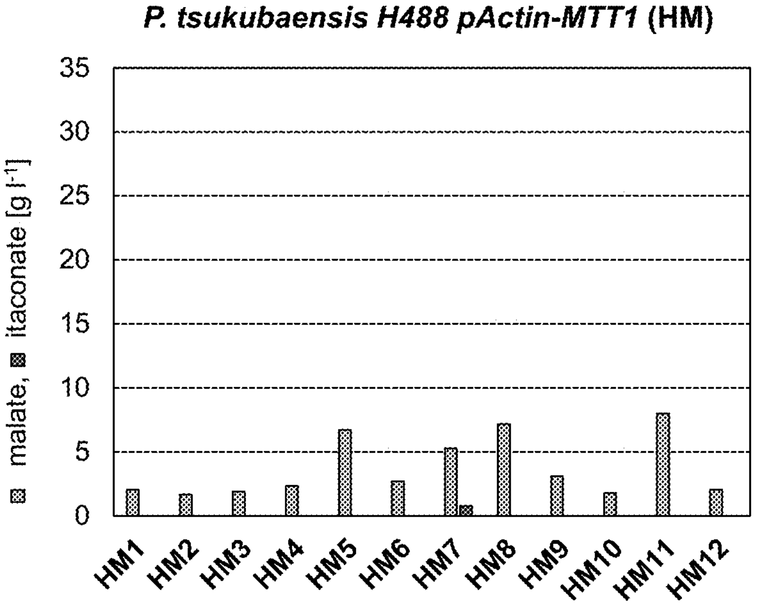

FIG. 21. Itaconic and malic acid production of *P. tsukubaensis* H488 MTT1-overexpression transformants after 10 d cultivation in 3 ml MG-IA medium.

Figure 22:
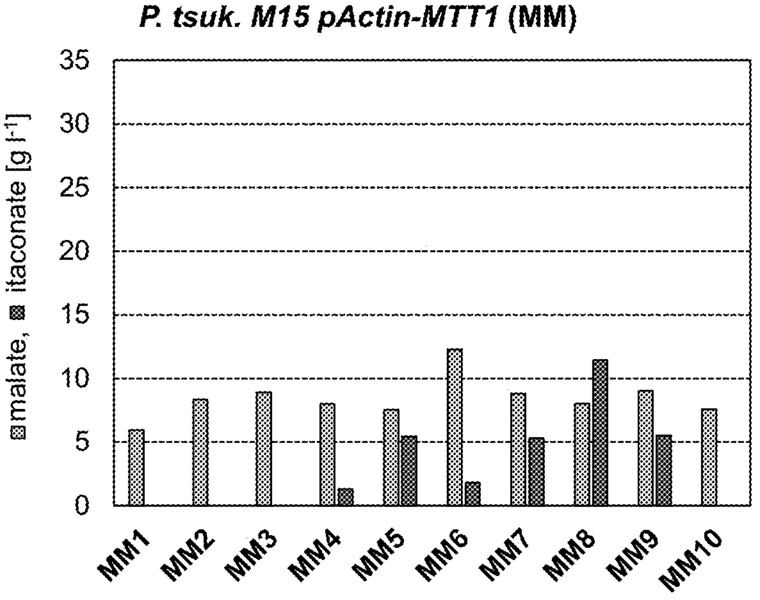
Figure 23:
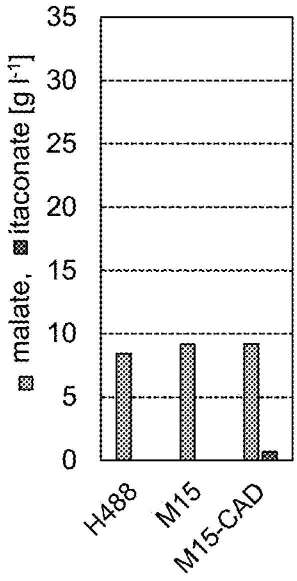

FIG. 22. Itaconic and malic acid production of *P. tsukubaensis* M15 MTT1-overexpression transformants after 10 d cultivation in 3 ml MG-IA medium FIG. 23. *P. tsukubaensis* reference strains H488, M15 and M15-CAD.

Figure 24:
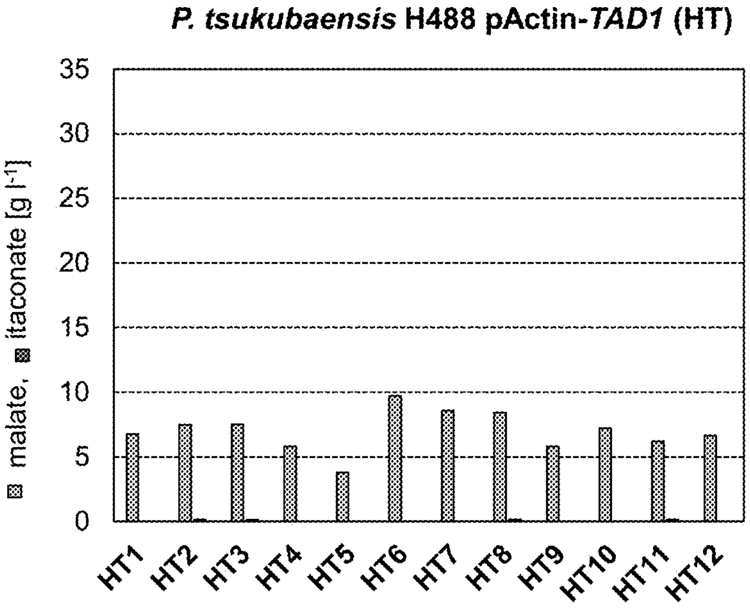

FIG. 24. Itaconic and malic acid production of *P. tsukubaensis* H488 TAD1-overexpression transformants after 10 d cultivation in 3 ml MG-IA medium.

Figure 25:
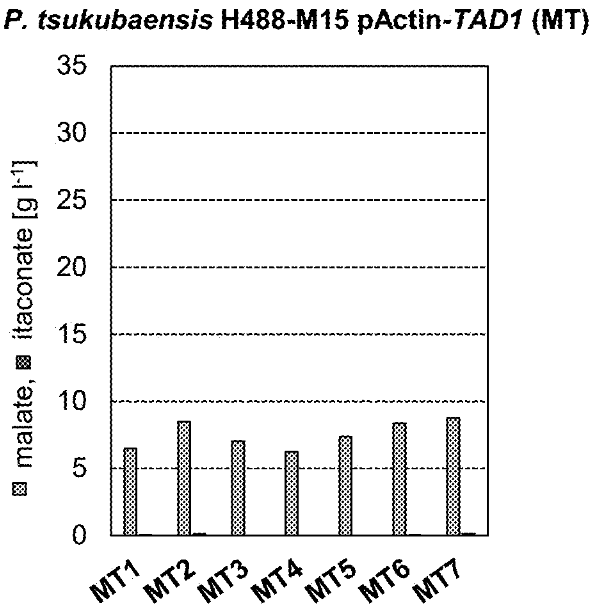

FIG. 25. Itaconic and malic acid production of *P. tsukubaensis* M15 MTT1-overexpression transformants after 10 d cultivation in 3 ml MG-IA medium.

Figure 26:
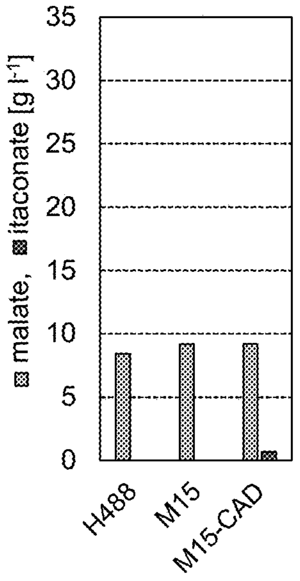

FIG. 26. *P. tsukubaensis* reference strains H488, M15 and M15-CAD.

Figure 27:
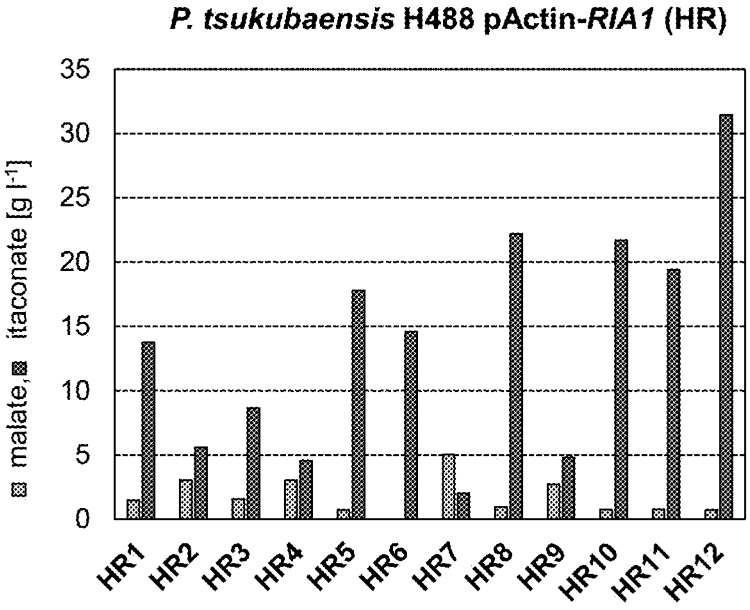

FIG. 27. Itaconic and malic acid production of *P. tsukubaensis* H488 RIA1-overexpression transformants after 10 d cultivation in 3 ml MG-IA medium.

Figure 28:
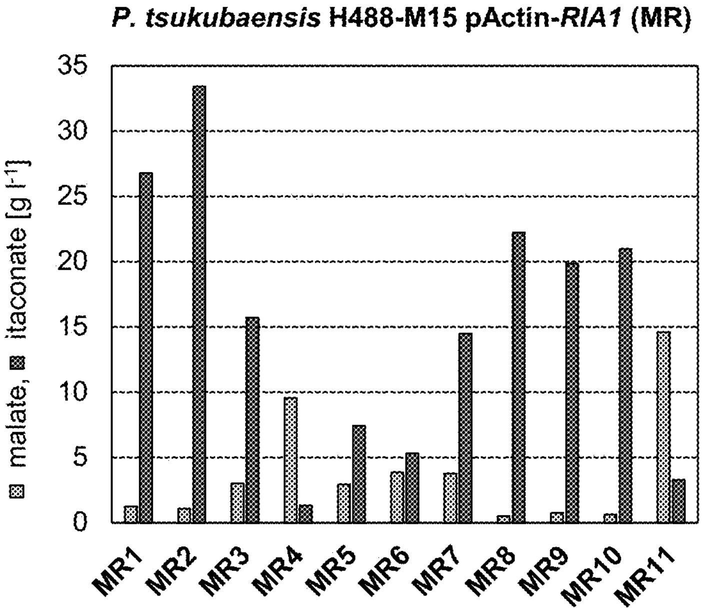
Figure 29A:
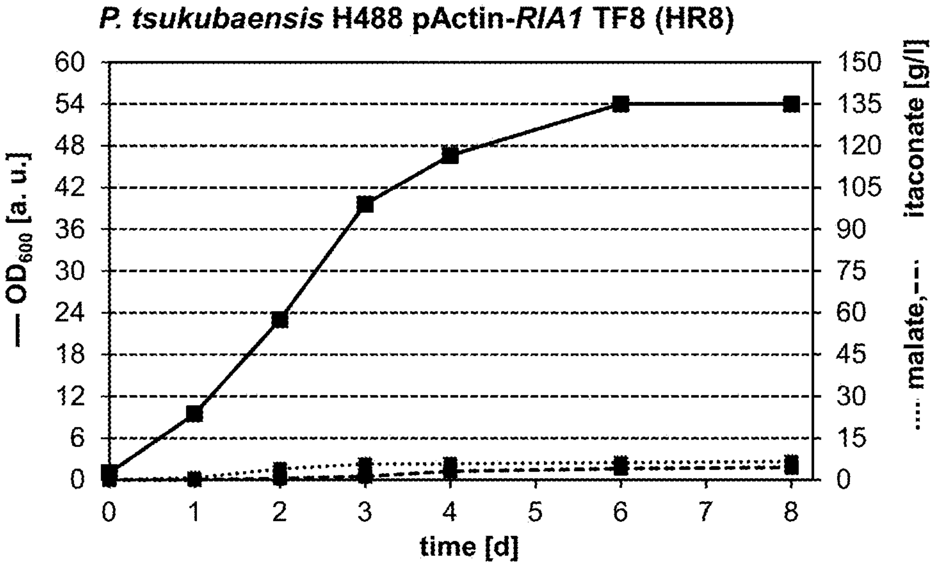
Figure 29B:
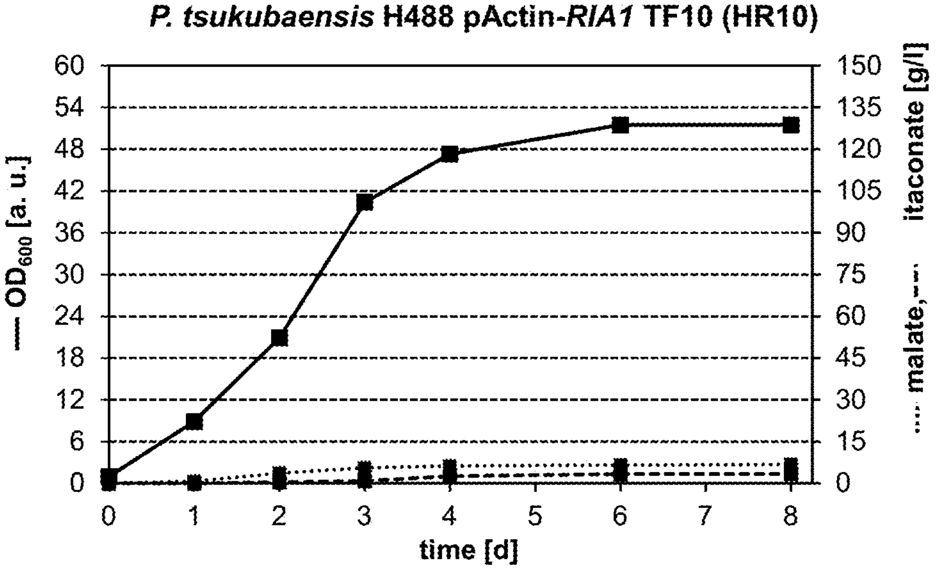
Figure 29C:
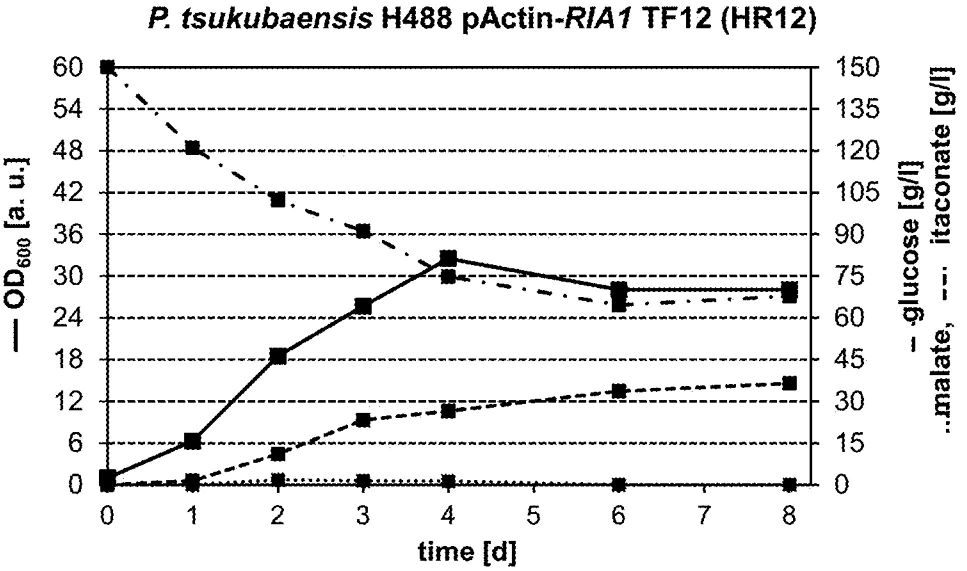
Figure 29D:
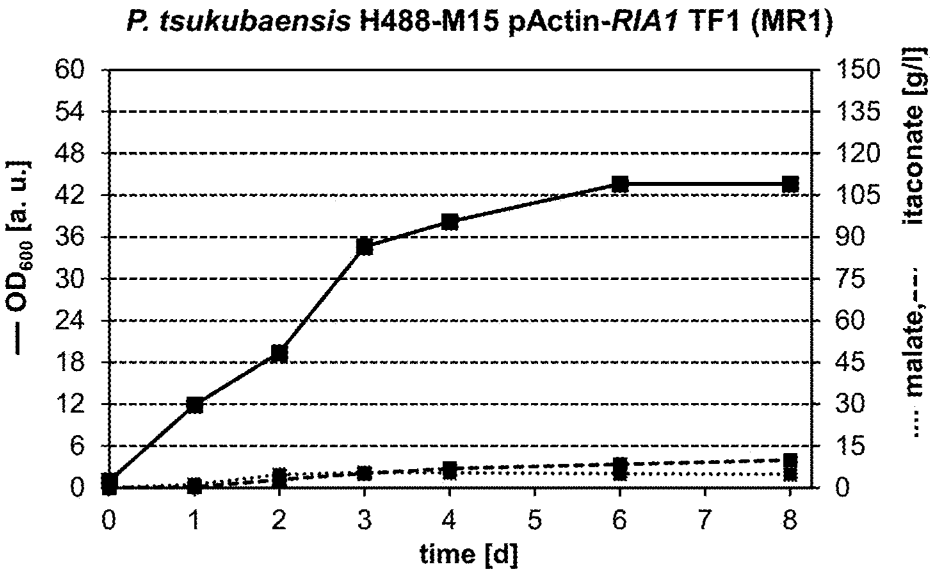
Figure 29E:
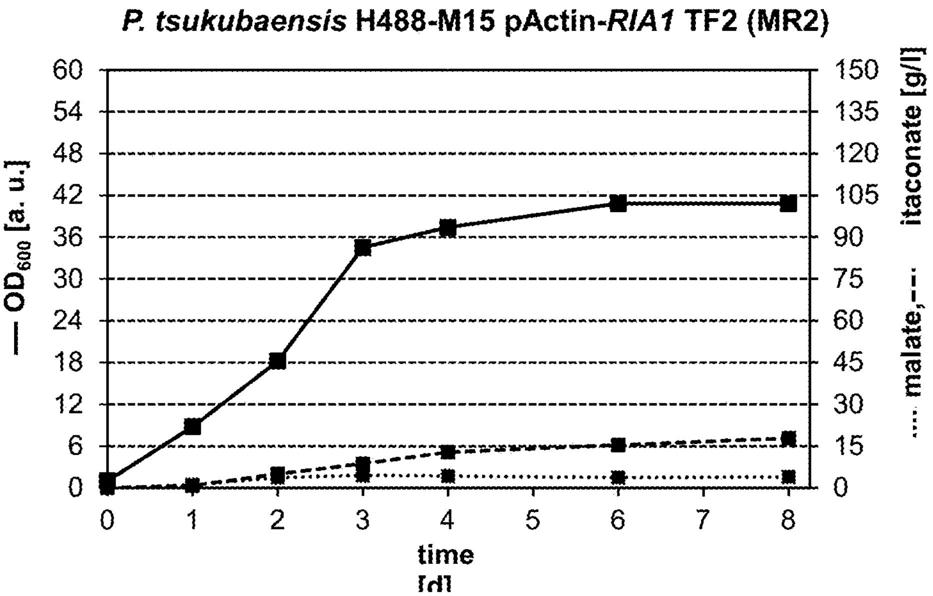
Figure 29F:
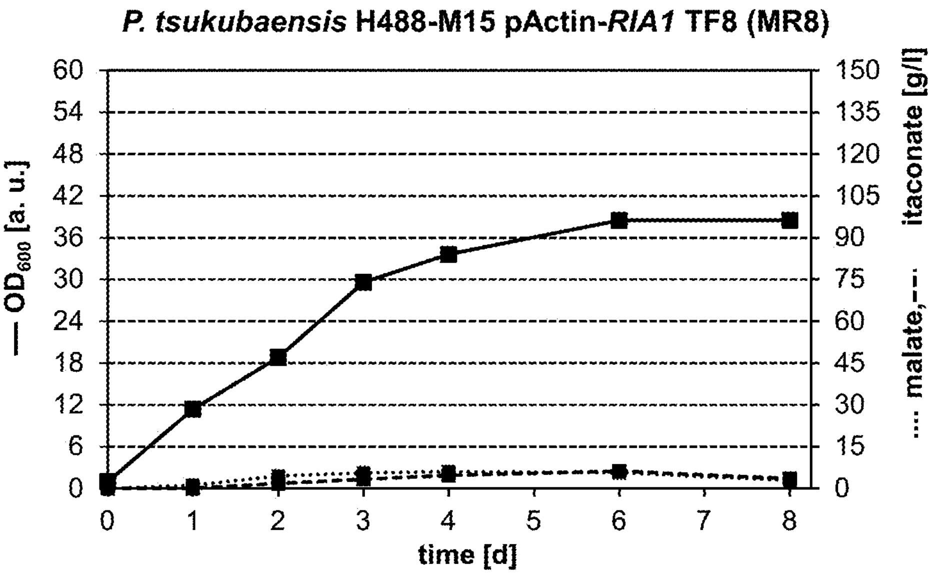

FIG. 28. Itaconic and malic acid production of *P. tsukubaensis* M15 RIA1-overexpression transformants after 10 d cultivation in 3 ml MG-IA medium.

FIGS. 29A-29F. Progression of ITA and MA production (g l-1) and growth (OD600) for six selected RIA1-overexpression transformants over the course of 8 d shaking flask cultivation in 50 ml MG-IA minimal medium (N: 2 g l-1, P: 0.1 g l-1, C: 15% w/v, no pH-control).

Figure 30:
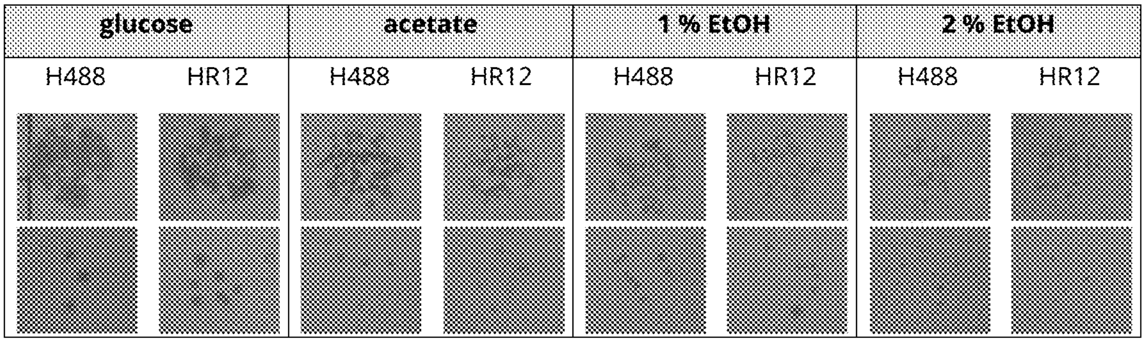
Figure 30:
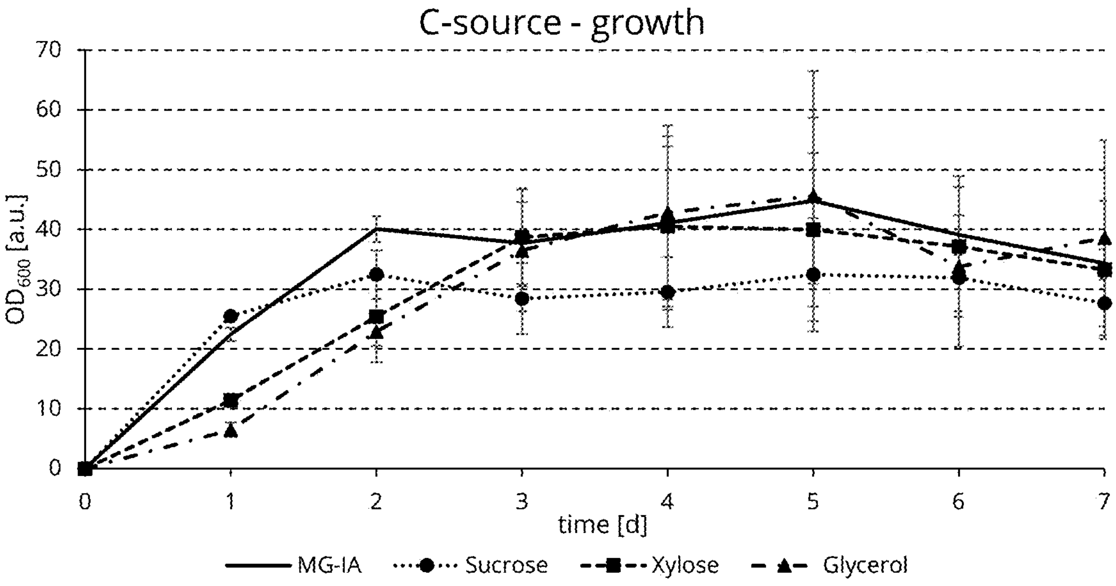

FIG. 30. Growth (OD600) pattern of *P. tsukubaensis* HR12 in MG-IA minimal medium (N: 4 g l-1, P: 1.0 g l 1) with either 10% (w/v) glucose (reference), sucrose, D-xylose or 10% v/v glycerol as sole carbon source. The cells were grown in baffled flasks for 7 d at 30° C. and 220 rpm. The medium was buffered using 3.3 g l-1 CaCO3.

Figure 31:
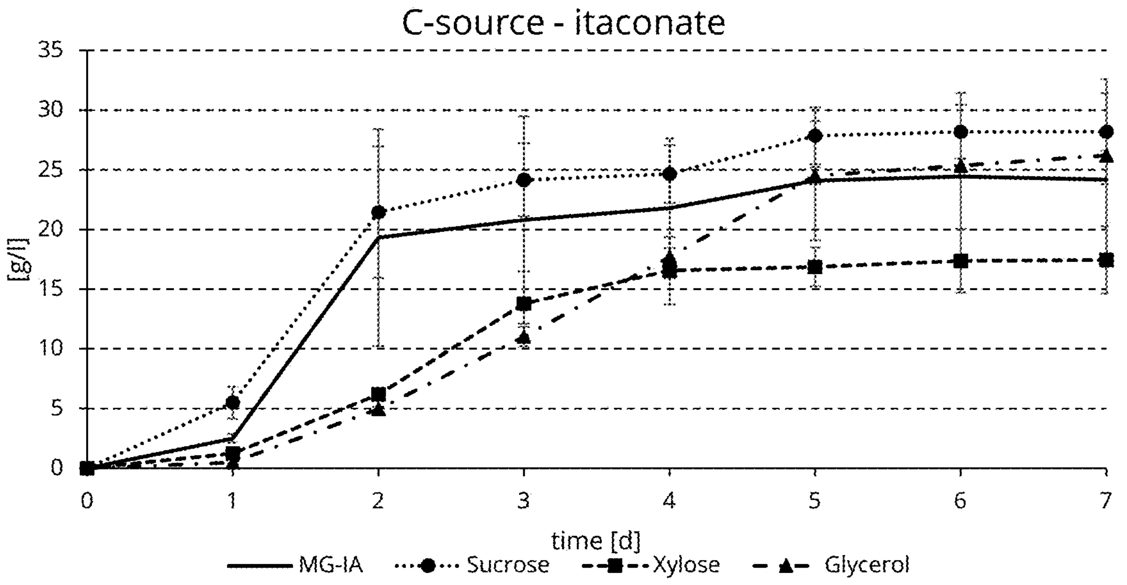

FIG. 31. Itaconic acid production of *P. tsukubaensis* HR12 in MG-IA minimal medium (N: 4 g 1-1, P: 1.0 g 1 1) with either 10% (w/v) glucose (reference), sucrose, D-xylose or 10% v/v glycerol as sole carbon source. The cells were grown in baffled flasks for 7 d at 30° C. and 220 rpm. The medium was buffered using 3.3 g l-1 CaCO3.

Figure 32:
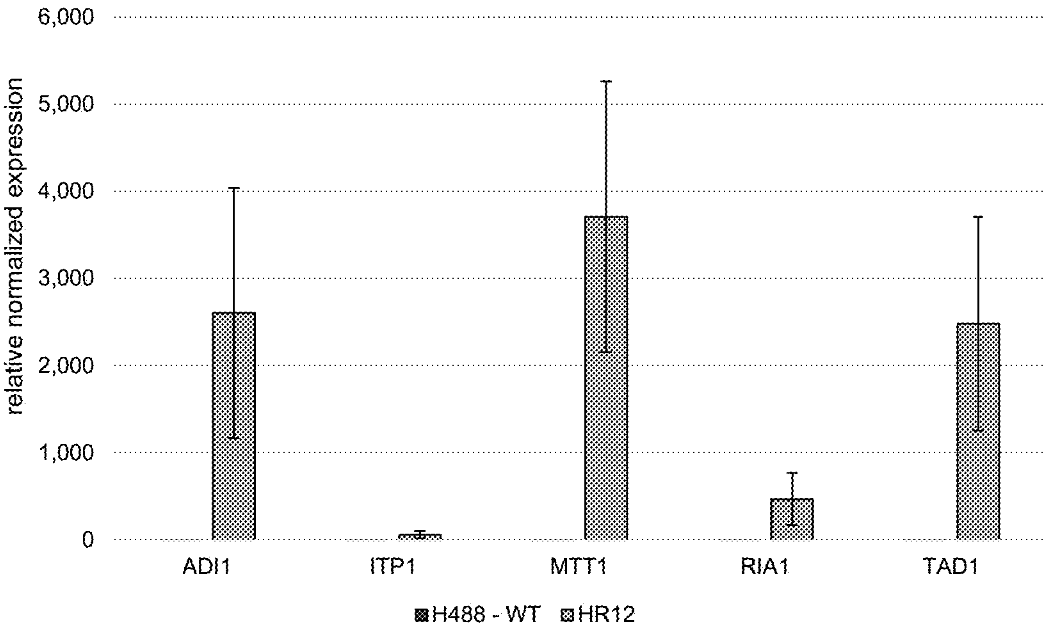

FIG. 32. Result of quantitative real-time PCR for the relative transcription of the itaconic acid cluster genes in *P. tsukubaensis* HR12 compared to H488. The cells were grown in MG-IA minimal medium until an OD600=2-3 was reached. The elongation factor 1 (EF1) and the ubiquitin conjugating enzyme (UBC6) were used as reference genes. Expression levels of HR12 were normalized for H488 expression levels. n=2, error bars show standard deviation.

Figure 33:
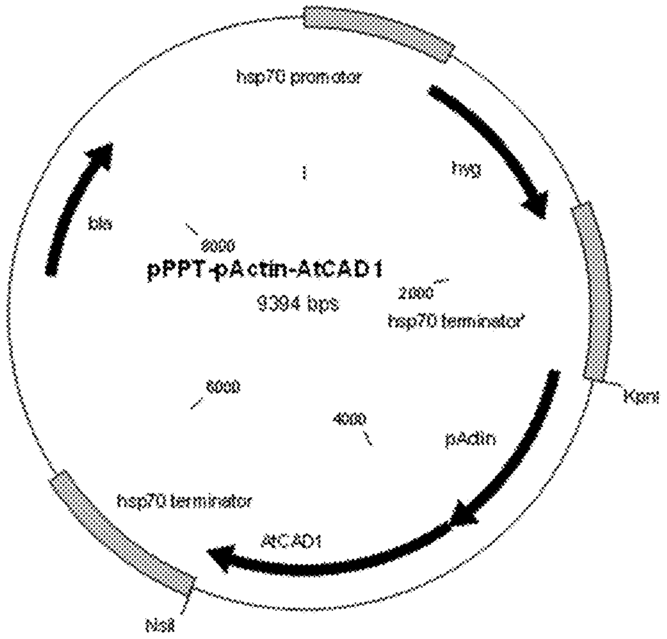

FIG. 33. Plasmid for the overexpression of the *A. terreus* CAD1 gene under the control of the strong, native Actin promoter.

Figure 34:
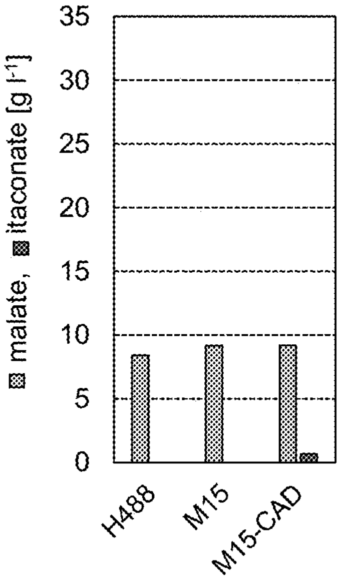

FIG. 34. *P. tsukubaensis* reference strains H488, M15 and M15-CAD.

Figure 35:
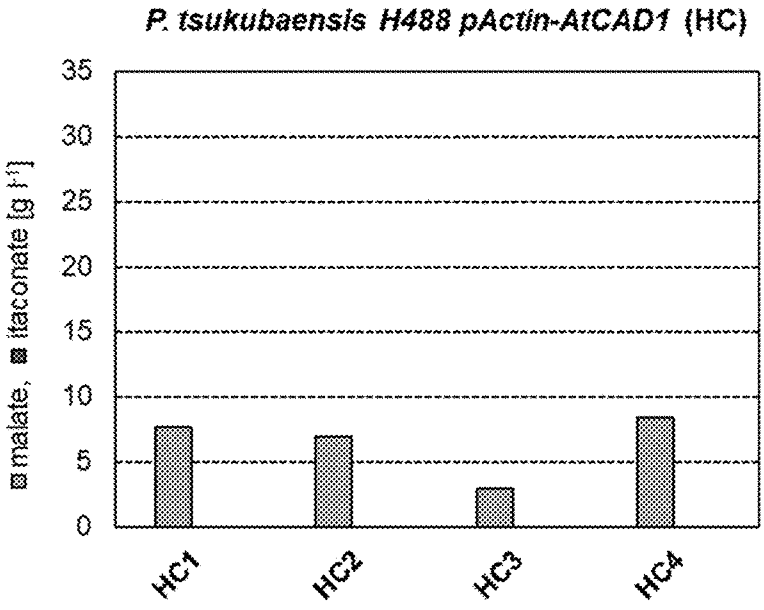

FIG. 35. Itaconic and malic acid production of *P. tsukubaensis* H488 AtCAD1-overexpression transformants after 10 d cultivation in 3 ml MG-IA medium.

Figure 36:
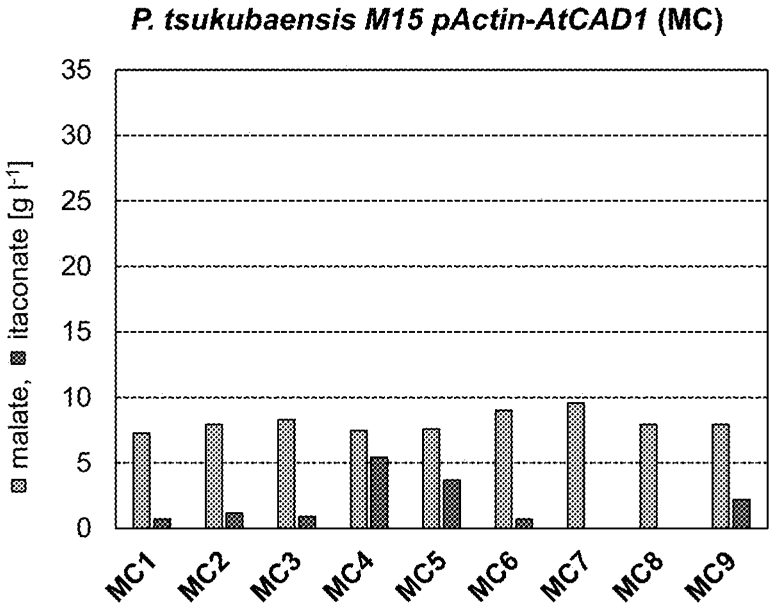

FIG. 36. Itaconic and malic acid production of *P. tsukubaensis* M15 AtCAD1-overexpression transformants after 10 d cultivation in 3 ml MG-IA medium.

Figure 37:

FIG. 37. Plasmids pPTT.Cbx.oACO1-Ex and pPTT.Cbx.oACO2 for the overexpression of the native aconitase encoding genes ACO1 (Pseudog3035, without the natural occurring intron) and ACO2 (Pseudog2814) in *P. tsukubaensis.*

Figure 38:
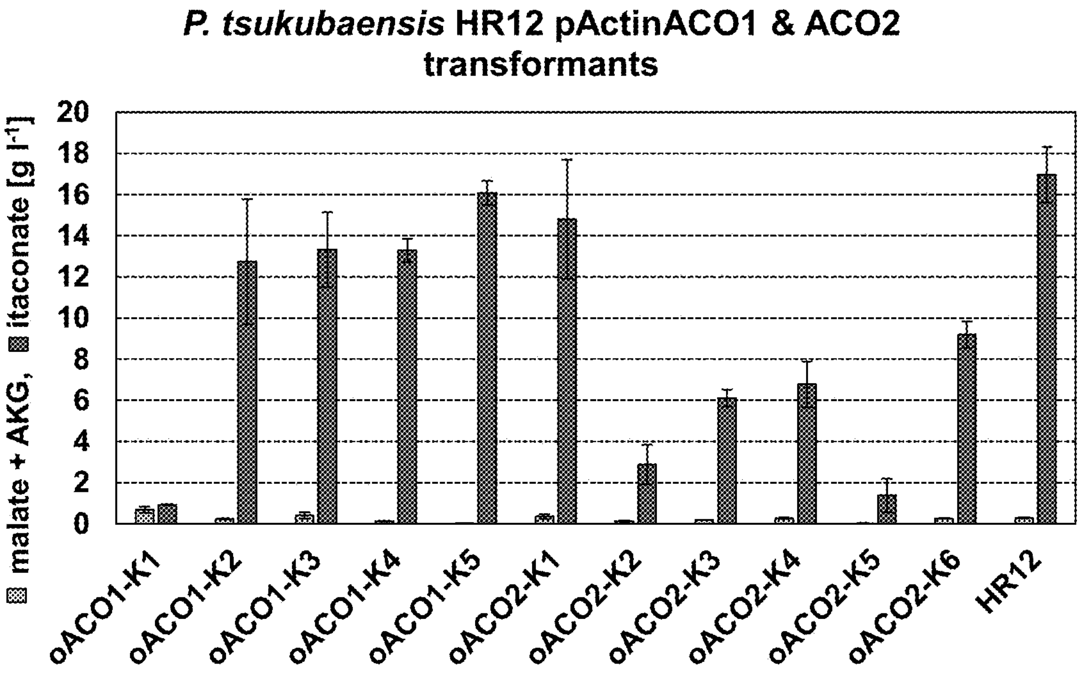

FIG. 38. Screening of ACO1 and ACO2 overexpressing *P. tsukubaensis* HR12 transformants. The cells were cultivated for six days in well cultures with 3 ml MG-IA production medium at 30° C. and 220 rpm. The medium was buffered with approx. 20 mg CaCO3/well. Error bars show standard deviation for two separate cultivations.

Figure 39:
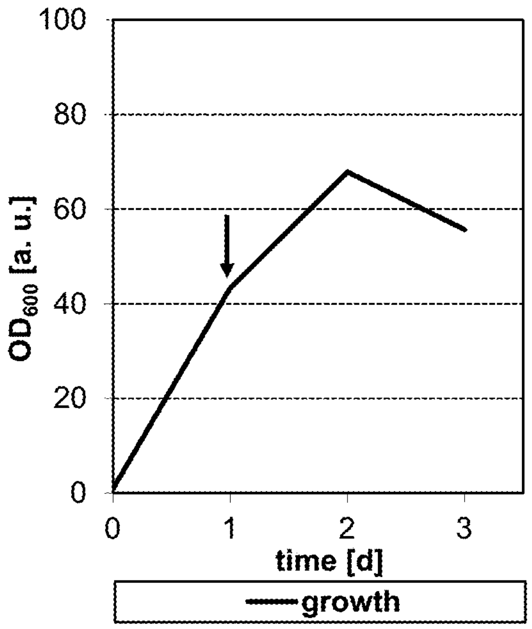

FIG. 39. Cell growth (OD600) of *P. tsukubaensis* H488 pre-cultivated in YPD medium and transferred into fresh 50 ml YPD medium. The culture was supplied with 20 g l-1 glucose at the first day of cultivation (marked by arrow). Cells were grown with a starting OD600=1 in 500 ml-baffled flasks at 30° C., 220 rpm.

Figure 40:
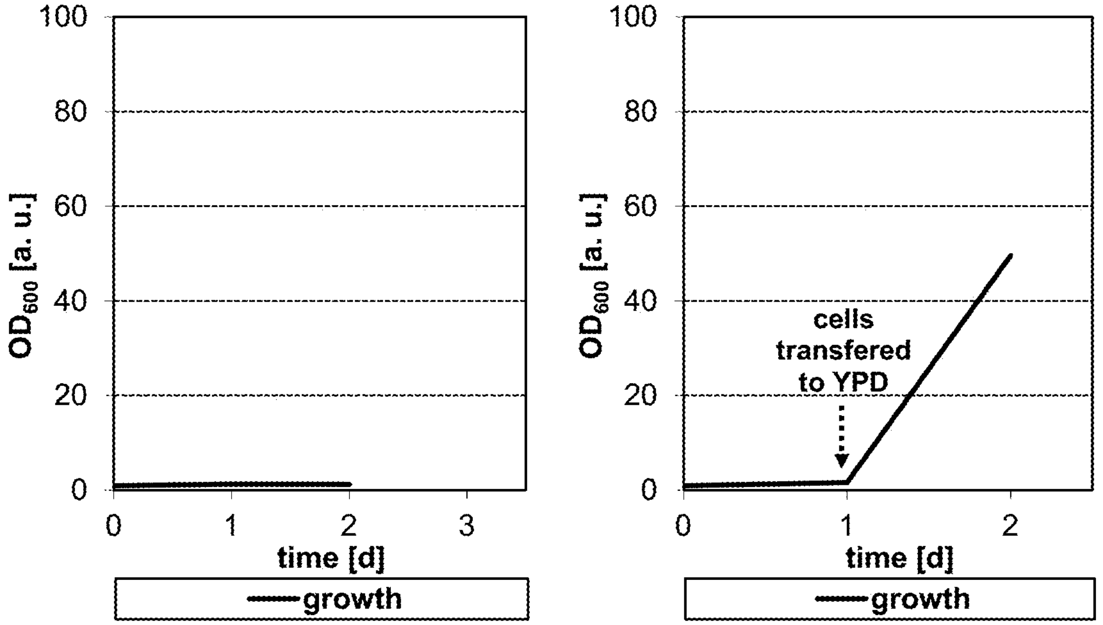

FIG. 40. Cell growth (OD600) of *P. tsukubaensis* H488 pre-cultivated in MG medium and transferred into 50 ml MG medium. Yeast cells were transferred a second time into 50 ml YPD medium (right graph). Cells were grown with a starting OD600=1 in 500 ml-baffled flasks at 30° C., 220 rpm.

Figure 41:
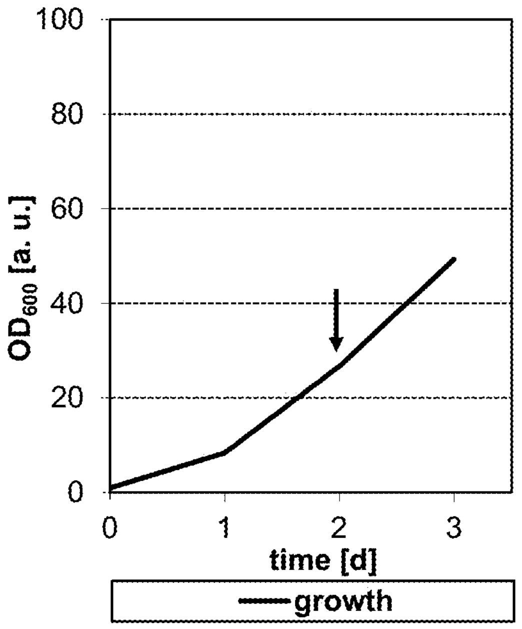

FIG. 41. Cell growth (OD600) of *P. tsukubaensis* pre-cultivated in YPD medium and transferred into 50 ml MG medium. Cells were grown with a starting OD600=1 in 500 ml-baffled flasks at 30° C., 220 rpm.

Figure 42:
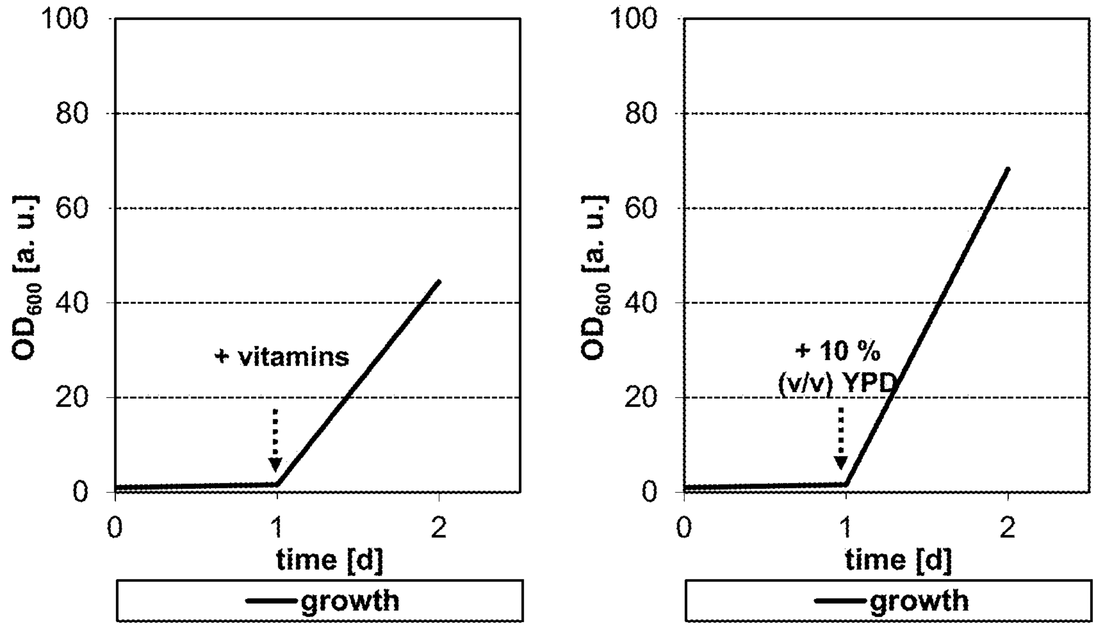

FIG. 42. Cell growth (OD600) of *P. tsukubaensis* H488 pre-cultivated in MG medium and transferred into 50 ml MG medium. Cell growth was induced by adding 10% (v/v) fresh YPD medium or 1× vitamin solution. Cells were grown with a starting OD600=1 in 500 ml-baffled flasks at 30° C., 220 rpm.

Figure 43:
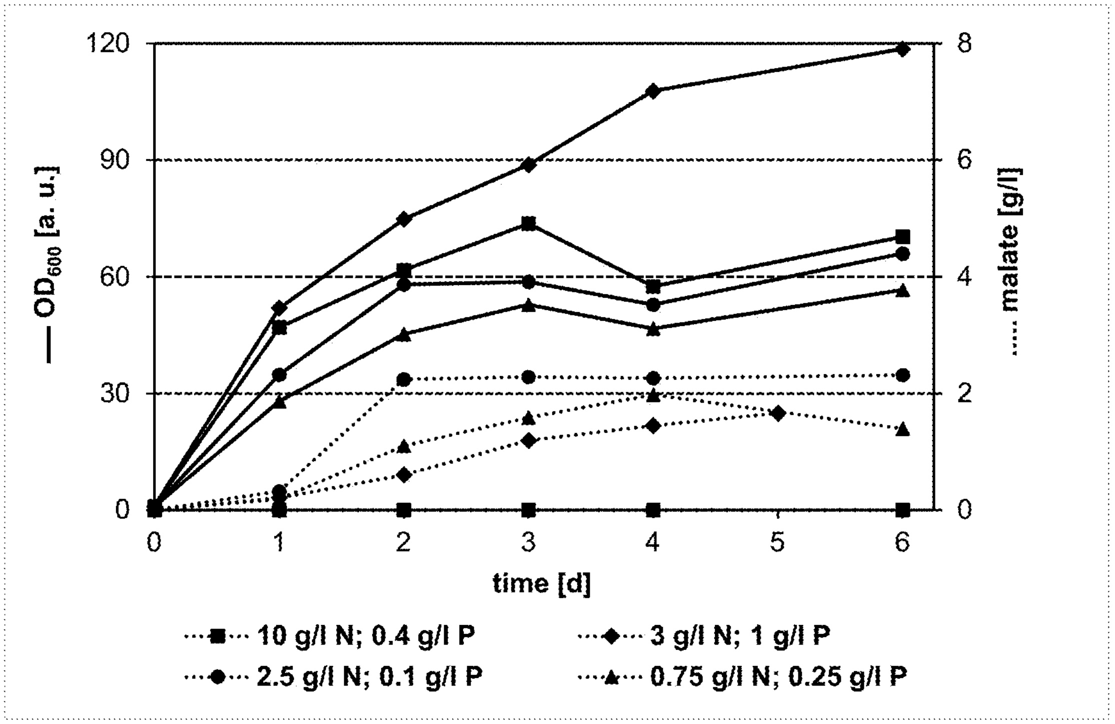

FIG. 43. Growth and organic acid production behaviour of *P. tsukubaensis* H488 in MG-T medium with various amounts of (NH4)2SO4 and KH2PO4/K2HPO4×3 H2O. The cells were pre-cultivated in YPD medium for one day and transferred into 50 ml of MG-T medium. Cells were grown with a starting OD600=1 in 500 ml-baffled flasks at 30° C., 220 rpm, medium was buffered using 3.3 g l-1 CaCO3.

Figure 44:
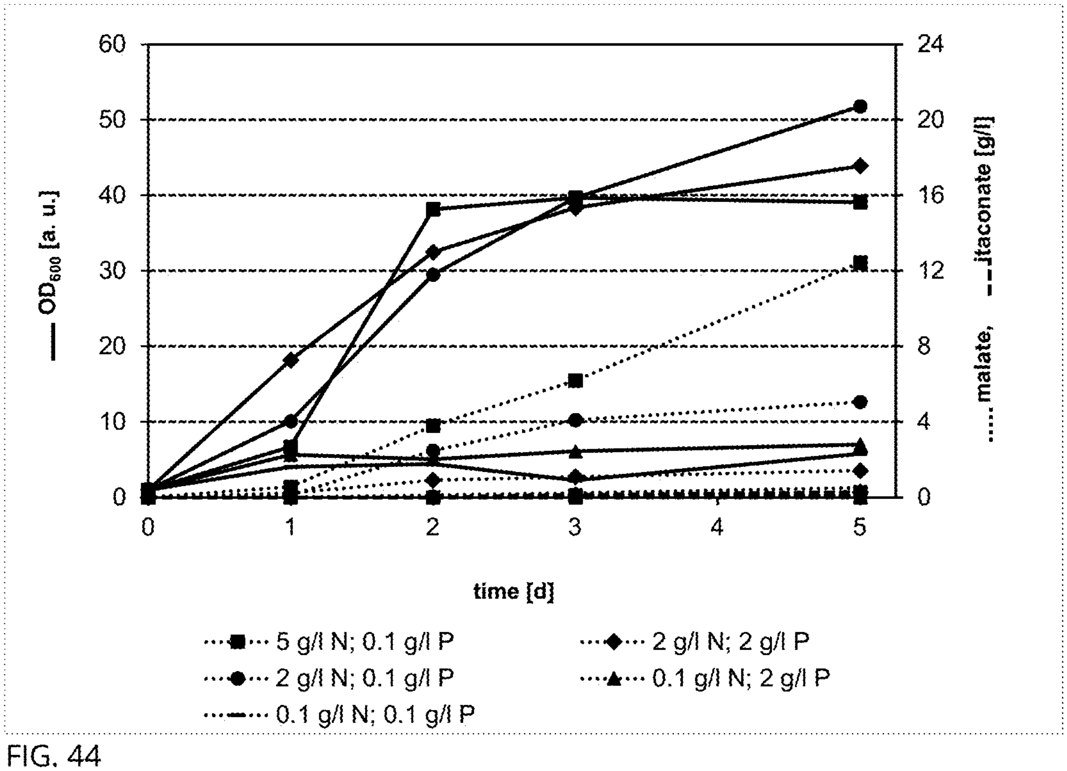

FIG. 44. Growth (OD600) and organic acid production (g l-1) behaviour of *P. tsukubaensis* H488 in MG-IA medium with various amounts of NaNO3 and KH2PO4/K2HPO4×3 H2O. The cells were pre-cultivated in YPD medium for one day and transferred into 50 ml of MG-IA medium. Cells were grown with a starting OD600=1 in 500 ml-baffled flasks at 30° C., 220 rpm, medium was buffered using 3.3 g l-1 CaCO3.

Figure 45:
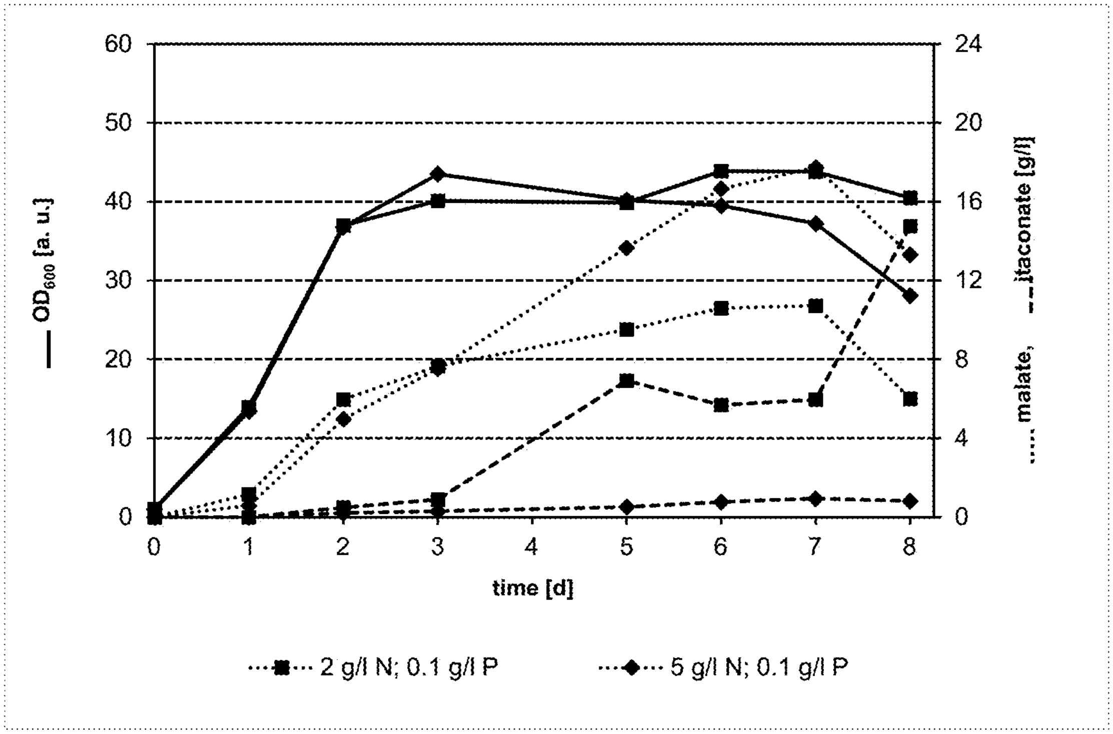

FIG. 45. Growth (OD600) and organic acid production (g l-1) behaviour of *P. tsukubaensis* M15 in MG-IA medium with either N/P-ratios of 2/0.1 or 5/0.1 (N=NaNO3, P=KH2PO4/K2HPO4×3 H2O). The cells were pre-cultivated in YPD medium for one day and transferred into 50 ml of MG-IA medium. Cells were grown with a starting OD600=1 in 500 ml-baffled flasks at 30° C., 220 rpm, medium was buffered using 3.3 g l-1 CaCO3.

Figure 46:
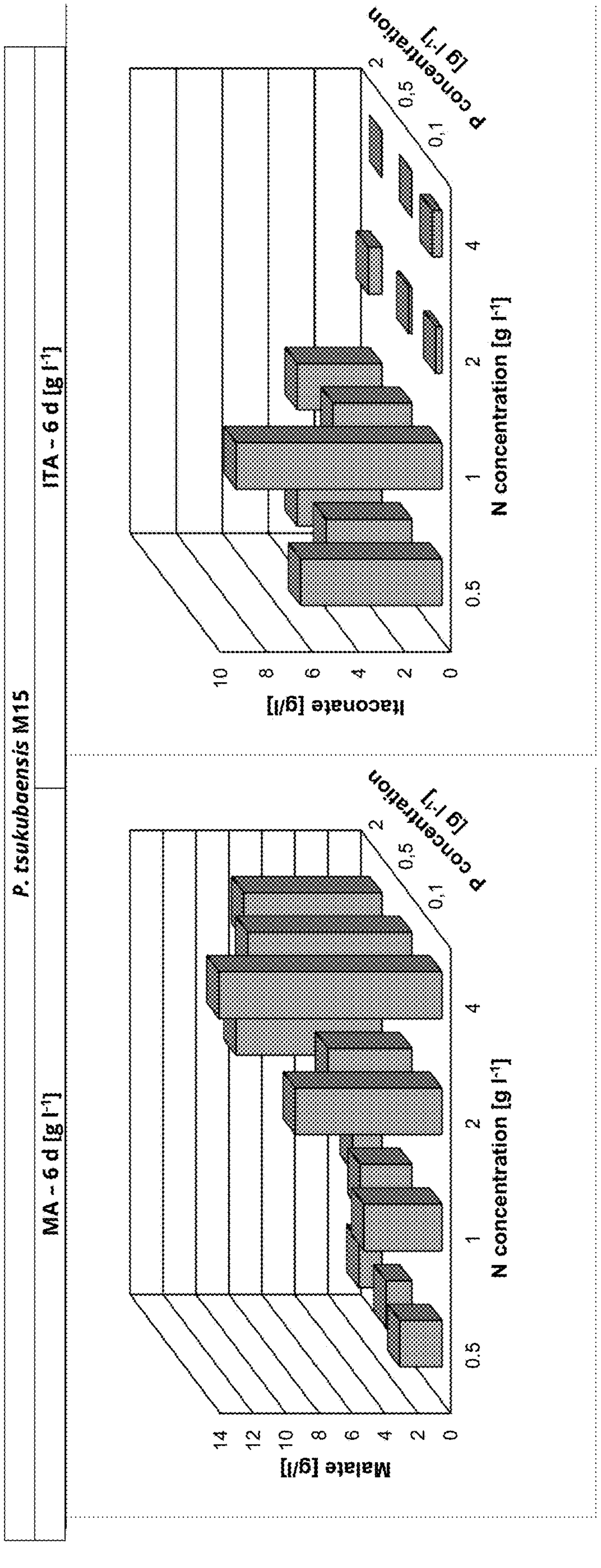

FIG. 46. Itaconic acid and malic acid production (g l-1) of *P. tsukubaensis* M15 in 3 ml-well cultures in MG-IA medium with various N/P-ratios (N=NaNO3, P=KH2PO4/K2HPO4×3 H2O). The cells were pre-cultivated in YPD medium for one day and transferred into 3 ml of MG-IA medium. Cells were incubated at 30° C., 220 rpm, medium was buffered using CaCO3.

Figure 47:
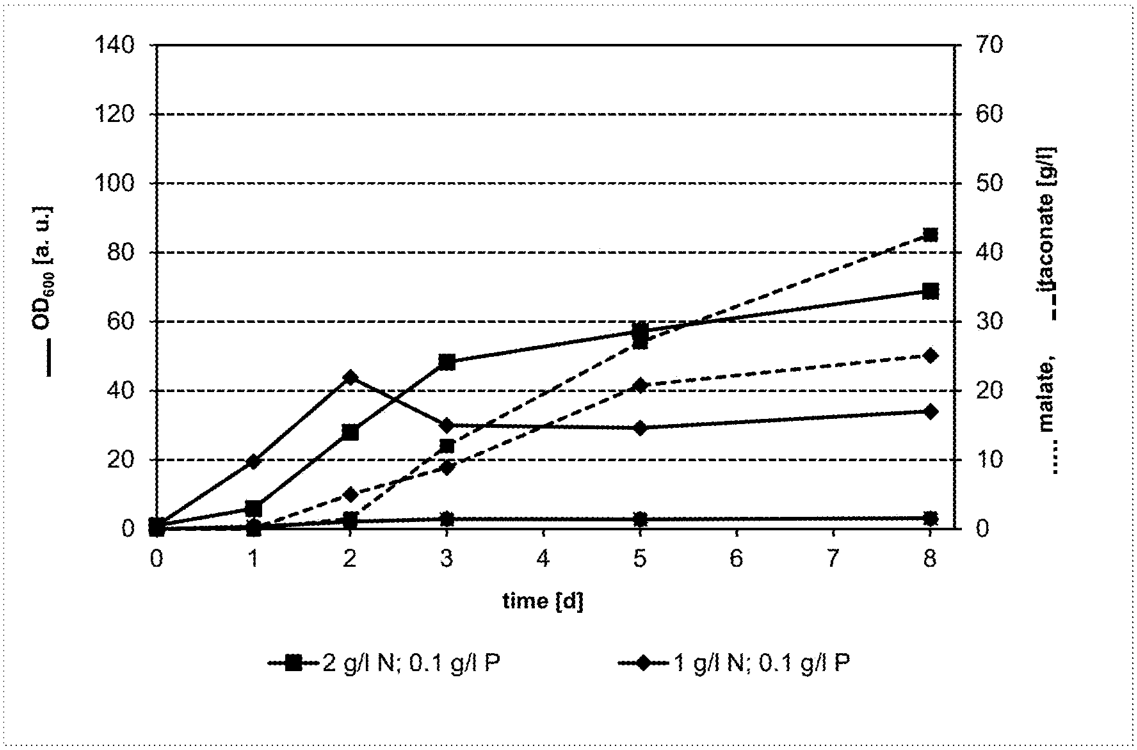

FIG. 47. Growth (OD600) and organic acid production (g l-1) behaviour of *P. tsukubaensis* M15-CAD in MG-IA medium with either N/P-ratios of 2/0.1 or 1/0.1 (N=NaNO3, P=KH2PO4/K2HPO4×3 H2O). The cells were pre-cultivated in YPD medium for one day and transferred into 50 ml of MG-IA medium. Cells were grown with a starting OD600=1 in 500 ml-baffled flasks at 30° C., 220 rpm, medium was buffered using 3.3 g l-1 CaCO3.

Figure 48:
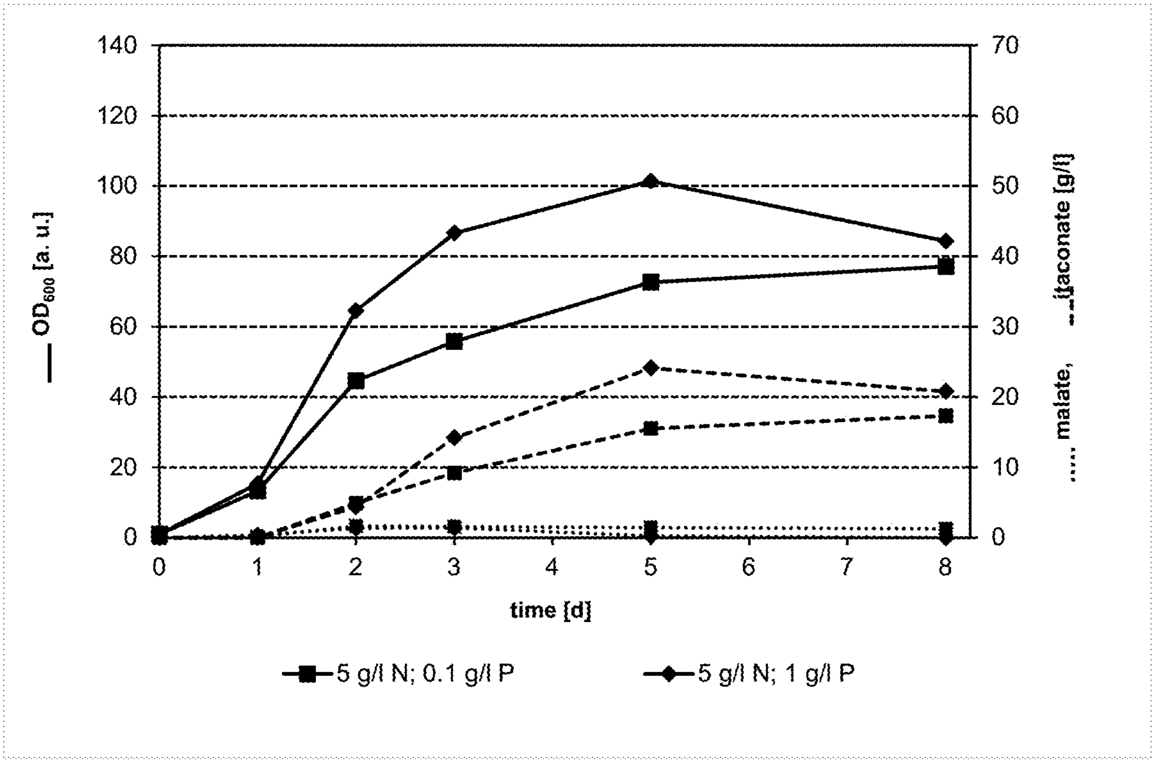

FIG. 48. Growth (OD600) and organic acid production (g l-1) behaviour of *P. tsukubaensis* M15-CAD in MG-IA medium with either N/P-ratios of 5/0.1 or 5/1 (N=NaNO3, P=KH2PO4/K2HPO4×3 H2O). The cells were pre-cultivated in YPD medium for one day and transferred into 50 ml of MG-IA medium. Cells were grown with a starting OD600=1 in 500 ml-baffled flasks at 30° C., 220 rpm, medium was buffered using 3.3 g l-1 CaCO3.

Figure 49:
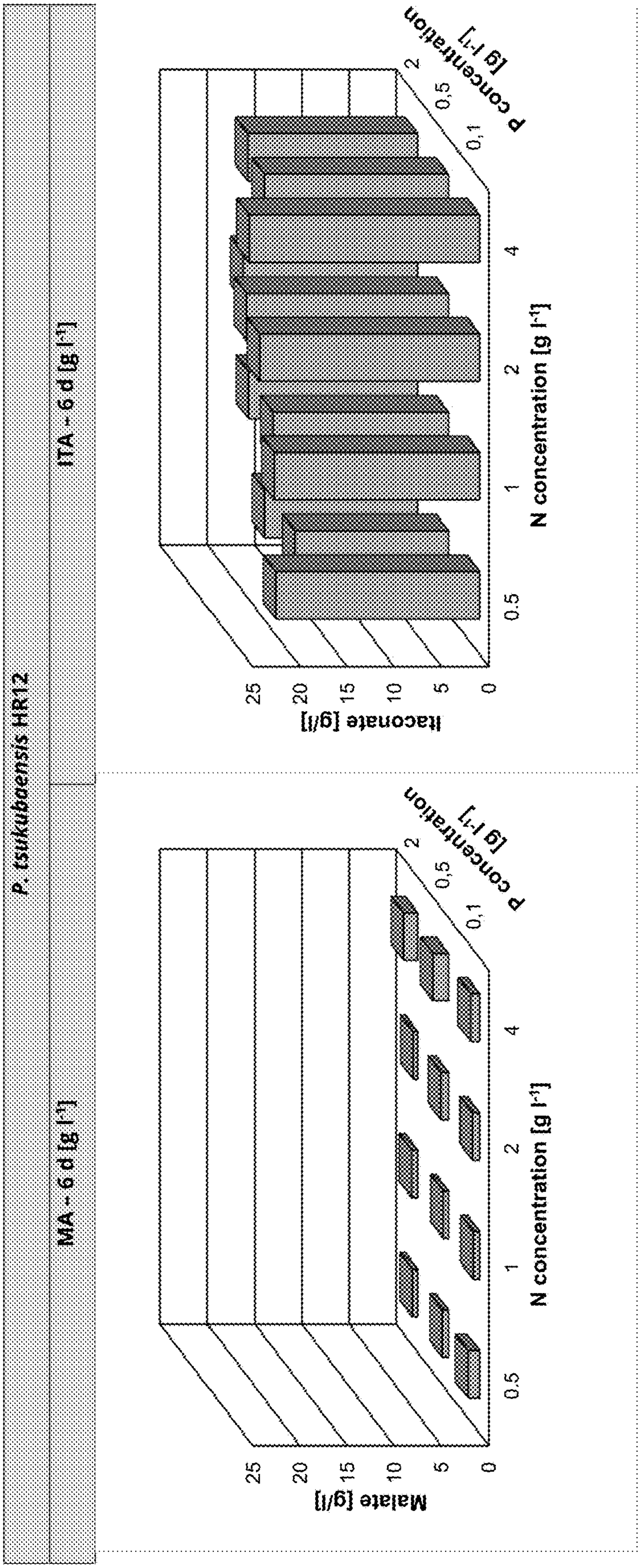

FIG. 49. Itaconic acid and malic acid production (g l-1) of *P. tsukubaensis* HR12 in 3 ml-well cultures in MG-IA medium with various N/P-ratios (N=NaNO3, P=KH2PO4/K2HPO4×3 H2O). The cells were pre-cultivated in YPD medium for one day and transferred into 3 ml of MG-IA medium. Cells were incubated at 30° C., 220 rpm, medium was buffered using CaCO3.

Figure 50:
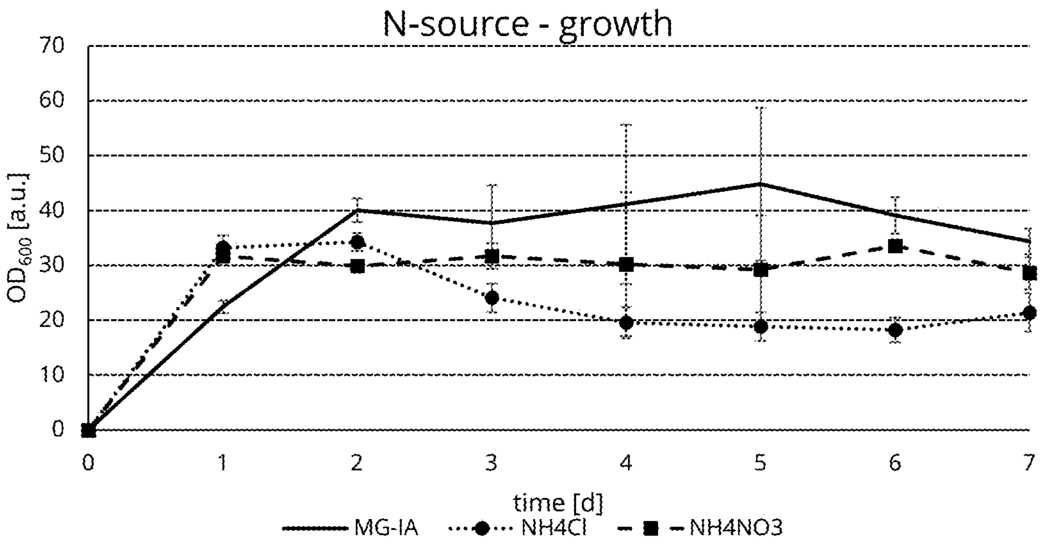

FIG. 50. Growth (OD600) pattern of *P. tsukubaensis* HR12 in MG-IA minimal medium (N: 4 g l-1, P: 1.0 g l 1) with either NaNO3 (reference), NH4Cl or NH4NO3 as N-source. The cells were grown in baffled flasks for 7 d at 30° C. and 220 rpm. The medium was buffered using 3.3 g l-1 CaCO3.

Figure 51:
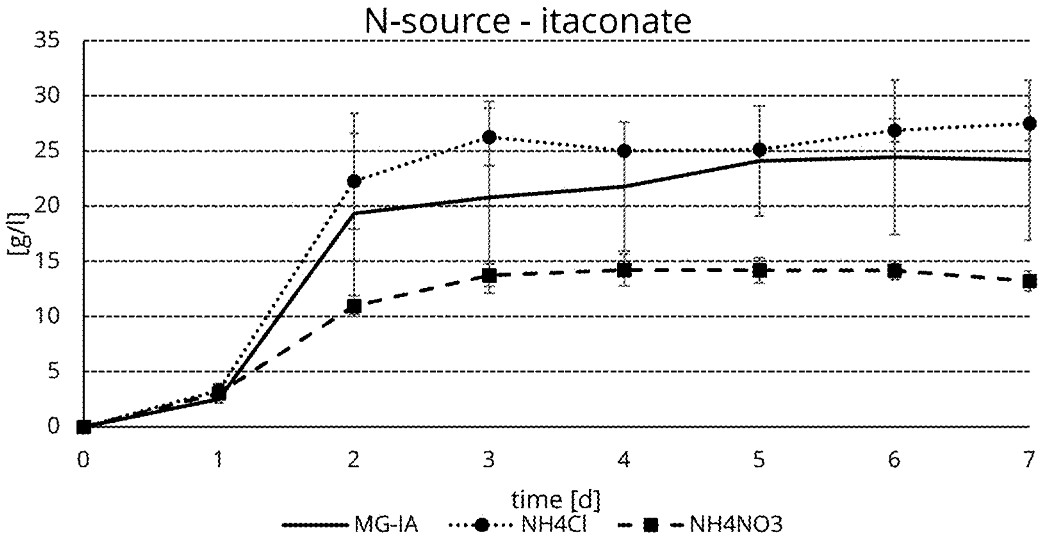

FIG. 51. Itaconic acid production (g l-1) of *P. tsukubaensis* HR12 in MG-IA minimal medium (N: 4 g l-1, P: 1.0 g l 1) with either NaNO3 (reference), NH4Cl or NH4NO3 as N-source. The cells were grown in baffled flasks for 7 d at 30° C. and 220 rpm. The medium was buffered using 3.3 g l-1 CaCO3.

Figure 52:
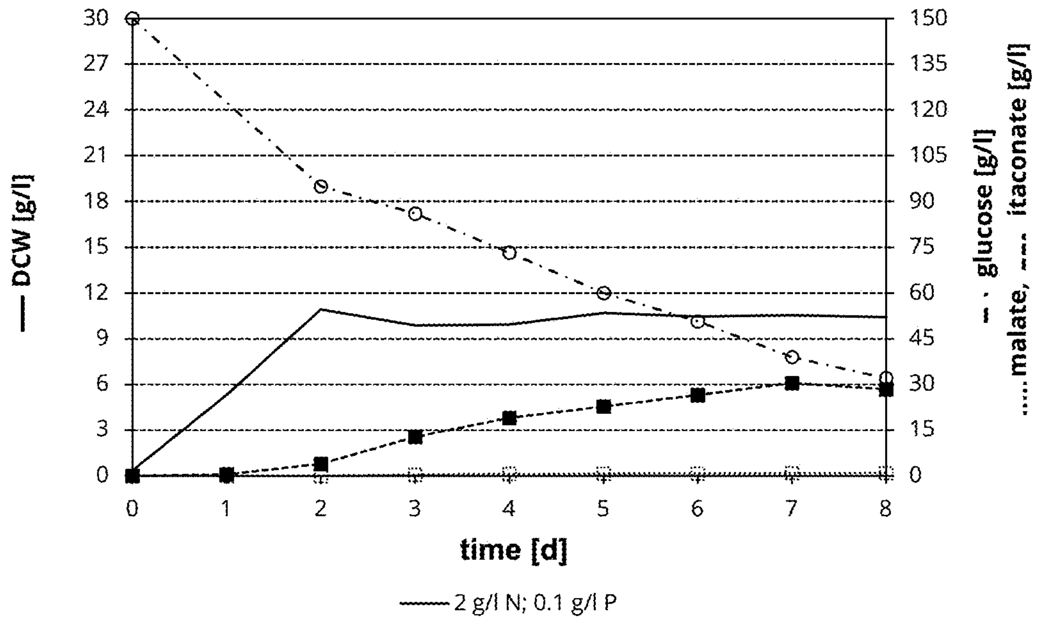

FIG. 52. 600 ml bioreactor cultivation of *P. tsukubaensis* M15-CAD in ITA production medium MG-IA-N/P: 2/0.1 g l-1 (NaNO3). The cells were cultivated for eight days at 30° C., pH=5.5, pO2=55% and an initial glucose concentration of 150 g l-1. Glucose consumption was monitored every 24 h. In the same interval the produced amounts of organic acids (ITA & MA) were determined as well as the dry cell weight (DCW).

Figure 53:
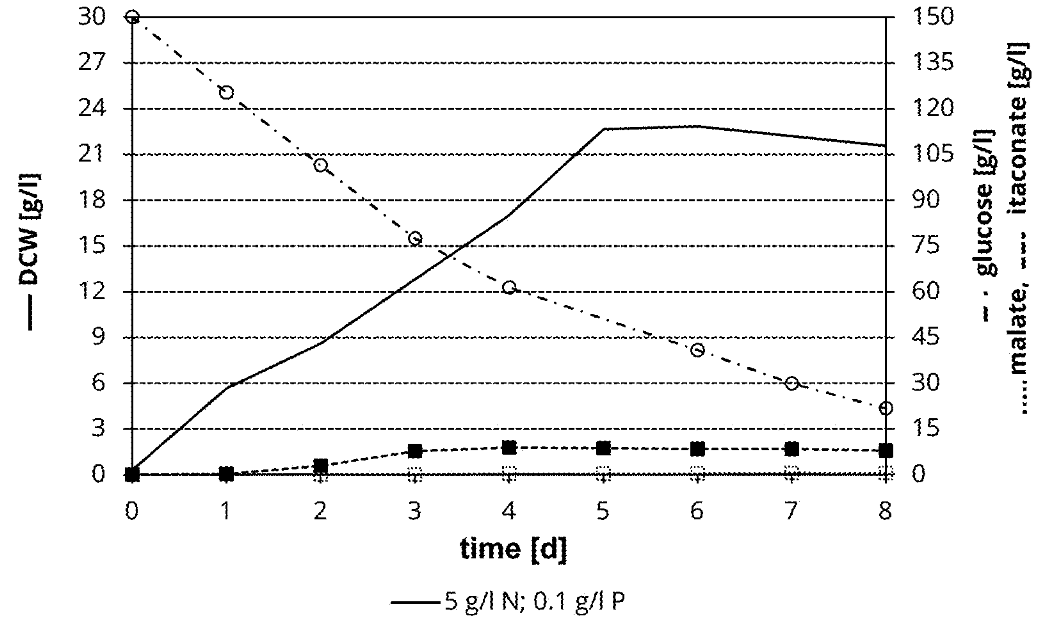

FIG. 53. 600 ml bioreactor cultivation of *P. tsukubaensis* M15-CAD in ITA production medium MG-IA-N/P: 5/0.1 g l-1 (NaNO3). The cells were cultivated for eight days at 30° C., pH=5.5, pO2=55% and an initial glucose concentration of 150 g l-1. Glucose consumption was monitored every 24 h. In the same interval the produced amounts of organic acids (ITA & MA) were determined as well as the dry cell weight (DCW).

Figure 54:
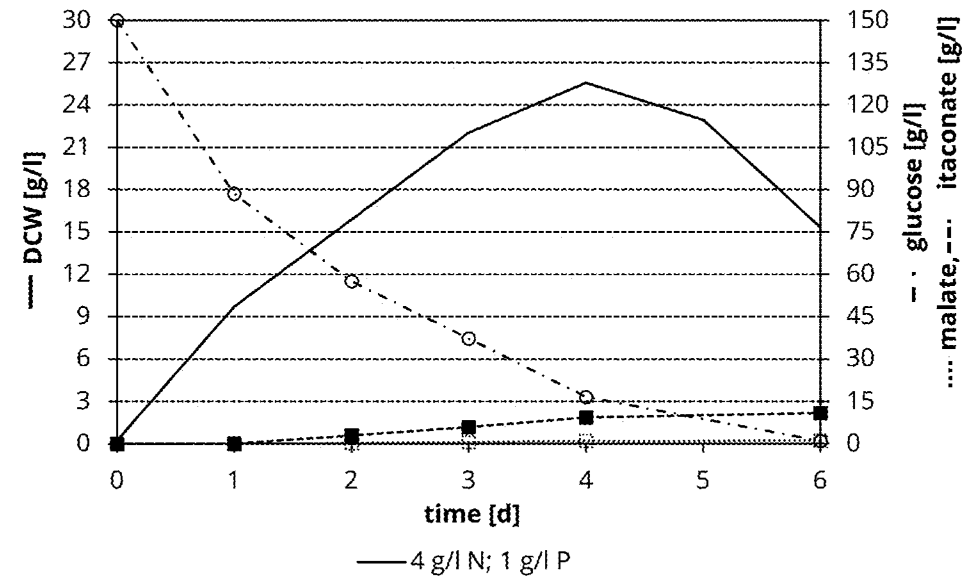

FIG. 54. 600 ml bioreactor cultivation of *P. tsukubaensis* M15-CAD in ITA production medium MG-IA-N/P: 4/1 g l-1 (NaNO3). The cells were cultivated for six days at 30° C., pH=5.5, pO2=55% and an initial glucose concentration of 150 g l-1. Glucose consumption was monitored every 24 h. In the same interval the produced amounts of organic acids (ITA & MA) were determined as well as the dry cell weight (DCW).

Figure 55:
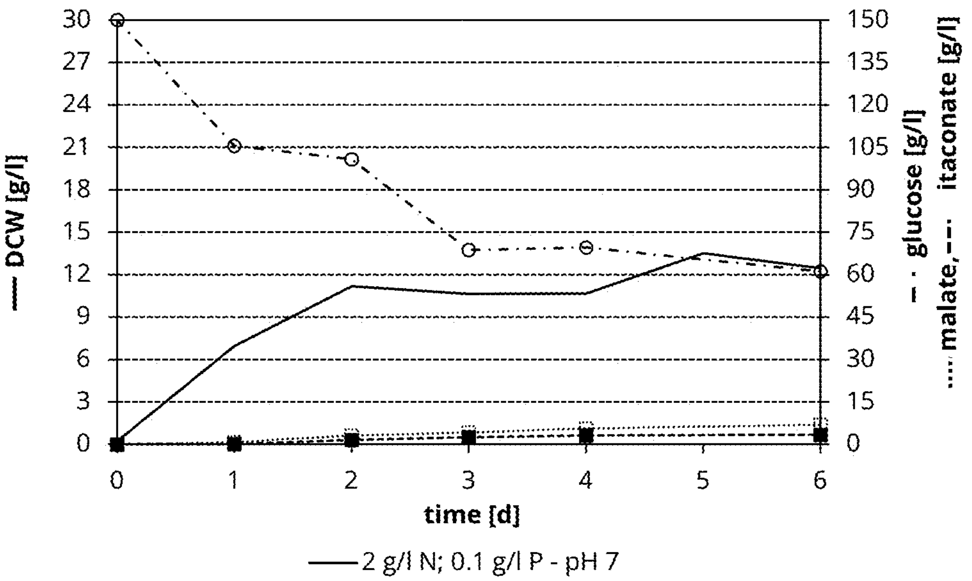

FIG. 55. 600 ml bioreactor cultivation of *P. tsukubaensis* M15-CAD in ITA production medium MG-IA-N/P: 2/0.1 g l-1 (NaNO3). The cells were cultivated for six days at 30° C., pH=7.0, pO2=55% and an initial glucose concentration of 150 g l-1. Glucose consumption was monitored every 24 h. In the same interval the produced amounts of organic acids (ITA & MA) were determined as well as the dry cell weight (DCW).

Figure 56:
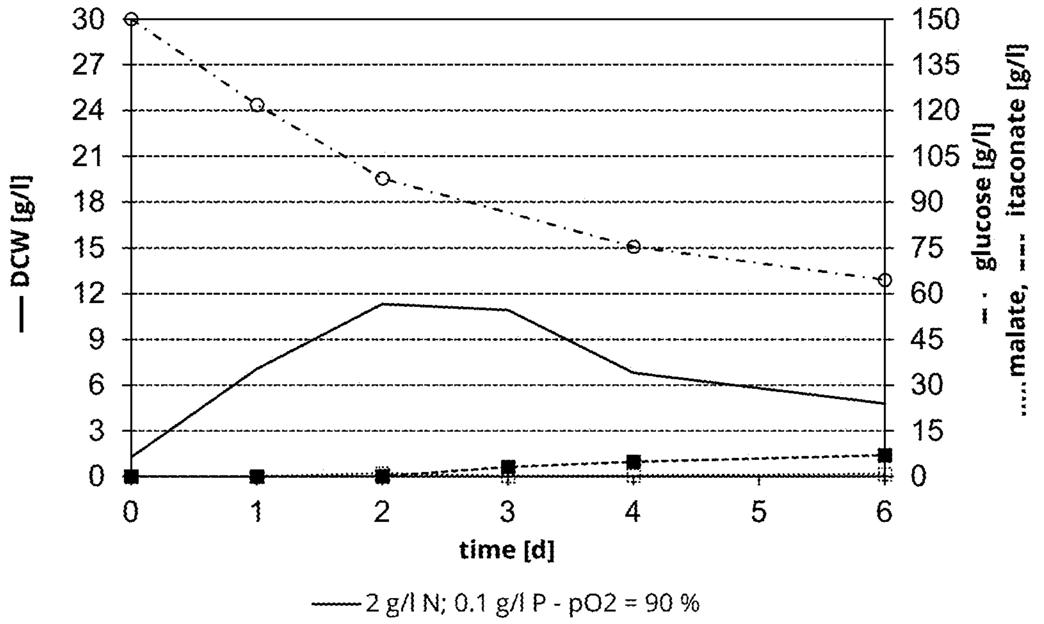

FIG. 56. 600 ml bioreactor cultivation of *P. tsukubaensis* M15-CAD in ITA production medium MG-IA-N/P: 2/0.1 g l-1 (NaNO3). The cells were cultivated for six days at 30° C., pH=5.5, pO2=90% and an initial glucose concentration of 150 g l-1. Glucose consumption was monitored every 24 h. In the same interval the produced amounts of organic acids (ITA & MA) were determined as well as the dry cell weight (DCW).

Figure 57:
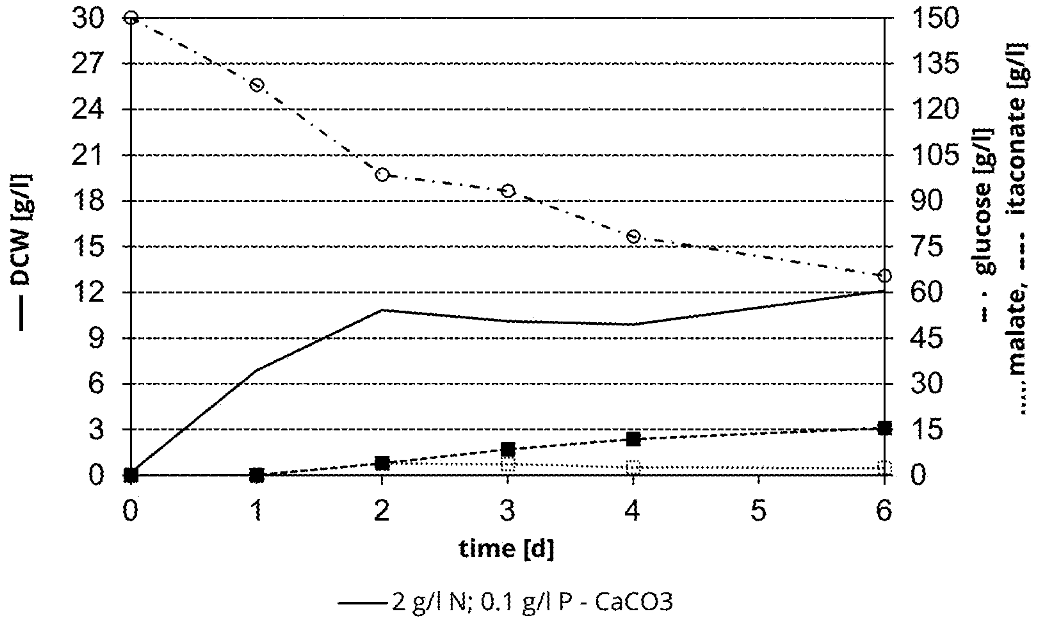

FIG. 57. 600 ml bioreactor cultivation of *P. tsukubaensis* M15-CAD in ITA production medium MG-IA-N/P: 2/0.1 g l-1 (NaNO3). The cells were cultivated for six days at 30° C., pH approx. 5.5-adjusted with 4 g l-1 CaCO3, pO2=55% and an initial glucose concentration of 150 g l-1. Glucose consumption was monitored every 24 h. In the same interval the produced amounts of organic acids (ITA & MA) were determined as well as the dry cell weight (DCW).

Figure 58:
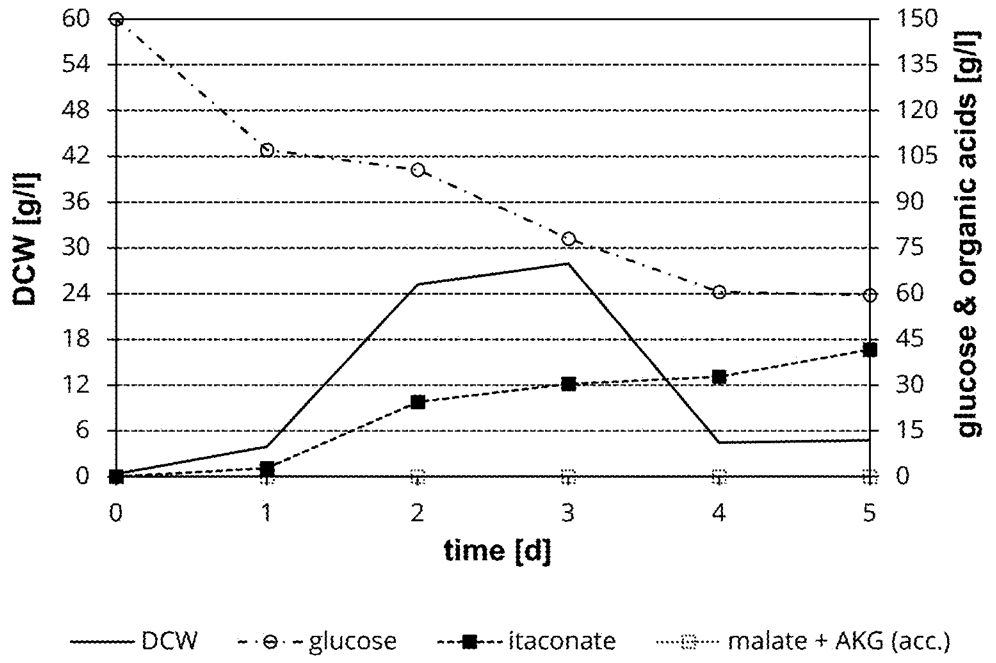

FIG. 58. 600 ml bioreactor cultivation of *P. tsukubaensis* HR12 in ITA production medium MG-IA-N/P: 2/0.1 g l-1 (NaNO3). The cells were cultivated for five days at 30° C., pH=5.5, pO2=55% and an initial glucose concentration of 150 g l-1. Glucose consumption was monitored every 24 h. In the same interval the produced amounts of organic acids (ITA & MA) were determined as well as the dry cell weight (DCW).

Figure 59:
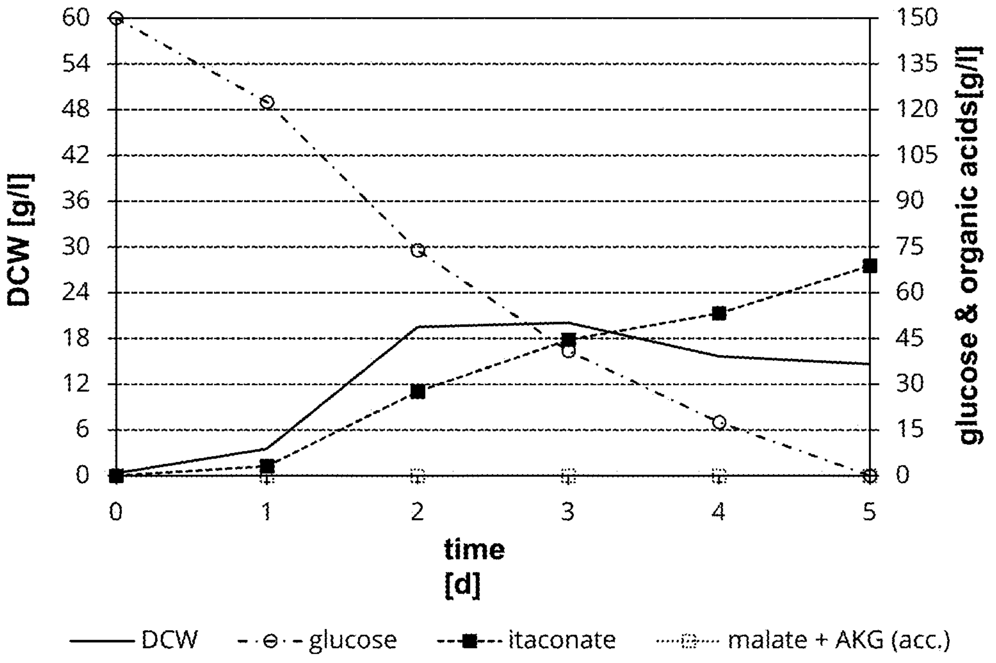

FIG. 59. 600 ml bioreactor cultivation of *P. tsukubaensis* HR12 in ITA production medium MG-IA-N/P: 4/1 g l-1 (NaNO3). The cells were cultivated for five days at 30° C., pH=5.5, pO2=55% and an initial glucose concentration of 150 g l-1. Glucose consumption was monitored every 24 h. In the same interval the produced amounts of organic acids (ITA & MA) were determined as well as the dry cell weight (DCW).

Figure 60:
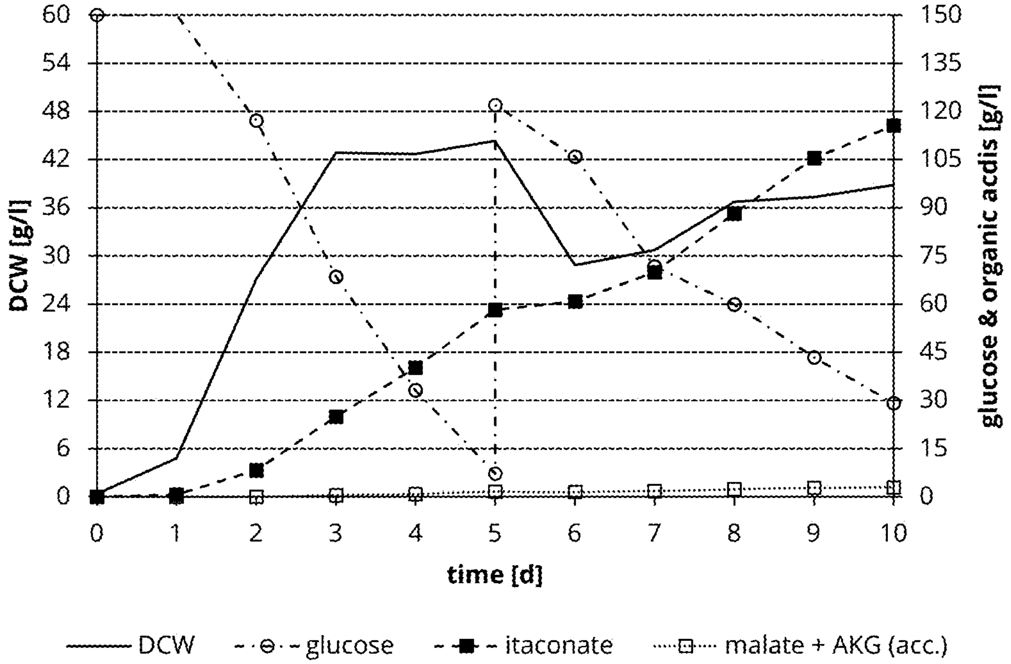

FIG. 60. 600 ml bioreactor cultivation of *P. tsukubaensis* HR12 in ITA production medium MG-IA-N/P: 4/1 g l-1 (NaNO3). The cells were cultivated for ten days at 30° C., pH=5.5, pO2=55% and an initial glucose concentration of 150 g l-1. At the 5th day 100 g l-1 glucose were fed. Glucose consumption was monitored every 24 h. In the same interval the produced amounts of organic acids (ITA & MA) were determined as well as the dry cell weight (DCW).

Figure 61:
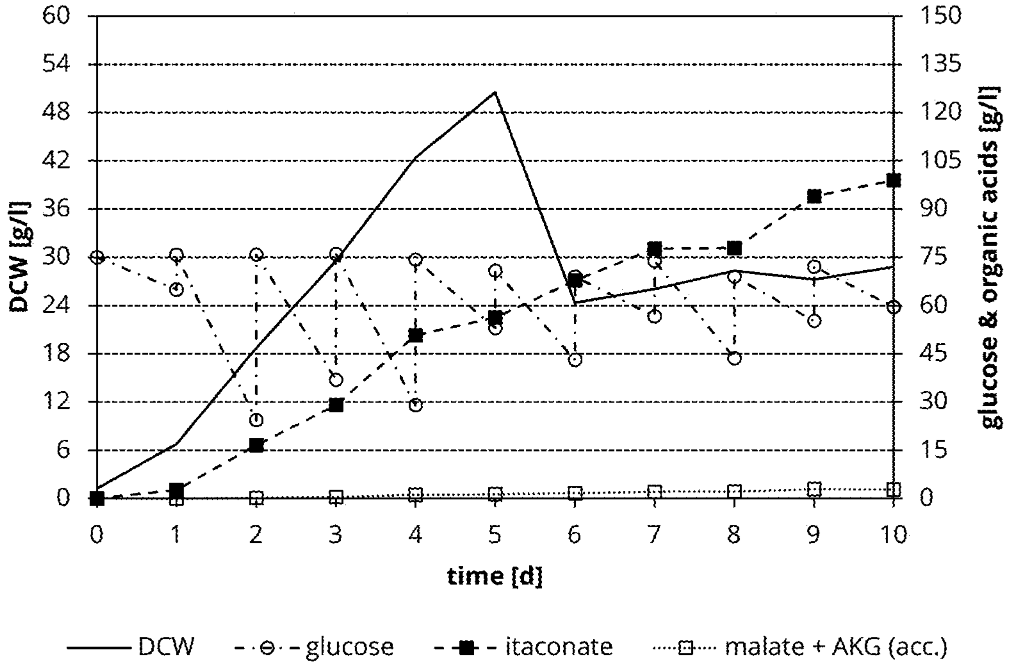

FIG. 61. 600 ml bioreactor cultivation of *P. tsukubaensis* HR12 in ITA production medium MG-IA-N/P: 4/1 g l-1 (NaNO3). The cells were cultivated for ten days at 30° C., pH=5.5, pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW).

Figure 62:
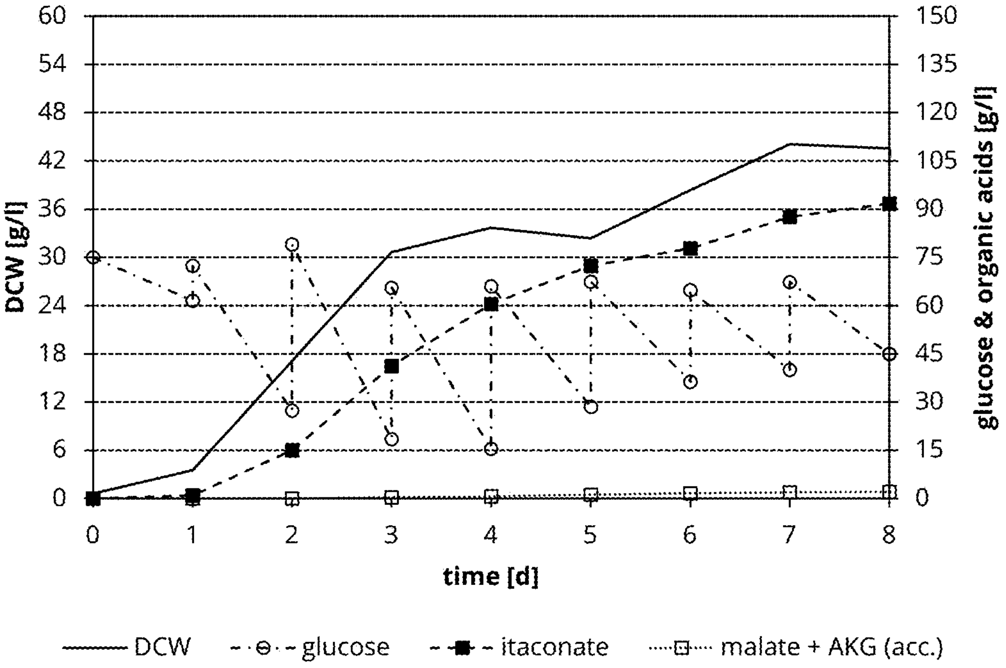

FIG. 62. 600 ml bioreactor cultivation of *P. tsukubaensis* HR12 in ITA production medium MG-IA-N/P: 5.5/1 g l-1 (NaNO3). The cells were cultivated for eight days at 30° C., pH=5.5, pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW).

Figure 63:
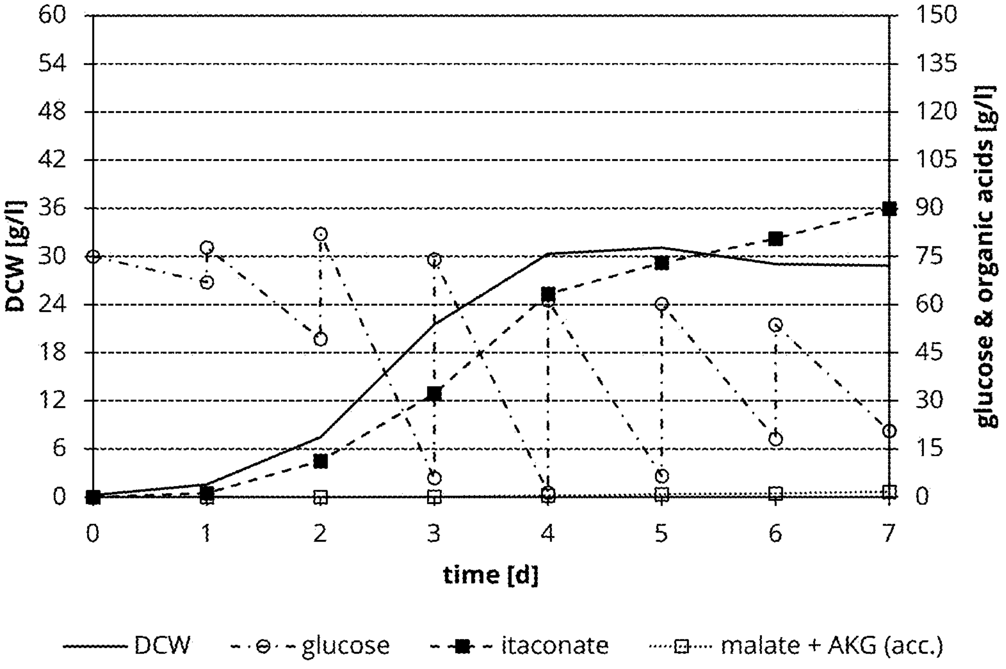

FIG. 63. 600 ml bioreactor cultivation of *P. tsukubaensis* HR12 in ITA production medium MG-IA-N/P: 8/1 g l-1 (NaNO3). The cells were cultivated for seven days at 30° C., pH=5.5, pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW).

Figure 64:
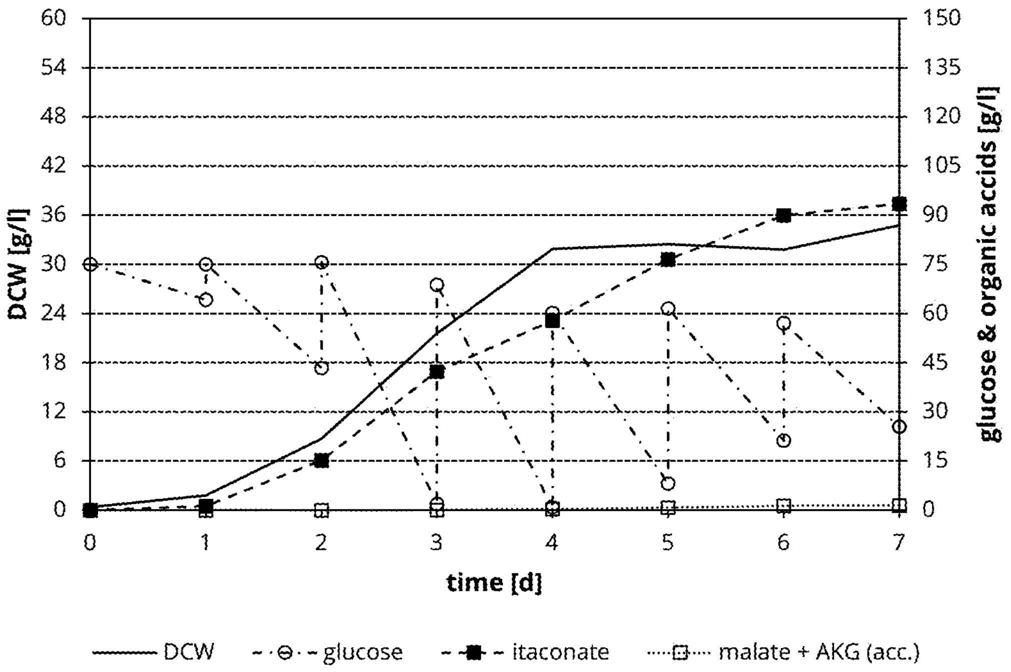

FIG. 64. 600 ml bioreactor cultivation of *P. tsukubaensis* HR12 in ITA production medium MG-IA-N/P: 8/1 g l-1 (NaNO3) & 1.75× mineral salts; trace elements; thiamine, FeCl3. The cells were cultivated for seven days at 30° C., pH=5.5, pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW).

Figure 65:
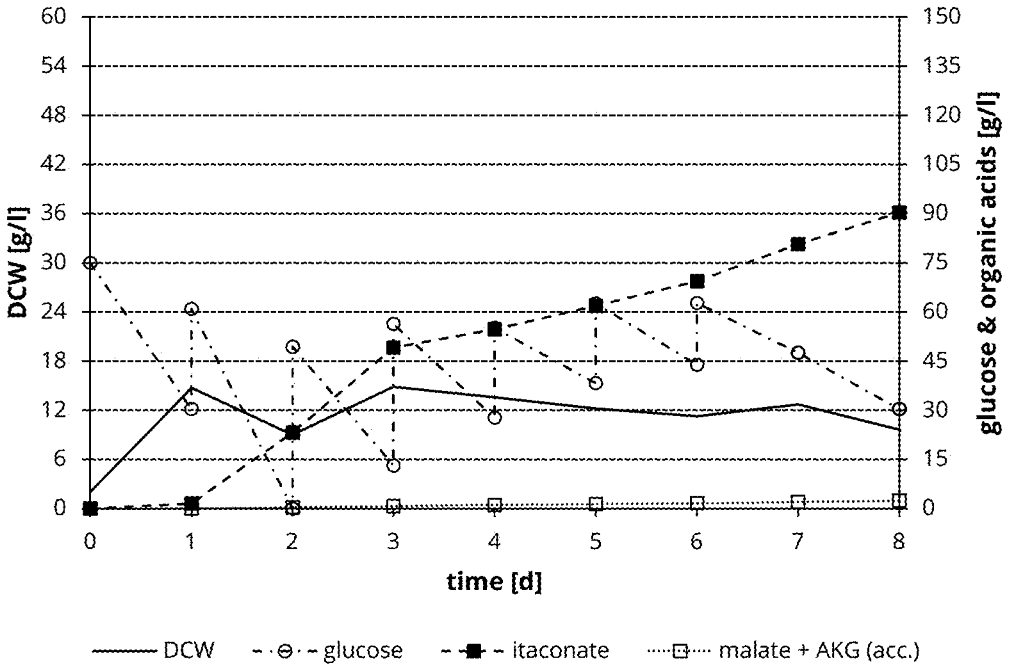

FIG. 65. 600 ml bioreactor cultivation of *P. tsukubaensis* HR12 in ITA production medium MG-IA-N/P: 4/1 g l-1 (NH4Cl). The cells were cultivated for eight days at 30° C., pH=5.5, pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW).

Figure 66:
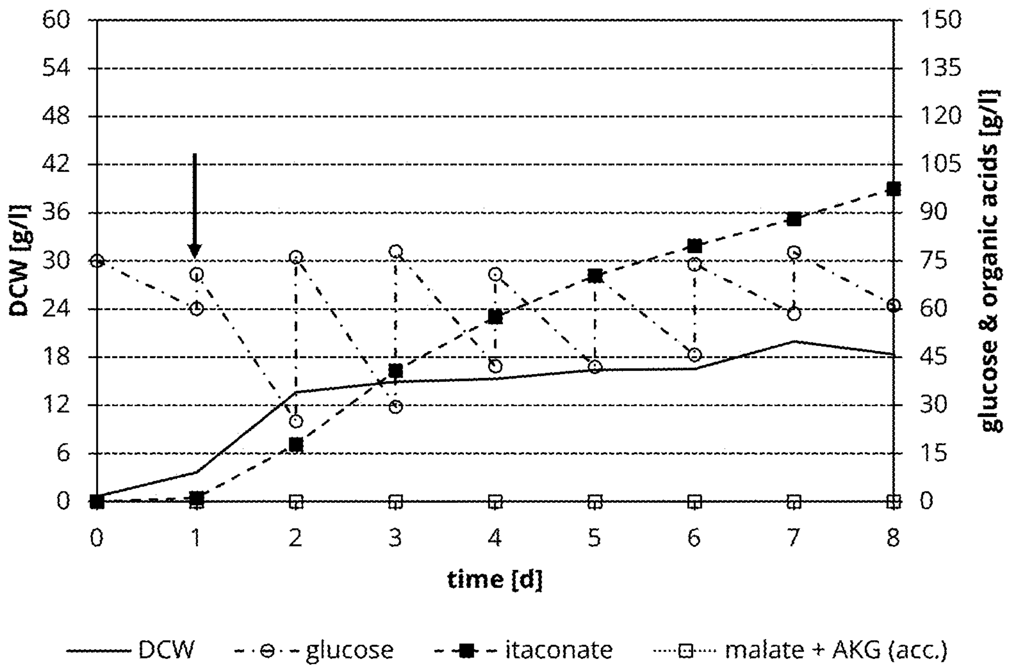

FIG. 66. 600 ml bioreactor cultivation of *P. tsukubaensis* HR12 in ITA production medium MG-IA-N/P: 4/1 g l-1 (NaNO3). The cells were cultivated for eight days at 30° C., pH=5.5→4.0 at 1st day (marked with black arrow), pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW).

Figure 67:
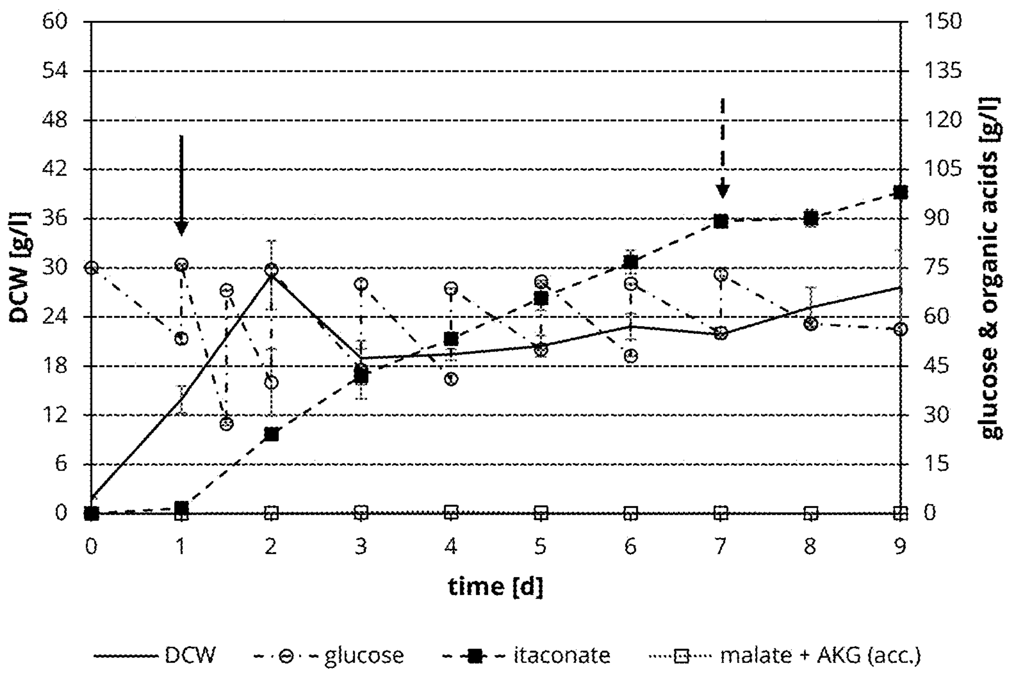

FIG. 67. 600 ml bioreactor cultivation of *P. tsukubaensis* HR12 in ITA production medium MG-IA-N/P: 4/1 g l-1 (NaNO3). The cells were cultivated for eight days at 30° C., pH=5.5→4.0 at 1st day (marked with black arrow), pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW). 1 g l-1 N-source was fed at the 7th day (marked with dashed arrow).

Figure 68:
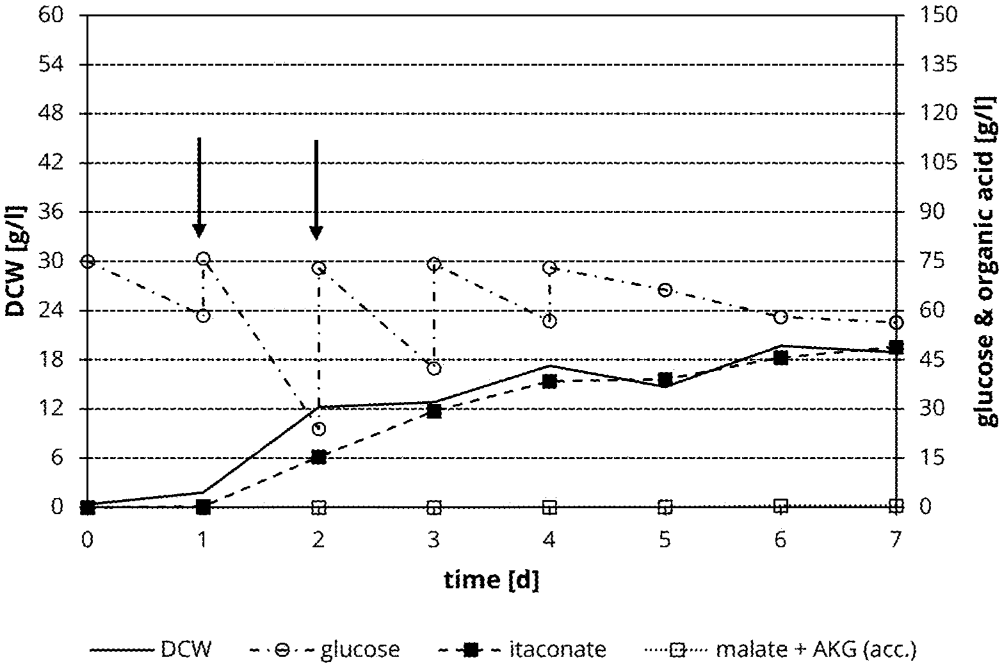

FIG. 68. 600 ml bioreactor cultivation of *P. tsukubaensis* HR12 in ITA production medium MG-IA-N/P: 5/1 g l-1 (NaNO3). The cells were cultivated for seven days at 30° C., pH=5.5→4.0 at 1st day→3.5 at 2nd day (marked with black arrows), pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW).

Figure 69:
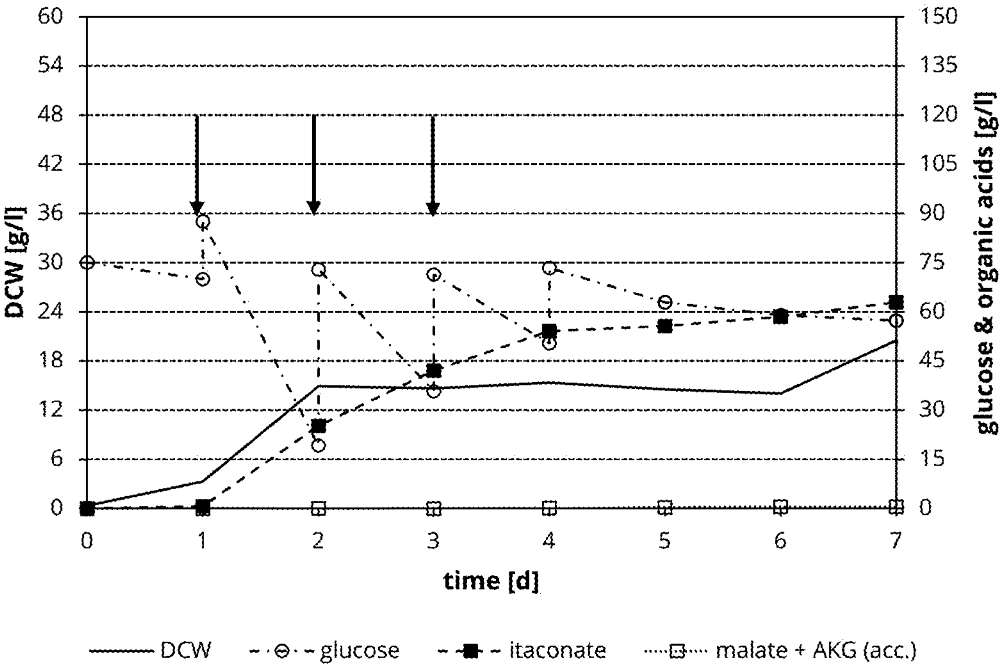

FIG. 69. 600 ml bioreactor cultivation of *P. tsukubaensis* HR12 in ITA production medium MG-IA-N/P: 5/1 g l-1 (NaNO3). The cells were cultivated for seven days at 30° C., pH=5.5→4.0 at 1st day→3.5 at 2nd day→3.0 at 3rd day (marked with black arrows), pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW).

Figure 70:
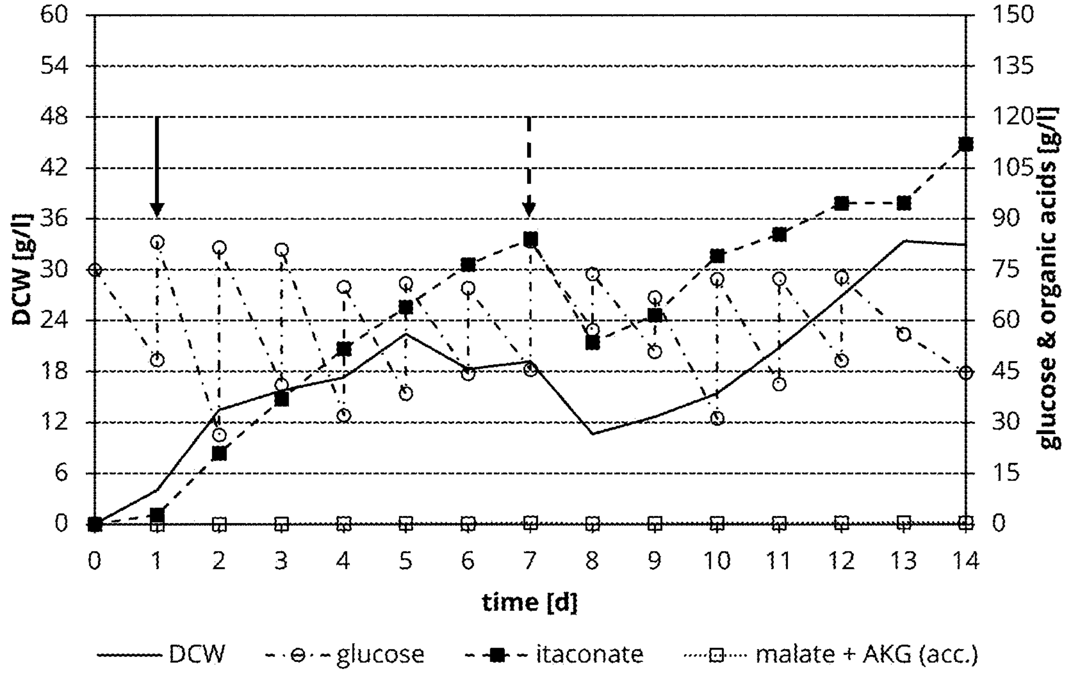

FIG. 70. Semi-continuous cultivation of *P. tsukubaensis* HR12 in ITA production medium MG-IA-N/P: 6/1 g l-1 (NaNO3) in a 600 ml bioreactor. The cells were cultivated for fourteen days at 30° C., pH=5.5→4.0 at 1st day (marked with black arrow), pO2=55% and an initial glucose concentration of 75 g l-1. Glucose consumption was monitored every 24 h and re-adjusted to approx. 75 g l 1. In the same interval the produced amounts of organic acids (ITA & MA) were determined as well as the dry cell weight (DCW). At the 7th day 50% of the culture broth was exchanged with fresh medium (marked with dashed arrow).

Figure 71:
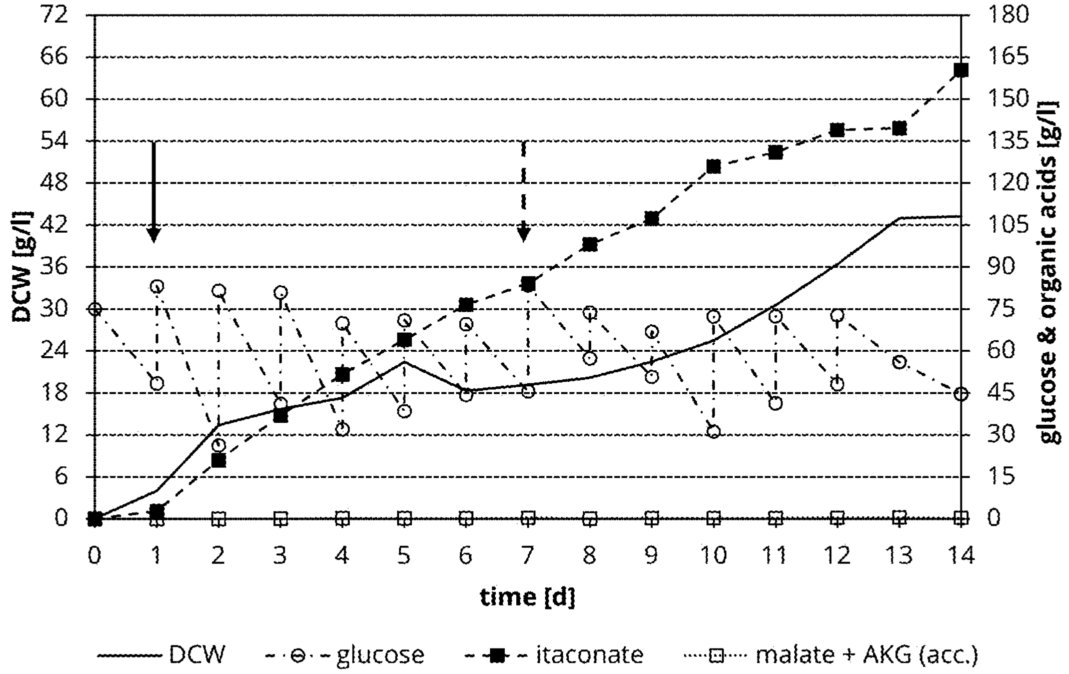

FIG. 71. Semi-continuous cultivation of *P. tsukubaensis* HR12 in ITA production medium MG-IA-N/P: 6/1 g l-1 (NaNO3) in a 600 ml bioreactor.—Adjusted for losses—The cells were cultivated for fourteen days at 30° C., pH=5.5→4.0 at 1st day (marked with black arrow), pO2=55% and an initial glucose concentration of 75 g l-1. Glucose consumption was monitored every 24 h and re-adjusted to approx. 75 g l-1. In the same interval the produced amounts of organic acids (ITA & MA) were determined as well as the dry cell weight (DCW). At the 7th day 50% of the culture broth was exchanged with fresh medium (marked with dashed arrow).

Figure 72:
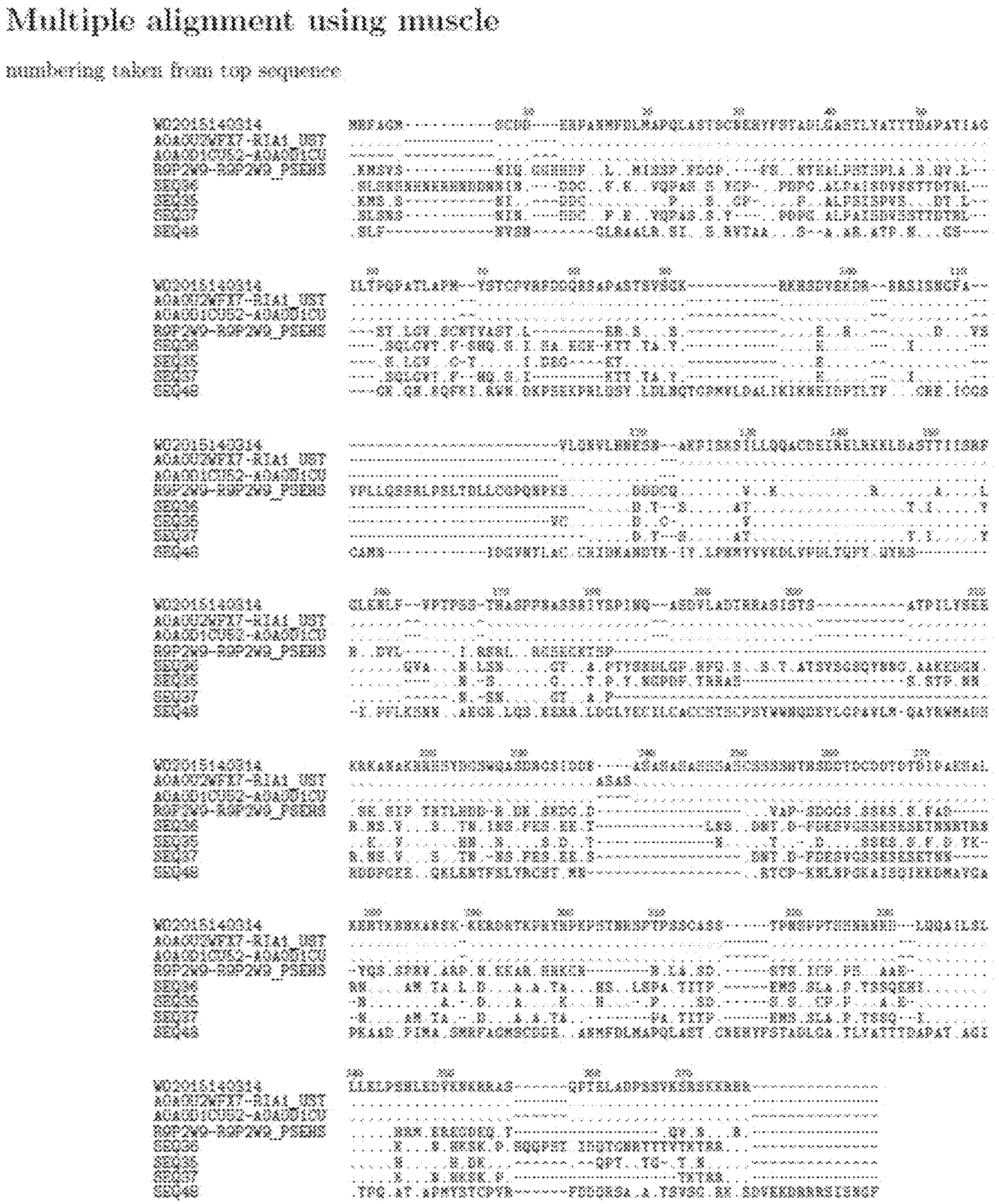

FIG. 72. Multiple alignment of RIA1 amino acid sequences. Only the topmost amino acid sequence is fully spelled out; for all other amino acid sequences only the amino acids differing at each respective position from the respective amino acid of the top sequence are given such that a dot indicates that at the respective position the respective amino acid of the top sequence is present. The proteins aligned are: "WO2015140314": SEQ ID NO. 16 of WO2015140314A1; Uniprot entry A0A0U2WFX7/RIA1_USTMD; Uniprot entry A0A0D1CU52/A0A0D1CU52_USTMA; Uniprot entry R9P2W9/R9P2W9_PSEHS; "SEQ36": SEQ ID NO. 36; "SEQ35": SEQ ID NO. 35; "SEQ37": SEQ ID NO. 37; "SEQ48": SEQ ID NO. 48.

DETAILED DESCRIPTION OF THE INVENTION

The invention is hereinafter described in greater detail. The description addresses the person of ordinary skill in the art of technical microbiology. The description is to be interpreted with a mind willing to understand. It is to be understood that the present description, like any other finite description of any technical fact or teaching, can by no means be exhaustive. In particular, features of any particular teaching or example of the present invention are to be understood as being meant to be optional parts of any other teaching of the present invention.

Unless otherwise defined, all terms (including technical and scientific terms) used herein have the same meaning as commonly understood by the person of ordinary skill in the art, which is a biotechnologist having ordinary experience in the art of fermentation. All terms should be interpreted as having a meaning that is consistent with their meaning in the context of the specification and relevant art and should not be interpreted in an idealized or overly formal sense unless expressly so defined herein. For the sake of brevity and/or clarity, well-known substances, methods, functions or constructions are not described herein in detail.

As used herein, the term "about," when used in reference to a measurable value such as an amount of mass, concentration, time, temperature and the like, is meant to include variations of 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19% or 20% of the specified amount. Unless otherwise indicated, all numerical values in the specification are to be understood as being modified by the term "about."

As used herein, the term "and/or" is intended to include any and all combinations of one or more of the associated listed items, as well as the lack of combinations when interpreted in the alternative ("or").

As used herein, the terms "comprise" and "include" and grammatical variants thereof specify the presence of a stated feature, step, operation, element and/or component, but do not preclude the presence or addition of one or more other features, steps, operations, elements, components and/or groups thereof. With regards to the definition of a parameter range in a composition or method, such terms denote that the respective composition or method does not comprise more than the maximum of the parameter value and less than the minimum of the parameter value. For example, a fermentation medium comprising 0.01-0.1% (v/v) of complex media components if a medium useful for fermentation, wherein the total concentration of complex media components is not lower than 0.01% (v/v) and not higher than 0.1% (v/v). As used herein, the term "comprising" also encompasses the term "consisting of".

As used herein, the term "consists essentially of" (and grammatical variants thereof), as applied to the compositions and methods of the present inventions, means that the compositions/methods may contain additional components so long as the additional components do not materially alter the composition/method. The term "materially alter", as applied to a composition/method, refers to an increase or decrease in the effectiveness of the composition/method of at least about 20% or more. For example, an expression cassette integrated into the genome of a production host microorganism or inactivated in said genome "materially alters" the microorganism if it increases or decreases the microorganism's itaconate productivity by at least 50%.

The "genome" of a microorganism according to the invention is the total of the replicating, inheritable genetic material—typically and preferably DNA—except such separate molecules that, albeit autonomously replicating, are like free viruses and free plasmids not constitutive in the definition of a microorganism species.

The term "expression" or "gene expression" as used herein refers to the process of synthesis of a gene product, preferably a protein or a functional RNA, and generally employs the steps of DNA transcription, optionally RNA processing and, in the case of protein expression, RNA translation. The term "expression cassette" (and grammatical or semantical variations thereof) refers to a segment of a nucleic acid, preferably DNA, that comprises a nucleic acid segment (also called "sequence") ready for expression of this segment. The expression cassette may also include elements that allow for enhanced expression of said nucleic acid segment in a host cell. These elements may include an enhancer, a response element, a terminator sequence, a polyadenylation sequence and the like.

According to the invention, a "promoter" is a contiguous nucleic acid section capable of initiating transcription in the host cell. A promoter is "functional" if it is sufficient to cause transcription of a corresponding gene in the respective microorganism under reproducible conditions. Suitable promoters can be inducible or repressible or constitutively active, wherein for inducible and repressible promoters transcription levels vary according to environmental or chemical conditions, and constitutive promoters are active under most conditions during fermentation. Also, promoters may be altered by replacing the native ribosome binding site by an appropriately selected different ribosome binding site. Preferred promoters are:

| Promoter | SEQ ID NO. | Characteristics | preferred minimal sequence identity to the respective SEQ ID NO. as determined by BLAST |
|---|---|---|---|
| pHSP70 | | promoter of the heat shock gene 70; strong basal activity, (stress-) inducible | 99% |
| pTEF | | promoter of the translation elongation factor 2 gene; strong constitutive promoter | 96% |
| pACTIN | 74 | promoter of the actin gene; strong constitutive promoter | 96% |
| pGPD | | promoter of the glyceraldehyde 3-phosphate dehydrogenase gene; constitutive promoter | 98% |
| pGLC | | 162 bp long promoter area of the α-glucosidase gene; inducible promoter | 96% |
| pGLCfull | | 1268 long promoter area of the α-glucosidase gene; inducible promoter | 95% |

Most preferably a strong constitutively active promoter according to the present invention is a pACTIN promoter and has a sequence identity of at least 96% to the sequence according to SEQ ID NO. 74. This promoter advantageously allows for a particularly broad expression of a variety of proteins in *Pseudozyma* and is further described in the examples.

The term "Hybridization" indicates that a polynucleotide anneals ("hybridizes") to a labeled nucleic acid probe, or the full-length complementary strand thereof, or a subsequence of the foregoing, under low, medium, high or very high stringency conditions. In order to allow hybridisation to occur, the nucleic acid molecules are generally thermally or chemically denatured to melt a double strand into two single strands and/or to remove hairpins or other secondary structures from single stranded nucleic acids. This formation or melting of hybrids is dependent on various parameters, for example the temperature. An increase in temperature favours melting, while a decrease in temperature favours hybridsation. However, this hybrid forming process is not following an applied change in temperature in a linear fashion: the hybridisation process is dynamic, and already formed nucleotide pairs are supporting the pairing of adjacent nucleotides as well. So, with good approximation, hybridisation is a yes-or-no process, and there is a temperature, which basically defines the border between hybridisation and no hybridisation. This temperature is the melting temperature (Tm). Tm is the temperature in degrees Celsius, at which 50% of all molecules of a given nucleotide sequence are hybridised into a double strand, and 50% are present as single strands.

The melting temperature (Tm) is dependent from the physical properties of the analysed nucleic acid sequence and hence can indicate the relationship between two distinct sequences. However, the melting temperature (Tm) is also influenced by various other parameters, which are not directly related with the sequences, and the applied conditions of the hybridization experiment must be taken into account. For example, an increase of salts (e.g. monovalent cations) is resulting in a higher Tm.

Tm for a given hybridisation condition can be determined by doing a physical hybridisation experiment, but Tm can also be estimated in silico for a given pair of DNA sequences. In this embodiment, the equation of Meinkoth and Wahl (Anal. Biochem., 138:267-284, 1984) is used for stretches having a length of 50 or more bases:

$$Tm=81.5° C.+16.6(\log M)+0.41(\% GC)-0.61(\% form)-500/L$$

M is the molarity of monovalent cations, % GC is the percentage of guanosine and cytosine nucleotides in the DNA stretch, % form is the percentage of formamide in the hybridisation solution, and L is the length of the hybrid in base pairs. The equation is for salt ranges of 0.01 to 0.4 M and % GC in ranges of 30% to 75%.

While above Tm is the temperature for a perfectly matched probe, Tm is reduced by about 1° C. for each 1% of mismatching (Bonner et al., J. Mol. Biol. 81: 123-135, 1973):

$$Tm=[81.5° C.+16.6(\log M)+0.41(\% GC)-0.61(\% formamide)-500/L]-\% non-identity$$

This equation is useful for probes having 35 or more nucleotides and is widely referenced in scientific method literature (e.g. in: "Recombinant DNA Principles and Methodologies", James Greene, Chapter "Biochemistry of Nucleic acids", Paul S. Miller, page 55; 1998, CRC Press), in many patent applications (e.g. in: U.S. Pat. No. 7,026,149), and also in data sheets of commercial companies (e.g. "Equations for Calculating Tm" from www.genomics.agilent.com).

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

The term "sequence identity" refers to a numeric indication of the maximum tolerable deviation between two amino acid sequences or two nucleic acid sequences, respectively, wherein one sequence (also called "benchmark sequence") is known and the other sequence is to be compared to the benchmark sequence. The deviation is determined by first aligning the two sequences to be compared and then counting the number of identical amino acids or nucleotides, respectively, divided by the total length of the benchmark sequence including all gaps in this sequence according to the alignment. Alignment is performed using the Needleman-Wunsch-algorithm (Needleman, Saul B. & Wunsch, Christian D. (1970): "A general method applicable to the search for similarities in the amino acid sequence of two proteins"; Journal of Molecular Biology. 48 (3): 443-453), with the following parameters:

- for amino acid alignments: gap open penalty of 10, gap extension penalty of 0.5, EBLOSUM62 (EMBOSS version of BLOSUM62) substitution matrix
- for nucleic acid alignments: gap open penalty of 10, gap extension penalty of 0.5, EDNAFULL (EMBOSS version of NCBI NUC4.4) substitution matrix For example, aligning a test sequence AAGATACTG (9 nucleotides) to a benchmark sequence GATCTGA (7 nucleotides) will lead to:

```
     Test: AAGATACTG-
                 ||| |||
Benchmark: --GAT-CTGA
```

Thus, there are 6 identical positions ("GAT" and "CTG"), and the benchmark sequence length is increased by 1 position due to the alignment, such that the sequence identity is 6/(7+1)*100=75%.

Where amino acids can be changed in a sequence according to the present invention, such change is preferably a conservative mutation. Using the standard one-letter code for amino acids, amino acid A is conservatively replaceable by amino acid S; amino acid D is conservatively exchangeable by amino acids E, N; amino acid E is conservatively exchangeable by amino acids D, K, Q; amino acid F is conservatively exchangeable by amino acids W, Y; amino acid H is conservatively exchangeable by amino acids N, Y; amino acid I is conservatively exchangeable by amino acids L, M, V; amino acid K is conservatively exchangeable by amino acids E, Q, R; amino acid L is conservatively exchangeable by amino acids I, M, V; amino acid M is conservatively exchangeable by amino acids I, L, V; amino acid N is conservatively exchangeable by amino acids D, H, S; amino acid Q is conservatively exchangeable by amino acids E, K, R; amino acid R is conservatively exchangeable by amino acids K, Q; amino acid S is conservatively exchangeable by amino acids A, N, T; amino acid T is conservatively exchangeable by amino acid S; amino acid V is conservatively exchangeable by amino acids I, L, M; amino acid W is conservatively exchangeable by amino acids F, Y; amino acid Y is conservatively replaceable by amino acids F, H, W. Particularly preferred replacements, using the standard three-letter code for amino acids, are Ala<->Glu, Ala<->Gly, Ala<->Pro, Ala<->Ser, Ala<->Thr, Ala<->Val, Arg<->Lys, Asn<->Ser, Asp<->Asn, Asp<->Glu, Asp<->Gly, Gly<->Ser, Leu<->Ile, Leu<->Val, Phe<->Tyr, Ser<->Thr and Val<->Ile.

The term "wild type" microorganism is used herein for comparisons of microorganisms and denotes a microorganism wherein the features in question for the specific comparison are absent. Typically such microorganism is an ancestor strain from which the microorganism in question has been or can be derived. For example, in an expression like "the production host microorganism comprising an insert between genes A and B which are separated by N nucleotides in the corresponding wild type microorganism" is to be interpreted as follows: The "wild type microorganism" is a microorganism identical to the production host microorganism except for the sequence connecting genes A and B in the relevant nucleic acid—typically called "chromosome" irrespective of its staining properties—of the of the wild type microorganism, such that in said wild type microorganism the 3' border—i.e. the stop codon—of gene A and the 5' border—i.e. the start codon—of gene B are separated by N nucleotides, given that gene A is located in 5' position of gene B.

References to Uniprot entries denote the respective sequence as of 2018-03-01 midnight CET.

While certain aspects of the present invention will hereinafter be described with reference to embodiments thereof, it is understood that various changes in form and details may be made therein without departing from the spirit and scope of the present disclosure as defined by the claims.

The present invention relates to the production of itaconic acid and/or salts thereof. Whenever in this description reference is made to itaconic acid, such reference applies as well to itaconate (and vice versa) if at all technically sensible.

The invention provides an itaconic acid production host microorganism. For the purposes of the present invention, the production host microorganism preferably belongs to the phylum Basidiomycota. As described above, microorganisms of this phylum have not been used industrially for the production of itaconic acid despite numerous attempts in the past. The present invention is based on the finding that contrary to the belief in the above mentioned prior art it is not sufficient and/or necessary to overexpress all genes involved in the production of itaconic acid. Instead, the present invention provides modified microorganisms characterized by the stable integration into their genome of an expression cassette for expressing a RIA1 gene, and/or suggests genes generally present in microorganisms of phylum Basidiomycota which should be inactivated for itaconic acid production. Preferably, such inactivation is performed by integration of an expression cassette for expressing a RIA1 gene. The present invention thereby makes available for fermentation a taxonomic branch of microorganisms which achieve a high productivity of itaconic acid without having to accept simultaneous high productivity of unwanted by-products, particularly malate.

According to the invention, the itaconic acid production host microorganism is alternatively termed "production host", "host microorganism", "production microorganism" and the like. The term "production host microorganism" and its corresponding terminological variants encompasses any progeny of a parent cell that is not identical to the parent cell, for example due to mutations that occur during replication or for example due to additional transformations.

The production host microorganism according to the present invention comprises an active metabolic pathway for producing itaconic acid. The host microorganism according to the present invention may naturally comprise such active itaconic acid pathway, that is, even before the at least one expression cassette comprising a RIA1 gene under the control of a functional promoter is integrated into the genome of the microorganism. However, the invention also provides, as described below, methods for obtaining itaconic acid production host microorganisms based on such microorganisms that do not naturally comprise an active itaconic acid pathway.

According to an aspect of the invention the production host microorganisms comprises an expression cassette. The expression cassette comprises a RIA1 gene under the operable control of a functional promoter.

Preferably, in the expression cassette the RIA1 gene is heterologous in view of the promoter operably linked to the RIA1 gene. A heterologous sequence for the purposes of the present invention is any of (a) a non-host sequence, (b) a sequence altered by (ba) insertion, (bb) replacement and/or (bc) deletion of one or more bases or amino acids, as applicable, (c) a sequence from a different host cell strain, or (d) a homologous sequence from a different genomic location of the host cell; for example, an artificial duplicate of a nucleic acid sequence is considered heterologous herein. A "homologous" sequence is a sequence that is found in the same genetic source or species, i.e. it is naturally occurring in the relevant species of host cell, and performs the same or similar function. Thus, the RIA1 gene in the expression cassette according to the invention preferably is operably linked to a promoter different from any promoter operably linked to a RIA1 gene in the wild type production host microorganism, if said wild type production host microorganism naturally comprises an expressed RIA1 gene. This way the invention allows to selectively influence the expression of the RIA1 gene according to the needs of the itaconic acid fermentation process. The description hereinafter provides examples and explanations of such particularly preferred expression cassettes.

The RIA1 gene preferably is heterologous in view of the production host microorganism. Preferably the RIA1 gene sequence is derived from a separate genetic source or species.

The expression cassette is integrated outside of an ip locus. While document WO 2015/140314 A1 discloses that overexpression of RIA1 lead to an increase in itaconic acid production, productivity remained lower than according to the present invention. The ip locus used as integration site according to WO 2015/140314 A1 is further described in Loubradou et al., "A homologue of the transcriptional repressor Ssn6p antagonizes cAMP signalling in *Ustilago maydis*", Molecular microbiology. 2001, 719-30. By avoiding this integration site, according to the invention a technically feasible itaconic acid productivity is obtained. For the avoidance of doubt, an integration is considered to have happened not outside of but at or in an ip locus at least in those cases where (a) the integrated nucleic acid is flanked on both sides by a (possibly truncated or somewhat mutated) duplicate of the ip locus as occurs, for example, by way of homologous recombination, or where (b) the microorganism contains the integrated nucleic acid at a position which, in the corresponding wild type strain, comprises or overlaps an ip locus; this occurs, for example by way of replacement integration. A method for identification of an ip locus in basidiomycetes and primers, vectors and methods for site-specific integration of constructs into an ip locus thus identified are described by Zambanini et al., Metabolic Engineering Communications 2017, 12-21, particularly pages 14-16.

According to the present invention, the ip locus is a region responsible for expression of a gene encoding an iron-sulphur protein subunit of succinate dehydrogenase. Such gene sequence is described for *Ustilago maydis* by Broomfield and Hargreaves, Current Genetics 1992, 117-121 and particularly in FIG. 2 of said publication. The publication and particularly said FIG. 2 are incorporated herein by reference for further description of the ip locus. It is important to notice that the present invention is not concerned with the function of the ip locus and the corresponding iron-sulphur protein subunit of succinate dehydrogenase as such; the inventors have found that the production of itaconic acid is improved by integrating at least one expression cassette as described herein outside of the ip locus of the respective microorganism. Preferably the ip locus of the microorganism does not contain an expression cassette as described herein, and even more preferably the ip locus does not contain a heterologous gene sequence.

The ip locus preferably is the locus of the inheritable genetic material of the microorganism coding for an iron-sulphur protein subunit of succinate dehydrogenase. Whether or not a putative polypeptide conveys the function of an iron-sulphur protein subunit of succinate dehydrogenase can be tested for example by reconstitution, i.e. a method comprising the following steps:

1. Inactivation of all genes encoding an iron-sulphur protein subunit of succinate dehydrogenase in a test microorganism to change the phenotype of the test organism from carboxin resistant to carboxin sensitive; a description of this is found in the above publication of Broomfield and Hargreaves;
2. Expression of the putative polypeptide in the test microorganism;
3. Determination of carboxin resistance in the test organism obtained in step 2; if carboxin resistance is reconstituted, then in the absence of plausible other explanations the putative polypeptide most likely conveys the function of an iron-sulphur protein subunit of succinate dehydrogenase.

The ip locus according to the invention in a narrow sense thus is a locus the modification of which leads to carboxin sensitivity, wherein expression of an iron-sulphur protein subunit of succinate dehydrogenase leads to reconstitution of carboxin resistance. Preferably the ip locus is a gene coding for a polypeptide having at least about 10% sequence identity to an amino acid sequence according to the Uniprot entry selected from the group consisting of P32420 (SDHB_USTMA), R9NZ36 (R9NZ36_PSEHS), M9MBS9 (M9MBS9_PSEA3), I2G708 (I2G708_USTH4) and V5F1L5 (V5F1L5_KALBG), even more preferably having at least 20% or even more preferably having at least 30% or even more preferably having at least 40% or even more preferably having at least 50% or even more preferably having at least 60% or even more preferably having at least 70% or even more preferably having at least 80% or even more preferably having at least 90% or even more preferably having at least 94% or even more preferably having at least 98% sequence identity to an amino acid sequence according to the Uniprot entry selected from the group consisting of P32420 (SDHB_USTMA), R9NZ36 (R9NZ36_PSEHS), M9MBS9 (M9MBS9_PSEA3), I2G708 (I2G708_USTH4) and V5F1L5 (V5F1L5_KALBG). If the microorganism is of genus *Ustilago*, then the amino acid sequence identity is preferably determined by comparison against Uniprot entry P32420 (SDHB_USTMA); if the microorganism is of genus *Kalmanozyma*, then the amino acid sequence identity is preferably determined by comparison against Uniprot entry V5F1L5 (V5F1L5_KALBG); if the microorganism is of genus *Pseudozyma*, then the amino acid sequence identity is preferably determined by comparison against. SEQ ID NO. 48. Even more preferably the ip locus is a gene coding for a polypeptide having at least 10% sequence identity to the amino acid sequence according to SEQ ID NO. 48, even more preferably having at least 20% or even more preferably having at least 30% or even more preferably having at least 40% or even more preferably having at least 50% or even more preferably having at least 60% or even more preferably having at least 70% or even more preferably having at least 80% or even more preferably having at least 90% or even more preferably having at least 94% or even more preferably having at least 98% sequence identity to the amino acid sequence according to SEQ ID NO. 48.

The ip locus according to the invention in a more preferred, wider sense thus is an ip locus comprising a gene coding for an iron-sulphur protein subunit of succinate dehydrogenase and consists of a nucleic acid sequence having at least 75%, even more preferably at least 50% sequence identity to SEQ ID NO. 50, which is the coding region of the EMBL entry Z11738.1, the *U. maydis* encoding iron-sulphur subunit of succinate dehydrogenase. In particular where the microorganism is of genus *Pseudozyma*, the ip locus preferably consists of a nucleic acid sequence having at least 75%, even more preferably at least 50% sequence identity to SEQ ID NO. 51, which is the equivalent of *Pseudozyma tsukubaensis* to the sequence according to SEQ ID NO. 50.

Even more preferably, at least one and most preferably all expression cassettes are integrated according to the invention outside of an ip locus that comprises a gene coding for an iron-sulphur protein subunit of succinate dehydrogenase and consists of a nucleic acid sequence having at least 75%, even more preferably at least 50% sequence identity to SEQ ID NO. 52, which is sequence of the EMBL entry Z11738.1. In particular where the microorganism is of genus *Pseudozyma*, preferably, at least one and most preferably all expression cassettes are integrated according to the invention outside of an ip locus that comprises a gene coding for an iron-sulphur protein subunit of succinate dehydrogenase and consists of a nucleic acid sequence having at least 75%, even more preferably at least 50% sequence identity to SEQ ID NO. 53.

It is particularly preferred when at least one and preferably all expression cassettes according to the invention are integrated outside of a sequence region defined by a first border region and a second border region, wherein the first border region consists of a nucleic acid having at least 50% sequence identity to SEQ ID NO. 54 and the second border region consists of a nucleic acid sequence having at least 50% sequence identity to SEQ ID NO. 55.

The first and second border regions are preferably distanced, in the wild type microorganism, by at least about 800 to 5000 nucleotides, more preferably 880 to about 2000 nucleotides and most preferably at least 1100 to 2000 nucleotides. Sequences SEQ ID NO. 54 and 55 are left and right border sequences adjacent to the sequence according to SEQ ID NO. 53 of *Pseudozyma tsukubaensis*. Most preferably all expression cassettes according to the invention are integrated outside of a nucleic acid sequence having at least 50% sequence identity to the sequence according to SEQ ID NO. 56.

According to the invention is provided a recombinant itaconic acid production host microorganism comprising an expression cassette (a) for expression of a RIA1 gene and/or (b) for expression of at least two genes selected from the group consisting of ADI1, MTT1 and TAD1. A microorganism having, like the host microorganisms according to the present invention, an active itaconic acid metabolic pathway will (at least under itaconic acid production conditions) generally express an MTT1 mitochondrial tricarboxylate transporter gene, an ADI1 aconitate delta-isomerase gene, a TAD1 trans-aconitate decarboxylase gene and an ITP1 itaconate transport protein gene. Preferably the microorganism of the present invention will (at least under itaconic acid production conditions) also express an RIA1 transcription regulator gene. As described herein, the RIA1 gene product according to the invention increases expression of an ADI1 gene, MTT1 gene, TAD1 gene and/or ITP1 gene, thereby leading to high itaconic acid productivity with advantageously low malate production. Optionally, the microorganism may express (at least under itaconic acid production conditions) a CAD1 cis-aconitate decarboxylase gene as is known for example from *Aspergillus terreus*, wherein such CAD1 expression can be co-occurring to or can be instead of expression ADI1 and/or TAD1.

If the species of the microorganism according to the present invention already comprises an active itaconic acid pathway, then it is possible but not necessarily preferred to have only one or more expression cassettes for expression of a RIA1 gene integrated into the genome of the microorganism at a location as described herein. However, the microorganism may comprise heterologous expression cassettes for a RIA1 gene and one or more of the ADI1, ITP1, MTT1 and TAD1 genes. In particular in those cases where a wild-type Basidiomycete comprises an ADI1, ITP1, MTT1 and/or TAD1 gene of which the expression is not induced by expression of the heterologous RIA1 gene expression cassette, it is preferred to introduce, preferably by way of stable integration into the genome of the microorganism at a site as described herein, an expression cassette of the respective ADI1, ITP1, MTT1 and/or TAD1 gene derived from the genome of a microorganism where such gene is inducible by the RIA1 gene. This way advantageously effectiveness of the heterologous RIA1 expression cassette (comprising a preferably heterologous RIA1 gene under the control of a functional promoter) is achieved which in turn facilitates enjoying the advantageous itaconic acid productivity and/or negligible by-production of malate.

The expression cassette is integrated preferably into the genome of the microorganism at an integration site which a) is located between a left border gene and a right border gene, wherein the respective first nucleotides of the respective translation start codons of the left and right border genes are separated by at most 51600 nucleotides in the corresponding wild type microorganism, wherein the left border gene codes for a protein having acetyl-CoA synthetase activity and wherein the right border gene codes for a protein consisting of an amino acid sequence having at least 21% identity to SEQ ID NO. 25, and/or
b) is located up to 6500 nucleotides of the nearest border of an open reading frame translating into an amino acid sequence having at least 30% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, and/or
c) is located within or replaces an open reading frame translating into an amino acid sequence having at least 30% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25 or an exon thereof.

As is shown in the examples, the invention has identified an integration site outside an ip locus which allows for a stable integration of the expression cassette and enables high itaconic acid productivity without having to accept substantial formation of malate as a by-product.

According to one way of describing the invention, the integration site is located between a left coding for a protein having acetyl-CoA synthetase and a right border gene which is an open reading frame coding for a protein consisting of an amino acid sequence having at least 21% identity to SEQ ID NO. 25. In case of a circular genome the term "between" is to be understood to indicate the shorter nucleic acid segment connecting the left and right border genes in the wild-type genome, that is without integration of the one or more expression cassettes. In wild-type basidiomycetes, the left and right border genes are typically separated by at most 51600 nucleotides, preferably at least 25800 and at most 51600 nucleotides, even more preferably at least 28000 and at most 42200 nucleotides, and even more preferably at least 35000 and at most 42100 nucleotides.

According to another way of describing the invention, the integration site is located up to 6500 nucleotides of the nearest border of an open reading frame translating into an amino acid sequence having at least 30% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25 or an exon of any of there sequences. As is shown in the examples, these open reading frames can be found in a location suitable for insertion of an expression cassette according to the present invention. It is understood that the aforementioned sequences are given only for describing the location of the insertion site according to the present invention, irrespective of any biological function. It is to be noted that for example in the genome of *Pseudozyma tsukubaensis* the aforementioned sequences occur in the order as given above. This allows to identify corresponding sequences in other basidiomycetes.

Preferably, the integration site is located up to 6500 nucleotides of the nearest border of any nucleic acid sequence having at least 30% sequence identity to any of SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26. These nucleic acid sequences have been found at a particularly preferred integration site in the particularly preferred wild type of production host microorganism *Pseudozyma tsukubaensis*; they correspond to the respective amino acid sequences SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25. Thus, the integration site preferably is located up to 6500 nucleotides, preferably up to 5500 nucleotides, even more preferably up to 2800 nucleotides, of the nearest border of any nucleic acid target sequence having at least 30% sequence identity to any of SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, wherein the respective target sequence at least hypothetically translates to an amino acid having at least 30% identity to SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25, respectively.

Even more preferably, the integration site is located up to 6500 nucleotides, preferably up to 5500 nucleotides, even more preferably up to 2800 nucleotides, of the nearest border of an open reading frame translating into an amino acid sequence having at least 30% sequence identity to any of SEQ ID NO. SEQ ID NO. 19, SEQ ID NO. 15 and/or SEQ ID NO. 29. These amino acid sequences are according to the invention expected to exert metabolic functions implicated in influencing the Krebs cycle. By integrating the one or more expression cassettes according to the invention, the respective target polypeptides are inactivated or downregulated such that their interference with the Krebs cycle is removed.

According to yet another way of describing the invention, the expression cassette is integrated within or replaces an open reading frame translating into an amino acid sequence having at least 30% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25. The amino acid sequences indicated above are derived from the nucleotide sequences according to alternative b) as described above. Again it is understood that the aforementioned sequences are given only for describing the location of the insertion site according to the present invention, irrespective of any biological function; it is not even necessary that a corresponding wild-type microorganism produces polypeptides with any of the aforementioned sequences. Preferably the respective open reading frames in the corresponding wild-type microorganism have a length of at least 6500 nucleotides.

Again, preferably at least one expression cassette is integrated within or replaces a target nucleic acid sequence having at least 30% sequence identity to any of SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, wherein the target nucleic acid sequence at least hypothetically translates into an amino acid sequence having at least 30% sequence identity to SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO.

19, SEQ ID NO. 21, SEQ ID NO. 23, SEQ ID NO. 25, respectively. And even more preferably, at least one expression cassette is integrated within or replaces a target nucleic acid sequence having at least 30% sequence identity to any of SEQ ID NO. 20, SEQ ID NO. 16 and/or SEQ ID NO. 30, wherein the target nucleic acid sequence at least hypothetically translates into an amino acid sequence having at least 30% sequence identity to SEQ ID NO. 19, SEQ ID NO. 15 and/or SEQ ID NO. 29, respectively.

It is to be understood that the microorganism according to the present invention can comprise two or more expression cassettes inserted into the same or different loci. In the examples one exemplary integration comprising two expression cassettes for RIA1 expression are integrated into the same locus. According to the invention it is preferred that none of the expression cassettes are integrated into an ip locus. Further preferably all expression cassettes according to the present invention for expression of a RIA1, ADI1, MTT1 and TAD1 gene, respectively, are integrated at a site as given in any of the alternatives a) to c) as described above.

A recombinant itaconic acid production host microorganism according to one aspect of the present invention a) comprises an active itaconic acid metabolic pathway for producing itaconic acid, and preferably
b) at least one gene
   i) coding for a protein having at least 30% sequence identity to and/or
   ii) the complementary strand of which hybridizes under at least low stringency conditions to a nucleic acid sequence coding for any of the protein sequences SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25 is inactivated.

As shown in the examples the mere presence of a plasmid for RIA1 expression in a basidiomycete does not reliably result in an increase in itaconic acid productivity compared to a corresponding wild-type strain. This is all the more surprising as the examples below show that even a moderate increase in RIA1 expression, as determined by qPCR, can lead to a significantly improved itaconic acid productivity without significant formation of malate as by-product. Comparing the invention with the prior art where heterologous RIA1 genes were integrated into genomes of Ustilaginomycetes in the ip locus (see for example Zambanini et al., Biotechnol Biofuels, 2017, 10:131, employing constructs that integrate into the ip locus of *U. vetiveriae* strain TZ1; integration specificity is described by Geiser et al., Microbial Biotechnology 2016, 116-126, see page 122) clearly lower itaconic acid productivities compared to the present examples were observed, and unwanted malate was produced in a roughly 1:1-3:1 ratio malate (g/l):itaconate (g/l) even under optimized conditions.

Thus, it is a teaching of the invention that the inactivation of at least one, more preferably two or more, genes coding for a protein having at least 30% sequence identity to SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25, respectively, is useful for obtaining the aforementioned advantages. Another way of describing this teaching is that the inactivation of at least one, more preferably two or more, genes is advantageous where the one or more genes, respectively, comprise or consist of a nucleic acid sequence which hybridizes under at least low stringency conditions to a nucleic acid sequence coding for any of the aforementioned sequences.

As described herein, inactivation is preferably performed by or in the wake of integration of an expression cassette for expression of a RIA1 gene and/or for expression of at least two genes selected from the group consisting of ADI1, MTT1 and TAD1.

According to the invention, the inactivated at least one gene preferably comprises or consists of a sequence the complementary strand of which hybridizes under at least medium stringency conditions, even more preferably under at least high stringency conditions and even more preferably under very high stringency conditions to a nucleic acid sequence coding for any of the protein sequences SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25. Also according to the invention, the inactivated at least one gene preferably comprises or consists of a sequence coding for a protein having at least about 45% sequence identity, even more preferably at least 60% sequence identity, even more preferably at least 75% sequence identity, even more preferably at least 85% sequence identity, even more preferably at least 90% sequence identity, even more preferably at least 91% sequence identity, even more preferably at least 95% sequence identity, even more preferably at least 98% sequence identity to any of the protein sequences SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25. Also according to the invention, a preferred microorganism comprises at least one expression cassette for expression of a RIA1 gene and/or for expression of at least two genes selected from the group consisting of ADI1, MTT1 and TAD1, wherein at least one of the expression cassettes is integrated into the genome of the microorganism at an integration site, wherein the integration site is located up to 6500 nucleotides, preferably up to 5500 nucleotides, even more preferably up to 2800 nucleotides, of the nearest border of an open reading frame translating into an amino acid sequence having at least 45%, even more preferably at least 60%, even more preferably at least 75%, even more preferably at least 85%, even more preferably at least 90%, even more preferably at least 91%, even more preferably at least 95%, even more preferably at least 98% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, and/or is located within or replaces an open reading frame translating into an amino acid sequence having at least 45%, even more preferably at least 60%, even more preferably at least 75%, even more preferably at least 85%, even more preferably at least 90%, even more preferably at least 91%, even more preferably at least 95%, even more preferably at least 98% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25. In each case, an inactivating integration is preferred as described above at or in one or more of the sequences SEQ ID NO. 19, SEQ ID NO. 15 and/or SEQ ID NO. 29 and respective sequences having, over the complete length, at least 45%, even more preferably at least 60%, even more preferably at least 75%, even more preferably at least 85%, even more preferably at least 90%, even more preferably at least 91%, even more preferably at least 95%, even more preferably at least 98% sequence identity thereto.

A preferred production host microorganism according to the present invention shows a characteristic gene expression level compared to the corresponding wild type strain cultivated under identical conditions. The expression level of a) the RIA1 gene is increased by a factor of at least 50, and/or
b) at least two genes selected from the group consisting of ADI1, MTT1 and TAD1 is increased by a factor of at least 1000, and/or
c) an ITP1 gene is increased by at most 500.

According to the present invention expression levels are measured using standard qPCR protocols on the corresponding mRNA as further explained in the examples. As evidenced by the examples, even a modest increase of RIA1 gene expression by 50-1000, even more preferably by 100-900 compared to the wild type strain allows to achieve the advantages of the present invention, particularly high itaconic acid productivity and a very low or even no production of malate as a fermentation by-product. Also, such increases of RIA1 gene expression can lead to increases in expression levels of ADI1, MTT1 and/or TAD1 by a factor of at least 1000. Preferably, the expression level of at least two genes selected from the group consisting of ADI1, MTT1 and TAD1 is increased by a factor of 1050-6000, and even more preferably the expression level of ADI1 and TAD1 are increased by a factor of 1000-4100 and the expression level of MTT1 is increased by a factor of 2000-5500.

Also preferably, the expression level of an ITP1 gene is increased by at most 500, more preferably by 0-300 and even more preferably by at most 200. It is to be understood that this applies only to microorganisms wherein the wild-type strain already exhibits an active itaconic acid metabolic pathway such that itaconic acid is released into a fermentation medium during fermentation. This parameter is particularly advantageous for selection of itaconic acid production host microorganisms, because those microorganisms which already exhibit a high level of ITP1 gene expression do not require any further genetic interference to increase itaconic acid release into the fermentation medium, thereby reducing the risk of unwanted side-effects by introducing an expression cassette for recombinant ITP1 gene overexpression.

According to the invention, the production host microorganism preferably belongs to the taxonomic class Ustilaginomycetes, even more preferably to the order Ustilaginales, even more preferably to the family Ustilaginaceae, even more preferably to any of the genera *Anomalomyces, Anthracocystis, Bromeliago, Cintractia, Dermatosorus, Dirkmeia, Eriocortex, Farysia, Franzpetrakia, Gymnocintractia, Heterotolyposporium, Kalmanozyma, Langdonia, Leucocintractia, Macalpinomyces, Melanopsichium, Moesziomyces, Moreaua, Mycosyrinx, Parvulago, Pericladium, Portalia, Pseudozyma, Restiosporium, Schizonella, Shivasia, Sporisorium, Stegocintractia, Tolyposporium, Tranzscheliella, Trichocintractia, Triodiomyces, Tubisorus, Ustilago, Websdanea*, and most preferably belongs to the genus *Pseudozyma*. The usefulness of *Pseudozyma* microorganisms and particularly of *Pseudozyma tsukubaensis* was surprising given the finding of a prior art survey (Zambanini et al. 2017, op. cit.) indicating that higher amounts of itaconic acid could be achieved using microorganisms of genus *Ustilago* (see Zambanini et al. 2017 table 3).

Further preferably according to the invention the production host microorganism does not express a functional orthologue for the *Aspergillus terreus* cis-aconitate decarboxylase (CAD1) gene nor any of the *U. maydis* cluster genes CYP3 and RDO1. These genes are thought to be involved in itaconic acid metabolism; strong expression of these genes can lead to a decrease in itaconic acid production.

Further preferably according to the invention the production host microorganism does not express a functional orthologue of the ku70 and ku80 proteins for nonhomologous end joining. This way the production host microorganism is particularly stabilised against unwanted spontaneous recombination, particularly where the production host microorganism comprises more than one expression cassette according to the present invention.

For the purposes of the present invention, a RIA1 gene is understood to be a nucleic acid sequence coding for a RIA1 polypeptide. Correspondingly an ITP1, ADI1, MTT1 or TAD1 gene, respectively, is understood to be a nucleic acid coding for an ITP1, ADI1, MTT1 or TAD1 protein, respectively.

According to the invention the RIA1 protein is, according to a functional definition, a protein capable of increasing expression of any of the genes ITP1, ADI1, MTT1 and TAD1 by a factor of at least 10 as measured by quantitative PCR of the corresponding ITP1, ADI1, MTT1 or TAD1 mRNA, respectively, compared to a corresponding strain that does not express the RIA1 protein. According to a structural definition, the RIA1 polypeptide has at least 46% amino acid sequence identity to the complete sequence SEQ ID NO. 35, preferably determined using the MatGat program and applying the following parameters: BLOSUM62 matrix, gap open penalty 12, gap extension penalty 2. Even more preferably, the RIA1 polypeptide has at least 55% amino acid sequence identity, even more preferably at least 57% amino acid sequence identity to SEQ ID NO. 35 as described just above. Such RIA1 proteins structurally correspond closely to the RIA1 polypeptide of *Pseudozyma tsukubaensis* as described in the examples herein, which further indicate advantages of such proteins. Further preferably, the sequence similarity of the RIA1 protein is at least 62% to the amino acid sequence SEQ ID NO. 35, even more preferably at least 64% and even more preferably at least 70%.

Particularly preferred are RIA1 polypeptides corresponding to those found in the genus of *Pseudozyma*, most preferably *Pseudozyma tsukubaensis*. In particular, preferred RIA1 polypeptides have at least 41% sequence identity to the complete sequence of SEQ ID NO. 36, even more preferably at least 57%, even more preferably at least 70%, even more preferably at least 73$%, even more preferably at least 80%, even more preferably at least 85%, even more preferably at least 90%, even more preferably at least 92%, even more preferably at least 95%, even more preferably at least 98%. Such RIA1 polypeptides correspond to the advantageous RIA1 polypeptides further described in the examples. Also preferably the sequence similarity of the RIA1 polypeptide to the amino acid sequence of SEQ ID NO. 36 is at least 46%, even more preferably at least 59%, even more preferably at least 70%, even more preferably at least 73%, even more preferably at least 85%, even more preferably at least 90%, even more preferably at least 92%, even more preferably at least 95%, even more preferably at least 98%.

It is particularly preferred when the RIA1 polypeptide according to any of the above functional and/or structural definitions comprises at least 1, even more preferably at least 2, even more preferably at least 3, even more preferably at least 4, even more preferably at least 5, even more preferably at least 6, even more preferably at least 7, even more preferably at least 8 and most preferably all 9 motifs corresponding to SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45 and SEQ ID NO. 46, respectively. Preferably, the RIA1 polypeptide contains each respective sequence motif with at most 2, even more preferably at most 1 amino acid exchange; it is in addition to this preferred that the motifs do not comprise a deletion or insertion compared to the sequences according to SEQ ID NO. 38 to SEQ ID NO. 47. Even more preferably the only difference in the sequence motif is that instead of SEQ ID NO. 38 the RIA1 polypeptide comprises the exact sequence SEQ ID NO. 47. Most preferably the RIA1 polypeptide sequence according to the present invention comprises all of the motifs SEQ ID NO. 47, SEQ ID NO. 39, SEQ ID NO. 40, SEQ ID NO. 41, SEQ ID NO. 42, SEQ ID NO. 43, SEQ ID NO. 44, SEQ ID NO. 45 and SEQ ID NO. 46, wherein the total of differences between the motifs in the RIA1 polypeptide and the aforementioned sequence motifs it at most 1 amino acid exchange and most preferably 0 amino acid exchanges.

According to a structural definition, the ITP1 polypeptide has at least 52% amino acid sequence identity to the complete sequence SEQ ID NO. 33, preferably determined using the MatGat program and applying the following parameters: BLOSUM62 matrix, gap open penalty 12, gap extension penalty 2. Such ITP1 proteins structurally correspond closely to the ITP1 polypeptide of *Pseudozyma tsukubaensis* as described in the examples herein, which further indicate advantages of such proteins. Further preferably, the sequence similarity of the ITP1 protein is at least 60% to the amino acid sequence SEQ ID NO. 33, even more preferably at least 83% and even more preferably at least 87%.

Particularly preferred are ITP1 polypeptides corresponding to those found in the genus of *Pseudozyma*, most preferably *Pseudozyma tsukubaensis*. In particular, preferred ITP1 polypeptides have at least 52% sequence identity to the complete sequence of SEQ ID NO. 33, even more preferably at least 70%, even more preferably at least 76%, even more preferably at least 79%, even more preferably at least 85%, even more preferably at least 90%, even more preferably at least 92%, even more preferably at least 95%, even more preferably at least 98%. Such ITP1 polypeptides correspond to the advantageous ITP1 polypeptides further described in the examples.

According to a structural definition, the ADI1 polypeptide has at least 63% amino acid sequence identity to the complete sequence SEQ ID NO. 32, preferably determined using the MatGat program and applying the following parameters: BLOSUM62 matrix, gap open penalty 12, gap extension penalty 2. Such ADI1 proteins structurally correspond closely to the ADI1 polypeptide of *Pseudozyma tsukubaensis* as described in the examples herein, which further indicate advantages of such proteins. Further preferably, the sequence similarity of the ADI1 protein is at least 74% to the amino acid sequence SEQ ID NO. 32, even more preferably at least 85% and even more preferably at least 98%.

Particularly preferred are ADI1 polypeptides corresponding to those found in the genus of *Pseudozyma*, most preferably *Pseudozyma tsukubaensis*. In particular, preferred ADI1 polypeptides have at least 63% sequence identity to the complete sequence of SEQ ID NO. 32, even more preferably at least 70%, even more preferably at least 78%, even more preferably at least 85%, even more preferably at least 90%, even more preferably at least 92%, even more preferably at least 95%, even more preferably at least 98%. Such ADI1 polypeptides correspond to the advantageous ADI1 polypeptides further described in the examples.

According to a structural definition, the MTT1 polypeptide has at least 53% amino acid sequence identity to the complete sequence SEQ ID NO. 34, preferably determined using the MatGat program and applying the following parameters: BLOSUM62 matrix, gap open penalty 12, gap extension penalty 2. Such MTT1 proteins structurally correspond closely to the MTT1 polypeptide of *Pseudozyma tsukubaensis* as described in the examples herein, which further indicate advantages of such proteins. Further preferably, the sequence similarity of the MTT1 protein is at least 59% to the amino acid sequence SEQ ID NO. 34.

Particularly preferred are MTT1 polypeptides corresponding to those found in the genus of *Pseudozyma*, most preferably *Pseudozyma tsukubaensis*. In particular, preferred MTT1 polypeptides have at least 53% sequence identity to the complete sequence of SEQ ID NO. 34, even more preferably at least 57%, even more preferably at least 70%, even more preferably at least 78%, even more preferably at least 85%, even more preferably at least 90%, even more preferably at least 92%, even more preferably at least 95%, even more preferably at least 98%. Such MTT1 polypeptides correspond to the advantageous MTT1 polypeptides further described in the examples.

According to a structural definition, the TAD1 polypeptide has at least 84% amino acid sequence identity to the complete sequence SEQ ID NO. 31, preferably determined using the MatGat program and applying the following parameters: BLOSUM62 matrix, gap open penalty 12, gap extension penalty 2. Such TAD1 proteins structurally correspond closely to the TAD1 polypeptide of *Pseudozyma tsukubaensis* as described in the examples herein, which further indicate advantages of such proteins. Further preferably, the sequence similarity of the TAD1 protein is at least 82% to the amino acid sequence SEQ ID NO. 31, even more preferably at least 92% and even more preferably at least 94%.

Particularly preferred are TAD1 polypeptides corresponding to those found in the genus of *Pseudozyma*, most preferably *Pseudozyma tsukubaensis*. In particular, preferred TAD1 polypeptides have at least 84% sequence identity to the complete sequence of SEQ ID NO. 31, even more preferably at least 85%, even more preferably at least 90%, even more preferably at least 92%, even more preferably at least 95%, even more preferably at least 98%. Such TAD1 polypeptides correspond to the advantageous TAD1 polypeptides further described in the examples.

A particularly advantageous production host microorganism according to the present invention is useful for converting glucose to itaconic acid a) with a productivity of at least 9.5 g itaconic acid/(I d) and/or b) with a yield of at least 25% (w/w glucose).

Preferably productivity is determined as the total mass of itaconic acid recovered from a fermentation broth after 8 days of fermentation, preferably fed-batch fermentation, divided by the final fermentation broth volume and the fermentation duration.

The invention also provides an integration vector comprising a RIA1 gene operably linked to a strong constitutively active promoter for integration outside of an ip locus. Such integration vector allows to achieve the aforementioned advantages of the invention when transforming a basidiomycete, preferably of the aforementioned class, order, family genus or species, to specifically and reliably integrate the RIA1 expression cassette (comprising a RIA1 gene operably linked to a strong constitutively active promoter) into the selected specific integration site. Preferred promoters according to the invention are the actin promoter, the HSP70 promoter, the TEF promoter, the GPD promoter and the GLC promoter, the actin promoter as described herein being most preferred.

Correspondingly the invention provides a method for alteration of an itaconic acid production host microorganism, comprising integrating at least one expression cassette for expression of a RIA1 gene and/or for expression of at least two genes selected from the group consisting of ADI1, MTT1 and TAD1, into the genome of a microorganism at an integration site other than an ip locus.

By integration of at least one expression cassette at the specific integration this method enables the person of ordinary skill in the art to turn a wild-type basidiomycete into an itaconic acid production host microorganism according to the invention, entailing the advantages described herein.

In the method the integration site preferably a) is located between a left border gene and a right border gene, wherein adenines of the translation start codons of the left and right border genes are separated by at most 51600 nucleotides in the corresponding wild type microorganism, wherein the left border gene codes for a protein having acetyl-CoA synthetase activity and wherein the right border gene codes for a protein consisting of an amino acid sequence having at least 21% identity to SEQ ID NO. 25, and/or b) is located up to 6500 nucleotides of the nearest border of an open reading frame translating into an amino acid sequence having at least 30% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, and/or c) is located within or replaces an open reading frame translating into an amino acid sequence having at least 30% sequence identity to any of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25.

Preferred integration sites and respective advantages have been described above and are further detailed herein.

Preferably the method is performed such that at least one gene i) coding for a protein having at least 30% sequence identity to and/or ii) the complementary strand of which hybridizes under at least low stringency conditions to a nucleic acid sequence coding for any of the protein sequences SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25 is inactivated.

Again, advantages of such inactivation and preferred inactivations have been described above and are further described herein.

The method thus leads to a microorganism which has increased itaconic acid productivity with respect to a control microorganism that does not include the at least one expression cassette integrated outside the ip locus.

The invention also provides a method for obtaining a recombinant itaconic acid production host microorganism, comprising a) cultivating a parent microorganism, b) performing, in any order and/or simultaneously, if so required: one or more transformations to provide the microorganism with any heterologous ADI1, MTT1 and TAD1 gene to obtain an active itaconic acid pathway in the microorganism, at least one integration of a RIA1 gene under the control of a constitutively active promoter, wherein integration is not in an ip-locus, inactivation of at least one gene i) coding for a protein having at least 30% sequence identity to and/or ii) the complementary strand of which hybridizes under at least low stringency conditions to a nucleic acid sequence coding for any of the protein sequences SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23 or SEQ ID NO. 25; and c) isolating the recombinant itaconic acid production host microorganism resulting from step b).

It is a particular benefit that the invention provides a production method for itaconic acid comprising a) fermenting a production host microorganism to produce itaconic acid, and b) recovering itaconic acid produced in step (a), wherein the microorganism is a microorganism according to the present invention and is preferably obtained or obtainable according to any of the aforementioned methods for alteration of an itaconic acid production host microorganism and/or is obtainable or obtained by transformation using an integration vector according to the present invention.

The fermenting process preferably is a submerged fermentation, and also preferably is a batch fermentation, a fed-batch fermentation or a continuous fermentation. Fed-batch fermentation is particularly preferred, particularly useful fermentation methods and materials used therein are described in the examples below.

The fermentation preferably is started in a minimal medium comprising at most 0.1% (v/v) of complex media components and has a pH of at most 5.5. As shown in the examples such minimal medium particularly supports reducing the amount of unwanted malate by-product and allows to increase productivity and yield of itaconic acid in a production host microorganism. According to the invention, complex media components are corn steep powder, corn steep liquor, corn starch, corn processing by-products, soy processing by-products, molasses, yeast extract, yeast autolysate and spent fermentation broth. Preferably, the minimal medium does not comprise more than 0.1% (v/v) of undefined media components. Most preferably, the minimal medium for starting the fermentation and/or for addition during fed-batch fermentation does not comprise more than 0.1% (v/v) of each of corn steep powder, corn steep liquor, corn starch, corn processing by-products, soy processing by-products, molasses, yeast extract, yeast autolysate or spent fermentation broth, even more preferably does not comprise more than a total of 0.1% (v/v) of corn steep powder, corn steep liquor, corn starch, corn processing by-products, soy processing by-products, molasses, yeast extract, yeast autolysate and spent fermentation broth, and most preferably does not comprise corn steep powder, corn steep liquor, corn starch, corn processing by-products, soy processing by-products, molasses, yeast extract, yeast autolysate and spent fermentation broth. For the avoidance of doubt, the host microorganism and the substances released into a fermentation broth are not complex media components of a fermentation medium.

The fermentation process according to the invention if preferably performed such that the pH of the medium, which preferably is a minimal medium as described above, during fermentation to at most 5, even more preferably to at most 4.5 and even more preferably to 3-4. Lowering the pH to below 4 leads to an arrest of dry cell weight (DCW) or at least to a significant growth retardation without compromising productivity and yield of itaconic acid and, surprisingly, does not lead to an unwanted increase of malate by-product formation.

The medium preferably comprises a polyalcoholic carbon source and the concentration of the carbon source during fermentation does not fall below 10 g/l for longer than 3 h. As shown by the examples, such fermentation conditions give rise to an advantageously high productivity and yield of itaconic acid with negligible formation of malate as fermentation by-product. Preferred polyalcoholic carbon sources are glucose, fructose, xylose, arabinose, lactose, sucrose, cellobiose, maltose, glycerol and ethylene glycol.

Particularly preferably the ratio of concentrations of itaconic acid to malic acid in the fermentation medium is at least 15:1 at the end of fermentation (batch or fed-batch fermentation), preferably at least 20:1 and even more preferably at least 100:1. According to the invention the formation of malic acid is unwanted. So far all previous attempts to fermentively produce itaconic acid in Ustilaginomycetes could not reproducibly avoid the co-production of malic acid, in several cases the amount of malic acid formed was even higher than that of itaconic acid. A reduction of the malic acid produced by the microorganism and preferably also a reduction of the malic acid secreted by the microorganism into the medium is beneficial because malic acid is a constituent of the Krebs cycle; a loss of malic acid thus reduces the capacity of the microorganism to fermentatively produce itaconic acid in high yields.

The fermentation method in step a) preferably is under aerobic or microaerobic conditions. It was particularly surprising that aerobic conditions would be beneficial despite earlier attempts to fermentatively produce itaconic acid using temporary microaerobic conditions (WO2009-1006627).

EXAMPLES

In this section, the abbreviation "ITA" denotes itaconic acid and/or itaconate, "MA" denotes malic acid/malate and "AKG" denotes alpha-ketoglutaric acid/alpha-ketoglutarate.

Strains, Media and Growth Conditions

The *P. tsukubaensis* strains H488 (CBS422.96, wild type, Kawamura, D., Saito, O., Matsui, H., and Morita, K. (1983). Producing of itaconic acid by yeasts: Ill Culture identification of itaconic acid producing strains. Shizuoka-Ken Kogyo Shikenjo Hokoku 27, 77-88), M15 (UVmutant of H488) and the newly constructed RIA1 overexpression transformant HR12 (H488-pPTT.pActin.RIA1, this work) as well as for cloning *Escherichia coli* strain DH10b were used. For cultivation, 12-well plates (3-ml micro-wells), 250-ml shaking flasks, 500-ml baffled flasks or a 600-ml bioreactor (Multifors, INFORS HT, DE) were used.

The yeast cells were streaked from a −80° C. cryo-conserve (emers) onto agar plates containing complete medium YPD or medium for selection (YM-Hyg, YM-Cbx) and grown at 30° C. for 2-3 d. Cultivations in liquid medium were carried out at 30° C. and 220 rpm. The strains were either grown in 50 ml complete medium YPD or in minimal medium for itaconic acid production MG-IA. For pre-cultures 50 ml of liquid YPD medium (in 500-ml baffled flask) was inoculated with yeast cells and grown for 1-2 d until a OD600 (Ultrospec 2000 photometer, Pharmacia Biotech) of 25-30 was reached. The cells were harvested by centrifugation (5 min at 3.500 g, room temperature (RT)) and resuspended in 2 ml dH2O (autoclaved). The subsequent liquid cultures were inoculated with the amount of cells suspension needed to obtain a starting OD600=1. In case of screening for transformants the cells were grown in 3-ml (MG-IA) micro-well cultures. The wells were inoculated directly with cell material from the agar plate and the well plates were sealed with an adhesive membrane. For cultivation in shaking flasks and well plates the pH of the medium was kept constant at 5.0-5.5 using 3.3 g l-1 CaCO3. For growth conditions in the bioreactor see Table 1. Sampling of the cultures was carried out every 24 h.

*Escherichia coli* was cultivated in liquid LB-medium at 37° C. and 220 rpm. The cells were grown on ampicillin (stock solution: 10 mg ml-1, end concentration: 100 μg ml-1) containing solid LB-medium at 37° C. to select for plasmid carrying transformants.

Media and Solutions

MG-IA

- N source: 1 g l-1 NaNO3 or NH4Cl (in particular experiments the concentration was selected from 1-8 g l-1)
- P source: 0.1 g l-1 KH2PO4/K2HPO4×3 H2O (in particular experiments the concentration was selected from 0.1-3.0 g l-1)
- mineral salts: 0.7 g l-1 MgSO4×7 H2O, 0.5 g l-1 NaCl, 0.5 g l-1 K2SO4 0.4 g l-1 $CaCl_2$)×2H2O
- trace elements: 0.5 mg l-1H3BO3, 0.04 mg l-1 CuSO4×5 H2O, 0.1 mg l-1 KI, 0.4 mg l-1 MnSO4×4 H2O, 0.2 mg l-1 Na2MoO4×2 H2O, 0.4 mg l-1 ZnSO4×7 H2O
- iron: 6 mg l-1 FeCl3×6 H2O (stock solution in ethanol)
- thiamine: 0.4 mg l-1 thiamine-HCl
- carbon source: 150 mg l-1 glucose, adjusted daily during fermentation YPD
- yeast extract 10 g l-1
- peptone (casein) 20 g l-1
- glucose 20 g l-1

YM

- yeast extract 3 g l-1
- peptone (casein) 2.5 g l-1
- malt extract 3 g l-1
- glucose 5 g l-1
- Hygromycin B (100 μg ml-1) and carboxin (25 μg ml-1) was used for the selection of plasmid containing *P. tsukubaensis* transformants LB (Sambrook et al., 1989)

- bacto-peptone 10 g l-1
- yeast extract 5 g l-1
- NaCl 10 g l-1

YEPSlight

- Yeast extract 10 g l-1
- Peptone (casein) 4 g l-1
- Sucrose 4 g l-1

Reg-medium

- Peptone 20 g l-1
- Sucrose 20 g l-1
- Sorbitol 1 M
- Agar 20 g l-1

SCS

Sorbitol 1 M

Sodium citrate 20 mM pH 5.8

STC

Sorbitol 1 M

Tris/HCl 10 mM pH 7.5

$CaCl_2$) 0.1 M

1× Mineral-Salt Solution 3 g l-1 (NH4)2SO4

1 g l-1 KH2PO4

0.16 g l-1 K2HPO4×3 H2O 0.7 g l-1 MgSO4×7 H2O 0.5 g l-1 NaCl 0.4 g l-1 Ca(NO3)2×4 H2O

PBS 8.0 g l-1 NaCl 0.2 g l-1 KCl 1.78 g l-1 Na2HPO4×2 H2O 0.27 g l-1 KH2PO4

General Techniques:

Sampling

Sampling of cultures was carried out every 24 h by directly removing 200-1.000 μl of culture broth in case of culture experiments in well-plates and shaking flasks. Bioreactor cultures were sampled every 24 h by removing 20 ml of culture broth through 2 three-way valves (to maintain sterility). The first 5 ml of broth were discarded (to avoid potentially accumulated dead cells in the sampling tube). The remaining 15 ml of culture broth were collected into a previously weighted 15-ml falcon tube.

Optical Density (OD600)

Optical density at a wavelength of lambda=600 nm was measured to track cell growth. The cells were pelleted by centrifugation for 5 min at 3.500 g, RT. The pellet was washed with 1×mineral-salt solution. After the washing step the cells were resuspended and diluted with 1×mineral-salt solution. Measuring was carried out in 1.5 ml disposable cuvettes (layer thickness: 10 mm) with an Ultrospec 2000 photometer (Pharmacia Biotech).

Dry-Cell Weight (DCW)

Dry-cell weight was only determined for cell cultures grown in the bioreactor. 10 ml of the culture broth was pelleted (10 min at 3.500 g, RT) in the previously weighed 15-ml falcon tube. The pellet was washed with 10 ml dH2O and pelleted again (10 min at 3.500 g, RT). Supernatant was removed. The pellet was then dried for 12 h at 100° C. and weighed to ultimately determine the DCW.

Glucose Enzyme Assay

Glucose concentration in the culture medium was determined by performing an enzyme assay with the help the enzyme assay kit Glucose UV test (R-Biopharm AG). It was executed according to the manufacturer's protocol.

Microscopy

The cells were centrifuged and resuspended in 100 μl fixation solution (4.5% v/v formaldehyde in PBS, PBS according to (Sambrook et al., 1989)). Visualization was done via light and phase-contrast microscopy at 400× magnification.

DNAse Treatment

DNAse treatmend was performed according to standard protocols using the following reaction mixtures:

DNaseI-re-treatment of samples HR12_1 and H488_1

DNase I—RNase free—EURx (Roboklon, E1345)

Reaction Mixture:

32/38 μl RNA (HR12/H488)

5 μl 10×DNaseI-buffer

1 μl Ribolock Ribonuclease Inhibitor 11.5/5.5 μl H2O 0.5 μl DNaseI 15 min at 37° C.

Purification of RNA with NucleoSpin® RNA Clean-up XS-Macherey-Nagel Elution (2-step) with 15+10 μl H2O cDNA-Synthesis with max. possible amount of 11.5 μl 11.5 μl RNA 1 μl Random Hexamer 4 μl 5×Puffer 2 μl dNTP s 0.5 μl Ribolock 40 U/μl 1 μl RT for RT-control without RT and only 10 μl total volume Preparation 2: 10 μl—Reaction Mixture 2.5/5.5 μl RNA (HR12_2/H488_2)

3.0/0 μl H2O 0.5 μl Random Hexamer

2 μl 5×buffer

1 μl dNTP s 0.5 μl Ribolock 20 U/μl 0.5 μl RT

RT-PCR

PCR with cDNA each as double determination, RNA and H2O-control as single determination 10 μl-Reaction mixture:

5 μl PCR-SYBR Green Mastermix 1.2 μl Primermix (je 2.5 pmol/μl)

1 μl cDNA/RNA/H2O 2.8 μl H2O

Read in 96-well plate

Lid-temperature: 105° C.

Protocol

1: 95.0° C. for 8:00

2: 95.0° C. for 0:15

3: 58.0° C. for 0:30

Plate Read

4: 72.0° C. for 0:10

Plate Read

5: GOTO 2, 39 more times

6: 72.0° C. for 2:00

7: Melt Curve 60.0° C. to 95.0° C.: Increment 0.5° C. 0:04

Plate Read

8: 20.0° C. for 0:01

Quantification

Step 3

Analysis Mode: Fluorophore

Cq Determination: Regression

Baseline Method:

SYBR: Auto Calculated

Example 1: Promoter Characterization

For each of the four genes TEF3, HSP70, Actin and Glyceraldehyde 3-phosphate dehydrogenase an approximately 1.050 bp long sequence from the immediate upstream region was amplified. The 5'-ends were complemented with a KpnI-restriction site and the 3'-end with the first 20 bp of the LacZ-ORF. Parallel to that, the ORF of the ß-galactosidase encoding LacZ gene from *Escherichia* (*E.*) *coli* was amplified while complementing the 5'-end with the last 20 bp of one of the promoter sequences and the 3'-end with a PstI restriction site. Both fragments were fused together during a second polymerase chain reaction (PCR). This was possible due to the homologous overlapping ends of the two fragments created in the first PCR. The overlap-PCR product was digested with KpnI & PstI and ligated into a linearized pPTT plasmid (The plasmid was KpnI and NsiI digested. Ends generated by NsiI are compatible to ends generated by PstI).

The created LacZ reporter gene overexpression plasmids, pPTT-pActin-LacZ; pPPT-pGAPDH-LacZ; pPPT-pHSP70-LacZ & pPPT-pTEF1-LacZ, were each transformed into *P. tsukubaensis* H488 and M15. HSP70 promoter from *U. maydis* (pUmHSP70) served as a negative (data not shown). The obtained transformants were cultivated either for 2 days in YPD complete medium or 4 days in MG-IT (minimal medium). The cells were harvested, lysed mechanically, extracted and tested for β-galactosidase activity according to Miller (1972). The absorbance of the cell free extract with ONPG (o-Nitrophenyl-β-Dgalactopyranosid) as substrate was measured at 420 nm for 30 minutes. To determine total protein content, a Bradford protein assay (Bradford, 1976) was carried out.

Most of the transformants showed elevated β-galactosidase activity in complete medium but minimal medium as well. The range of activity for every tested promoter was quite high. While pHSP70 and pTEF1 transformants underperformed compared to the HSP70 promoter from *U. maydis*, pActin was the only tested promoter that showed elevated enzyme activity in every scenario (see FIG. 5-FIG. 8). The reasons for such differences in promoter activity are still unclear.

Due to the overall relative high activity under the control of pActin, this promoter was used for subsequent overexpression analyses.

Example 2: Generation of Overexpression Strains

The itaconic acid-overproducing strain *P. tsukubaensis* HR12 was created by the heterologous introduction of the whole circular plasmid pPTT-pActin-RIA1.

The strong constitutive Actin1 promoter was used for all overexpression transformants. The native promoter sequence and open reading frame (ORF) sequences (genes to be overexpressed) were derived from genomic DNA of *P. tsukubaensis* H488 by polymerase chain reaction (PCR) using the primers listed in the sequences table. The promoter sequence was then fused to the respective ORF by overlap-PCR. The ORF of ACO1 was cloned by amplifying the two exons separately and fusing the promoter and the two exon fragments simultaneously during one PCR. The overlap products were then cut and ligated into the according plasmid which was cut and previously dephosphorylated (for restriction enzymes used see FIGS. 4A-4D).

Example 3: Transformation of *P. tsukubaensis*

The transformation protocol was adapted to Gillissen, B., Bergemann, J., Sandmann, C., Schroeer, B., Bölker, M., and Kahmann, R. (1992). A two-component regulatory system for self/non-self recognition in *Ustilago maydis*. Cell 68, 647-657; and to Schulz, B., Banuett, F., Dahl, M., Schlesinger, R., Schäfer, W., Martin, T., Herskowitz, I., and Kahmann, R. (1990). The b alleles of *U. maydis*, whose combinations program pathogenic development, code for polypeptides containing a homeodomain-related motif. Cell 60, 295-306.

For the transformation of *P. tsukubaensis* only freshly prepared protoplasts were used. To obtain protoplasts, *P. tsukubaensis* cells were grown overnight in 3 ml YM medium at 30° C. and 220 rpm. The next day 1 ml of the culture was transferred to 50 ml YEPS light medium and grown at 30° C. and 220 rpm for at least 3 h until an OD600 of 0.5 was reached. The cells were harvested by centrifugation (5 min at 3.500 g, RT). The cell pellet was washed with 20 ml SCS, pelleted again and resuspended in 2 ml Glucanex® (6% w/v in SCS, sterile filtrated). For the enzymatic lysis of the cell wall, the cells were incubated in a 50 ml-falcon tube at RT and soft shaking for 30-45 min until 50% of the cells were present in the form of protoplasts. Harvesting the protoplasts was done by centrifugation (10 min, 2.500 rpm, 4° C.). The pellet was consecutively washed in 20 ml SCS, 10 ml SCS and 20 STC (icecold SCS & STC). After the last washing step, the cells were resuspended in 0.5 ml STC (icecold) and ultimately aliquoted into 1.5 ml-reaction tubes with a volume of 80 μl per tube. The protoplasts were gently mixed with up to 15 μg circular plasmid DNA (max volume: 10 μl) and incubated on ice for 10 min. As a control 10 μl of dH2O was used instead of DNA. The cells were overlaid with 500 μl PEG4000 (40% w/v polyethylene glycol 4000 in STC, sterile filtrated) and incubated on ice for 15 min. In the meantime, the selective agar plates were prepared: Reg-medium was liquified and cooled down to approx. 50° C. and mixed with the doubled concentration of Hygromycin B (200 μg ml-1) or Carboxin (50 μg ml-1). 10 ml of Reg-Hyg/Reg-Cbx was used as a base agar and overlaid with same amount of Reg-medium (no marker) as a top-agar. The protoplasts were gently plated and incubated at 30° C. for 3-15 d. Colonies obtained after transformation were streaked onto selective plates for purification. Single colonies were then screened phenotypically for itaconic acid production. Genomic DNA was isolated from suitable candidates. The genomic DNA was used as template for PCR to check for integration of the respective overexpression plasmid. The itaconic acid overproducing strain *P. tsukubaensis* HR12 was confirmed by sequencing of its genomic DNA.

The sequencing showed that the regulator gene for itaconic acid, RIA1 under the control of the strong constitutive promoter pActin was integrated two times in tandem orientation with parts of the vector backbone (see FIG. 12). The first copy consists of 82.2% of the overexpression plasmid (1.627-9.167 bp) and the second 85.1% (1-7.804 bp). Integration of the two vector fragments occurred in the ORF of Pseudog4086 while deleting an approx. 34 kbp long sequence consisting of nine other ORFs (Pseudog4087-4095).

All known native genes responsible for ITA production in *P. tsukubaensis* were used to create respective overexpression plasmids. Since the Actin1 promoter demonstrated overall highest observed LacZ-activity in previous tests, this promoter sequence was used for overexpression analyses of the ITA-cluster genes (itaconic acid metabolism gene cluster).

Similar to tests for promoter activity, the genes were fused with the pActin sequence while simultaneously adding restriction enzyme sites on both the 5'- and 3'-end of the promoter-gene fusion product. The created PCR product was digested and ligated into an accordingly linearized pPTT-plasmid (see FIGS. 4A-4D). For the created plasmids see FIG. 13.

Resulting plasmids were each transformed into *P. tsukubaensis* H488 & M15 according to Bodinus, 2011, plated onto hygromycin B-containing Reg-plates and cultivated for 3-10 days at 30° C. Transformants were then streaked onto hygromycin B-containing Reg or YPD solid medium to obtain pure single colonies. The single colonies were then screened phenotypically for ITA production in 3 ml-well cultures. In each well of a 12-well plate a spatula's tip worth of CaCO3 (approx. 20 mg) was added and then filled with 3 ml of liquid MG-IA minimal medium (N: 1 g l-1; P: 0.1 g l-1; C: 15% (w/v)). Using 1 μl-inoculation loops each well was inoculated with a single colony. The well plate was sealed with a semipermeable membrane and cultivated for 10 days at 30° C. and 220 rpm. On the 3rd, 5th, 7th and 9th day 1 ml dH2O was added per well to compensate for evaporation.

The cells were harvested at the 10th day by centrifugation (18.000 g for 15 min at 4° C.). Ion chromatography of the diluted supernatant (1:200-1:2.000) was carried out for the quantification of produced malic acid (MA) and itaconic acid. Overexpression of ADI1 resulted in total only four transformants (HA1, HA8, HA10 and MA7) with a slight increase in ITA production compared to the reference strains H488, M15 and M15-CAD. These four transformants produced 0.2-1.0 g l-1 ITA after 10 d of cultivation. Malic acid was still the main organic acid produced in those mutants (see FIG. 14-FIG. 16).

Overexpression of the itaconic acid transporter (ITP1) had no effect in the *P. tsukubaensis* wild type strain H488. There was no ITA production detected only similar amounts of MA compared to H488 (see FIG. 18).

The same overexpression led to different results in strain M15. Out of 12 transformants tested, 10 showed increased levels of ITA production. Three of those, MI8; MI9 and MI11, even secreted ITA as the main product (see FIG. 19). Those three transformants produced 9.9-12.5 g l-1 ITA and 6.7-9.0 g l-1 MA. The difference observed between the two strains while overexpressing the same transport protein, ITP1, could potentially mean, that the export of ITA is bottleneck in strain M15.

By overexpressing the mitochondrial cis-aconitate transporter MTT1 in H488, only one transformant showed increased levels of ITA (0.8 g l-1 ITA, 5.3 g l-1 MA). The other mutants solely produced MA (see FIG. 21). However, the same overexpression led to several transformants demonstrating elevated ITA productivity in strain M15, with mutant MM8 producing ITA as the main organic acid (11.5 g l-1 TA, 8.0 g l-1 MA) (see FIG. 22).

Similar to the aconitate-Δ-isomerase (ADI1), by overexpressing TAD1 only a marginal ITA production (0.03-0.16 g l-1) could be induced in strain H488 as well as in strain M15 (see FIG. 24 & FIG. 25).

Only small, if any, increases in ITA production could be achieved by the overexpression of the two enzymes ADI1 and TAD1. Although, the introduction of the upregulated transporters ITP1 and MTT1 led to higher producing transformants. The effect of higher ITA production by overexpressing one of the two transporters was most prevalent in strain M15. This could mean that an increased cis-aconitate transport out of the mitochondrion or the export of ITA are on their own not leading to higher ITA production but crucial for an increased ITA synthesis if other factors are already in play.

By transforming *P. tsukubaensis* H488 and M15 with a constitutively upregulated copy of the RIA1 gene a significant change in ITA synthesis was achieved. All screened transformants showed increased levels of ITA. 20 out of 23 transformants produced ITA as the main product (see FIG. 27 & FIG. 28). Despite the high induction of ITA production, the range of formed ITA between transformants was substantial: 2.0-31.4 g l-1 for H488 transformants and 1.3-33.4 g l-1 for M15 transformants. Only transformants HR7, MR4 and MR11 secreted more MA than ITA.

Cultivation of the generated transformants in shaking flasks and quantification of the produced amounts of itaconic acid:

The six highest producing transformants, HR8; HR10; HR12; MR1; MR2; MR8, were later cultivated in shaking flasks with MG-IA minimal medium to further characterize their ITA production capabilities. The cells were grown for eight days in 50 ml MG-IA medium (N: 2 g l-1, P: 0.1 g l-1, C: 15% w/v) in baffled shaking flasks. Interestingly, only transformant HR12, showed a similar ITA productivity compared to the pre-screening (see Table 5 & FIGS. 29A-29F). HR12 was therefore the main transformant used for further studies.

Characterization of Transformant HR12

In order for the yeast cell to be capable to grow solely on acetate or ethanol as carbon source, Coenzyme A (CoA) has to be acetylated to acetyl-CoA. Pseudog4086 encodes for a potential acetyl-CoA synthetase (AMP-forming) catalysing this reaction. Pseudog4086 was partially deleted by the insertion of the plasmid. To check if ethanol/acetate metabolism was affected by this deletion, the cells were hence grown on minimal medium with either acetate or ethanol as sole carbon source (see Table 6).

There was no detectable difference in growth behaviour between the wild type and HR12. Despite the partial deletion of Pseudog4086, the yeast is still able to utilize acetate and ethanol. This observation could be explained by a compensatory effect of the gene product of Pseudog3222. This gene potentially encodes for an acetate-CoA ligase (ADP-forming), which also catalyses the acetylation of CoA.

It was also unclear whether *P. tsukubaensis* HR12 is still able to grow and produce ITA on other carbon sources than glucose. The yeast HR12 was therefore grown in liquid minimal medium with sucrose, glycerol or D-xylose as carbon source (see FIG. 30 & FIG. 31).

The data clearly show that all of the tested substrates are being used by the yeast for growth and for the production of ITA. The highest cell densities were reached with glycerol (OD600=45.6) and glucose as a reference (OD600=44.8). Despite resulting in the lowest cell density, *P. tsukubaensis* HR12 produced the highest amounts of ITA with sucrose as carbon source after seven days of cultivation with an end-point concentration of 28.2 g l-1 ITA. Glucose was equally fast converted into itaconic acid but reached a lower end concentration of 24.2 g l-1. Potentially because more of the carbon was used for cell growth or storage in form of lipid bodies or mannosylerythritol lipids (MEL). Production of ITA with glycerol was much slower in the beginning but reached comparable amounts of ITA to that of sucrose (end-point concentration: 26.2 g l-1). Growth on D-xylose was a bit delayed like in the case of glycerol but ITA production was overall the lowest with 16.6 g l-1 at the 4th day and only 17.5 g l-1 at the end of the cultivation.

Quantitative real-time PCR provided the evidence that, in fact, all of the five ITA cluster genes are highly upregulated in HR12 compared to the wild type H488 (FIG. 32 and Table 6a).

The overexpressed RIA1 gene showed a 470-fold higher transcription rate in HR12 compared to H488. The expression of the genes encoding for the two metabolic enzymes ADI1 and TAD1 and the mitochondrial transporter MTT1 was even higher with a 2.500-3.500-fold increase. Expression of the itaconate transport protein (ITP1) appears to be only slightly increased. This is due to the fact, that the transcription was already relatively high in H488 compared to HR12 (data not shown).

Considering the data, it seemed unnecessary to further overexpress MTT1 or any other ITA cluster gene, because the expression level of every analysed gene is highly upregulated.

Overexpression of a cis-aconitate decarboxylase gene (CAD) e.g. from *Aspergillus terreus* controlled by a strong native promoter FIG. 10 shows the pathway for itaconic acid production in *P. tsukubaensis* and *A. terreus*.

The difference between the two species is how cis-aconitate is converted into itaconic acid.

In *P. tsukubaensis* cis-aconitate is metabolized in a two-step process into ITA, with trans-aconitate being the intermediate. This process is a single-step reaction in *A. terreus* and catalysed by the enzyme cisaconitate decarboxylase (CAD1). *P. tsukubaensis* transformants were constructed with additional copies of the AtCAD1 gene under the control of the *U. maydis* HSP70 promoter. By doing so the ITA overproducing strain M15-CAD was generated.

To ensure a high transcription of the AtCAD1 gene in *P. tsukubaensis*. Therefore, the AtCAD1 was fused during a PCR with the native, constitutive pActin promoter while simultaneously adding KpnI- (5'-end) and NsiI-restriction sites (3'-end). The 2.589 bp long amplicon was KpnI- and NsiI digested and ligated into an accordingly linearized pPTT-plasmid creating the pPPT-pActin-AtCAD1 plasmid (see FIG. 33).

The circular plasmid was transformed into *P. tsukubaensis* H488 and M15. In total 13 transformants (4 transformants in strain H488, 9 in M15) have been created and screened for their ITA production capabilities (see FIG. 35 & FIG. 36).

All of the transformants still produced malic acid as the main organic acid. There was no observed induction of ITA production by overexpressing AtCAD1 in strain H488. Seven out of nine M15 transformants produced higher amounts of ITA ranging between 0.7-5.4 g l-1. The M15-CAD transformant behaves similarly with an ITA amount produced of 0.7 g l-1 under the same conditions.

Overexpression of the Native Aconitase Encoding Gene Controlled by a Strong Native Promoter The question was whether the production of ITA in transformant HR12 could be further increased by additionally overexpressing aconitase to obtain more cis-aconitate which would then be supplied to the deregulated ITA metabolic pathway.

First the respective enzymes were identified by conducting a BLASTP search against the NCBI database. Two candidate genes had been found: Pseudog3035, this gene was named PtACO1 and Pseudog2814-PtACO2.

Although the ACO1 ORF contains an intron, the gene was amplified without the intron. The approach was similar to the fusion of the pActin promoter for the genes described above: First the two exons were amplified. The first exon was complemented at the 5'-end with the 3'-sequence of the pActin promoter (21 bp) and 3'-end with the 5'-sequence (20 bp) of the second exon. The 5'-end of the second exon was hence complemented with 3'-sequence (20 bp) of the first exon. All three fragments, pActin (complemented with a hygromycin B resistance cassette it harbours a carboxin resistance cassette.

The native ACO2 gene does not contain an intron. With the help of an overlap—PCR the gene was fused with the pActin promoter while also adding a PfI23II (5'-end) and a NsiI (3'-end) restriction site. The digested PCR product was ligated into a PfI23II & NsiI digested pPTT.Cbx-plasmid. The resulting ACO1 & ACO2-overexpression plasmids (see FIG. 37) were transformed into *P. tsukubaensis* strain HR12.

In total 11 transformants have been obtained: 5 ACO1 and 6 ACO2 overexpression transformants. All transformants were screened for ITA acid production. Not one transformant showed an increased production of ITA. HR12ACO1-K5 and HR12ACO2-K1 produced equal amounts compared to strain HR12. All the other transformants produced less ITA.

Identification of a Minimal Medium for *P. tsukubaensis*

Kawamura et al. (1981, 1982, see above) described a medium for the cultivation of *P. tsukubaensis*. This medium was modified for the production of ITA with the *P. tsukubaensis* wild type H488 and originally contained corn steep liquor (CSL) as an essential component for the induction of ITA production. Since CSL is a complex ingredient with varying composition, it is unwanted for a strict standardized process. It was therefore necessary to find a component to substitute for CSL in a minimal medium.

*P. tsukubaensis* cells cultivated in rich YPD medium show fast growth in the form single cells. In a 50 ml YPD culture with a YPD preculture in baffled flasks they can reach a cell density of up to OD600=68 after two days of cultivation. If the yeast cells were pre-cultivated in MG minimal medium for ascomycetous oleophilic yeasts (see Table 7, modified according to Mauersberger et al., 2001: Mauersberger, S., Wang, H.-J., Gaillardin, C., Barth, G., and Nicaud, J.-M. (2001). Insertional Mutagenesis in then-Alkane-Assimilating Yeast *Yarrowia lipolytica*: Generation of Tagged Mutations in Genes Involved in Hydrophobic Substrate Utilization. J. Bacteriol. 183, 5102-5109) and transferred into the same minimal medium, no growth was observed. If the yeast was transferred after one day of no growth into YPD medium, the cells showed rapid growth again, meaning that cells were still vital. When the cells were pre-cultivated on rich medium (YPD) and transferred into MG medium, without transferring any of the YPD medium, cell growth could be observed. The growth was still slightly retarded. That indicated that a certain compound in trace amounts could be enough for the cells to grow in minimal medium.

To observe if growth in MG medium could be induced, the *P. tsukubaensis* H488 cells were pre-cultivated in MG medium and transferred into fresh MG medium. After one day of no observed cell growth, the medium was supplied with either 10% (v/v) YPD medium or 1× of a composite vitamin solution (see FIG. 42 & Table 8). In both cases cell growth was observed. In a follow-up cultivation the single vitamins used in the composite solution were tested. Two out of the eight vitamins, inositol and thiamine, enabled growth of *P. tsukubaensis* H488 in MG medium (see Table 9).

Using MG minimal medium containing only inositol or thiamine as a vitamin, *P. tsukubaensis* H488 was stably grown for five passages. The yeast cells even accumulated lipids in the form of large intracellular lipid bodies (data not shown). Although no organic acid production could be detected in MG-1 or MG-T medium with *P. tsukubaensis* H488. MG-T was used as a transitory minimal medium.

Optimization of the Cultivation Medium for the Production of Itaconic Acid

A basic composition for a minimal medium for the growth of *P. tsukubaensis* H488 has been found in this project but it was crucial to develop it further regarding its nitrogen (N) and phosphate (P) content, to ensure ITA production. Testing the MG-T medium with different N/P-ratios it was clear that not just the growth but also the organic acid production was greatly affected by different N/P-ratios (see FIG. 43). Nevertheless, malic acid was still the main acid secreted by *P. tsukubaensis* H488.

The composition of the MG-T was adjusted in the amount of carbon source and the concentration of P- and N-source were set as variables to test different ratios. Also (NH4) 2SO4 was exchanged for NaNO3, because the sulphate anions were perturbing in the analytics of ITA quantification. This medium was named MG-IA (see Table 10).

*P. tsukubaensis* H488 was later cultivated in 50 ml MG-IA cultures. Despite just the small amounts of ITA, it was the first time that ITA had been produced in minimal medium with the *P. tsukubaensis* wild type H488. The highest ITA concentration of 0.3 g l-1 was achieved with a N/P-ratio of 2/0.1 g l-1. In the same time 12.4 g l-1 MA were secreted (see FIG. 44).

*P. tsukubaensis* strain M15 was cultivated in the same medium with the two N/P ratios deemed best (N/P: 2/0.1-5/0.1). After five days of cultivation in MG-IA (N: 2 g l-1, P: 0.1 g l-1) strain M15 secreted already significant amounts of ITA (6.9 g l-1) but malic acid was synthesized in greater amounts (9.5 g l-1). By prolonging the cultivation to eight days, the ITA/MA ratio reached a tipping point with ITA being the main acid produced: ITA: 14.8 g l-1, MA: 6.0 g l-1 (see FIG. 45).

*P. tsukubaensis* M15 was therefore screened in 3 ml-well cultures with various amounts of N-source (0.5-4.0 g l-1) and P-source (0.1-2.0 g l-1) for ITA production. With high amounts of nitrogen and low phosphate concentration mainly MA was synthesized but malate production was greatly reduced at low to moderate nitrogen concentrations. At lower N-concentrations ITA was the main organic acid instead (see FIG. 46). These results indicate that nitrogen and phosphate limitation trigger ITA production in strain M15. In shaking flask cultures with N: 2 g l-1, P: 0.1 g l-1 the ITA synthesis was also greatly enhanced when nitrogen was depleted, and the cells entered stationary growth phase (see FIG. 45).

The ITA overproducing strain *P. tsukubaensis* M15-CAD was subsequently cultivated in MG-IA medium with N/P ratios of 2/0.1 and 1/0.1. After eight days of cultivation a threefold increase in ITA—42.6 g l-1 (3.2 g l-1 MA) was achieved compared to strain M15. At the end of the cultivation 20.9 g l-1 of glucose of the initial 150 g l-1 were left, resulting in a yield of 33% (g itaconate/g glucose). With a decreased amount of nitrogen (1 g l-1) a lower cell-density was achieved that resulted in a lower ITA production of 25.1 g l-1 and a yield of only 24% (see FIG. 47).

Increasing the nitrogen amount to 5 g l-1 led to much higher cell densities while simultaneously drastically decreasing the ITA production: 15.5 g l-1 ITA has been produced with 0.1 g l-1 phosphate-source (MA: 2.9 g l-1; ITA-yield: 15%) and 24.1 g l-1 ITA with 1.0 g l-1 P-source (MA: 0.5 g l-1; ITA-yield: 16%) (see FIG. 48).

All of the described strains show a clear connection between the ratio of nitrogen and phosphate source in the medium and the amount of secreted itaconic acid. If the screening of the different overexpression transformants is considered, it is already apparent that transformant HR12 behaves different regarding ITA productivity. HR12 was screened in 3 ml-well cultures like *P. tsukubaensis* M15, to test if this transformant is also dependent on a certain amount of N- and P-source (see FIG. 49). After six days of incubation the transformant produced high amounts of ITA: 16.3-24.4 g l-1 and only modest concentrations of MA: 0.5-1.7 g l-1. It seems there is a decoupling effect by the introduction of the upregulated RIA1 copies in transformant HR12. For this transformant there is no limitation in N- or P-source needed to induce ITA production. Although, with higher amounts of nitrogen and lesser P-concentrations slightly higher ITA-concentrations have been achieved. The MA concentrations have been higher in these samples as well.

Despite successfully uncoupling ITA synthesis from nitrogen or phosphate limitation conditions, it was still unclear if different N-sources have an impact on the ITA-production with the help of strain HR12. *P. tsukubaensis* HR12 was cultivated in MG-IA medium with either NaNO3 (reference), NH4Cl or NH4NO3 as N-source to check for a potential relationship. (NH4)2SO4 was undesired, because of the resulting [SO4]2-anions.

A slightly faster growth could be observed with NH4Cl and NH4NO3. Cell density subsided with NH4Cl and was the lowest observed after seven days of cultivation. Strain HR12 produced however the highest amount of ITA (27.5 g l-1 at the 7th day, MA&AKG: 0.18 g l-1) with this N-source. Cells grown with NaNO3 reached highest cell densities but produced less ITA: 24.2 g l-1 at the 7th day, MA&AKG: 0.44 g l-1. The growth behaviour was not impaired with NH4NO3 as Nsource, although transformant HR12 produced considerably less ITA: 13.2 g l-1 at the 7th day, MA&AKG: 0.26 g l-1.

This behaviour of drastic decrease in ITA synthesis with NH4NO3 is surprising. It cannot be described by the amount of cell mass. The amount of cells produced is right between that of NaNO3 and NH4Cl. Neither is the relative amount of nitrogen present in the medium determining: NNaNO3: 16.5%, NNH4Cl: 26.2%, NNH4NO3: 35.0%.

In the case of NH4Cl it appears to be that there is a negative correlation between cell density and ITA production. This is a beneficial effect, because that way more resources can potentially be converted into ITA instead of cell mass. The composition of MG-IA was therefore changed by replacing NaNO3 with NH4Cl in later cultivations (relevant cultivations have been marked accordingly).

Cultivation of the Most Promising Transformants in a Fermenter and Quantification of the Produced Amounts of Itaconic Acid Cultivation of yeast in shaking flasks is indispensable in science because of the operational simplicity and the prompt results it offers. The main disadvantage of this cultivation method is the lack of control of certain influencing variables e.g. aeration. To be able to reliably cultivate yeast in large quantities (pilot plant and production) a gradual up-scaling process is necessary, since the microorganisms may behave in an unexpected manner in larger volumes.

*P. tsukubaensis* strain M15-CAD and HR12 were cultivated in a 600 ml-bioreactor under different conditions to get a first impression, whether ITA production can reliably be upscaled from shaking flask level and if so, how certain factors affect ITA productivity.

For fermenter cultivation cells were streaked form glycerol stock (25% v/v) onto YPD plates. With these cells (max. four weeks old) 50 ml YPD medium was inoculated and grown for one to two days at 30° C. and 220 rpm until a cell density of OD600=25-35 was reached. The amount of cells needed to obtain a starting OD600=1.0 in the fermenter was harvested by centrifugation at 3.500 g for 5 minutes and resuspended in 3 ml sterile H2O. Start of fermentation was point of inoculation. Cells were cultivated under the following conditions if not stated otherwise:

temperature: 30° C.

pH: 5.5-adjusted constantly by addition of 1 M HCl & 2.5-5.0 M NaOH aeration: 55% pO2-11 min-1 air supply and adjusted by dynamic stirring >400 rpm in case of foam building, TEGO® antifoam KS 911 (Evonik Industries AG) was automatically added N-source: NaNO3 (or NH4Cl in the accordingly labelled fermentations)

Sampling was carried out every 24 h by removing 20 ml of culture broth.

Cell growth was determined by measuring optical density (OD600), and dry cell weight. Glucose concentrations were estimated enzymatically using an UV-test kit (R-Biopharm AG, DE). Measurement of organic acid concentration were carried out by ion chromatography. Additionally, cells were observed microscopically for changes in morphology and potential presence of contaminants. Losses resulting from the removal of culture were later taken into account for the calculation of yield, productivity rate etc.

Itaconic Acid Production with *P. tsukubaensis* M15-CAD in a 600 ml Bioreactor

Strain M15-CAD was cultivated in 600 ml MG-IA medium with N/P-ratios of 2/0.1 or 5/0.1 g l-1. Compared with shaking flask cultures, there was a clear effect on the ITA productivity by the N/P-ratio. The amount of cell mass was relatively low with only 2 g l-1 N-source but higher amounts of ITA of up to 30 g l-1 have been produced. Biomass production was doubled with 5 g l-1 N-source but ITA concentration was only ⅓rd compared to the lower N-source.

There were not only large differences between the two media, the ITA production was significantly lower in the fermenter than in shaking flasks. With 2 g l-1 N-source 30.5 g l-1 ITA (1.0 g l-1 MA) was produced after eight days of cultivation in the fermenter, compared to 42.6 g l-1 (3.2 g l-1 MA) in shaking flasks. This constitutes for only 72% of the acid produced in shaking flasks. The effect was even more substantial with an increased N-concentration. After eight days only 58% of the concentration of shaking flask cultivation could be achieved: 8.9 g l-1 ITA (0.3 g l-1 MA). It appears that with more nitrogen available more biomass is created, thus less of the carbon source is converted into ITA.

Shifting the N/P-ratio to 4 g l-1 N-source and 1 g l-1 P-source led to a rapid cell growth with a maximum of 25.6 g l-1 DCW after four days. The cells died often quickly afterwards. The ITA production was comparable to a N/P-ratio of 5/0.1: 10.9 g l-1 TA after six days (1.1 g l-1 MA).

Just by increasing the pH of the medium (N/P-ratio: 2/0.1) during cultivation to pH=7.0, drastic changes in organic acid production could be observed. Although the yeast cells showed a similar growth behaviour to the previous fermentation at pH=5.5, only 3.4 g l-1 ITA were produced after six days. Even the ratio of organic acids turned around, since MA was the main acid produced with 6.9 g l-1 at the end of cultivation. In this case the amount of produced biomass appeared not to be the problem. Rate of glucose consumption and biomass build-up was very similar to that of pH=5.5.

The solubility of ITA increases with higher pH-values. That should facilitate the production of ITA. In order to potentially increase ITA by elevating cis-aconitate synthesis in the TCA cycle, dissolved oxygen was raised during the fermentation process to pO2=90% (aeration: 2 l min-1). The idea behind this was to supply enough oxygen to ensure NAD+ and FAD-regeneration in the electron transport chain. Both NAD+ and FAD are essential electron carriers needed to maintain the TCA cycle. By doing so the overall ITA production was immensely reduced. After six days only 7.0 g l-1 ITA and 0.8 g l-1 MA have been produced. It is possible that the TCA cycle was indeed more active with elevated oxygen supply but the generated cis-aconitate was simply used up in the TCA cycle, instead of being converted into ITA.

During the last bioreactor cultivation with strain M15-CAD the pH-control was shut off. 4 g l-1 CaCO3 was used to maintain the pH instead. CaCO3 is the salt of a strong base (Ca(OH)2) and a weak acid (H2CO3). It is insoluble in water. When an acid (stronger than H2CO3) is present in the medium its anion replaces the carbonate anion while forming the corresponding Ca-acid salt and H2CO3 (ultimately H2O & CO2). In the course of the fermentation process only the amount of CaCO3 is used up to maintain a pH of 5.5-6.0.

By doing so, the ITA production was again greatly reduced. After six days only 15.5 g l-1 ITA and 2.4 g l-1 MA has been formed. This was really a surprising effect, considering it was a very similar fermentation compared to the first one (see FIG. 52). The only discernible difference was the method to maintain the pH around 5.5. Again, a comparable amount of cell mass was formed but less glucose was consumed: 96 g l-1 in the first case and 85 g l-1 with CaCO3 as buffering agent. This difference in glucose consumption is similar to the difference in produced ITA: 26.6 g l-1 (at 6th day)-15.5 g l-1. Usage of CaCO3 seems to impair the product formation for still unknown reasons.

In summary for the production of ITA with the *P. tsukubaensis* strain M15-CAD, it is important to restrict the available nitrogen and phosphate supply. This is true for the production in shaking flasks and larger bioreactors, although the optimal N/P-ratios seem to differ between different culture volumes. Phosphate limitation is an essential part to induce ITA production in this strain. The amount of available nitrogen is also a critical factor; if there is a N-excess, most of the glucose will be used up for biomass, instead of ITA production. Furthermore, it is important to also find the optimal oxygen saturation and pH to minimize inhibitory effects or competing metabolic pathways.

Itaconic Acid Production with *P. tsukubaensis* HR12 in a 600 ml Bioreactor

Itaconic acid overproducing strain *P. tsukubaensis* HR12 was cultivated in the 600 ml bioreactor as well. At first the conditions deemed best for strain M15-CAD were applied. The yeast was cultivated in batch fermentation with initially 150 g l-1 glucose, pH=5.5, pO2=55% and a temperature of 30° C. The initial N and P-concentrations were 2 g l-1/0.1 g l-1 and 4 g l-1/1 g l-1, respectively.

It is apparent that HR12 behaves differently than M15-CAD. As was already shown in well-cultures, HR12 produces itaconic acid with no dependency for a certain N/P-ratio. ITA is being formed from the start until the end of fermentation in a consistent rate.

In the case of lesser amounts of nitrogen and phosphate (N/P: 2/0.1 g l-1) 41.6 g l-1 of ITA and no malic acid were produced after five days while only consuming 90 g l-1 glucose (see FIG. 58). This corresponds to an average productivity rate of 8.3 g l-1 d-1 for ITA. Cell growth was rapid. It reached its maximum at the 3rd day but declined quickly, although the production of ITA continued.

FIG. 59 shows that the increase of initial N- and P-concentration (4/1) was very beneficial for the production of ITA. Instead of a drastic inhibitory effect of high N-&P-concentrations observed with strain M15-CAD, the ITA productivity rate was raised by 66%. With an average productivity rate of 13.8 g l-1 d-1 in total 68.8 g l-1 ITA have been synthesized with no detected amounts of MA over the course of five days. It reached its maximum at the 2nd-3rd day and slowly declined afterwards. Considering the consumed glucose and the resulting 68.8 g l-1 ITA, a yield of 46% (g itaconate/g glucose) was achieved. Cell growth was less intense and more steadily even with more resources available.

In a follow up cultivation, the fermentation described above (N/P: 4/1 g l-1) was repeated as a fed-batch fermentation for a total of ten days and feeding 100 g l-1 at the 5th day (see FIG. 60). Contrary to the previous cultivation significantly more biomass was created. DCW reached a maximum at the 3rd day, maintaining this amount until the 5th day. After glucose was fed the cell amount decreased but slowly recovered until the end of fermentation. At the 5th day glucose was almost fully consumed and approx. 60 g l-1 TA was formed. This is in accord with the previous cultivation. ITA production rate remained with 11.6 g l-1 d-1 almost constant for the whole period of cultivation. During the first five days negligible amounts of MA and α-ketoglutaric acid (AKG) (accumulative 1.6 g l-1) were produced. This amount rose to 3.0 g l-1 after ten days. Almost 30 g l-1 glucose remained in the culture broth. Overall 115.6 g l-1 TA with a yield of 28% w/w were produced.

From FIG. 61 it is evident that lowering the initial glucose concentration to 75 g l-1 and introducing daily feeding intervals, led to a rapid increase in cell biomass. Surprisingly, DCW greatly declined after the 5th day and remained constant afterwards. By applying glucose more frequently the overall ITA productivity was marginally lowered to 9.9 g l-1 d-1 with a promising yield of 39%.

Elevating the nitrogen concentration to 5.5 and 8.0 g l-1 showed similar end results. A large amount of cell mass (DCW ≥30 g l-1) was built up (see FIG. 62 & FIG. 63). Itaconic acid production increased slightly as well. After seven days of cultivation approx. 90 g l-1 was produced in both cultivations. By shifting the N-concentration from 4 to 5.5 g l-1 the productivity rate could be enhanced from 9.9 g l-1 d-1 to 11.5 g l-1 d-1 while also sustaining yield: 36% w/w (previously 38% w/w). With 8 g l-1 N-source productivity was even higher: 12.8 g l-1 d-1 but ITA yield dropped to 32% w/w.

For the fermentation described in FIG. 64 all resources despite glucose were initially present in a higher amount: N/P-ratio: 8/1 & 1.75× the amount of mineral salts, trace elements and thiamine. That way the ITA productivity was increased to 13.4 g l-1 d1 (yield: 33% w/w). After seven days 93.5 g l-1 ITA and 1.4 g l-1 MA & AKG were synthesised.

Since NH4Cl tested beneficially in shaking flasks, its use was analysed in the bioreactor as well (see FIG. 65). After eight days of fermentation 90.3 g l-1 ITA and 2.3 g l-1 MA & AKG were produced. This corresponds to a productivity rate of 11.3 g l-1 d-1 and a yield of 41% w/w for itaconic acid. Simply by switching the N-source productivity and yield were increased.

For the downstream processing of organic acids, it is very beneficial to already cultivate at a pH as low as possible. The effect of lower pH-values on the productivity was therefore analysed. To keep the resulting stress by lowered pH moderate, the fermentation processes were started at a pH of 5.5 and lowered at the first day to 4.0 (and gradually further to 3.5 and 3.0 at the second and third day for the respective cultivations).

FIG. 66 shows that cell growth was much more restricted but very stable over the course of fermentation at a pH of 4.0 compared to the neutral pH. Considering cell morphology, the cells appeared smaller in size, formed pseudohyphae more frequently and showed less lipid storage activity. If any lipid bodies were formed, their dimensions were minor compared to cells grown at pH 5.5. The inhibition of lipid storage was substantiated by the observation, that these yeast cells did not afloat at latter days of cultivation because of changes in single-cell density by lipid accumulation.

These results were later confirmed in an almost identical fermentation, with the difference that 1 g l-1 NaNO3 was supplied at the 7th day to potentially maintain cell viability (see FIG. 67). Cell growth was very rapid at first but dropped after lowering the pH. After pH adjustment a similar stable growth behaviour like in the previous cultivation could be observed. End concentration after nine days was 98.1 g l-1 ITA (productivity: 10.9 g l-1 d-1, yield: 40% w/w) and accumulative 0.06 g l-1 MA & AKG.

By further lowering the pH to 3.5 or even 3.0, both cell growth and ITA production were negatively affected in a significant manner (see FIG. 68 & FIG. 69). 48.9 g l-1 and 62.9 g l-1 ITA were produced after seven days, respectively (0.5 g l-1 MA & AKG acc. in both cases).

Although the average productivity ranged between only 7.0 and 9.0 g l-1 d-1, yield was between 31-38% w/w. It should be considered that the ITA productivity rate resembled that of cultivations with higher pH during the first days. In both fermentations the ITA synthesis almost halted after the 4th day. This was also to be seen in the glucose consumption. This indicates that the yeast cells converted glucose into ITA at a rate comparable to previous fermentations but slowed down upon lowering the pH. At a pH of 3.5 and 3.0 the cells were not able to sustain ITA production or even basic cell metabolism for a longer period.

So far it was demonstrated that *P. tsukubaensis* HR12 is a robust itaconic acid producer in batch fermentations of a shorter period. For larger scale production it is however often more cost beneficial and more practicable to cultivate in a continuous or semi-continuous way. By fermenting semicontinuously a large portion of the culture broth is removed after certain time, filled again to the initial volume with fresh medium and cultivated further. This bears the advantages of higher efficiencies due to longer cultivation times. It is also possible to completely convert the substrate. Furthermore, set-ups must be carried out less frequently and the associated risks (e.g. failed inoculum) are thus minimized.

To investigate if strain HR12 would be a suitable candidate, a semi-continuous fermentation was carried out. The yeast was therefore cultivated with an N/P-ratio of 6/1 (N-source: NH4Cl) at pH=4.0 for seven days. At the 7th day %72 of the culture broth was removed and replenished with fresh medium. As shown in FIG. 70 HR12 continued ITA production for the whole 14 days of cultivation. Even after refreshment the rate of productivity seemed stable. At the end 112.0 g l-1 ITA (0.4 g l-1 MA & AKG) were produced. If the large losses in products by culture replacement are taken into consideration, theoretically 160.4 g l-1 ITA were produced at a rate of 11.5 g l-1 d-1 with a yield of 35% w/w (see FIG. 71).

TABLE 1

Comparison of genomes of different unconventional yeasts and *Saccharomyces cerevisiae* in regards of the number of their chromosomes, genome size, GC-content, number of encoded genes and number of resulting proteins.

| Species | Chromosomes | Size [Mb] | GC [%] | Genes | Proteins |
|---|---|---|---|---|---|
| *Pseudozyma tsukubaensis* H488 | 38 scaffolds in sequencing | 20.28 | 53.6 | 7017 | |

TABLE 1-continued

Comparison of genomes of different unconventional yeasts and *Saccharomyces cerevisiae* in regards of the number of their chromosomes, genome size, GC-content, number of encoded genes and number of resulting proteins.

| Species | Chromosomes | Size [Mb] | GC [%] | Genes | Proteins |
|---|---|---|---|---|---|
| *Ustilago maydis* 521 | 23 | 19.86 | 53.7 | 6671 | 6.548 |
| *Ustilago hordei* Uh4857-4 | 23 | 20.72 | 51.9 | 7230 | 7.111 |
| *Sporisorium reilianum* SRZ2 | 23 | 18.48 | 59.5 | 6806 | 6.673 |
| *Yarrowia lipolytica* CLIB122 | 6 | 20.32 | 49.0 | 7357 | 6.472 |
| *Saccharomyces cerevisiae* AWRI796 | 16 | 11.46 | 38.2 | 5153 | 3.681 |

TABLE 2

Homologous scaffolds or part(s) of the scaffolds of *P. tsukubaensis* compared to the chromosomes of *U. maydis*

| *U. maydis* chromosome | *P. tsukubaensis* scaffold | *U. maydis* chromosome | *P. tsukubaensis* scaffold |
|---|---|---|---|
| 1 | 1 + 27 + 25 | 13 | 17 |
| 2 | 12' + 2 | 14 | 15 |
| 3 | 3 | 15 | 29 + '12 |
| 4 | 7 | 16 | 19 |
| 5 | 9' + '4 | 17 | 18 |
| 6 | 5 | 18 | 20 |
| 7 | 6 | 19 | 16 |

TABLE 2-continued

Homologous scaffolds or part(s) of the scaffolds of *P. tsukubaensis* compared to the chromosomes of *U. maydis*

| *U. maydis* chromosome | *P. tsukubaensis* scaffold | *U. maydis* chromosome | *P. tsukubaensis* scaffold |
|---|---|---|---|
| 8 | 14 + '10 | 20 | 4' + '9 |
| 9 | 24 + 10' | 21 | 21 |
| 10 | 13 | 22 | 22 |
| 11 | 11 | 23 | 23 |
| 12 | 26 + 8 | | |

TABLE 3

Reported strong heterologous and native promoter sequences available for P. tsukubaensis

| Promoter | Origin | Characteristics |
|---|---|---|
| pHSP70 | *Ustilago maydis* | promoter of the heat shock gene 70; strong basal activity, (stress-)inducible |
| pTEF | *Ustilago maydis* | promoter of the translation elongation factor 2 gene; strong constitutive promoter |
| POTEF | *Ustilago maydis* | modified TEF promoter |
| pACTIN | *Pseudozyma flocculosa* | promoter of the actin gene; strong constitutive promoter |
| pGPD | *Pseudozyma flocculosa* | promoter of the glyceraldehyde 3-phosphate dehydrogenase gene; constitutive promoter |
| pGLC | *Pseudozyma tsukubaensis* | 162 bp long promoter area of the a glucosidase gene; inducible promoter |
| pGLCfull | *Pseudozyma tsukubaensis* | 1268 long promoter area of the a glucosidase gene; inducible promoter |

TABLE 4

Results of protein BLAST for the deleted genes in *P. tsukubaensis* HR12.

| gene | potential function | organism | identity-query coverage | e-value | accession |
|---|---|---|---|---|---|
| Pseudog4086.t1* | acetyl-CoA synthetase | *Moesziomyces antarcticus* T-34 | 86%-78% | 0.0 | GAC72024.1 |
| Pseudog4087.t1 | alcohol dehydrogenase | *P. hubeiensis* SY62 | 91%-99% | 0.0 | XP_012188027.1 |
| Pseudog4088.t1 | hyp. protein | *Moesziomyces antarcticus* T-34 | 74%-100% | 0.0 | GAC72021.1 |
| Pseudog4089.t1 | aldo-keto reductase | *Moesziomyces antarcticus* | 87%-98% | 9e−30 | XP_014656423.1 |
| Pseudog4090.t1 | hyp. protein | *Sporisorium reilianum* SRZ2 | 50%-89% | 9e−49 | CBQ72812.1 |
| Pseudog4091.t1 | prob. 2-deoxy-D gluconate 3 dehydrogenase | *Sporisorium reilianum* SRZ2 | 89%-100% | 0.0 | CBQ72814.1 |
| Pseudog4092.t1 | adenylate kinase | *Moesziomyces antarcticus* | 83%-99% | 2e−152 | XP_014656419.1 |
| Pseudog4093.t1 | voltage gated potassium channel | *Moesziomyces antarcticus* | 65%-93% | 0.0 | XP_014656418.1 |
| Pseudog4094.t1 | hyp. protein | *U. bromivora* | 30%-57% | 7e−27 | SAM83131.1 |
| Pseudog4095.t1 | hyp. protein | *P. hubeiensis* SY62 | 38%-76% | 8e−40 | XP_012188014.1 |

*Pseudog4086 has only been partially deleted.

TABLE 5

ITA and MA concentration and ITA productivity of 6 selected RIA1-overexpression transformants after 8 d shaking flask cultivation in 50 ml MG-IA minimal medium (N: 2 g l-1,P: 0.1 g l-1, C: 15% w/v, no pH-control).

| recipient strain | transformant | ITA conc. (8 d) | MA conc. (8 d) | ITA productivity |
|---|---|---|---|---|
| H488 | HR8 | 4.4 g l-1 | 6.6 g l-1 | 0.6 g l-1d-1 |
| | HR10 | 3.4 g l-1 | 6.8 g l-1 | 0.4 g l-1d-1 |
| | HR12 | 36.4 g l-1 | 0.0 g l-1 | 4.6 g l-1d-1 |
| M15 | MR1 | 9.9 g l-1 | 4.9 g l-1 | 1.2 g l-1d-1 |
| | MR2 | 17.8 g l-1 | 3.9 g l-1 | 2.2 g l-1d-1 |
| | MR8 | 3.5 g l-1 | 2.9 g l-1 | 0.4 g l-1d-1 |

TABLE 6a

Induction of ITA metabolism genes

| gene | | function | relative norm. expression |
|---|---|---|---|
| Pseudog6288 | ADI1 | aconitate-Δ-isomerase | 2.606 X ± 1.437 |
| Pseudog6270 | ITP1 | itaconate transport protein | 65 X ± 42 |
| Pseudog6267 | MTT1 | mitochondrial tricarboxylate transporter | 3.708 X ± 1.555 |
| Pseudog6266 | RIA1 | regulator of itaconic acid | 471 X ± 299 |
| Pseudog6271 | TAD1 | trans-aconitate decarboxylase | 2.482 X ± 1.226 |

TABLE 7

Composition of MG minimal medium for the growth of ascomycetous oleophilic/lipophilic yeast. This medium was the basis for the development of a minimal medium used for the ITA production with *P. tsukubaensis*.

| | |
|---|---|
| mineral salts | 1 g l-1 KH2PO4, 0.16 g l-1 K2HPO4 × 3 H2O, 3 g l-1 (NH4)2SO4, 0.7 g l-1 MgSO4 × 7 H2O, 0.5 g l-1 NaCl, 0.4 g l-1 Ca(NO3)2 × 4 H2O |
| trace elements | 0.5 mg l-1 H3BO3, 0.04 mg l-1 CuSO4 × 5 H2O, 0.1 mg l-1 Kl, 0.4 mg l-1 MnSO4 × 4 H2O, 0.2 mg l-1 Na2MoO4 × 2 H2O, 0.4 mg l-1 ZnSO4 × 7 H2O |
| iron | 6 mg l-1 FeCl3 × 6 H2O (stock solution in ethanol) |
| carbon source | 50 g l-1 glucose |
| pH buffer | 3.3 g l-1 CaCO3 (insoluble, heat sterilized) |

TABLE 8

Composition of 100 X vitamin stock solution.

| 100 X vitamin stock solution | | |
|---|---|---|
| 200 mg l-1 p-aminobenzoic acid (PABA) | 2 mg l-1 folic acid | 400 mg l-1 pyridoxine-HCl |
| 2 mg l-1 biotin | 2 g l-1 inositol | 200 mg l-1 riboflavin |
| 400 mg l-1 calcium pantothenate | 400 mg l-1 niacin | 400 mg l-1 thiamine-HCL |

TABLE 9

Growth of *P. tsukubaensis* H488 in MG medium with different vitamins.

| medium | growth |
|---|---|
| MG | − |
| MG-A | − |
| MG-B | − |
| MG-C | − |
| MG-F | − |
| MG-I | + |
| MG-N | − |
| MG-P | − |
| MG-R | − |
| MG-T | + |
| MG-vit. | + |
| YPD | + |

wherein
MG minimal medium with 5% (w/v) glucose
MG-A +0,2 mg l-1 p-aminobenzoic acid (PABA)
MG-B +0,2 mg l-1 biotin
MG-C +0,4 mg l-1 calcium pantothenate
MG-F +0,2 mg l-1 folic acid
MG-I +2 mg l-1 inositol
MG-N +0,4 mg l-1 niacin
MG-P +0,4 mg l-1 pyridoxine-HCl
MG-R +0,2 mg l-1 riboflavin
MG-T +0,4 mg l-1 thiamine-HCL
MG-vit. +all vitamins

TABLE 10

Composition of MG-IA minimal medium with varying concentrations of nitrogen and phosphate source.

| | |
|---|---|
| N-source | x g l-1 NaNO3 (NH4Cl) as given below |
| P-source | x g l-1 KH2PO4/K2HPO4 × 3 H2O as given below |
| mineral salts | 0.7 g l-1 MgSO4 × 7 H2O, 0.5 g l-1 NaCl, 0.4 g l-1 Ca(NO3)2 × 4 H2O |
| trace elements | 0.5 mg l-1 H3BO3, 0.04 mg l-1 CuSO4 × 5 H2O, 0.1 mg l-1 Kl, 0.4 mg l-1 MnSO4 × 4 H2O, 0.2 mg l-1 Na2MoO4 × 2 H2O, 0.4 mg l-1 ZnSO4 × 7 H2O |
| iron | 6 mg l-1 FeCl3 × 6 H2O (stock solution in ethanol) |
| carbon source | 150 g l-1 glucose |
| thiamine | 0.4 mg l-1 thiamine-HCL |
| pH buffer | 3.3 g l-1 CaCO3 (insoluble, heat sterilized) |

TABLE 11

| Compilation of sequences | | |
|---|---|---|
| SEQ ID NO | nomenclature | remarks |
| 1 | | preferred RIA1 expression cassette insertion region in Pseudozyma tsukubaensis |
| 2 | | genomic itaconic acid metabolism gene cluster in Pseudozyma tsukubaensis |
| 3 | Pseudog4085.t1 | Uniprot: Pc13g02200 protein (1.4e−110) |
| 4 | Pseudog4085.t1 | |
| 5 | Pseudog4086.t1 | Uniprot: AMP-binding protein 5 (1.6e−172) |
| 6 | Pseudog4086.t1 | |
| 7 | Pseudog4087.t1 | Uniprot: Alcohol dehydrogenase (4.1e−214) |
| 8 | Pseudog4087.t1 | |
| 9 | Pseudog4088.t1 | Uniprot: Putative uncharacterized protein (2.3e−206) |
| 10 | Pseudog4088.t1 | |
| 11 | Pseudog4089.t1 | Uniprot: 2,5-diketo-D-gluconic acid reductase B (4.7e−106) |
| 12 | Pseudog4089.t1 | |
| 13 | Pseudog4090.t1 | Uniprot: Putative uncharacterized protein (4.8e−104) |
| 14 | Pseudog4090.t1 | |
| 15 | Pseudog4091.t1 | Uniprot: Planta-induced rust protein 8 (3.2e−79) |
| 16 | Pseudog4091.t1 | |
| 17 | Pseudog4092.t1 | Uniprot: Adenylate kinase (1.3e−116) ADK2 |
| 18 | Pseudog4092.t1 | |
| 19 | Pseudog4093.t1 | Uniprot: Related to TOK1-Voltage-gated, outward-rectifying K+ channel protein of the plasma membrane (2.3e−303) |
| 20 | Pseudog4093.t1 | |
| 21 | Pseudog4094.t1 | Uniprot: Conserved hypothetical Ustilaginaceae-specific protein (2.5e−21) |
| 22 | Pseudog4094.t1 | |
| 23 | Pseudog4095.t1 | Uniprot: Conserved hypothetical Ustilaginaceae-specific protein (5.6e−20) |
| 24 | Pseudog4095.t1 | |
| 25 | Pseudog4096.t1 | — |
| 26 | Pseudog4096.t1 | |
| 27 | Pseudog4097.t1 | Uniprot: Uncharacterized protein (6.6e−06) |
| 28 | Pseudog4097.t1 | |
| 29 | Pseudog4098.t1 | Uniprot: Conserved hypothetical Ustilago-specific protein (2.1e−06) |
| 30 | Pseudog4098.t1 | |
| 31 | Pseudog6271.t1 | Uniprot: Uncharacterized protein C8E4.05c (1.1e−161); corresponding Uniprot entry A0AOU2UYC4/TAD1_USTMD Trans-aconitate decarboxylase 1 in Ustilago maydis |
| 32 | Pseudog6268.t1 | Uniprot: Putative uncharacterized protein (1.2e−159); corresponding Uniprot entry A0A0U2X0E4/ADI1_USTMD Aconitate-delta-isomerase 1 in Ustilago maydis |
| 33 | Pseudog6270.t1 | Uniprot: Putative uncharacterized protein (4.8e−225); corresponding to Uniprot entry A0AOU2UXG3/ITP1_USTMD Itaconate transport protein in Ustilago maydis |
| 34 | Pseudog6267.t1 | Uniprot: Mitochondrial substrate carrier family protein Z (7.1e−48); corresponding to Uniprot entry A0A0U2IR85/MTT1_USTMD Mitochondrial tricarboxylate transporter 1 in Ustilago maydis |
| 35 | | synthetic RIA1 sequence |
| 36 | Pseudog6266.t1 | Uniprot: Putative uncharacterized protein (2e−42); corresponds to Uniprot entry A0A0U2WFX7/RIA1_USTMD in Ustilago_maydis and Uniprot entry R9P2W9/PHSY_003267 in Pseudozyma_hubeiensis |
| 37 | | synthetic shortened RIA1 sequence |
| 38 | | 1st RIA1 motif |
| 39 | | 2nd RIA1 motif |
| 40 | | 3rd RIA1 motif |
| 41 | | 4th RIA1 motif |
| 42 | | 5th RIA1 motif |
| 43 | | 6th RIA1 motif |
| 44 | | 7th RIA1 motif |
| 45 | | 8th RIA1 motif |
| 46 | | 9th RIA1 motif |
| 47 | | 1st RIA motif as found in P. tsukubaensis |
| 48 | Pseudog4640.t1 | Uniprot: Iron-sulfur subunit of complex II (2.6e−146); corresponds to Uniprot entry P32420/SDHB_USTMA Succinate dehydrogenase ubiquinone iron-sulfur subunit in Ustilago maydis |
| 49 | Pseudog4640.t1 | Pseudozyma tsubukaensis |
| 50 | | coding region of Embl entry Z11738.1 |
| 51 | | Pseudozyma tsukubaensis genomic sequence corresponding to Embl entry Z11738, aka SEQ ID NO. 52 |
| 52 | | Embl Z11738.1 |
| 53 | | Pseudozyma tsukubaensis extended ip locus |
| 54 | | Pseudozyma tsukubaensis upstream of SEQ ID NO 53 |
| 55 | | Pseudozyma tsukubaensis downstream of SEQ ID NO 53 |

TABLE 11-continued

| SEQ ID NO | nomenclature | remarks |
|---|---|---|
| | | Compilation of sequences |
| 56 | | Pseudozyma tsukubaensis most extended ip locus |
| 57 | | Artificial, Actin promoter (pActin) fused to ACO1, (BsrGl)-pActin-olapACO1 |
| 58 | | Artificial, Actin promoter (pActin) fused to ACO1, (BsrGl)-pActin-ACO1-(Nsil) |
| 59 | | Artificial, Actin promoter (pActin) fused to ADI1, (Kpnl)-pActin-ADI1-(Nsil) |
| 60 | | Artificial, Actin promoter (pActin) fused to CAD1 of Arabidopsis thaliana (AtCAD1), (Kpnl)-pActin-AtCAD1-(Nsil) |
| 61 | | Artificial, Actin promoter (pActin) fused to ITP1, (Kpnl)-pActin-ITP1-(Nsil) |
| 62 | | Artificial, Actin promoter (pActin) fused to MTT1, (Kpnl)-pActin-MTT1-(Sdal) |
| 63 | | Artificial, Actin promoter (pActin) fused to ADI1, (Kpnl)-pActin-olapADI1 |
| 64 | | Artificial, Actin promoter (pActin) fused to AtCAD1, (Kpnl)-pActin-olapAtCAD1 |
| 65 | | Artificial, Actin promoter (pActin) fused to ITP1, (Kpnl)-pActin-olapITP1 |
| 66 | | Artificial, Actin promoter (pActin) fused to MTT1, (Kpnl)-pActin-olapMTT1 |
| 67 | | Artificial, Actin promoter (pActin) fused to RIA1, (Kpnl)-pActin-olapRIA1 |
| 68 | | Artificial, Actin promoter (pActin) fused to TAD1, (Kpnl)-pActin-olapTAD1 |
| 69 | | Artificial, Actin promoter (pActin) fused to RIA1, (Kpnl)-pActin-RIA1-(Nsil) |
| 70 | | Artificial, Actin promoter (pActin) fused to TAD1, (Kpnl)-pActin-TAD1-(Nsil) |
| 71 | | Artificial, Actin promoter (pActin) fused to ACO2, (Pfl23Il)-pActin-olapACO2 |
| 72 | | Artificial, Actin promoter (pActin) fused to ACO2, (Pfl23Il)-pActin-ACO2-(Nsil) |
| 73 | | Artificial, Vector surroundings |
| 74 | | Artificial, Actin promoter of Pseudozyma tsukubaensis, last 4 nucleotides: start codon + G of genomic DNA coding for Pseudog6713.t1 |
| 75 | Pseudog6713.t1 | genomic DNA, Uniprot: Actin-3-sub 2 (1.2e−230), Actin (1.2e−230) |
| 76 | Pseudog6713.t1 | Translated; Uniprot: Actin-3-sub 2 (1.2e−230), Actin (1.2e−230) |
| 77 | | Pseudozyma tsukubaensis genomic region of pActin promoter and gene |

The invention claimed is:

1. An itaconic acid production host microorganism of genus *Pseudozyma*, wherein the microorganism comprises at least one heterologous expression cassette integrated into the genome of the microorganism outside of an ip locus, wherein the expression cassette comprises:

a) a heterologous RIA1 gene encoding an RIA1 protein, wherein the RIA1 protein comprises at least 90% amino acid sequence identity to SEQ ID NO: 35, under the operable control of a functional promoter, and/or b) a RIA1 gene encoding an RIA1 protein, wherein the RIA1 protein comprises at least 90% amino acid sequence identity to SEQ ID NO: 35, under the operable control of a heterologous functional promoter.

2. An itaconic acid production host microorganism of genus *Pseudozyma*, wherein the host is a recombinant microorganism comprising an expression cassette for expression of a RIA1 gene encoding an RIA1 protein, wherein the RIA1 protein comprises at least 90% amino acid sequence identity to SEQ ID NO: 35, and for expression of at least two genes selected from the group consisting of ADI1, MTT1, and TAD1, wherein said expression cassette is integrated into the genome of the microorganism at an integration site, wherein the integration site a) is located between a left border gene and a right border gene, wherein the respective first nucleotides of the respective translation start codons of the left and right border genes are separated by at most 51600 nucleotides in the corresponding wild type microorganism, wherein the left border gene codes for a protein having acetyl-CoA synthetase activity, and wherein the right border gene codes for a protein consisting of an amino acid sequence having at least 21% identity to SEQ ID NO: 25, and/or b) is located up to 51600 nucleotides of the nearest border of an open reading frame translating into an amino acid sequence having at least 30% sequence identity to any of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, and/or c) is located within or replaces an open reading frame translating into an amino acid sequence having at least 30% sequence identity to any of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25.

3. An itaconic acid production host microorganism of genus *Pseudozyma*, wherein the host is a recombinant microorganism a) comprising an active itaconic acid metabolic pathway for producing itaconic acid, wherein the active itaconic acid pathway comprises at least one RIA1 gene encoding an RIA1 protein, wherein the RIA1 protein comprises at least 90% amino acid sequence identity to SEQ ID NO: 35, and b) wherein at least one gene coding for a protein having at least 30% sequence identity to any of the protein sequences SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, or SEQ ID NO: 25 is inactivated.

4. The itaconic acid production host microorganism according to claim 1, wherein the expression level, compared to the corresponding wild type strain cultivated under identical conditions, of a) the RIA1 gene is increased by a factor of at least 50, and/or b) at least two genes selected from the group consisting of ADI1, MTT1, and TAD1 is increased by a factor of at least 1000, and/or c) an ITP1 gene is increased by at most 500.

5. The itaconic acid production host microorganism according to claim 1 for converting glucose to itaconic acid a) with a productivity of at least 9.5 g/(1 d), and/or b) with a yield of at least 25% (w/w glucose).

6. An integration vector comprising a RIA1 gene encoding an RIA1 protein, wherein the RIA1 protein comprises at least 90% amino acid sequence identity to SEQ ID NO: 35, operably linked to a strong constitutively active promoter for integration outside of an ip locus.

7. A production host microorganism, wherein the microorganism is transformed with the vector of claim 6.

8. A method for alteration of an itaconic acid production host microorganism of genus *Pseudozyma*, the method comprising integrating at least one expression cassette for expression of a RIA1 gene encoding an RIA1 protein, wherein the RIA1 protein comprises at least 90% amino acid sequence identity to SEQ ID NO: 35, and for expression of at least two genes selected from the group consisting of ADI1, MTT1, and TAD1, into the genome of a microorganism at an integration site other than an ip locus.

9. The method according to claim 8, wherein the integration site a) is located between a left border gene and a right border gene, wherein adenines of the translation start codons of the left and right border genes are separated by at most 51600 nucleotides in the corresponding wild type microorganism, wherein the left border gene codes for a protein having acetyl-CoA synthetase activity, and wherein the right border gene codes for a protein consisting of an amino acid sequence having at least 21% identity to SEQ ID NO: 25, and/or b) is located up to 6500 nucleotides of the nearest border of an open reading frame translating into an amino acid sequence having at least 30% sequence identity to any of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, and/or c) is located within or replaces an open reading frame translating into an amino acid sequence having at least 30% sequence identity to any of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25.

10. The method according to claim 8, wherein at least one gene coding for a protein having at least 30% sequence identity to the protein sequence SEQ ID NO: 19, SEQ ID NO: 15, and/or SEQ ID NO: 29 is inactivated.

11. The method according to claim 8, wherein the microorganism has increased itaconic acid productivity with respect to a control microorganism that does not include the at least one expression cassette.

12. A method for obtaining a recombinant itaconic acid production host microorganism of genus *Pseudozyma*, the method comprising:

a) cultivating a parent microorganism, b) performing, in any order and/or simultaneously, if so required: one or more transformations to provide the microorganism with any heterologous ADI1, MTT1, and TAD1 gene to obtain an active itaconic acid pathway in the microorganism, at least one integration of a RIA1 gene encoding an RIA1 protein, wherein the RIA1 protein comprises at least 90% amino acid sequence identity to SEQ ID NO: 35, under the control of a constitutively active promoter, wherein integration is not in an ip-locus, and inactivation of at least one gene coding for a protein having at least 30% sequence identity to any of the protein sequences SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, or SEQ ID NO: 25; and c) isolating the recombinant itaconic acid production host microorganism resulting from step b).

13. A production method comprising:

a) fermenting a production host microorganism to produce itaconic acid, and b) recovering itaconic acid produced in step (a), wherein the microorganism is a microorganism according to claim 1.

14. The production method according to claim 13, where the fermenting is a submerged fermentation.

15. The production method according to claim 13, wherein the production method is a batch fermentation, a fed-batch fermentation, or a continuous fermentation.

16. The production method according to claim 13, wherein the fermentation is started in a minimal medium comprising at most 0.1% (v/v) of complex media components and has a pH of at most 5.5.

17. The production method according to claim 16, further comprising lowering the pH of the medium during fermentation to at most 4.

18. The production method according to claim 16, wherein:

the medium comprises a polyalcoholic carbon source, and the concentration of the carbon source during fermentation does not fall below 10 g/l for longer than 3 h.

19. The production method according to claim 16, wherein the ratio of concentrations of itaconic acid to malic acid in the medium is at least 15:1.

20. The production method according to claim 13, wherein the fermentation in step a) is performed under aerobic or microaerobic conditions.

21. The itaconic acid production host microorganism according to claim 1, wherein the microorganism is *Pseudozyma tsukubaensis*.

* * * * *

SEQUENCE LISTING

```
<160> NUMBER OF SEQ ID NOS: 77

<210> SEQ ID NO 1
<211> LENGTH: 51574
<212> TYPE: DNA
<213> ORGANISM: Pseudozyma tsukubaensis
<220> FEATURE:
<223> OTHER INFORMATION: preferred RIA1 expression cassette insertion
      region in Pse udozyma tsukubaensis
<220> FEATURE:
<221> NAME/KEY: misc_feature
<222> LOCATION: (38477)..(38501)
<223> OTHER INFORMATION: n means a or g or c or t/u

<400> SEQUENCE: 1

ccccctgact cgtcgctcac cgctaccacc tccgaagctg gtgtcaagaa cacgctgggt      60

gcaggtgacc gatcgtaccg cttcatggat gcgggcgctg cctttggtgg tcacgacgta     120

tttgacgaca ttccaggcga ggctcctaca gctcctggca cagctccacc ttcgcgcccc     180

atgtcgccag ccaatgcgct cgagcaaggc cgattgcgaa acaccgccgg cttgcccact     240

tcgtcgtctg gtcctgctcc gccttacata gcttcatctc gccgtgctgg cggcgtaagc     300
```

-continued

```
gagtcgtacg agctcactga tccgcccaac cgcatctaga caccccatgc attttcgttg    360
aaacagtgaa tcgtgctgtc ttctatctac tcaccacacc ctcattgcat tctcgttcct    420
tcaggcatct catcaaaatc attatccccg taacttagca ttctcggaca ctaactattc    480
atctctctct acatagcttc catcgcaatg aatcttgcat cttacccatc tggagctgtc    540
tatgagtgcc gatcgtgcct gccatgcaac tagcttgcgg atgcagtatg ccttgatccg    600
tgtcgtcgag gattgaaggt gtgaacatgc caacaacgca aacagagacg atcagaatgc    660
aagtacggaa tataatgaca ttatgacgcc aaatcgcagc gctacagacc agtggcggag    720
tggtcaatcg cgcgaggttt aagcgcgatg ctgattttat ttctcgtcct tcgggttcgt    780
gggttcgaac cccacctggt ctattcgagt tttttttcc cttacttccc ttttcaaccg    840
tttcgtcatc accactcatt cgcattcttg ttgctacgca tggcacatga tgtatggtct    900
ccatctgaag ctgcaggggt atatgtattg cgtcatgaag ctgctttcga gttggaacgc    960
tgtgtgtgaa agtcgtaaat gatatcggcg gcagctttca tgccggcctg gttggggtgg   1020
tatgcgcatc tgtttttgaa gttccagaac gagccgtctg atacccaagg ctcttttgat   1080
ccgagtgcgt gcttgagctt gctctcttct gctagcggaa cgacatagac gttattcctc   1140
ccttccgctg ccttggcgta gagcgattga agctgttcgg ccatctcgat gtacttttgc   1200
acttgttgct gatcccaaca tacgtccctc cacgcttttg tatcgggtcc catcatggcg   1260
tggtattcga ccaggtagat cgtcgctttt ggatactttt tctggacgcc atcgatcaag   1320
gttgcgaatc tttgggagat ctcgtctggc gaagcgatgg tggggtgttc aaagtgctcc   1380
ttctcttctt tcgacaagac aaaatacgac aacaatctac cccaccatgt gttcttgaac   1440
gtcagaccga acatactccc gatgtagaac atgtcattgc ccccaccggt gatcgtgact   1500
atcgcatcgc tgccatcatc tccttcctta agttcgggaa gaagacttag ttgaggggcg   1560
tagactttct ttccagtatc ttgcggttcg gagatcaaat tgagtagcgt cgcacttgac   1620
accgaaaggt cgagaaattc atccgtgttg ttcgggtcga gattgagtct acgcgccaag   1680
tagttgggat agttgtttgc acttcgacca gcgtcagtgt ctacttgagg agggatgcct   1740
ggcccagcgg cgaacgatga gcccaacgcg atcaaccttg tcatttggac ttgttatggc   1800
acagtgttga tattgccaag atcgacgtcg aagatgcaat gatgaagcaa aacggagcga   1860
agtgcaaaca gggtctcgat aagatgaatt gacgagttca aaggaagggt tcccgatatg   1920
aagactaacg acttcatcgg caggcttcta gcggaaaccg gactggataa ggcgggcagc   1980
gtgtaggtgg gtctgtgcgt ttgcgtcaac cccgcatttc ctcggcaaag aaaaagcaag   2040
aaatttgaga aaaaggcggg aaaattgtaa cacaggctaa ggaccggttg tcggaggtca   2100
aattgaagcg ttgagccggt acgacctaga gaatggggaa actcatcacc agccgtgtca   2160
ttctcttttg ctgaggttgt gatcagattc tcatctacat agcttgtcgt tcgaagcaac   2220
cgggcactta ttctacctct atgcgtccat catgatgaat cttcgcgagg ctgtgtaccc   2280
atgggtacat ttgggcgaag aaaggacgtc gcacgaccga cagcctaaga agcatagcgc   2340
accaaagtaa cggttgaatg actgcaaatg tagagccgtg tcaagttcgc gatcatagcc   2400
gaagcgagtg agggatgtct cgagctatgt ggccggcatg ttctcagtgc cccgcaattt   2460
tttgtgtgtg ttcttgtggc acgagcaatc ggctcaaccg agtctgcagc aaaactgagc   2520
catttacccg tcgtggccga cttgaccgtg tgcgagccaa gagcaagccg aaaacgtgag   2580
tcttcgccga gtctcttcct tcctttgctt cactaacatc agtagccgtc actatagatc   2640
```

-continued

```
ccttatgagc agctagccgg cagattttgg ctgcgtttcc tccccaccat catcgcattc   2700
ctgcatcacc ttgcctactc cgtcacgatg ccctacacac caccacgttc gtcgcagcct   2760
cctaaaggtt taccctttga gctttcgctc tcgacgcatc ccggcgcgca gcacaaccga   2820
tcttcgctca cacccgtgtc gttcctcttg cgtgccgcgc tgattacgcc tcgcaaattg   2880
gcaatcactc atcctgaaaa gggctactca ttcacctacg agcaatgggc agcacgtact   2940
ctctcgctcg cctttgcact tcgcagcctt cccgccttca agattggtga tcgcgtcgct   3000
gttatctcgc ctaacgcacc tctgatcgca gacgctcact ggggtattcc tgctgttggt   3060
ggtatcatta cgccgatcaa cattcgaaac acgcccaagg aggtcgctta cgtcttggag   3120
cactcgggta gcactgtaat cttggtcgac cacgagttta cacacctcgt ccccgagaac   3180
cctggcccag gcatcaccgt catcgtcagc aaagattcgg gaggacaaga agctgacgat   3240
ccatacgaga aatttctcga tcgtggcttc ctcgaatggc agcgtgctga gcaggctgag   3300
ctcaaagcct acaagtctcg cactcgacct tctgctgaac caaagacggg atggaaactc   3360
atcgaggcgc ctcaagacga agaacaaccc atcgccctct gctacacctc gggtactact   3420
ggtcgaccca aaggtgtgct cactaaccac cgtggagcct acctttctgc cgtagccaac   3480
gcttttgaag cccacctcac gcaggatagc gtctatcttt gggttcttcc catgttccat   3540
gcttgtggat ggacgtaccc ttgggctgtt actgcttctc tcgctacgca tttcaccatt   3600
cgcaaggtcg acaacaccgt tatctgggac gcgttgctca atcacggcgt atcgcactac   3660
tgcggtgccc ctacagttca gatcggcctc gtcaaccatc ctaacgcacg caagctcaac   3720
cgtcgcgtga acgttgccgt cgcagcttcc gcacccaccg ccaacctcct cgccaagatg   3780
gagggtctaa acttgcaccc agtccacgta tacggcttga ccgaaacata cggtcctttc   3840
accaggaggt acttcgagcc cgaatgggcc aaactagatg ttgatgctcg agcacgaatg   3900
atggctcgcc aaggacactc ctacctcact tcagatgagg tacgtgtcgt tcgtactgct   3960
tcttccaccg acgcctctac acctgacctc gtcgatgttg agcgcaacgg tcaagaaacg   4020
ggcgaaatcg tcattcgagg aaacatggtc atggtaggct actacaacga tcccgccgcc   4080
acttccaaag ccgtcatgaa aggctggttc cacactggcg acctagccgt ccgtcaccct   4140
ggcggcgaaa tccaaatcct agaccgaggt aaagacatca tcatctccgg aggcgaaaac   4200
atctcctcgc tcatggttga acaggaactt gcctcccacc cttccgtcct cgaatgctgc   4260
gtcattgcac gaccgcacga aaagtggggc gaacgcggcc agtcgtttat cgtgctcaca   4320
gaacaggcga aagcgaaact caacttcgca gagataaaaa agaagggttc accggagaac   4380
aaggcgtttg ttgaagaggt gaaaaagcac tgcgtggaaa ggatgtccaa attcgccgta   4440
ccggaatggt tcgacgtagt ggacgaattg ccaaagacaa gcacgggcaa ggtgcagaag   4500
aacgtgctcc gagctaggtt cgctagtaag ttgtaaaagt agatcgtgtc gcgtggaatg   4560
agagcaatgg aagtgtcatc tattcttggt cgatgcaacg gtgcgatgtg tgtctcttgg   4620
atgcgtcggt aacgtgcttt tgacaacttc gagaagattc acccgacgac agagggtaat   4680
gcactgacaa gcgcatagca cggaggggca aagagctgcc tcaacagccc aatcctgtac   4740
gaccatacga gcaagagtga gacacgtctt cattgtttga cacgaagaag tttacggcaa   4800
ggaggtaact ttttttacgc cagagaagga tggttcgttt ggtggtggag ccgcgcttct   4860
ccgcacagcg agaagagggg cgtaggtgtg ggggaggaca gtccaagtcc aagtccaagg   4920
tgtcgcgtga aattgaccga ttttggcagg ttttgcggct ttgtgcagat cactttcaaa   4980
agccgccgcc gccgccgcct cctgcgccca gaacatgtgt ggagttttcg tttttcgctc   5040
```

-continued

```
gtgccacctt ttccttctct ttgtgtcgta cattacatcc actcaacctt ccttctcatc   5100
cttccacctt tcgttctctt atttctatcc ttctcaccat caccaccagc ttccacagcg   5160
tctatcggaa ccatgacttc catcctgcgc gacatccttt ccacctacgt cacaggtggt   5220
aaagacccct tccgcaacct ctcgtacgcc gctgtacccc tctccctcct cctcgctgcc   5280
ctccctcact ggtacaccat ctaccttgcc gaatcgaaca aagtccaagg aggatggagc   5340
aacgtcaacc cccgcttttg ggtccaaact ctcaccgcca aggctctcac caagaagttg   5400
accccgcttg aaaaccagat tttgaggggt caaagttgcc aagccaacgc gtttgagaac   5460
gtgccgctgt tcatcgccac cgttgtatgg gcgaacgtaa gcggcttgga gagggaaacg   5520
attaacaact ttgtagtggg atatctggta agcagggctg cgtacacggt gttgtatttg   5580
aagacggagg ggtatgcgaa cagttttgct aggacggcgg ttttccaagt gggaatcatc   5640
tggattatta ccgtttggat gaagggggct tttaggggtt tgccgctcgt caagtgagcg   5700
tatgatcgag gcgagaggag agggagctag gaaagaagga ttggcaaacc catagaagca   5760
cagagtggag agcgaacaag gggtccacac tcaagacgta acgccccgcg aatcagcccc   5820
acgcttcgct ctcactctcg ttcccctcct caaatctaca ctgacgatag ccaagcagca   5880
atcacacaaa agttcgaacg ttcgagtata agacagctat ccgtttgtgc acaacagcat   5940
ttgagttgcg atacatcttt ctcttgacaa gaaactaatc attgagcacg ggtgaaaaca   6000
cttagtaaga cagactcttc tccagaatcc tagccaagtg ttcgtggcca tcgctgccca   6060
tcacgtcacc gatacccgga gccaaatcca acaccctcct ctgtggaatg gttcctttta   6120
cgagggcctc cacatgttcc tgcccgtacc cgatcttagc cagacccctc ggcacgccca   6180
agtcggccaa gaaggacgcg atcctatcgt acacaagtgc accaacctcg gagtcgggca   6240
gacgagcgat atccgtagcc tccgcaccgc tgtcgtaacc cgcaaaaata gctgctacgt   6300
cacggtgacg gtcgggcgcc gaaggcgccg taaagtcaaa tactgcaggc ccagtcaaag   6360
cgaccgagat accgtggggt acgatgggat ggtccacctc gtaccccggg tgctggtatt   6420
taccaaattt cttgttcaac cccgaaatag ggtagctcat gccgtggcaa aggtggacgc   6480
cagcattacc gaatccaata ccagcaaacg tggaggccaa aagcatctgt ccacgggctt   6540
caaagtcggt tttgtccttc gcaacgcgcg ggaggtactt aacggtctgc ttgagcgccc   6600
agagggagaa aacgtccgag atggggttac gtccttggta agcgggacgt tggagcgggt   6660
ttgcggggcg aggcatgcgt tcgttgtacg ggatggcggt gtacgattcg agtgcgtgga   6720
acaacacatc caatcccgaa ctgatgtgga cggcggtagg gcaagtttcg gtgttgagag   6780
gatcaacaat acccaacagg ggacgaaggg ctcgggaggc aataccggtt ttggactcgg   6840
tagcggtatg atcaaagatg gctgtaccgg tggtttcgga tcccgtacca gcggtggtgg   6900
gaacgcaaag cagaggcttg agaaccttgt cgatgggggt accacgaccg ataggagcgt   6960
tgacgaattc gagcagatcg gcgtcagggt agcagctgaa aaggttggcg actttacacg   7020
tatccattac cgatccacca cccaccgcca aaaagtggga gaagtcctgt tcacgtgcga   7080
acctgatcgc tgcctcccaa ctcttctcat tcggctccac cctgacctga tcaaagatct   7140
cgtacttaac cccagccttc tctagtccat cgatactctg cttcatcgcg gtcagattcc   7200
tcaccgttgg atcggtgaaa acacccacct tcctcgcctt catattggcg aaatccatac   7260
cgacttcctt ggtgacacct tcaccgtacc taatgttgga agcggcaagt tcaaaggcgt   7320
attcgcgttc aacggcgtga tcgacgggag tggcgtatcc gcgtgcgttg gcaccaggtt   7380
```

-continued

```
gagcattgtg tttggcaatc atgttcattc cggcacgagc gaggttggct ccacccccgag   7440
caaccgagca tccgtgacag gggcatccac ctgcatgcga catgcgcatg aggttggcga   7500
tggagctacg ggaagctggg cctggtttgg gcattgttgc tgcgatgaat cttcactttg   7560
gggtcgatga agaggcagaa aaaaggaagg gtaatgatga agaagggaag agaaaggcaa   7620
acgaggcaag ggcgaaagag taaagtactt tggtgtgtgg agacgggaaa tgggggatgt   7680
cacgagaaca cgatccttgg agtgcagggc agacaaagac gagattccgg ggaatgggtt   7740
gccaggttgt aatgtagcgc agagaggtca tgcggggaag gggccgagtt gccgacagag   7800
taatcatccg ttcttgaagg cagtagagca cagtggtgtt atggcgatgc ataagcggta   7860
ctgtaattga cctttttatt cgccttttc cgccttctcg ctttagccgg tgccggtggt   7920
gcacggttac gaaagagcga cagcagtcag tgacagcagg gcagaggcag agcgcgcgtc   7980
gaaaatagac atccacgacc acatacgaca aaagcggagt cgaaaacagc tcagacacac   8040
agagaggaag aacgagggct cgtgcggggc acagcacggg tctatcggtt cttccaccga   8100
agaaggatac atcttaaccc gcttctacag ctgcggagaa aagggtatat acgcacgtcc   8160
ttgttacaca cgacatcgat ggcaaccact cccgattctg acgagttgac gatcgtagcg   8220
atatgcacct gaaagctttc agtgctcctg cttgacagca tgcatgctcg gctgtcaaag   8280
agagcctcgt ccacatacaa agcgaccacg tcagtgaagg aaagatggta tgataaatga   8340
tttcgttgtg tggggggaat ttgcaagtga atggaactct ataacaggtc catcagatag   8400
tgtccgtgtt cgtaagcatc ctcgaccagc aagagatgcg tatatcagtt ttgttcgtgg   8460
tgagtatcac ccggtgtcat tgaaaacgag aaggccaaga ccagctcaaa gcaagctcaa   8520
ggcgaaagca agcaccgctc ctgctcctag agtcacaacc ccacccgtga ccatggacga   8580
tgccgaactc ttcgacccag cactgcttcc actaccaccc ttcttcgccg tactgctcgc   8640
actgctccca ttgttcgccg ccgtcacgtt cgcagcaccc gtcggcatct cctggaacaa   8700
tctatacagc gaaatgttgt acgacaacat ggcgtaatcc tcgtgcgaaa cattgggcat   8760
aaagttagcc gtctgcgtca cgggcagctt cccattcccc gtcaaactgg cgagcgattc   8820
aacaaagtga catcctcttt cgaggtggtt tgcgccttgc agagaagctt cgcatgcggt   8880
atcgccttga ccgttgtcga ggaggccgta gttgtagtgg acgttacgcg attcgaacgt   8940
ggtcaggagt tgctgtttgt tgttcttgac acggtcgcga gcgtagttgg ggacgccgga   9000
gccatcgagg ccgtacgccc agtcgtctgc ggtggaggcg cagctggtgt tggagttgtt   9060
gggacgagag gaggtgagcc agacgtaact gccggggttg ccgacccaaa agatgatgtt   9120
ggagtcgtag gcgtcgggtt tcttgacgac agagtagcgt tggaccattt gggcgcccat   9180
cgagtgaccg gccatgacga cggtgttgag ggcggggaag gtggttttgt cgaagagtgc   9240
atccatgaag gagtccataa cctgataaga cgagatggcg gtgttgccgg gtcctcgcga   9300
agccataccc gattgccact gcgatccgtg ccagtacagt tcgccagact ggatggcgcc   9360
cgctttggca tcatcggaat tcatccagca gggacccaag atcagcactt gatcttttcc   9420
aagtcttcca ctgtcatcgc ctgtagtcga tccgtccgca ctgctaccag cgctctgcgg   9480
gttggtctcg aacacattca acgcgttctg gatgagcgaa gtgtacttcc agcaatctct   9540
tggtttgcct ggcatgatca taacagctct cttgatcttg gtagcgtcaa atccttgggt   9600
ctggtagaaa ggcatcacag ctccaggtgc aacagcaaag gtgcggttga gcgtcatacc   9660
ttggatctcg ggtaatgctt gccagcctcc atcgacgctt ccgttgactg cggcttcagg   9720
agtgaaaggc acattggcgt tccaaggaag ctgcgtattg tccgggacaa tgttgtagcg   9780
```

-continued gtaaagacct ccggtagcgt attggcctgc gatgtagggg agtgcattgg cagctttggc 9840
agcagcaaca ggatcggtga aagcttgttg atagatggct tcttgagaag cggtgctgcc 9900
gttagggttt ggggatgatt gtctgcggtt atggagcttg gaaggtcgat acgaggcgtg 9960
agaggaaggt tcggcgatga cggtcgaggc agaggcgagc aaggtgagag ccagcaccaa 10020
ggctgatgag gatgcttccg acttcatgat tggtggtcct tcttcctcag tgaggtgttg 10080
tgagagatgg cagaggtctt agttgtggtg acggtggtgg tgaggaaggg aagggaggat 10140
gaaaaagtaa ggaaagagta agaagcgacc tcggatgtgc cgctacgtca gatgagctct 10200
ctcatcattg gtgttcgata gaagcagaaa gggctgcaga agcaccaatg atcgtcaggg 10260
acaaacgtca caaagggcaa gaaaagaaat acaggcacgg gagccaagca tgcatgtctc 10320
tgcgccaaga tgcttctttc ttgtggtgct tctgttgctg attcttcgct cccctccttc 10380
gcctccgtgc ttttctactt cggctgctgc cgaggatcaa cggaggtgcc gcgaaagatg 10440
cagcgttggt tctgctgctt ctacgtctcc gaagcatctc atgcgatatg aaacaagaaa 10500
gcgagaaagg ggcatcagcg aaaacggaga agcgagaagt gaggaggcgg caaagacttt 10560
gctccattca gctgagctcg aaaacccggc actgttacac tgtaccaaat cacgctgcat 10620
gtgtggttgt gtgtgtgttt caactctgca tcacatgcac atctgcgctt gtctaagtca 10680
ctgtttgcga atgtggaatg ctgcgctgca gtgtctgtcc gagcttatcg tgagacttcc 10740
atcggaacct gtcactgttg ccagcagcag tgcagtagtg cagcagcgcg gtgaaatttt 10800
caaggagaga cgcgttccga caatcctctc ctctcctctc cctttgttcg gcagattcgg 10860
cgcgtactcc gctcccgtgc ctttgccata ttcaattctg tcggcacact tccgagatga 10920
tcggcatcga cagcaatcca aagctcgagc gcacaacttt gcagccgttt gaggcgactg 10980
acgatacaga cgttcacgca cagcatgatt gacaagtgag ctcggaagcg aagagaggca 11040
atgcagaatc gctgtctcga aagcaacacc aagaccggag aaaaacacgc tgcccagaag 11100
cttggcaatc tgcacatcgg tgaaagtaac actcagattt ctctcggcgc tgcaagcctc 11160
acttctctct tctttctttg tcccgattga atttcgattc cgtttccaat atttggtgat 11220
ctgagcttac atcgggcgga gaaagcaata caccatgctg agtgaagagc ttcactcgca 11280
gtcaacaggg ttaggagcaa cggcaccttt agcgccctga tccttagcgt cgagggtagc 11340
catgtcttcg tcgtcgagct caaagttgaa gacgtcggcg ttggaggcga tacgcgaagg 11400
tgtgtccgac ttgggaagag ggacgaagct gttaggacaa acgatgtgtg cacagcaaag 11460
aggtcagtac tcagataaaa agagagcttg agagaatgaa gcaggacacc gctgaactca 11520
ccctttctgc aacgaccatc ggatcaacac ttgcgaccag tccaccttgt gcttggcagc 11580
gatcttgagg agttcttcgt cgtccttgtg ctcgcctcga acgattggct gcaatacaca 11640
tcaaagaaat gcacagaatg tcagttgtct tccctcgcac agattacaat gaaagggaag 11700
agtgggagag agggagagta acatacgcag taagcctgga gaacaatgtt gtgcttcttg 11760
caaagctcaa cgatcggacg ctgctggcac caaggatgaa gttcgatctg gttgacagcg 11820
ggtgtctcgc cggcgtcgat gagttcttgg aggtgcttga gaccgctgtt gggatccatg 11880
caaaggaaga aggattctgg tcagcatcac ctaagccttg tagccaatga caattgatgg 11940
gagctactca ctagttgcta acgccgatag taacaacttt gccttcggac tgcaactcct 12000
tgagcgcttc ccagaggtgc ttgcgtccct cgggacccga agtaggcgtg tggatgagga 12060
agcagtcgac gtagcctgtg gttccagagt tactcgtttg ttgatcagca ttgcatctat 12120

-continued catcgaatct ggaaaggtta aggagggaga cttaccatcg aggttaatct tcttcaccga 12180
ctcgcgcaac gactcgagcg tctcctcttt cgtcttggaa gggaagatca ccttggtcgt 12240
cacaaagata ccacgacgcg agacctgctc ctccttgcac cactgtcgaa cggcgtcgcc 12300
gactctaaga tagcaccaat gcgaaaagag tcaagagcaa aaccgtcagc atcgtctttc 12360
ctttcctcta agtcagctgg aaaagcggga agggccgcac tcactccttc tcattctcat 12420
agtactgcgc cgagtcaatg tgcctgtatc cagtcttgag agcggtagtt accgagttga 12480
cgcaaacatc cgaaggactc aggtagacgc cgaaacccaa aacgggcata tcgacgccat 12540
cgccgagcga gtaagttgac tgcagagtaa gcttcgacat cgtgcgtgct gctgtgcgat 12600
gtagtagtcg ggtggtaacg atacgaagaa tgatgtatga atgagaggag gaaaagaagt 12660
tcaggtggaa ggggaacaga aggtgtggag aagaagctca gcaagggccg tgcgtcaaaa 12720
ttggagaaga agattggacc ctgaaaatgc tgcacgagtt ggtcagctgc gagcaagggc 12780
gatcttggtc tgcatggcac gcgtcggaat gagattttcg cttgacgaga ggaccacctt 12840
tgacgctgag taggtcacac aacgttgatg gggcaagttc aagcttgtcg cagagcatgc 12900
ttcagtctct tgttcgtcct ccgaaacggc tagaaggatt cggtcgatgg gggaggaaac 12960
aaggcagcac gaaaggaaag gaccgatggc agtctaaatt gatactgaga aattagacga 13020
agcagaaatt gcgaaataaa ccggcacaaa aaaccacgaa aaatcatcat agaaaaagca 13080
tcacagcccc tgtcaaaccc taagttgacc ctcagcgata ctgacgagaa gtacgtcaac 13140
atggcgacta tctcaccatc aagcctgctt tggcttctcc ggcttcgctt caaccttggg 13200
ctgcggctgt gttggcggtg gcgtcgttgt cagcccacca tcaggtaaag gtaccaacgg 13260
atcgttcggg tcgaattgtc caccaccacc tcctgttgct gtctcaccgt caccgcggcc 13320
tcctgtttgt gctcctccgc tagtacctcc ttggacggcc gccggctttc ccttggttgc 13380
agccccattc ttgcccgcgc catcgttccc tcccgccttg ccgccgtcgt ccagatcagg 13440
ggccgggacc gtatgcagcg tgtacccgtc gcttcccttc aacgccatac agaagcgatg 13500
caagtcgaag ggaggttcgt ctagccaacc tttgacgagg tgtagggggc aatcggcgcg 13560
gactgcgaga gtgagcttgt tttcgcagta gtcttggaat tctgagatcg cagcttcgag 13620
ttcggggtct tcggaaaagg tgttatcggg aggattatcg gcagttgtgg tggtggtaga 13680
gcccaacgga cgaggtgtag taccgtgagt cgatgcgaca gggttgatgt ctggcttcgt 13740
ttcggagtcg ggaccaggga tccaaggatc attgggatcc gcgccgcctc tctgaccagc 13800
gtcgttagcc gtggtcgttc ctgatccagt cttcgtacct tcttgttgct tactttcgtc 13860
acgcttctgt aaagccacca accctgcatc ttccccttcg agccctatcg actccatctt 13920
cttatgcatc ttcttatgct tctttctacc taacttccca cttggcgcct tacccttacc 13980
cgcatgcaca cctcccaagc tcatactttt gaccccgttc ttctccctca cagcatcaca 14040
cctctgacac gtaggtagcg ccgtgtgaca ctggacatgc tccgtactct gaaacgccac 14100
cagcgtgtta caccaagcga tcgccttatt cgtattctcc ggatggtaga gcacaaccac 14160
gctatctccc atacccgtta agcgcttctt acttgcatcg tcggcattga tcgtattctt 14220
gcccttgggt tggattccgc gtggctttgt gggtggatcg ggcgagtcac ccatacaata 14280
ggtgaagttg cgaatggcga gccaaccgaa actgttggct tgcgcttgga gggggtcttg 14340
gacgacggtg tctgcttgtg cgcgataggc gttttgggtg agaaggaggg tgaaaaggga 14400
ggcgaagagg agggttagcg agggcggttt gggtatggat ggcatggcga acgagaccag 14460
acgaggacgg tgatggtgtg gtggtcagaa gcgaagcgcc aaactagagg aacgagcggg 14520

-continued taaggagaag ggggataagg tggccgtca aacaggctcc aaaccaatga gggtattcga 14580
gccgatgttt gagtcagaac aaagttgtga ggggcggata tgaagtcaat gtcaacccac 14640
ccaaccgttt caccgccacc gtgtccctcg cagcccatgc taccatacaa cttgctccat 14700
aaggcggtgg tcaccgcatt cgctgtagac gccacagcaa caacacgtcg gcctttccgc 14760
actttgcgcc gaaaagtctc cgaaccattc aattgaccga gcaaacacca ccttcttcac 14820
accgatacac tcgcacacac gttcacaaca acaagagttc gaaaaaaatg ccaaaggaat 14880
gtgtatgatc gcaagtgcta ctttgcaaca ggcaaaggag cgtaagaaga gtactgcctc 14940
tgataggagc tatactcatt tctacctctg tatgagctat actcttcgcc acctccctca 15000
agtctacctt gcttctgcag ctgtatctgg gtcattaccc tcctttgctg ctctttgagc 15060
ctctgtcttc gcgtcatgga atcccaaatg tgctgcgtca tggtatcgtt cgactcggtc 15120
tgtttgtgaa tggtttcggt cgaatcgtgg acacggggag tatcgaagag ctcgaaactt 15180
tcttcgaggc cgttggcgag ttcttcttcg agctgtcgag gacgaagctt cagctttggg 15240
tatcgacgaa gagagcgagg ttgatgagga gacgaaaggg acttgggaga gtgaggagtg 15300
ggaagggccg aaatgatggt tagaaagagc gtgaggaagg gtaggacgag aactgggact 15360
actgtgaaac gcatcgttgt tctttaaggg gcgaaagtgc gcccggcacg aggtactgaa 15420
gtgtccggtg gagcgagtgt atgtatagtg ttcatgcggg ttgctgcctc agtttcgggt 15480
cagaagcgga gtgtttttat ctacatcgag gacgatgcta aagtaaaaca agccggcggt 15540
aaaggatgca catcggcgaa cagccgcatt caaccacgcc gaagctttca tagcctctcg 15600
agcagaggtg atgacacaaa gctctgcaac atggccgatg acaacccgtg aaaggctgtg 15660
cacaaccgct ggtcaaagtg aaagggcttg ccgagcggta ccatgaagtt tgtgggtcat 15720
tcaacaaggc ggcaataccc acctccactg ttcgccgctc tcttgacgac agagaggaga 15780
gaatgccgac tccaagtcat tagttgaatt gccaaagcag gcacggtcat cacgacgtca 15840
ggggtagcaa tcaggtggga ataaggcaag gcgcacaatg atacgcagga ccctctatga 15900
taccaaccac tctattcgcc agccagtact tggcgtaggc gaacgtcagg caccacagtg 15960
accttcgacg ctggtcagtc tgggaagttt gctgatctct catgtgtcga cattgcgacg 16020
catagcctga tgctgagcac cgagttcgac cgtcctcgaa gccaaacgag ctgacgccca 16080
atgcgatttt ttcaaaatgt tagacatgca catacgacaa tttgcgattc gaaaaaatct 16140
cgccgacatc ggcggatcca acttcctgag cttacggagg agcggtccgg cgcgtccggt 16200
cttgcacctc tttcgcttga ccgcacagac gcattttgag tgcaaagctt gactcttccc 16260
ccgcaccgaa agcgctccac cgccggccta gtgacgcttt gtagaagaaa gcaggctcaa 16320
ctctgcgtgt gaccgctttg ggtttataag gttggtcggt caaacacact tcctctaagc 16380
tctctcgaac ctaaaccttc ttctcgtcga tacaaccttt catttgggac cacgggagca 16440
cgttgcctta tctccacatc gttcatcctc gctttcattc tcaggatcag tcgctcatcc 16500
tctttcctct cgataacctt ctcgctcaac agcaagactt tgaacaaaat ggcatccacc 16560
gacgtagcct gcgaaaagac cccctcgtcc tccgctttgg gacttttcaa cctctctggc 16620
aagaccgcat tgttgaccgg tggtactaga ggtattggtc aagcatgtgc cgttgcactt 16680
gctgaagctg gtgcatcggt catcctggcc gttagaccag gtaccgctcc tggcgctgat 16740
ggcaaccacc ctgccctctc ccccttgctt gctgtttccg accagacttc ctcgcagaag 16800
cactcgaccg tcgaagccga cctctccgat ctctcctcgg tcaagtctct cttcgaccgc 16860

-continued

```
gcgcttcccc tctccccttc aggcggcatc gacatcctcg tcaactgtgg aggcatccaa  16920
cgccgtcacc catccaccga cttccccgaa tccgattggg acgaagttct caacgtcaac  16980
ctcaaagctg tctggcttct ctcccaagct gctggtcgcc acatgatccc ccgccgctcc  17040
ggcaagatca tcaactttgg ttcgctgctt acattccaag gtggcctcac ggtcccagct  17100
tacgccagcg caaagggagc cgtaggccaa ctcacgaagg cacttagcaa cgaatgggca  17160
aaacacaacg ttcaagtcaa cggaattgct cccggctaca tcgcgaccga catgaacgaa  17220
aaattgcttg ccgacccaac gaggttgagg cagatcagcg agaggattcc tgcgggtagg  17280
tggggtgagg ccgctgattt taagggccca ttgctgtttt tggccagtca agcgagtcag  17340
tatgtcagtg gtgaaatgtt ggttgttgac ggtggatgga tgggtcgtta agcgcagctt  17400
ctaacagaaa aagtttgttt cgtatagagc atgtgttgaa gcagtcgcaa tcaaaaattg  17460
tatcgtgtcg tttcgtattg aggcccgatg atgtgtctgt ctgtgggtga agagcctgat  17520
tattgtagcc ggtgtgcggg tcaaaaagtg gggaaaaaag cgagccgcga ctgccccgca  17580
aagcgaagaa gagggagaga gagacgcgtt ctgccggtgt gtggctttct tttgccggac  17640
cgtcgacggc gaaacttgcg cagggtccat cttccggacc ctccgactcc acaacatcat  17700
ctcttcggac ccttgttcac tcttctcttt tcgaccatca tcaccattac cgtatccaca  17760
ttccagtcat ccatctactg cgaatatggt cgcttcaatc ggcaggctcc aaagcattgc  17820
ttccacctcc ttcctgcgca gcgctgcacg ctcatattcc tcaacgcgca atgtttcttc  17880
ctcatcagcc gactcacaaa tgcgaatgct catcgttggc tctccaggat caggcaaagg  17940
cactcaatcg acacgcctcc tgaaacacta ctctttttcg gtcctctccg caggcgacgt  18000
actgcgatcg cacatccaac gtggaaccga aataggccaa cgcgcagatg cagtcatcaa  18060
gcaaggcgga ttgatgccgg atcaggtcat gatggatctc gtaggagctg aagtcaaaac  18120
attagcgggg agcgactggc tgctggatgg attcccgaga acactggggc aagcagaaat  18180
gttggatgag atgttggagg accaagagaa agggttgagg ttggtggtga atctggatgt  18240
gcctgaagag gtgattttgg ataggatctt gcgtgagtca caaaccccat caaaccgcaa  18300
tcagatcgag tgcgagctta tacactgacc cgacatcgat gactgtactt gttcctggcg  18360
aacaacagaa cgatggacgc acttaccctc aggacgagtc tacaacctct ccttcaaccc  18420
tcccaaagtc gaaggcaaag acgacataac cggagaacca ctggtcaaga gggaagatga  18480
caacgtcgta cgtatcccct cctttcccct tccccgcctg ctgtttcatt tatcttacac  18540
tctctaactc ctcctcatcc ccgtcatcat gctacgccgt tgctactgca ggaaaccttc  18600
ggcaaacgcc tcaaaacatt ctacgcacaa accgaaccca tgctcgacca ctaccgtcgc  18660
aaaagcggct ccatcaccga gatcgattgc cgtaccgaaa caaacgctga tctcgcagca  18720
tcaggcaaga aggatctatt tgtcaacttg aagggcgaaa cttcgaaaca gatctggccg  18780
cacttggtca aaattgtaca cgagcgattt cccaacctaa aggcagcagc ggcggcgcag  18840
tgaatcgcag ataccacgtc agaagaccta agggaagcca aatacaaata cattccattt  18900
gcagaaaagc ggaaggcgat aaaaagttat ggtacaatgc gatacatgtt tgctattccg  18960
acggtgccgg tccttccggt tcttggttcc ttccgtatgg ttgttgatgc tcatgctcgt  19020
gcccctgctg atgctcatgc tcgtgttcgt gcggatgaaa cagatgcgcc aacgtcggat  19080
gatgctcctc tccatccgcc tctcccaccg tttgccccct cctccgcctc atctccgtcg  19140
tccgctgctt gaacccctcc accctatcct tcaacccctg gaactgttct agaaacacct  19200
tcagatgatg ctcaaactcc agattggcaa ctaccaactt cgccaccttt tcatactccg  19260
```

-continued gattcgcaat ttgctggatc gccgcatgga ggttttgcaa cgctgtttcc gggtctgttt 19320
cctccccgtc tttactttt gaggttcctt cggaggagtc ttgtggggca agatcggtcc 19380
ctgagagcga agaagacttc tgacgcgagt tgtagtagtg tcgcagggcg gggacgtcgg 19440
tcatggctgc agagatggct gtgtcgtgta agcgaagtac gcgaacagag tgttggaagg 19500
tgagcagggc ggcaagggcg agtttttgag gtgctgagac gagggtgtct tccacacgcg 19560
cggctgctcc gacgggcaat tggacttcag cagtgatgag accagagtcg gtaacaccag 19620
aagcattctt aaggatgaaa gaggggatgg cgagaggtac accgtcaggc gtgtcgagat 19680
ctcgttcgag ctcctctaga ggttcgggtg aagatgtgtg ccggtcgcgt gcaaaggtgg 19740
cttccatact ctttcgctct acttttgtcc gctctcctgt gtcattggat ccggcttcga 19800
ccatcttgaa cttctccctc ttgacgtcac tttcgctttt gcggtgagat cgcgttcgtg 19860
accgtcttcg ctttcgcatc gctgatgctc ctgctgtagc acctctcgtt tccacatcct 19920
caccttcctc ctccgcgtcc gcttgacgct gctcgcgctg catttgctcc ttcttcaacc 19980
gcctcttcct agccctctcc tctgctcgat cgaacaacct cgacgtggat tgcgttagca 20040
ttcgatgcag cactccacca aacgcatcct gaacaaccgc caacaagatc gtcaacacag 20100
caacacccat caaaccccat atgacaaaga tcgccctacc gatctgcgtc gtcggatgat 20160
agtctccata cccaatcgtg atcatggcga tgaagcagaa ccacattgca ccaccgtaac 20220
tccatctctc tgcataagta aaagcaacgg cgccgaggag ccagaaagca gcggtgacgg 20280
aggcggccag gacgagtttc atgcgtgcgg ccatgatggc ttcgtgtcgc gcgtgttctt 20340
cgtaggtgag gaagtcttgt tctgtgcgtt tttttgctgc tagaagttcg gtttgaaggg 20400
cgtggatttg gtgttgtaga gcggggtcgc cgacggttgc agttgctggc ttttctgctt 20460
ctgcgagttt gggttcgtca ttggaggcgg cgttgccgga ggaggcagca gtggtggtga 20520
tggaagacgc aacattgtcg gctggaggtg caccaccggc agcagcttgc ttctccatct 20580
gagccaaagc ttcagcgaat tcgttgttgt tgctatcgtc atccggcgaa ttactgacag 20640
cgttggagtt gggtccaaac gtgaacgtgc gaggcatgat cctccgtatt gcacggtcct 20700
gcctcttgtg ctctttaacc gcagcttttc gttctgctat tctcctacgt cgctcctttg 20760
tcctcgcgat gagggccgct tggaaagtct ctaggatcgt gctcctcgcc gaagatacga 20820
caagcgcaac gaggatgatt ccgattggcg catacaagat gaccaagact ttgccgcccg 20880
gacttgtcgg taccacatct ccaaaaccaa ccgtcaatac tgttgccgtc gaaaagtaca 20940
gcgcagtgat gaaatcgatc ttgatgaggt agacaaagat cagacttccc agcgacagat 21000
acagcagcag tcccatacct gccagcacca gtccctttttg cagctgtgtc aaccccgagc 21060
ctgcgtgctt gaaatccttt gtcctgacgt agtcggcaac caagctgatg gtgacgatcg 21120
tcgacgtgat ggtcgaagcg cagaccatcc agtaactggc actgagactg aggccgtcat 21180
gtttgggtcc atagatacca ccaaagacag ccaaggcgac gacattgatg atgtcgtgaa 21240
gagcgaaacc cgcaatggca agcgcaatac ttgctctcgg tttcaagaac tcgagaaatc 21300
gaaagatgat cgctgcgttg gccacgactg ccgcactaag cgagatggcg agtccaacgg 21360
ttaggatagg cggattatcg atgtatcgtt ccacaatacc gtctgcatcg atcttggcgt 21420
accatttgga cgtcaaacct ggcacttcga gtacgatgga gaaaggggcg agaagaccgg 21480
aaaagatcgg tgttttgcgc accctccatc cgtgacccag gtctgcactg tgcgctggtc 21540
catctccgct gtcatgtcga tgaaagtgat gatgagtgtt gtaatggaca gcatggccga 21600

-continued

```
agtgtggtac gtcagtgaca gtgaggaaag tctgaagagt gtttgtgttg ggtagacctc  21660
tatgtttgta tgcgggctgt gcaggtggtt tctctgacgg tggtgtaatg tcttttcgac  21720
gtcgaaacgg cgacctgtca cgacttgcag agtgattgtg actttgcaac gacttgagtg  21780
gtggaagatg cgaggtgata tgcgtgggtt gcaacgacga ggcagctggc aacaaagccg  21840
gtcgctcagc aggcgacaca gatgtttcgt ggtcggccat actgttgtat gttgttgtcg  21900
aatgtcgacg ctgctatgag caatttagca cttttgctga tgtatgtgtt gaaagcatcg  21960
caagaaggtg tttcagctgc gatttgcgaa ggtgtatcga tgatgttgtt ggtggtgtgg  22020
agatggtgtt acgaaatcaa gcaacgtgag aatccacaat tcgagcgcct cggcagcagc  22080
ggcggcaatt cgattgccgc gcttttccca cgcagggtcc aattaaagat aaatcggagc  22140
ttactttttt ggaatttcgc aagaatcggg gaaatttagt gcagcagaca gcggaacggc  22200
agagcccacg tgtttgcttt tcgaaaaaga actcgggatt tcgctgtacc tcgcctcgac  22260
atatccttat ccttatcaag tccccgctcc aagctatcaa ggttggaatc tagaacctgt  22320
ttgtaccttg cagcgcctat ctccatctga tacagacagt gagacagcga tagctctctt  22380
ctagcaagtg ccccaaaaag tcaatccagg cgaggctaaa gcagaattga agtacagaca  22440
cgatgcaagg aatcaccgac gcccgtgcaa cagcattggc aacgctgccc taacggttcc  22500
cgcatcatac agcacctgag ttgcctccct tggaagatcc atcgctccca aataagctag  22560
tctgtatcca tcgcctccca ggtgttgccc taccactcct tcgaagaaca accaaagctg  22620
cgaattttgt ggctcacgct ccgtcatcac atctctccac caagaatgtg ctggaaccat  22680
caagatgtgc ctctccccg ctgttgtggc aacgcctaga tggaagagag tggaatgcgt  22740
ccgtcctcgt cttgcgggca gaagcctagt gattctgttg ggaagatttt gtcgaggtac  22800
atctttgttc acaccaagcc cactcttatc ctgcaagact tggactggcg gccagagatc  22860
ttcgccttct tccaagcttg atacatggtt catgcgcctg ttgtccctgt cactccatac  22920
aggcatcggc ttcattctgt gtgctaccat ttgacaagca atagtctggt gaatggcgtc  22980
gagtatctga ggctcgggtc ggtagataat ctcgtcgccc agaaagcggt gttgctcgct  23040
acggtcttcg aaattggccg gaacgagatg gtcgttctcg cagaggtgct tgaagaacgg  23100
aatgtcgagc gggtaagtca cgggttgact ccgatagtaa cccacctcca gaggtccata  23160
ctctcgacca tctcgcaact tgaccgcatc gagatggatt acgccggata attcctcgtt  23220
gactcgccag ccacttccgg cagtcaatga tccatctgtt agctcctttg taggagcgtg  23280
aaatggatat cctgcatacc acaacatgat ggctggatct tcgcgtccaa attgatcgat  23340
gagtgtctgg tatggggtgt gaccccatgc gattgcttcg tttgctcgag cgccccaagc  23400
accagaagcg gtgccaccaa ttgaagcttg acgctcggca gatggagagc cgaatgcgtc  23460
ggcagaaagt tgttcagatg tgcctggtgc tatgggctgt actgcagcag agtcagatcg  23520
ataatgaacg cttgttggat cgtcaagacg ggtaggaaag catcgtgctt ggctgaccac  23580
catctcctgc cagccatgca atcgagtgac aacactattg taggtagaca gacgggacgc  23640
acagacgaga cacgaacgac actcttgtcg gtctactgaa gcacaaagcg aagcagctgc  23700
acagtgatat acttgatcaa agacagtgat cacaatacat ttgcacaaga cgcacaacgc  23760
ccctaaggca gggtgaaagt gggctacgct gtactttcag gttcactttc aggttcgttc  23820
gaagcacaag gggtctgctt ctcaggcagc cagcagagcg aattgcagcg tccagcagca  23880
acgtcagaat cgaacggtag tggtccaggc aggtcgcata cgcaaggacg aaagtagcgc  23940
ctctttggtc tctttcgaca ggaaggcgcc acctagcaaa gccaccattg gctgtctatt  24000
```

```
ctctcctgcc ggttggatgc cttcatgaaa gacccaaaag tccaaattgg tagcttggcc  24060
atttgcgagc tgggtgtatg tctgataagg tagagtagtc atcatgatat gccttttttcc 24120
ttggttcgag acgatctcaa gatgataaac cttcgaaaag tccctctgat gcgcagagat  24180
ctgcgtcaag acagccttcc tgaggtcatc acgtagattg cgggtgagtg tcagccgacg  24240
gacctcttcg ctttggagct gcttgggtat gatatgagct ggtggccaca gaagctggcc  24300
ttccatcaga tcgtgatctg gactgacacg ctgtggggtt agtccgccaa acgacatgtg  24360
cgcccggatg gcgcgatgaa tgtcatccaa gatcttcggc tcgggtcgat aaactccgtg  24420
aaagtttcgg tagctagcct tgttcttgtc gccaaggacg aaatcttcga agttggcaaa  24480
aatgagctga tcgtactgat acaggtgacg gaggacggga atgtctagcg ggtaggcagc  24540
tatctggaac ttgtcctttc ccacttgaag cggaccaaac tgtcttccgt ctctcaatgc  24600
gaatcgtgga atcgtgtatc gaagagctcc atctcgcgag ggcgtagggg ctaccagctc  24660
actcactggc agcttagtgt cggggtgtac tgaataggtg ggttggggtg gaggttgagc  24720
tgtgacaagg acttgggcga aggatggctc tggagcgtgc ccaagaacgt gcccatgctg  24780
catcccaggg acgacttgga aagggtacat agggacgaga gcaacctggt ttccaacagc  24840
aggaggcgaa aacaagggtc gcatgcggga gtcgtaccaa gcaagtggct caataggctg  24900
cggactggga ggaagggctg cgtggtggta ttgcaactcc ggatcgtacc gctgggtggt  24960
atcgatcttg agtcgctcga gacgcgaaga aagatccggt ctgcctgatg aaaatagtct  25020
gtagtcggag tctccttcct cgctagagct ggttggggcg ccgatgcagc ccgctatcag  25080
cactgtgccg agtgctatgc tcagcggaag ttttggcatc ttgactctgc ctgacttgtg  25140
atggaaatga tgcttagtag ccttcgtctg gttggcgtag cagaaagcat ccttcttctg  25200
gaacgaatcc tctttttgtt ctgcgatgaa ccaaacgagg caaccctcag ccctgacttg  25260
actcgttgct cgaatttgcc cacgtcatct tcgagctgca gctgatctga gcggctgctc  25320
gacaggggct gctgcttcat tgaaggtgac aagtcgtcac cgtagatcgg agtagcaacc  25380
aaaaaggctg catttggtgg cgacttcttt gctttctgca agaacccact tagtcagtaa  25440
tttgtcgagc aaccgaagtc ggtggagcag ctcagtatgt tgtgacgttt tgggatgagg  25500
ggcccacccg acgatgccag tcaagcgaaa ccgggaggca aaagtgtgga acgtttcttc  25560
tgaatagcat agcgtcagca cagagcacgc ctttacacag atgagcgatc acggtgatga  25620
aaggcatgca ttcgaacgtc gaggacacgt ccttcaagct catagagtgt taattaaaga  25680
ggtaggtcaa gcatgagcga gttcgagaag ctgaggaaac gccggacgga tgagtccagc  25740
ttcaagcatg cttcttttcc ccgtccaagg tagaaatgtt ccgcccaaaa gcgccaactt  25800
tggcctactt gcgtattggc gcgctacagg gtctagactc tcagtgaaga tccagagatc  25860
ggagtcgata ggaagattgt tctcgcccag atagtcttca gggcgcacag ggattgcgag  25920
gacgtgtcta gctttgccat cgacttcaac ttccatgtga taaagctttg gcgtttgagc  25980
cgagtgagtt ttgagacggt tcctggtgga tgctcgcaca cctttgctca ttagggacga  26040
cttgacgtct agtccgttga tgatccagcg agatggagag actgatggca agaggaaatt  26100
accttgacga acgtcgggtg tttgcgcgtt gataggcttt ggtggaaggt ggctgccaaa  26160
aagatgatga cccaacttgt tcttgatagc cttgagcagc tcgggctctg gcctgaacac  26220
cgatcctctt actgcaagct tgttcccaac aagccgactt tcaaagttac ttggcacgta  26280
agctttcgat aagtataggt gtcggaactc agcggtgtcg agcggatatg tctgcagctt  26340
```

-continued

```
gaaagtgtac tctttcaacc tcacagctcg atcagccttc ttcgcgttgt gcgcattttg  26400
ttgaatcgga gccacctgca ggtgttccgc tggaccttga cttgggccag cttcgagtaa  26460
catgtcagct gcagcaggat agtggttgta gttcggctgt ttgacaatag gtctctgatc  26520
aacgatagat tgaatctggg tttgcgcccg cgaagaaggc accacatagg ttggtgcgac  26580
gtttgagaac gtgtctggcc cgggtcgcgg gatgcccgtc catatagatc tgtctgtagc  26640
atgcgtatac tggatcaaag ctgccacgaa aagcagcaag caagctgaga gcctcctcag  26700
cgtcattgtg aggctcgatg gttgtcgaga ggccaggatg acgatctgga tgaattgaca  26760
gaggtgctct gtagaggagt cggcaaggat gcgcacttta aatgggatac agtcctcgag  26820
gggtttaatt cagggaagat cgcttgacga ggccactcgc tctgtccctt cgtgttttga  26880
cctgctgacg tagcttcaac gtgccgggct atatgaaagt actggtggac tcgatctcga  26940
tgcagatgat atcaatgaag tgctcgagct tcatgcatag caatagtgga tccgacatcg  27000
atgcaatctg catgaatgaa gtgcctgagc ttcaattgct ttcattgtta taatatcagc  27060
actgacacgg cgttgtccag tgcagagtga ctatgatcac ctcagccaag agctcctcac  27120
aaggtgtgcg aagcccttac gatcacacgg cttttcgaac tatcgcctct agcgagtatc  27180
gaaaatgctt tcaagcttat cttgctaaaa ctggtgggtt gaaacaaacg taagtggatt  27240
gcacgaggag agataacgaa ccggggatgc cgagtggaca acaagccttc ttacgagcgc  27300
ctcgcactcg ctgtgaatgg ccaagaacgc caaggaagtc aaggacgtgg aagctctagt  27360
atgcttggaa aagccggctt catcgtctga gcagccatga gcggcatgtg ggcgtgtaca  27420
gggaggaaca tacctcccaa ggacgatttg cctgcctcca tccgtgaccc ttctcggagt  27480
cttcatgcct tcgaagaaga tccagaagtc cgagttgccc ggtgcccatg tctgctctat  27540
gaagtcacca ggtcggacag ggaacgttag aatatgcctg agttctccgc tcgaaggaag  27600
tgtagatgaa acagattggg tgcaaggtgt gaatgcgttc gaaaacgaga tgggatcgat  27660
cgacgtagac gatttgtgag tatctcttgg ggaatctcga gcccgttagg tacatctttg  27720
gagttcgtga cagctggcca aagatattca ccttgattga tctcgtgaga cagagggtcc  27780
atgtcaacgc gctcagggta gaagttgtag ttcttaagct gactccagat ccgttccttg  27840
atcgaagtta gcagagatgg ttcaggtcga aagatcattc cccggaattt caacgtttgg  27900
ccgtctagga acgtctcaaa gttggctggc tcaagatagt gcgaagtcgg cccactgtac  27960
aggtgctgga agaccggagt atcaagttga tatgtctgtg gaaggaaagt tttataatgg  28020
cgaagactcg cgacagctgc ataccgcgaa ggctgcaagg tagtcagagg ctcggcagtc  28080
aaaggctctg tcgagctggt tggatctgcg ttagaagcgc taccgtcgac cagctgagaa  28140
gtcagggtgg tagagtgagc ggctgtcgct gagtctctag cgacagaatt tccagctgcc  28200
gagccacttg ctgatgtact agcctgagat aggacatgat caggattggg aaacagctcg  28260
agtgttgttg tcgaggtctc cgactcgtca gtattgcccg ttgcctgcgt ggccgtagca  28320
aagatcgaca ggaggagaag aaaggctgct ggcagcatca gcctgaccat attgctcgac  28380
agatagattc tctgcagaac aacggctgga cacgtcgaca ctcgagagcc ctgactgatt  28440
gcaggtctcg attcagcgac gccttatgta gccatataca ccagattggc gtaagaacga  28500
gtacaaatgg gtcaagcatc gctacagctt tacttgcgct cacggtgtca atcttctgct  28560
tgatgacctc gtaaagagga caaggttcat tgcgcatgcg aaagtgaggc tgaaactccc  28620
acggatgtca cacacaaagg tgaagtccag gcaagtgaac tgctgttgca atgctgatgg  28680
tgactaggtg tcggcctgcg gtgtccacca ggaagctcgg agcagcctcg agatgcaggt  28740
```

-continued ggcttgagaa agcttccaca tacgtgtaca tcggatatgg ccgtgattat tcacacagct 28800
gatgccagga ccgtggtagg agaagtgact tcacacaggc cttgaagaac accgaagcaa 28860
acattcagct caaagcattg aattgattga agaggttgaa tcaccggtgc ctatgcttca 28920
aagcacgctg cggctcgatc tacttgagct ctgaaaaagc aggtttgaag gctccgatag 28980
ctaagaaagg ctcttggatt ttcttcggaa gaaacgaagc acctaagaag gctaacggtc 29040
gcctgtacgc aagtccaaag cgcgctggtg cctggaacgc ctcgaagaaa agccacagat 29100
ctgaatcgat aagtcgatgt cggccgacga aggagccagg ctgcgctggt gtcatcatga 29160
tgtgcctaac gcgtccatcg acagacactc ccagcttgaa catattgggt cgttggactg 29220
tgtttgtgcc aagccggttg gtgatcaatt gacgaaagcg tttgccgagg gacttggccg 29280
ggaaatggag ccttccggac ccggtcttgt cctgtacagg cggccaaaga aaatcgcctt 29340
gcatcagctc aacgtcaccg ctgacgcgca aaaaccgcct ttctattgcc ttcagatgcc 29400
ccccgatcgt ctcacgagtt gcttctagga ccgctggctc cggacggtaa agcatgcctt 29460
ctgtgtggaa tccgtatttg gtcatgaacg tttcgaaatc gagtgggacc agatgatcat 29520
tgtcgtaaaa gtgacgcagg gaagtagtat ctaagggata agaacgcatt gcaaattctc 29580
ccaaaccatc aggagctctc cgtcgcccag ttttggtagg cttcaaggac tgcggatctg 29640
tggtctgtga tgtgcttgcg atgtctccag gaggtggagc attaagatcg aagactgctc 29700
tctggccgct acttgccgca tcaaccccag gtggagaatc tgtcgttcga tgctcgctca 29760
cttgtgggta cgaatgggac cagtgccgga cgcctgtctg cctgatgttt gtcaccggat 29820
agctcggttc ttgaggaatg ggctgacggg gtaagttttg cggctggttc tggacagtct 29880
gcagctcatc aattggaata cccatccatc gtggtctgcc tgctgcgagg acgcagcttg 29940
ttaccaaaac aatgtaagct actacgggct gcaccttcat gctgacgtga cgagaaagaa 30000
tgggttgtat ggccagatgg tgcgaagaag gagaaggaac aaaggttgga gattggcgat 30060
caattaataa aaccttcgag tagactttgt ggcttgtgga cgaaatgctg tgaaggagca 30120
cgcattgagc ggtacatggc tgatcacaaa ttcattgcgc gtttacttgt tcaaagctta 30180
acctctcttt gcagcatctt actcctccga atgaactacc tagtctacac tgcaaccaaa 30240
ggaatcgaag ctcgactcga ctcgctcaga agtggtacag tagaatgaga tgtcccacca 30300
actaatgtcg tcacgaaatt tgcggtgtca aagcggtgaa ctaagtaata gccttcgcat 30360
tcatatcttt gcgagctgta cataggctgc cgttcagctc gaagaatgtc ttcggcggat 30420
cactcaaaaa caattgcggc ggcatttgcg agcaatagaa gcagacatag aattgcttga 30480
ttaagatcaa agtatggctg gaagtagtga ataacactca acgatgtagg accggcaagg 30540
agaacctatc ctgagaagga tcacacctta cgcgacccaa acttgtaggc tgtcgtctct 30600
agtgcgctgt acgcagggct tcttcaaaag ctggtctgat ggtgtgtgca tcaccaagta 30660
ttttgctcgc atctgcagga agaaacgaag ctccaagaag ggccagcttc ttcctgtcgg 30720
catgctcgac tccttggaag aagagccaca tcctagaatg aaccggtctc gttggcagtg 30780
agatgtggta cgaagctggt acctgtatca tcagaatctt ccgttgaccc tcaggagacg 30840
gtaacgtcaa agtgaacatc ttgggttccg tgagcgtgtg ataaggccat ttctggtttg 30900
gcaagcggcg ataatggtac aacttgcgga ttggcacgtt cactgcccca tttaggtcga 30960
tttcagtggg tggccagagc cattggcctt cactaagacc accttgcaag gcgctcggct 31020
gccttctaaa gcttcgcagc gtagaccaga ttgtgttctg aatctcgtct agccttttgg 31080

-continued gctctgggta gaagagaggt ccccaagcgt gcaagaatcg aaccgggttt tgggatctga 31140
ttcctccgcg attcttcaga aacttttcga agtcagcatc tctgacgtcg cgcgaatctt 31200
cgtacagatg cttgaattca tccatttcaa ctttttggaa gccttttggc tcaaagtctt 31260
tgttccctac cgggaagggt ccccagtttc gatcggtcct gaatgccgga atctcaggcc 31320
tatcctgact ctcttgaggc gtgctggtgc tggattctgc ttgatgaaac caaggcctag 31380
agtcgaaggc tgcagcaatg gtaccggtgt ctctgccaac ttgagagtga gggattatac 31440
cagcgttcga ctgctgctct gcttgtggca gggcatatct gctgtcgtgc tcccagacag 31500
gaagcatggc cctttgcggt atattccaat acggtcggtc ctccataggt cgagcacatg 31560
cagctggaag tgccgctagg aggcaaaggc ctgcaagcag acgcttgaga cacatggcaa 31620
ggggatagct ggctagtctg tacgtggtct tgcgggaagc gtgcaagaca agcagaaaca 31680
tcgggagggg tgaagcctat atagcgatta ctcactcact gtaccttctc aacccactgc 31740
gctggcacta gaggaggctt tgcattcgcg atcagcaatg cgaataagct cttgcaacga 31800
acgaaagatg tctcatctgc cacacgtgaa agacaatgca cggtatgatc cagcaccgta 31860
tcggcaacgg atgtgggcat tgacctggga ccccacatgg ttacgttgcg tgtgaattga 31920
caactctctc atatagcaca aatgacctca gcgagaacta cgtgcgatcc gtgacaccgg 31980
attgcatgcg attcagttgc atcaggtcag gcctgcgtat tgagcgtgtg cctcactcag 32040
gggctaaacg ctcatcaaat tgcggtccga gacgggcgtt ggcagctcaa ttagtgctac 32100
atgagtattg ctgtatagga gcgagcctgt ttggccctcc cacacagtgc ttttgcgaag 32160
caacgacgtc atttgaggca acaaaggtgg tctcaggtcc tgccgtgccc cacccacagc 32220
agcccatcac ctcttcaacg tgagctggca cagtcaaggt tcgcagattg ggaccgtcag 32280
aagccacaca gacatctgaa gaggtgggct tcaagactag ctttcgagag attgtgcatt 32340
gtctcgtacg aatggctatg ggtgataaga atgagcgcgt cgaaaggatg ggttggagac 32400
catgaaatat tgctgatcga atatcctcat gacagcgttg caatatcagc gtggctgaga 32460
gctcaacgag cgcagggcct cctcgaaagc cggacggatg gtcctagcat cgagaagaac 32520
ttgattggct tcatttggta ggaaggaagc accgagaaaa gcgatcttgc gttctcgtcc 32580
ttgctgtaca ccctgaaaga agaaccaaag ctgtgaatca ggtggatcaa aaggaaagga 32640
aatgtgatcg tgcgtccgac cttccatcat taggatctgc ttgtttgaaa aaatggaagg 32700
gacatcgagg tgaaatagtt ttgcatcggg aagcatgtgt ctgttccatc gctctgcagg 32760
cattcgacga tagcgttgaa ctagtagctg agcaggcaga ttgagtcctg cattgtttgc 32820
agctatctcg gtgggcggcc acagccattg gccctcactg agaccatctt gaagctgccg 32880
agcctgccta ccagcatttc gaagcgtgtc ccagatcgtg gcctggatct cgagtagtct 32940
ctgtggctct ggataataca agctgcctct ggtaggaaag gtatggcgcg acgcagcgtc 33000
cgcatctgta gccaagaaag tttgatagtc tgcatctctg acgttaggca aggcgtaaag 33060
atgctgaaag acattgatct tgacagggta gcccttcggc tcgaagcgtt cgtttccgat 33120
ggggaagggg ccccactttc tgtttgtgtg aaaagcaggg atctcgagcg tcgtgccata 33180
caggttccga ctcgaaccag cctcggacat cctgcgccaa ggctgaggac tgagattcgg 33240
aacagcttca ttgatgacaa cgaaacgact ctgggatggc agaggtatga ttgactgtgt 33300
gttccagtca aggttgcgct tcagttgctc ttccatcaac ggatcagcac cagcttcgag 33360
acggggttgg tttgtcgaag caggctggtg ttctgatggg ctcagggcgt atctactgtc 33420
atgctcccag acaggaagca tggctctttg cggtatgcca ccaaacgacg catcgtccat 33480
tgcttgcacc cagcctgccc aaaaggccat tattgatagt aggacgagca tccttagctg 33540
aagcaaaaaa tgcgtgatta tcggtcaccg tggtctcaga tgatgctcgc tgtgagcgtg 33600
aagaaagagt ccaacccttg ccaccacctt gacggaactc tccttggacg aggctcttac 33660
ggccgctgtc tttgcgcaac aggtccactg ctctgtttga gcaacgaaga tctcagaccg 33720
tccacgtcga cagcgcgatt ttgttcatgg caacgccctg aagtggctca gacaacgaac 33780
gcaaaagtcc catcaatcac gcacagtact gcccaccaac ggcgagcaca tgaaatcgaa 33840
actttaaaca cgaggcgtgc gaatcgagcg cggtttttgg ttcacatcgg tccgagcact 33900
gtgagagatg tggccgtgct tctggtctgc gaacgagtga ctgtcgtctg accaaacggc 33960
tgtctgtctg atggcttcaa tttctcagtg cctgcgtgaa caagttcact gagcggaacg 34020
atgatcactt tatttctacg caagccttta tggacgctgt gctctgtcca cgcacactgc 34080
gcaagccaag cttcgactca catgttgttg aacgcccaac aacaagtgcc gtttgacctc 34140
ttcgaaatga agtcaagtat cgttcaaaca gacagctagt ctctgaagac agcagagcag 34200
cagattgtag tgagagagga tgagcgcagg gtcacattac agctcggtag gctggagatc 34260
ggtatcgtag ctctgaattc aggtaatcag atgtgagtca cgggtgcttt acaaaaaagt 34320
agttcgcaaa ggaagggtgg cgagaaccgt agtgcccgag gctgagggac aactaggcta 34380
gatgattaaa aaccatggtc aggtctccac tatccagtaa gcgcttcgca ctgtcccttg 34440
gaaggaacat agcacccagg aaggccattc gctttctaaa acctcgacca ttgattggct 34500
ctctaccttc aaagaagaac cacaaattcg agcttgtcat tgtccgcgat gtgggagccc 34560
aattaccaac gcttgttggc atggctgcaa tgtgtcgcac ccgcccatca ggaagaagga 34620
cagcaaggtg atacaagctc gagaccttgc cttcgtgccg gttcctgtcc ttcaaagcct 34680
tatggatgcg aggattcaaa acgtctgccg gcatttgcag gtccccttcg ccctgccttc 34740
gctctacggg cggccacaag aattgtgcct cgcgcagatc gaaatttgga aacacccgct 34800
gagggggcaa ctcaaggtct cgaaggcgtc ctgtaaggcg ttgctgtatc gctcgcaaaa 34860
gctcaggctc cggtaaaaat gtcaagccat tgatgggtag tctgcctctt gaaacaaagc 34920
ctctgaagtt ggtcgggtat gtgtctgggt tggcgtgaag atgttgaaag ccttgccaat 34980
ggagcgggta tgactgcaat gcgaacattt tgtcgccgat gtcatagggg ccccatttgt 35040
agcctaaatg gtccgtgaag gagatggact cttttgcagc tggttgctgg cgaagactag 35100
acccggctcc aggagcaaat gcgttggtaa gctcgggatg atggcttgaa gtgcccacat 35160
gttcgtactc gctcatcgtg ccgatgtttt gtgctgtctg cggtgaagag gtcccggagc 35220
catcgctgct cgctgcagga ggacttggca tggattggtg gacagtaggc tgattatgcc 35280
agtactgcgg tgaagctgga cgaggaagtt gaggcggata gggtcgatag tcgtgctctt 35340
cccacgcagg aacgaattgt gagaatggta catttgagtt cctgggatcc attggagccg 35400
atagtaccaa gcctaccatg gatatcaagg tcaaatagaa gtagatccac gcttgaatca 35460
tcttggcaag aaagcaatgt ggaaaggtgc actcgaccgg tcttgtgtat cggtgctgtc 35520
tggtctgagt cagagtccgc catggcagta tttatgccct tgcaaaatgg gaaggctcgc 35580
atacttgagc ttgcagcaca acgatgtaag actgcttaac cctctgagct tgttgtcaga 35640
gtcgatcgat aacttagtac tcaacgcatg tcagaagcgg tgggcctcgc ttctcgtgtg 35700
caggatgcgc tcccgattcc gactaagccc acaagagacc tgttgtgctg attcccagac 35760
tcatttcgag gttgactttg atctttgtgt gcgaatcagg agcacttgca gcacttcaca 35820

-continued

```
ggcgtatcaa gggccggtgg gtgcccgagc aagaagacgt actgtccata attttgatca  35880
cacaagtgtc gcgatgaagt ccccgttgtg tggcaacttc atcaacattg agacaactgc  35940
tcgatcaagg ctgcggtcac aaagagcctt cttggctgca accttgccgc aaaaggggca  36000
ctcggtcctt tgttcgcctt cctcctagct agtacaaagg tcagcgctga tgcatgatac  36060
attgtgagcg tcgacggcag tcgctactgg ataccagacc gtgaagtcag gcaggtgtta  36120
tgagtgtcag ttgtagcaac aaagaatcgc atcgatagga gcacaattac ggtgtttgtt  36180
tgacgtcgga cctacatcat actaagtgga aagacagaga ctacattctc tgcaaataca  36240
agccgtggcg actaggtgtc acttggatga agggatcagg tggcgctgaa agggaggtgg  36300
taacatacag gcgcgaaccg cagtcgacga gctagaccag tgcgtcatga tctgtcaagc  36360
agcgaaagtt gaaattacct tggctctgag cagcgtttcg tgtgctgaac tcggcaaaaa  36420
catggcgcca agaaaggcca tggtcttttt gcctatcacg ttgcttgtca acctcttgcc  36480
tctgtaggat tggatcccat cgtgaagctt tctgccttcg tagaagagcc acagatctga  36540
gtctcctccc gtgctggttg tccagacctc ggtcacagct ggagtcatga tgatatgtct  36600
gtctccagcg gaagaaggaa ctgtaaactg atagatgttc ttggcacgca tcgtacgaaa  36660
gcgatttcca ggagcaacgg agatgcgatt cgacaggagt gcctcgggca tttgaagaac  36720
cgactttgtg tgggtcaaag gcggccatag gtacattccc tcgcggaaaa acttgttctt  36780
ggagtcgata ggcttcgcgc tgatcccttg atccgtaagc gtgttccaaa tggtcgatcg  36840
gatgtgctta agaacttctg gttcgggacg gaagctaatg ggccgcacct gcagtcggaa  36900
cggctggcct ggtacaggct cgtcgatggt cgctggaatc gtgccgtcgg gctggtagag  36960
gtgtttcagt cgctccattt ccaacgggta ccatatcagc tgaaacttct tggagttgag  37020
tttatacggt ccccagatga cgcctgagac atctttgaaa gcgggaatga tagctcgggt  37080
cctagtggta ccctccggac ctcgtcgagg acccgagatg gttctcccgg ctttctcctc  37140
ggcgtcaggc tcccaagagt ccgagctgct cgcctgacgt cgccagaagg gaggatggac  37200
agaaccgtcg cggtgaccca aacgctcagt cggcgacaaa tcaggagcag aggcgtgtcc  37260
ttggttgtca aatgtcggaa caccagtgac caccatggcc aacaagccga ggagcacaca  37320
tagctgcaca ggtctgtaca tactatcttt catgccgcag gacgaatgca aaccttgact  37380
tgagctacga gatgtgaaga ggagggtcac gcgatggagg gaaaggatga gaggatacga  37440
gacggtcgat caagaaaggc caatcagtat cagcttttat ggttttgaga ggcttcggtt  37500
tcttcttggc aatcgaagct caagcacaaa gtcgatcata cttccttcgc aggcttggaa  37560
agttcatgtg cagcgaagcc tcgcatcttc tgcttagaaa gttgtcacag cctcaagctc  37620
tggaacggag agcgacgtgg cctacggtac atggtcgtgc ggcggttgca gccaaagcga  37680
atgacatacg aggctgttgt cttggccata cacagaacgg taatcgagcc atagaagcga  37740
tcatcggttc cacctgctcg cgtgacccga gtatgacaat cagcctggga tcccagcact  37800
attcctgaat agcttcgtgg cgaaactcga gagctctcgt gcgcttagat cttcattagt  37860
gggcctgttc atcttggtat tgcaatccgt tcttaccaaa cagccagagg tcacctctcg  37920
atgctgaagc caagcggtct atgagcttca acatccgtct atgaggtcga ctcttgggac  37980
gcctcaagtt gccgagactc gcggaccggt cgggtttcgg accggaagtg cctaagggca  38040
atcggagttg gccgcactct cgacttgagt tcatcatctc acccacatac aatgctgcat  38100
ccgccttcaa agcctctcat gcccgtgtag ccacgcattc ctggtagtgt tgttgtcaca  38160
accaatgggc aatgggtcac cttgacaccc gtggtgggct gcatgactgc tttgcgacaa  38220
```

```
cgaccgaaaa atctgttgcg ttggcaagaa caaacacgct gcctgctttc gtctcttctg  38280
cacaaatctc agcccattcc cgcattcaag tgttgatgcc gagaggcgac cgctacgcag  38340
aacagagtcg atcaagttgc ccagcactgc cagcttcgaa aaagtgcttt gcgcaactac  38400
tgtacgagcg atacagaaat gaattaatgc gtcctcgtag tttcccgtcg cgacttggga  38460
agaaggaaag cttccannnn nnnnnnnnnn nnnnnnnnnn nggaaaaaaa aaaaaaaaaa  38520
gacacgatgg ctaaaggtgt caaaatgtgg ttgcaagaaa agcactggaa aaacaagtaa  38580
aaattaagaa aaaaaggtta tgtcaggaat cgagcagaag gtggccgaag aacaattaag  38640
ttagtaaagt aaaatactgt atcaacgaaa agacaaacaa aaaatgcaaa gcgaaaaatc  38700
ccaccataca gcccagcatg ctccctcgca accgagtcgt tgtaacagcc tatgagcctt  38760
caacgctgcc gatcgagggg ccttgtggac gcttgctgac tagtcgtgct cggttcgagt  38820
ctatcgcagg gatctgaagg atcgatagcg gctgtagact gatataaatg atacatttag  38880
ccctcggtag gctgctcttt ccctcacttg gtcatcggct tctacccccct tcctcgcttg  38940
caaaactcgc ctctattgag ctgagatgct ctctctccta cgtatcttcg gcatcagcgc  39000
ctgtgtcttc atctctcttg ctcatgcgat cgatccaagc aagttcgaca aacctcagga  39060
gaggtcgtgg ctagccgcaa agtcatttat cgagcttgct cacgaacata attctgtggg  39120
ctaccgagca gcctatcctg accatctcga gctcaactcc gaagacgcag aaagggcttg  39180
gaatttggct caacagccag gccatggacc tctgaacact tttggttccc gagagaccaa  39240
ggctcgcgct tgggcacttg cacggatccc gtttggccac gaagttattg ctccataccg  39300
catcggcgaa aagcaagctt atttgttttg ggaggttgaa cacaatagtc acaagctact  39360
tggcatggag ctttggccgc ctggaggaat attccctgcg ggccacgtga gcttcagcga  39420
attgatggca tcgctaccca agagaaacgt ggtcaacaaa ttcatgaaat ccttcagggg  39480
ttgaaggatc cgacgttttt ctctgttgtg ctcggctgca aacgctattt tcagtggctg  39540
gcgaaatctg gaccctgcat aaaataaggc tggaccctgc ataaacaaaa atttagttcc  39600
gacaaaagct taaacacggc atcatacata tttgtggcgg tttgaggagg agtgttgatg  39660
tgacacggat gttattgtgt tggtgcaacc ttatcaagcg aagtataaca tattcgtgtt  39720
gttgatgtca tacatatgca tagctagcta cttgttcgcc cctttccttc gctccttatc  39780
gaattgatct ttatttctaa taagttggcc gtctgtgaat atgagcgcct cagcatcgac  39840
tttgcctgtc tcataagggc aatcttgttt cttgtggggc tgtttctcga tctcgaaggg  39900
cgcgacgaga gactagtaac gctactgact tgaattgacc ttaaaagctg gccgcaatgt  39960
tgggccacgc acacatcaag ccccatccga tacgtgtctt gctgtccatg gatactcttg  40020
cattctgtca actcgcaggc accgaacaga atcaatttga gtgcagaact cggtagacag  40080
ggatttcttt gagtctgatg acgaagctct gtcatgggcg agagcgaacc aggaaccacg  40140
ccgcaaaatc ggtatctcga tggcttaaag ccgatgaata gaaggacttg catctctaga  40200
gcagactttc tgcggttgaa cccacacaaa gatcaagtcc agtggatcgg cccaccaaca  40260
tcggcgcaag cgcttcatat gagttgttgt aggatggcaa gattgagcgc aactggtttc  40320
ctctcctacg taacggcttt ccagtggcga ggcaacgctt ttgtcggaca tgcgttctgt  40380
acatcgacac accagacact cgcatgtcca taggtccctt ccttgtgagg agctgacatc  40440
tcacctgtgc gtggcttgac agaaggatac aacgagcaac cacgcttctt attgtctagc  40500
atcgagccca ctcaaatgct gtcacaatct tctgggttgg cctcaaggcc gcgttcttct  40560
```

-continued

```
ttatgtgaga tgtacctcct gcaactgctg ctggcatggt gataagcaaa gcatcggtgt  40620
tgtcaagctt gcacgatcgg tgttgatatg taggaagaca accagccgaa acaatgcgac  40680
gagcgccatc atagaaacaa ccgtctcaag ggtgcctctt tagccgcttt ggactgttgt  40740
cgcctgcttg caagctgcaa agccctttcc tgaaccgcct ctgatctgtc tttcgagctt  40800
ttgagacgat gtagcattag attgctgtct ggattgaagc cataaataga gtcaattaag  40860
tgaaaagtcc gactcacttc cttcacggca ccccaatcgt tttcccagct catcgcccag  40920
tcaagttgct ccgatggttc tctcgactcg cattatcatc catctattac tatccatttc  40980
cgtccttacg actgcgactt tcgctgtgag ccaaccaagt ctgacaagcg atgccaagaa  41040
gcactacaag caacaccata tcacgtatat cagggacagc ctattgccag cggtcatcga  41100
cccagagagc cgtgttgaat actactccca tctcgtatct ggaaaaccgc tggctccggg  41160
tcaagcgtac gaccattcaa agtcgctagg aaacggaccc atccacgtca cctacgaccg  41220
caagcatgaa aatgcatacg cgaccaccaa gattccgttc aattctgatg ttggccataa  41280
gtggggtatg aatgtacgtt tgaatgacgg cgcaggcaat gaagagcaca aagacatcta  41340
tgctttctgg cacaagccta tagggcatcg tccagttttg ctgcgactgg atgcctggcc  41400
agcccgtcag caggctcacc ctgccctttc ttgggaacaa gtcgaaggag tcatgcgggc  41460
tttacagcgc cgatcttagc ttccctgcct tgccgcagta ccaccacttc tttgtaccct  41520
acaaatcctc gctgatcctg tcgacaataa ccgtagctcc cgtcagattt ttgcttctga  41580
gcgtctttgt aacgtatgtc aaccgctttc taagcaacat gctgctatcc gagtcagtaa  41640
cacagctctt tgatctcaac ccaaaatcaa acagaagcga tattccaggc gtgtgcgaca  41700
aactctgtgt agaatgatga ctgttttcac gcaaacatat tcgttgagcc gacagtttgg  41760
ttctgacagg acgccacgag gccagtggca ggacatttca taaagcgagg acaacatcgg  41820
cttattgagg gtctgaacgt ccggcagctt caaacacgtg acagatagca gaatgggatc  41880
tggtattgct cccagatcta cacaaggtcg atgagataac tgagagaagt ctgttccttg  41940
cacttagata gtggtagacg ccgaaggccg aaggagagca agaaatcgct gtgaaccagt  42000
attatggcat gttgccaata tgttacagtc aaccgacggt agaccgattc atgtgggcgg  42060
tgtcaacgcc acaaagtacc gtcccgccta ccgccacaca gaacgtggca acggcagtgc  42120
taagaaccaa ataatgccga gaagccgcga agagccgaat tcaggggttg ctgggcaccc  42180
agtcggcatg gaaggacgag ccccaaaacg ccaagtgaga tgcatcgagc tacaatataa  42240
gcagcttgcg atctgcgatt ccagtgtcga ccggcaagca cggcaatca caccgcctac  42300
tacaccaaga tgatgctctt ccgcttgttg ctcctgcttc tgggcgctgc cttggtttct  42360
gccttctttg aaagcgatta cgtcaatctc aaagggacag accgaagcat gtggctaaag  42420
atgcacgaac gattcgaccc ttccttcaag caaggtcttg cacgagaaca tatttcttct  42480
cctcgagtgg tcgccttcgg ccccgaatgg taccagtcgg ccttgcagca tgcacgcgac  42540
aagggagtgt tggttcttgg cgttcacagt cctctcacat cattgacggg gaacaagaag  42600
acgtattttg tcacgctgat ccattatgac gatggagttg ttgcacgtca gctccaattg  42660
catcctcaaa gcatggtggg tgcagtcttg tggaagcaca gtaaaggtca aaacaagatt  42720
gtttcgattg acaggttaat taggaagacg gagatgaact gggatccaga ggtactggaa  42780
agtgtcctac aacgcgagca ttgacaccaa catctcaaga agggagcgac cccgatcgga  42840
gctttcgtac gtattcccat cttgatcttc aggcgccgtt gtacgtgtcg attgtctttc  42900
tggctgatca gctttgtact catccttctt cacactgact caggattgaa cggctctctc  42960
```

```
ccacgatggt cttgtctcga cccttcggta cccacgtcaa cgcatgcaaa gtgggctcac  43020
tgagcacctt gcagtgaatt gaaagccaca aagttgcttc gcattgatgt ggccctggtg  43080
acaatagaga aataatgtgc tcttacattg caacgaatgt atgaaatcgt gttgtctgct  43140
cacaaacaac aacgatatat gaaacaagct catatgcaat ccggcatcgt tgcgcttgtg  43200
ttcaatgctg gctcggcgcg agtcttagca cacgtttacg aactgtagct gccccttteg  43260
agcttctgtg actgtgcaaa gagcacagcg agctgcatag ttgcccacgt tagcacgact  43320
gttaagcgct attgttaccg gtgttgtccg atatcacacg attgcgacct gggcggcatt  43380
cagcgatgct cgtgggaagt cactggcaag actgaaagta ctcgagggcg agcttgaaag  43440
aggcgattgc gccagatgcc aaaaggcata taagctcgtc gatctttcac tcagattcaa  43500
gtctgaacgc atcaaattct cccacgggga atcagctctg tatctctcaa ggacttcaag  43560
atgaacgcct ttacagctcg tacgatctta tgcctcgtat tcatcctctc cgtccttgct  43620
gccagcgtct ccgctgcccc accactttca agcttcgatc gtaatatgat caacgagcac  43680
gaagctcagc aggagaggct gtacagagac agcgggtatg catggaaccg tccgcagcaa  43740
ttcgagtact ttgcagtacc caattttgaa cggaaggctt tagagctcgc tgatggacgt  43800
ttccgtcaca tcgggaccca aggaatcggt cctttcgcta gaaacgctgt ggagacttac  43860
tacttatcga gcttgattcg tcctggcacg cttcttggtc acgatatggg gcttggaccg  43920
ggaagaatag caagtgcgct ctggaaacac cataatggag aggccaaagt gttgggtgtc  43980
acaatcacgg agcaccagcc caatcttgat tggcaaatgt ccgcgctgcg cgacatcatc  44040
agtcgtcatt agtggatctt gcctcccctt ggctcttcgg acgagagtag aagcccaaag  44100
ggctgtggct ttcggttcga gcttgcatgg ttctgcgagc agtgccgctc tcggactcgt  44160
gcgaaaagct gcaaacagct aggtcgccag ccagatatcc gcttctttca gcccatgctg  44220
ccgtgtccaa cgccttttca atcatcacac ccactgtcat cctctctgcc cactacctct  44280
gtctcgctta tgctttcaca ctttcgagct cgtgtataga ctcccgtccc tggcattgcc  44340
tacaactcgc tgtgttgacc ttcgaaccaa gcctgctagc ctgaccaggc gaagggagtc  44400
gttacgtgta ccgaaatgca gacgaattta accatcgaat ttatacatta tttacagaaa  44460
agtatgtgat acttgctagc tagttgtttg tgagctgacg cacctatgcc gatcggttca  44520
ctgtctttgt ccatcattgt cgctgtgtgg gtcagctaca atggacgttg gagcccacct  44580
tcaggggcgc cagggccgca caaacgatgg gcgatatttg ttccgtctga ttggaaaccg  44640
acagtgggcc tgcattgctt cattcgccca cgtttgtgcc atggtcgccc ctagccatgg  44700
tcactctttc ggcgagcgtg ggcctcttga tggacatgct ttgctgactg agcaaagaag  44760
tatcgagagt gtggcaagaa catataagta ttcccataca tgttgcgtct acggcaaatc  44820
attgagtgca agatctgctt gtccgcatga gaagcctatc tcgcccttta ctcctgaaac  44880
cggatcaaga tgaccgccat cctccaacgc tatactcttc tggtcgtact cttcttatcc  44940
ttgacacttg gtgtatcagc gacgccggca tacaccctct ctaagaccga cggtgagatg  45000
ctcaaaaaag ctcagcttat gcaaatgagc cttcacaccg atcacggaga tagatggaag  45060
aacgttcagc ccgacatcga ctactcccac gtcaacaacc tccagtggga agcggcggcg  45120
gacggcaagg cgagaaaata tactcatgtc gaaactgtct cctctgtcct ccccttcaga  45180
agcaagaagg tctacttcta cagcctaatt catcctggat cccacttagg gcagatgatg  45240
agactgcaac acgatcaagt cgcaagcctc ctttggaagc acgagaagga cgagccgaag  45300
```

-continued gtcattcaca ttgataccct gaaacacagg ccaggcgtga actggggcag tatgcaagac 45360
ctgagggagg tgctgcttat gcactgagca agcagatcat cggcatgccg ttgaacgata 45420
gaatcatccc atagatccac tcagctcaca agagcagctt ttgagctgcc tgagcgcgac 45480
ttgtttactt atgaagtctc tgctacacat caaaccgttt gactcttcaa ggagattgct 45540
cattcgctga agggtaatga cactgcatat acttctgatt tcactgttgc ttgcgtatcg 45600
tgctcttcct cacgaataga cacttcccga gcgtgtgttt cagaagagca atgtgtgagc 45660
ctcatttacc ttccagtgag ggcgtcgtga attaatgtag gatgggtttc gacccacata 45720
cacttccact aagacgttca tcaggctcga agcactgctt tgtgggcagg tgccagcggc 45780
acagagcgct agtggcactt aaaaggaaga cagtctgaga cggagttctc cggcaacagc 45840
tgagcgataa cagctgcctc ctcctcactt tcttctccct acgtgttact acacaagtca 45900
agaagcgcct tcgtcagcac gcaagcgacg ttcacacaat gatggtccta cccaggcagc 45960
tgctttgtct ctgtgtactc tcttttcgat taccatgctc gtagcagcag acagtagctc 46020
accggccacg gctaggcaag tggatgagca aggctttcct ttactgtcag agacggaata 46080
caacatgctc aagactgcta ggcttcgaca gcacaaagtc accttcaagc aaggctatca 46140
cgatcaagcc gcatcctttt accggcaagg aagtttccca aagcctgcac tacgttcgag 46200
tgtatatgct gttgaggacc tggaagctca agcactcagg gaggctaaga ccgaaggagt 46260
cacttacgtc ggcaaacaga aactatcgaa acagccagcc tggttgggcg gaagaaggca 46320
actctatttc tacagcgtag ttcggcctga aggtacctta gggaaacaga tgcgggtagg 46380
cgagaattct ggggagcaga gagccgcgag catgctctgg aaacacgaca ccaagacagg 46440
cgagacaagc ttggtgcaca tcgacgagat tccgtatcat gcagaccttg actggggact 46500
cagcaagttc agaaaggtgt tgtggcttca ctgaagcgca ttcccaatac aaagcgcctg 46560
gcaccggtcc cccgatcaat gcttcggctg cacaggtctc gactcacgcc gctttcctaa 46620
acaccgttac agcctcgttg ttctgcttac cagagagacc cctcttctat cccaagtgac 46680
gaccgatgtg acatacacag tagctaaagt gtgatgcatc ttcggtgact cgacgcaatt 46740
ttaattttat tggtagcttt gcagcagtac cgatgtgcag tctctcaagc accgattggc 46800
ttcctgattg tcgaaggtga gcacagaggg caagtacctc gactgaacga cgcgttgatg 46860
tctcgtgaca tccgaagtat ccactgcaac ggttgcagcg tttgtgagca ccctctctct 46920
caaccttcgt ttcaatagtc aacaacagct agatgagtgc tcagactttg tacgcatcct 46980
tgactctgct ttaggctcga gatcattaac gctttcgcac gaccacctca acgagactgt 47040
cgcacgatcg acttataata ctaccgttgc attgcggatg agtctgtcga gcaacattga 47100
ctcatttgat cgagtcaaca attcgcatct tctggtacaa gcgaccctat ctcatctcat 47160
tttagactct tggggaacac atagctgtcc aagaccggaa gcaacgctcg tgtcgctcct 47220
gtacggccgt caacaccttt gtgatcgctt tctacctgcg ttgattagtg cccgtttcgt 47280
gtcagagcat gtagactctc tccgcgttta ccgaagcaga atcgaagtgt acaaaatgcg 47340
cccctgacgg ctgagcgagt ctctgtcttg ttcccctcag aagctttgca ttcttgtctc 47400
ttcaactttc caacatggtc gtctctttga agcgtcttct cgacctcttc atcctctctg 47460
tccctcttgc catctgcgta gtctcagctg ggaattgggg cagcaagccc aagtcatata 47520
ctggcttcag gctccaagat gaatatgtaa gcaccgaagg acagctgaat cgcatcgaaa 47580
aagagatgct caaaactgcc agggacaagc acattcgccc tatctacgat cgtgctggca 47640
gcgagtggaa atctttcact ccggagccct ttcttcgaga ctacacacac atccctaggt 47700

-continued

```
tcaataccaa ggtgcttgat tccgccacta tgtatggggt cacgtatgta ggccaaaaag  47760
tgtttccagg cgcaaggagg cttcccctca accttgtgaa cggcagaact ggagtaggag  47820
gtgatcggga catctatttc tataccgtga tcccacccca caccgagctc ggacgcgaaa  47880
tgaagcttga cgaaagacgt cggatcgcga ccgtgctcta caagtggaat ccaagtgtta  47940
atgagtggac actgattcac gttgatgagc tccggaactt cgacaacttg aagtgggacc  48000
ttaaagggat aaattctctc aagtttgtct agatcgcaag cctttgcggt gacttttgct  48060
ttacgaggca tcgcccacct tcccgatcgg tagcgctccg tttctagatt tgagtctcat  48120
atacaatcat gtgacagttc tgggctttgt tccaaaagtg tgaagctcgc ttctctgttg  48180
ccttgagcgt gaaagctagc tctgtctagg aaggattgta ttgattgagg atgctaccgg  48240
ttgtgtactg ccggttgtgc tgagcgagaa gaacaggact agcaaggttg acctcatcaa  48300
cggaaccagc gacaagcctg acctatatca ttcggcggta tcaggggctg acaatgtaag  48360
gacgcccatc aatggtcgca atgaagctct agctgcacaa cagcccttga ctacctatcc  48420
accgctaaat gcagagagcc accatccagg agcgagttga ggtggggctc cgatattgta  48480
aagagagctg ctttgcaaac gagtaaatag tctgtaccaa atgtccgacg atactgttcg  48540
ctctctgaga agcccttgat gaccttcttg gcccgtcgcc gtttcctcca gacccaatct  48600
cgcagcatgc tggtcttttc gtcgaagcgg ctcttctgcc tctttatgtc tatgcttttg  48660
ctggtcaatc tcattgaagc agccggcagc tcgaaaggtg ctacagccgg tgacgccgcc  48720
agcgcttcag ccggcacgac tgacctcgcg gccaatgacg ctagacgcct caccaaagac  48780
gatctggaca tgcttttccg agcccgacaa gaacacgccg taccagtcta cacgaacgct  48840
ggagagaaat ggcttcccac actaacgtgc cttatctcgt ccagtaccca aacgctccca  48900
actttgaact tcgggcgctc gaaacagcac acgaatacgg agccaggtat gtcggaaagc  48960
ctgcagacaa tatatccact tcttggaacc gtatctgggg acgagtgagc aggccgcaga  49020
aagacacata ttttctcagc gtcattcatc ctcagcacaa gctcggacag gagatgggct  49080
tagccgataa caaacggatt gctactttgc tttggaagta caacaaggcg aaggatgaag  49140
caaagttggt gcatgtcgac gagctgaatt acgccaaagg cctgaagtgg gagcttgatc  49200
ctttgaaact agtcatccag catcactagt cccacatgaa aggcgagtag tctgaggcgg  49260
cagtctgcct cgacacaaac gctgctttgc ccaccttttg cagaactcgt ctaaagctcg  49320
ttcgcaagat ttctcctatt tcctttctct tcaacccaag atgtgttctt ccttttgtgg  49380
acatgatgaa cgacgtgggt ctgttcggaa gcgacaatgt ttcgtcttct ccataaccca  49440
ttcacactga aatatagcag gggcagaat cacgatgtgt tgcacacaaa gtagggggc  49500
gaaagtgata gttggaggcc cggttcctgt gggcatcggt ctggctttcc cactgttggc  49560
agcagacaaa gacaatcctc tcgtcgtcac gggcaaaagc gagcctctca gtagcagtgg  49620
gctaattttt tgtctatata tgataaagtg attcgccgag gatctagatg cggtcgacct  49680
tcccgtccat cacagaagct ccccattcca tacttccctg cctcagccca atcttccctc  49740
cagtcacgat tatctccgaa tgcaggttct ctctaaccgc ttcctcggcc ttttggccct  49800
cctcttctca cttgtcatcc tgggtgtcgc tgccacccgg cttagtgata aagaggaaga  49860
catgctcaat caggcacgaa gtccttacca gtctcccatc tacgaaaatg ctggtcatgc  49920
atggcagacc tggacacttt atcctaaact tcaggattac tcgcacatcc ctgactttga  49980
gcgtgatgct cttgaaatgg cttataggaa aggtgccatg cacatcagcg acaccatgga  50040
```

-continued

```
cgacaacgac atccgaaaca gggcatggcg ttctggtagc cacagtggta gcaagttggc  50100

cagagatgga catatctact tttacagtat tgttcctcct cgatcttaca tgggactcca  50160

gatgggactt cccgagaaaa accgggtcgc tagtctgctt tggaagcatg atccgggaac  50220

ggggcagacc aagttgattc atgttgacga acttcagcac tataagaacc tacagtggga  50280

catggataag ttggaagaca ttctcaggca tcactgagac agatcattgg ttcagatttg  50340

gcctgcgttg ctacccgttc tagcttctcc tcttagcgac gcacgagttc tttccgccat  50400

caaacaacgt ttcgttactt ctgcctccga gctagtcatt gttagtcaat cgctttccct  50460

gcaatcttag tctcattgac ctcctaatcc aggcctgagc gtttcagatc aaccggtgaa  50520

agcagccaag tagcgcgcgc acaatagtga aggatgttga caaacgcatt caattgcaac  50580

agtgcatgta acggttgttc ccaatcttgc ctaccggctc acctcttcca acaatggtcg  50640

atctgtagca ctctggagtg agcccactag agagacgcga tgaaggacgt gggctatgtt  50700

ggcggtagca ctgctactcc cgctcaacgc acgcccacta gctcaggatc agatgatcaa  50760

gggtgctttc tggtttggga cttgacgctc tgctttcaac cgtctttggt gccgttgaag  50820

cacctccagc tactagcttt gctttacgaa gaggtcaatt tgagtcagag gcatggtata  50880

taaggcccac ctcgaccttt tttccttctt gtcctctcaa gtcattccac cattcctcga  50940

tacttgtcgc agctcaagcg attcgtcaat atggttgcca ttcaccgccg tctcttcctt  51000

ctcctgctcc ttggcgtcat ctttgcaatg accgccaccg ccgcccccacc ctacatcaat  51060

ccggacgaag agatgatcca acactctatc ggcaaacttg gcactgtcta cgccgattcg  51120

ggtgtcacat atgcaccggt caacgccgcg ggcaaatatc gcgtctacaa ctttgaagaa  51180

aaggcgtggg acatggctca cggtggcgca acctatgtcg gtacgcgtca acacttccga  51240

ggaggtcaaa agtatggtca accttggaag tatttctatt ccatcattcc tcctgacaca  51300

ccgttgggac gggagatggg cttgcctgac cacaaactcg cgacggtgct gtggaggtac  51360

gggaacggtc gaaagtcgat ggtggaactt caggaggcgg ataactatat gcatcattct  51420

gggttcaatt ggaacgggat gcaggagctg aaggatgtaa ttggacatca ctgaagctcg  51480

tctgttctgg actggtgatg gtctcgttgc ccgcgctctg acagctgtcg tcgaccagtg  51540

gttgggacgt ggatcgctcc cgcctctcaa gcaa                              51574

<210> SEQ ID NO 2
<211> LENGTH: 18268
<212> TYPE: DNA
<213> ORGANISM: Pseudozyma tsukubaensis
<220> FEATURE:
<223> OTHER INFORMATION: genomic itaconic acid metabolism gene cluster
      in Pseudozym a tsukubaensis

<400> SEQUENCE: 2

ggctgagcgt tttactcgac agaatgcttg aaccaattct tcatcgacgc caactcgtaa     60

cgccagtttg cggcgatcaa ggtgtattgg gattggagaa gaccaaggat gatttagcgg    120

tagatctggg acaggataga gatcggagga ggaggaggaa atcgaaccag ataggtgacc    180

atagggacga atttcctttc ttttttttt ctctttcttt tttcttttct ttttcatttt    240

ctttttttctt ttctttctct ttctcttacg gctgtgctca ctccgagcaa tcaatgtttg    300

tgttctcttt tacagtaaat gtgctcactt cggcggcatg cactaaacat gtcgcaagcg    360

gaagcttaac acgcagcctt aaatcttaca atatctagga tgccggtgtt cagtgtgtgc    420

cttttccttt tccgaacgtc aaaacggata ttgacagagc cagctgttcc ggagatgtgg    480
```

-continued

```
ttcttgtgta agctgcagat acccgggcaa aaggtacaag caggactgcc gggtaggttg    540
aaaggcgatc ccccttgttc ttaccgatgt caatattgat aagagccgat aagtgcaatc    600
acgcaatcag gtagcggatg gtcttgatgt ccgcttcacc aatctcccat tatttgaggc    660
agagccagag gagtacttct acgtccacgg ttaagttagt caagcggaga gctgatagtc    720
atgatcgttg gcgcacgccg aggctgagtt tagactctag atcatacatg attaacctca    780
atagaatgag ttatgcaaaa aaacgggtcc agagcctcgt cgattcaaga tcagcagtga    840
gccgattcaa gcacgaactg aagatcaggt gcaagataac tctgggccta ggacggtcga    900
aggcgcgaac aagcgaggtt tcgagtggac aagtacgaaa cgggggagga actagtccac    960
gatgatcgga tgcacatggg ttacagtcaa gaaggaggga gttcgcaaga agagcgtgat   1020
gcctacaatg tagccgaaac gaaagctatg tgtgtgttcg ggtgggggta aggagccaat   1080
tcgagagaaa gagagagaga gagagagaga gagagagaga gaggaaggga aagagagaga   1140
gagagagaga tggggaggaa ggcagccagg tcgcatcttc tgccctagga gcctgacgaa   1200
cagtatatca acgtatttac tctggttgga ttcaatgaga tagaccagca aatcctcagc   1260
tgttcgcaaa ataccatgta ctggcggagt gatactgaca tcacaacgat tgatttcctt   1320
gcggttggac aatcaaatta gactagtgac ctcgcttgtg tgcgcattag ctgctgcctc   1380
aagatagttt atcataagga attgtctcgg atgtccacgt tgatggtctt ttgcctcgtg   1440
cccgactggc ctttgtgtgc ctgatcttga tcaaagatct ccattcgcac caagaaaatt   1500
tgtacccgac atccgaatcc gaacgtgcag tctattatac acatttcgaa gatggcagct   1560
ttcctgttgc cttagtctct cgcaacgcgt tctcctgctt gctaggaacg cttgagctaa   1620
tttcaatggt tcttagaccc cgaaaagtcc tattaatatc cagtcttttg cgaaatcagt   1680
gtcaattttc acagacgaat cttgcaggcc tacttcattt cgcaacctac agcttcaaca   1740
agcaggtaca aagggttcac ctttatcgat acgtcggttg tataacgcag attttgccgg   1800
aatgactggt ccgatgtgtt tctatggtgt cgaggagcgc aaaaagctcg tcctgccatg   1860
cgtctgaacc gtgcgaatct tgaaccattg caacgagctc agctcggtcc catttttata   1920
tattcaaagc aatccactct gagccgaatg gtcccgtagt gtctcccctc ctgtccatca   1980
atctcgacga aaagaagcga caatgagcct ctcgaacagc aatcacaacg agcgccacaa   2040
cgacgacaac aacatcaatg acgatgattg tgctaacttc tttgagctga tggttcagcc   2100
tgcctcttct tcttcttacg gcccctactt tcccgaccca ggactggcgc ttccagcaat   2160
ttccgatgtc tcatcaacaa cagatacgcg actaccgtca cagctcggag tgaccccatt   2220
cagtcatcag acatcgccca tccgatccgc agatgaagga gagaagacga caacaaccgc   2280
atcatacaaa agaaagcatt ccgaggtgga gaaagaccgt cgaagaatca tctcaaacgg   2340
atttgcagtg agtttccctc ttcttctacc ataaagttca ggctggttga gctgaagtcg   2400
acgtttggca atatttgtgt agatcttgca gaacgtcctc cataacgact caacttccaa   2460
acccatctcg aaagcgaccc tacttcaaca agcgtgcgac gaaatccgtg aactgcgcaa   2520
aaaacttgat acgagcatta ccatcatctc ccgctatggt ctcgaaaatt tgtttcaggt   2580
ggctccaacc cccaattctt tgagcaatgc ttctcctccc aatggtacga gtagggctta   2640
ccctacctat tcgaacgacc tcggcccgga tcgtttccaa gactcgcggc gtagttccac   2700
ttcggcgacg agtgtgtctg gatctcaata taacaatggc gctgccgcta aggaggatgg   2760
aaacgagagg cgtaattcca acgtgaagag gagaagttct tacaccaaca gcatcaacag   2820
cagcttcgag tcatccgagg aggacactct gaatagcagt tgcgacaaca caagtgactt   2880
```

-continued cgacgaaagc gttggcagca gcgaaagcga aagtgaaaca aacaacagga caagaaacag 2940
aaacagaacc aagagggcaa tggcaacagc aaagctcaaa gaccgagacc gcgccaaagc 3000
tcgaaccgca cccaagccac acagcaatcg cttatcgcct gcatccacta taacgccaag 3060
tgagatgagc agcagcttag ccagcccaaa cacctcttca caagagcata tccagcaagc 3120
catcttgtca ttgctcctcg aattgccgaa acatctggag aatgtgcaca agtcgaagcg 3180
tccttcctct cagcagccaa gcacacagat tgatcaaacc ggaaaccgga ctacgacggt 3240
aacgaagacc aggagacggc accgatgatc ttgatcaacc ctgcttgcct ccacttccgt 3300
tgtgtagata caaagtctga caaccctaat ctatgtgtat atgggcgtga tcccacttca 3360
tcgactacgt tcgtgcgtta ccgagagcgt tctgttgtga gatagtatga ttgctgtctt 3420
gacaaaggca tacgctcttc ggcctttttc tggtgtgtgt gcttgacaca aattcgggga 3480
tcatgctagg ctcggtggtg gccaaacact cacatacatg cagtggaggg tgggagacga 3540
atcaaagttt cccaacttgt gagtgagtcg ctaacgagct tcaagccgtg gccataagag 3600
gttcgattgc aagaaagcag taaaggcaat gtagagaagc gaaacaaggg cggaacgcaa 3660
gggagagtgc aaaaaggaac gaagatgctg gatcgcctcg gaggcgatca gcagcgaaga 3720
attgatacgc atgacggctg caggcatcga gctgagctgt gtctctgctt agtccacgcc 3780
tcaagcctag tgaacctagc actcatatca agcgctctgc atggctaatt cgttacagtg 3840
caaatctgaa cgcgaccaag cctggaagac ggatcatctt gtatgtacag aagaaattca 3900
aaccctaacg aagaacgcca aagccaacag gaatcaaaac tcgggaccgg cgagaagcca 3960
aactacctgt tcatacacgc taaaaatgac tcctccacta acgatgaggc gcatactacg 4020
tgatacggaa ccacgccaca gagctgctat gccctctgta ccgatggtgt cggtcaagca 4080
gtgccacgtg gatcggtagc gcgaagcgtc gatggcctgc atcctcgttt tgagaacgtc 4140
aaatggcatg gtcccataca cggcgacaac gccagatgta gcaccgatgg agaaagtggt 4200
caaccaattg acgaaggatg aacccttgcc ttgggctttg ggaatgaaat ctcgcatagc 4260
agagtatgta cctagtcgga tcgctgaggc cgagccttgg cgtagaatga ctggaaatac 4320
acctttgtag ataccgccaa acccttcttg tcggatgatc gaggcggttc cacggaagag 4380
accctgttcg tagcgtggtt tggcacgctt gccgtcgtcg atgagttttg tttctggtga 4440
aagcaataca gcgcaaggtc agtctgtctc gcccttcttt ggttctgttc tgcgagtttg 4500
cgtgggcact cactgatcgt ttcactcggt gtcacagcga atatggcttc cagcgtgcca 4560
gcgcccattc ctgcaatgta gttgctaccg ctcgataatt tcccctgcga aagatttcag 4620
tgtcagtcta tttcctaatg catccatgct aggggaaaac actcactgtt gatttgttct 4680
tgagcatatt tcgaaaattc tcaaaagcca aaaagcgaac accagccttg gaagcgttgc 4740
cgacaactac agccgaacaa ccacgaaaga gccctctagg cccttctttt tcaagtgttg 4800
atcggaaaac atccaatggt gaaagacgtt cacgattgcc gtgagtatct cgctgtgcga 4860
actgtgtaac tgtcttgaga tactcgatgg ggaaagtggc cactaaggaa gacaagaaga 4920
ttgtaaggta aaattactag caaaatggac gaggcgaaag cgatagaact cacctccttc 4980
aacagcgcct gcagtcgcac cggccagcac cgagactgaa ggagagatgt tgcgttgaac 5040
ggacggcatc ctagctgatt ttgttctttg ctgtttgtaa tcgggaaagg cgctgtcccc 5100
gctcaggaca agcagagagt gtttgggcct tatgaacctt tcagcgagga ccagctctct 5160
tactatttgt tttcagggtt ttccaagaga cacaggaaaa tagcctcctt actcaatcta 5220

-continued

```
tggtgttcga acccggtcgt ggccatatag gctacctatg caatcacaca agttattcgg   5280
cgctcagttg tggcgatcgg tctgagataa tttgctgagc tgcagctttt cgtgcagggc   5340
gacctcgtca cgctcatgct ttttcaagcc aagcactatc acgcttgact aggagtaccg   5400
tggtggtctc tcagaatgtt gtgtccaaac cacgtgttgt gcccgaacca gctatcaagt   5460
gctcgcacga ttcgcaaagg aaactatcga gctttgctca gcatattcag cgtgacaagc   5520
acgatgcctc atgtcaattc agctcaatct catgcaagac ctgcgacaga gagtgcgacc   5580
atggggagta aatgaacgtg accaagtaag tcagataaga gaccaggaag gcataaatct   5640
gccacctcca cgaggtgttt gagacctgat aggagcatga caaggagcag acaaaagcga   5700
acgagatcag gctttcacac agttgcacga gagattatga ggatttgaat ctgacgatat   5760
gattggaccg gcaaaatgtt gcgatgagca aaatggcact gtaaggatgt gaaagactgc   5820
tctcataggg ctgtggaatg cgtgccgcgg tagctagaca cagtgctgtc cggcatattg   5880
taatatagct cactttcctt cccttccgaa ccaagtggaa tgatgtgaga tctatcttta   5940
cctcttccca atgcgagcgc cagcgactga tatgccctat cgagcatctc cgcgctggtt   6000
ggagtgacgg gtgagatgat cggtatttca accgaagggt gccgatcagg catagtataa   6060
tagacgcggg cgtgtgcaat cagggctacg gaacgctcaa cgtgggcaat atctagcgaa   6120
cggggtgagt cgctttcggc ggctgtaagt ccaatctcga gaacgccact aggatgttcg   6180
atagagatgc gacgctgagg cgtgtaggga ggggtggtat cgccaggcga tgaagagagc   6240
gaaggagtgc gtgacgaaaa gatgtccgag accaccgttc caggtacata ggcggctccg   6300
gcggtgcaga tggcaccggt gacggcgtgt gcgttgtggc aagttttggg agtgaagtct   6360
gttggacaaa aaggaactga gaatcagcag ccgtcaatca ttcaacaagg tacggtcaat   6420
tcagcgttga gaacttacac cgtgccgtaa aagtggtgca attggaacct ggtccgatga   6480
gagacaattt gggcaccacg ctagaagaaa catcacccca gcccattcgt cgacctgcct   6540
ccaggcgtac acgttccagt cgagatagca aggcagtgtc cgcattgagc gtcgctgggg   6600
tctcgaaacc tgtgatacca acatcggctt gacgaacaaa aacaacaggg atggccgaat   6660
cgatgacgga tacctcgagt ccctcgattg agtcagtggc attgccagtt ggaagaagct   6720
tgcctgtgca tgcacccacg gtattaagga agcgtaagct gacgcgagcc gaaggacgct   6780
gcaagcccgt atcgtccaca tctttgtagt ggactcgacc atcttgaacc ggaatgagga   6840
gctcggatgc ctggttggag ttgagattaa agatgcgcac aaggcaggtg gtgtcggatg   6900
gatgaggctt gactagacct cgctcgatcg cgaaggcagc caccccgctc atcaaattgc   6960
cgcagttggg tgctgtgtcg acgatgcgct cattgatgcc aacttggcaa aagaggtagt   7020
caacatcgga gtgatcgctc tgtgcacttg gcgagactat ggccactttt gaagtcagag   7080
aattgccacc ccccataccg tcgatctgca gtggatgtcc ggaacccatg atggacagca   7140
gcgccgcatc acgagcgctt ggctcggatg gcaggtcact tgccaagagg tataagccac   7200
gactggtgcc agcgcggtaa attgtggtct caatgcctcg cagcatcgtg aagctgtcag   7260
tgtgactaac gacaaaagcc aataagatgg acggctaacc aaaacgtcgt tatatgatct   7320
ttcttcgcct gagttcttcg gtcgaggcca tggaagtacc tactatcctt ctgaaccact   7380
tgacacgtcc cgcaagagga ttcgacattc tcgattgacg taggtgtcaa attgtgcgtg   7440
aaccaccacc accacttcaa ggcacgaggg ctagacgtga gatttagact agtagacaat   7500
gagcctggct gggagaatgc gtgcaacgct gtcaaacagt gcatttgccg gcggtgtcct   7560
cagaagctgc acgcgatggt cacgctcctg aattgtgggt gagagcggac gtagcctgat   7620
```

-continued

```
ttaaaattta tctaaaggta ttattaatat taaaaatgag atacgttcaa cgatcagcag   7680
aagaatgctt ttggctatcg cagtttgtat cgaatttccc atcggcttta ttgaaattat   7740
aatacggtgt attatactgt tcagtacagt acagtagtac tgtacgtaaa tgaccatata   7800
ctgcgcccgc tcttacttag cactgctatt ttcaaagctt ttccaatgga acgacaggag   7860
acgttctctt gttgatcgac gctgaatttt gtttaccgac aatccgccta cgccgctgca   7920
gcaaggaatt tcacacagta gcgtagcatg aaccgtttcg tcggacggtg tcggatttcg   7980
aaatcgagaa cacggcggac aaggtgtcaa ttgctaacag cgtgcaaatc cgctgcacaa   8040
gaagagcgtg cccatgcttc ttggccctac atactgctct tatcgaccct tcggacatgc   8100
aaagggtcat cttctgcctg aagaacatgc ttcgtctgac ccaagaatgt acggcctgtc   8160
caggtcaggt actcgtctcc gatccaagga ggatgataag cttcgtggca ctaagcggtc   8220
ggttcgtctc acaaacgcca taccaccgcc tttgccgtgc attcccatag tggccttccg   8280
aagctcgacc acttcacatc ccaatgtagc tataaaatcc aagcttgaag agctcattac   8340
tgatgcctag gagtggcgtt tactgctcct tccttcgaag cgcccatcgg ccctcacttc   8400
cgtagacatg cttccacaga cacctgttcc agattaccgt ctcagcatga gatattcgac   8460
agacagcgtc gcagcatcgc aagcgttaac aacgcctgaa gcagctccaa gtatttccca   8520
tcacgcagac acgggcgagg ttcaacaggc gcatagcggc gatgacggcg cgctcgaaga   8580
gggcgcaatt gctcactcaa gtaaggaagg gtcacaacga gatcagcaaa cggagcttta   8640
ctgtgctttc acaaagggca ccaagctctt cgtcgtcttg tccgtgtcta tcgcgggctt   8700
tttctcgcca ttctccatca atatatatat ccctgcgttg cctcagatct cgaagctact   8760
acatacatcg gaaggtgagt gagacgattt ctcgtagaga cagtttccca gaagcagctc   8820
ctcatcatca tattttgtct tattgtagcg gctactaatg taacggtaac cgtctacatg   8880
atcgcacaag gcctctcgcc ggtcatctgg gcacctcttt cagatgtaag tccccatttt   8940
atgtgacgcc tgtctctgtt gtaagatgtt tccacaggat caatctctga aatttctcgc   9000
ctgtcaaatc ggcacgtaca ggtttttggc cgcagaccca tctacattgc aactttcctc   9060
gtttttttcg tcgccaatct tgggctttcg ttcaccaatg tctactggct cttggtcgtc   9120
ttgcgtatgg ttcaagccgc aggagcatgc agcgccatcg ctattggcgc aggaacgatt   9180
ggcgatgtta ccgagcgcaa ggaacgagga agttatatgg gctattatgc gcttgcccaa   9240
tatactggtc cagccatcgg gcccgtaatt ggaggtgcgc tttcgcaaag atgggattac   9300
cattctacct tcttcttcct cagtgccgtt tctggtgtct ttctgatctt catggccttc   9360
ttcttacttg aaacgcttcg tgttctagtg gggaacggaa gtgcacgcac attcggcatc   9420
tatcgcactt tagtgggacc cagactggtc aagtcgacgg caaattcgat gcgtccaagg   9480
atgaagagtc cgcttgaagg tcgactcgaa tttggattcc atcgtccatt tttggtgttt   9540
gcacgccccg agactagcct ggcaatcctg gctttttcga tggtgtatgc aacatactat   9600
ctatcgtctg cctctttgcc ttatctcttc aagcaagtat atggtctaca cgagctactc   9660
attggggtat gcttcgtgcc tagtggtgtt ggttgtgcct tgggcacggt gctcgctggc   9720
aagatcctcg attcggacta tcgacgcgcg ttagacaaga acaagtcggg tgtcaaggtt   9780
acgcgcgcac ggctgcagtc ggcctggatc tacttgccag gctatgcctc ctcgcttcta   9840
gcgtacggat ggtgtgttcg ggcgcatacc cacatcgccg ctcccatcct tttcagtttt   9900
acacgtaagt gagaattcaa tcttccgaat cgtggatcct gttcgtgtac agcagtgctg   9960
```

-continued

```
actctgcctt tcaattaatc tacgaaacag tcggcatgtt ttcaacaatg tacttcacca  10020
acatcaacac actcgttgtg gatctgtacc cgggcaaggc agctactgcc acagctgctg  10080
ttaacgtagg gcgttgctta ctcggcgctg tggctgtggc catcgtacaa ccaatgaccg  10140
atgctatggg cgctggatgg acattcacag tcggcgcgct ccttgctctg ttcatcggtc  10200
tgatttgcca gacactcatt cactttcatg gcgagaagtg ggcagctcgc aagcactctt  10260
gatttgattt ctacaatgct atcgctctgt tcaacatact gtggactcaa ttcacatgcc  10320
tctgaaatgc aaaatcatat cacccagctg gtcgttaaat tcttcagaaa ttacctggac  10380
tttgaaaatg ttcatcttca gtagcgggtt tctcattcag cagatctggc atgaaatgct  10440
ccggacctac ctgaatcggt cgcgaagcaa gaccatatga ctagggggtc cttcgtgtgt  10500
gcctcggggt tggtatgtac agtacatctg tcatgatcag atcaattttc atgataagag  10560
acgtttgcgc agcggcaacg gcacccttca cgtgatttgc acggtccatg gaacatgaac  10620
catgcgtgat ttgcacgcag acgaatctga gcgtcctctc accttcggcg acagcgactt  10680
ggtcacgcga acaaggcatg gtttcaacat cacaccacga ctgcctcgcc ttgttcgaaa  10740
ctgcttcaac actcagtatc actgtactga ggtgactggg gtcgcggttg aagatcaagg  10800
ccggcctggc aaattttgta taaaattgta aatgaaccag gcagtcatgt tgtcactcac  10860
ataggaagtt gtccttggag ccagaatcga ccaagttcct tacctcatca tctcactatg  10920
gcaccttctc tcaacgcgaa ctcaacagcc gatcggcgga acgccactgc tgcccctgac  10980
cttctatccg gcaataaagc cggtggtggc ctcaagcttt ccggattacc agacctctcc  11040
gactcggcag gcaccttgag cgacgtattt ggaacgccgg ccatgcgcct catctggtct  11100
gaccaaaatc gagttgcttg ctacctcgag atcgaggcag cgctcgccgt tgtccaagct  11160
gaactcggta tcatcccaaa gcacgccgct caggagatcg tcaaacactg ccgtgtagat  11220
gagatcgatt gggctctgta caagcaaaag accgaattga tcggctatcc tgtcttggga  11280
atcgtccagc agctggttgc caactgcaaa gatggcttgg gagagtactg tcattggggc  11340
gctacgacac aagatatcac cgacacagct accattatgc agattcgtca gtcgctcgcc  11400
ctcgttaagg agaagctgtg cagcatcgtt gcgagccttc ggtacttggc ggaaaagcac  11460
cgcaaccttc ccatggctgc gcgttcgaat ctcaagcaag ccgtgccaat aacttttggt  11520
ttcaagatgg cgcgcttctt ggccactttc cgccgacatc aggagcgtct ggccgagctc  11580
gagaagagaa catacacact agaattcggc ggtgcggcgg gcaacttgtc ctcgttaggc  11640
gaaaagggta ttgcgacgca cgatgcactc gccaagatgc ttgacctttc acccgctgac  11700
atcgcctggc ataccgaaca cgatcgcttt gcagaggtag gtgccttcct gggtcttctg  11760
acgggaacgc tagccaaact cgccacagac atcaaactca tgtcgcagac cgaggtgggt  11820
gaggtcgggg agccattcat ctcaaaccgt ggctcatcgt ccaccatgcc gcagaagaac  11880
aacccgattt cgtgcgtgta tattcatgcc tgtgccgcca atgtccgtca gggaactgct  11940
gcgctgttgg atgccatgca gtcggatcac gagcgtggca ctggaccttg ggagatcatc  12000
tgggttcaac tcccgctcat gatgaactgg tcggcagcgg ctctggccaa tgccgacttc  12060
attttgaagg gattgcaggt cttccccgat gccatggtcc gaaacctggc cttgtccaag  12120
ggcttgatcg tctccgaagc agtcatgatg gcgctcggcg acactctcgg ccgccagtac  12180
gcccatgacg ccgtctacga gtgctgtcga gcggcctttg agcataacag accgttgctt  12240
gatgttcttc tcgagaacca agaaatagct agcaagctga agcgtgccga gctagagagg  12300
ctttgcgagc cagccaatta tcttggacaa tgctcccaat ggatcgatcg tgtcttgcta  12360
```

-continued

```
cctccttcca cgtgaattaa gtagtgcgct tcagttcaac ttgttcaaat gctcaccgca  12420
tttgatgctt ctttgcttgc caacctttct tttaatgtag ctattgttta attgtatata  12480
ttacgggttc atttttgaag atgacggttc caaggcttca ctctcacgga ggcatgttac  12540
tcaccatcac cattacaagg ctgcgtcagc gaagtcaacc atcatcaaga cgatacaaaa  12600
ggtgggcatg gctcggcagc caccaccact acttctagtg caagtgcagc tgctacctct  12660
gctactgcag cggctcagga agccagccag accgccaaga cctcgacaga atgccactct  12720
cacgccgatg gctctcttca ctgcggctcg cactgaacag atctttggca tcggccacgg  12780
aatctagatt cgatttgagc cactaccaat caattacttc tgcaaaatgt atatagttcg  12840
cagcaacatt gacatggttc gaacaaacac aggaagcagt gcagaggcga acgtccttcg  12900
atactttctg cacagcgccg aaatccatga gcttgcccgt gatggaatga agatgaaaat  12960
aagactcaaa tgaagccaag caactcattt gcaggcgatg cactcactct ggaaagttat  13020
tgaccaacac atgaattgcc atgcgaatcg tggctgaaca agagtcgacg tgtcggaccg  13080
acgaaagact tgaaggtcac cagaggttgt ggttcagttt tctgttcaag cgctatatca  13140
caacttgcct gtggaattag actgttccac caatgttcca taggccatga ttgagtgtct  13200
gttccagcaa caatggatta gcttgtggaa cacgtttcaa acattgaaat tttttcgttg  13260
tgtcacaaat tttaatataa atgttgacgt cacatttgtt ttgccagaca gatgtacacg  13320
aaattccgac gaatatcccg gctggcgagg ttccagagtc tcggctgtcc aacattgcca  13380
aagatcgacg gaacgccgta acgaatgcgc ataaaaccgt tggcactaca gaaattccgg  13440
gaacacgctg accggatcaa acaacggctt ttgacccgtc ctcttgaagc tgtccaccta  13500
ctcatcagct ctggtctaag cttgctggaa tcttatgtag aggcatggct gcagtcagct  13560
ccggaacaag atcgtcaagg aagaagtttt gatcatcttt tgaggcctct ccctgaatct  13620
acttggaaag gacggcgtct attttggccg ggtctagcct cggaactcca aacaattgtt  13680
ctagagaaag aaaaaaataa aaaaatgtac aaattatact tcacgtttga agcctgtatt  13740
aagtgacccg taccctcatt tgtaccagag cagcggttag ccttgatcga ctgagcaata  13800
gcgccgaaat ggtggaaaag tgtgccgccc gtttgccgag tctggacgcg ctatcccgaa  13860
caattctctt tggtaagggt tggttgggct tttaaatgac gtttgaaggc cgtcgtcacc  13920
tcggacgttt tgtgggagta atgatggatg actctgttca ctcgcggtct tgtgtccttt  13980
cacggctccc ccgctgtggc tgaattctgg tacagggtgt tctgtaaccc aaccaaactg  14040
aagagtgttt tgtctttgac agcagactat gcaccataat gggatacttg acacgaaggg  14100
atataaaatg aaccacccta atcagcaaac acagcccaaa cagctcctac ttccgaacaa  14160
ttcgaacctc gagctaatcc acggctcaaa tcaagcgaga accaaccaac caagatgcct  14220
ttcgctcgaa ccctgctgct ctcggccata gtgggctcgg ctgccttgac cacagcagct  14280
cccgtttccc ctgcttgtca accagccctt cggcaatggg gtcaaatcac cttcaatgaa  14340
attgctctca gcataggcga cgacggcgat tttgtgattg gtgggccgaa tcccataaat  14400
tttgcagtcg ccacctgctc gaaggaatac catggtaaat acgaggttca gggcgaagcg  14460
taccttgtcg acgctacaga ctccagtcaa tgcctgactg cgagcaatct tgaccagcag  14520
aactcaacgt tctcattcca agattgtcgt tacaacggcg ctggagatat ctcggcctcg  14580
caattctttg catattacac tgactacgat gcagccaata ccctgaaagc gtacttcaac  14640
ggcgaaatcc ccagagtagt caatgccact cagcctccca tctacaatct caagagtcaa  14700
```

-continued

```
tatgataagc tgagctttga aggcagtctc gggaaattga tggtcgatta cacccccaac  14760
ctctcttcgg ttccttcggc ttcgctcgca ataccgaaag gataccttcc cgtgactgca  14820
cctccgcaga ctgatgatcc tgcgctgaag tgtggcactt atcaagtcgg ccagctccac  14880
ttcaacaatc tgacttcgag ctcgaatcag tataatgggc ctctgaatag cggatgggag  14940
gccgacccac acactaagga caagttcatc tttgaacagt gcgactactc accctcgggt  15000
attaaggttc aaaacgacgt tgtttatggt cgtctccgtc ctgcaaccga gcttcaagac  15060
tgcaaattcc aatgctatga gttcatgggt caaggggacg gaggttggat catgggtctc  15120
caagaacaac cctgcggata cgcgaccgct tcctccaaag aggccgccca ggagagcttc  15180
gacgtgatca agctcgacaa gtcggacaac acggttgaat gggtcacctt caagaacgga  15240
actcaaacca gcgtgtattc ggcctacact caagtcgact atgaccagga gtatgacgtg  15300
tctcaacaca tttggaaccc gctcgggatc ggctatattc agctctcccc ggacaatgca  15360
aacctgacca aatttccgcc tggtaaagtg agcttcgtcc ccaatgcgta agtcaaccag  15420
tcctcgcagt ccaagcttcc agtctctctc gctgcactca gtcatgcaaa taggatgcga  15480
cctcttatcc caagctccgc tttgagtaat tcttcgtatg ccttgttgca atatgcgagt  15540
aagttttgct gtgcctaatg ctgcggcact gagattatgt ttagttgact acgtctatcg  15600
agaaattctg gtggacttgg tcgcatgctt gatacgagta ggtaagtgta aagatgccga  15660
caagggatgc aatgccctag cattcattgc tggacctgga acggagtcct gttggagtgg  15720
cgccgactga attgcttcag tctgagcgct accattctgc gtccacaggc cgaaattcgc  15780
gtttcgggcc gagcgtgctt cgagacaccc cctttgctgg aaggagactg ttggttggac  15840
ccaacgaagc gtccgtcaag tttacctcgt ggatatactt tgcggaggca ctgcatagct  15900
tttgcatcaa ggcatcagct tgcttgggga gcaatggggc atcgaggcac agatcctgcc  15960
agacgaaacc accaaagagc tctttgcatt tggcgattgc cacgatagtt ccacctgggt  16020
gtttgcgcgc agcggttgcc aaagcgcaac caaaggcaga gcgggcagcg ttatcgtgtg  16080
agctcatacc ggcgaatcgc tccatcgcag ccatcagcac tgcgtcaaag gctggctgtg  16140
gtgcgtctaa caactgagtc aatcgttcac tcgcgtgtgc aaatccatgt agaagttgtg  16200
gctcaagttc agggcgtgcg gctgcctcag ccaacagtgc aatcacaatg tcctcgatgg  16260
agactcttcc agatgaatcg ctgacggtag ggatcggcaa atcatcaagc aaagtaagcc  16320
ggccttgggt gcactgtcct cgttcttgaa gctcaagctg tcgtaattcg taaaggaagc  16380
gggggttggg ctccacctgg ggtcgagaag atctgagttg ggctagggcg tcagccaaag  16440
agatcttttc ccagatgata cgtactgcca agacgagggt agcgctacgt gagacgcctt  16500
cgtagcagtg cactagcacc tttccgcccg tctggcatgc ttgctcgatc cattttgcag  16560
cgtcagcaaa gtaaggaaaa aggcgctcgc tagtgctgtc tctgacatac agatgccagt  16620
attggaattg gtcgggatgg aggtcttgaa cttcgcgagc cgcattgagg atgtgagtga  16680
tgccaagcga tttgaggcac tgcgcgtcag ctgcctctcg cacacctcca agataaaggc  16740
catccacgag aaaggatggc ggatctgaat agattttcag catgcgtgga acggcaatgg  16800
tggcaatgtg gatgaatgtg aactcctaat gcgcgaaccg aaggctttca aaagaggcgg  16860
tctctttatc gatcttgcag taccaagcac cctgctgtaa gacgagcgca gactgtatgt  16920
gagagcggac ggaagtaacg aagtgtcata caaggattgc atctaggagg aggttgatac  16980
ttcaactagc tcccattcac aagacagagt cacgttagat tctcgagcga gcgcacgatg  17040
tgagaacccg taagcgtgac acctgatgag aagtgacgca cgtgccaaca gcagtgaaca  17100
```

-continued ttttcggcta aacgccaaaa gagcctggac tagatcaccg ggatcggcac cacatgtcat 17160
ttagaatgct tagaatgcgc aagggaaaat ctgtttgact ggcagccaag tcttctgaaa 17220
gtatagtgca tcactgtcac aggcgtcccg agtcagctgc ggaaaagtcg gactcaatct 17280
ctttcgatcc gaaacggatt ccacaccatt taggcggtgg tttttgggga atatcaacct 17340
gcttgctgaa acaagacggg tcttgctgga ttttgaggaa atgtcacagc agcagagtgc 17400
gatctgaatt tgctggaaat ttcaaaagtg gaggcagcac agcgcagcgc agacgcgtca 17460
aatttggatt gggtggaggg aatacaaatt ccaaccacag cggtggcaca gcggtggatg 17520
gtcggactga aattttgtat tgcccagatt tgggagacgg tcaacactgt tgtggtgcac 17580
ctcaccagat gaattgcaac aatttggcac gccatcctga gaaggcaggt tgcaacaaat 17640
ttttgaatat cagcatagca ggctgtaaca aaaaagacgg tctgtaacaa caataatatt 17700
cattttcaga tgacaggtag taacaagtgg aaggcgggct gtcaataaat ttttcaaatg 17760
ccttcatttc aagcatgacg gtctgtaagc cccagtatca atttggattc aaccaaaata 17820
gcagtttggc ataccagact gcttgaaaga tgacggtcta tcaatatctc tgtgcagttt 17880
aaatagagat gtgagagaat tctgttggtt gactgttgtt tgtcagcccc accacatccc 17940
aaccaaccat gttgtttaca acctgtcctg cctgcactta cacatattca accagcaaca 18000
tcaccaacca catttgcaaa gctcacaagg gtgtgtctgt gacagcagca gcagccaaag 18060
cttgtggatt ggttgcatgc ttgtgtggac agacgttgct caacaaggca gcgctggcac 18120
ggcaccaggg aataaggaaa tgccagcttg ctgtctccca gcctttgcaa ccatctccgt 18180
tggctgctgt tttaaatttg cagccatcag ccaccccgtt gctgttgccg ttgccatctc 18240
caatttcaag tccatcgact cccaccag 18268

<210> SEQ ID NO 3
<211> LENGTH: 283
<212> TYPE: PRT
<213> ORGANISM: Pseudozyma tsukubaensis
<220> FEATURE:
<223> OTHER INFORMATION: Pseudog4085.t1

<400> SEQUENCE: 3

Met Thr Arg Leu Ile Ala Leu Gly Ser Ser Phe Ala Ala Gly Pro Gly
1 5 10 15

Ile Pro Pro Gln Val Asp Thr Asp Ala Gly Arg Ser Ala Asn Asn Tyr
20 25 30

Pro Asn Tyr Leu Ala Arg Arg Leu Asn Leu Asp Pro Asn Asn Thr Asp
35 40 45

Glu Phe Leu Asp Leu Ser Val Ser Ser Ala Thr Leu Leu Asn Leu Ile
50 55 60

Ser Glu Pro Gln Asp Thr Gly Lys Lys Val Tyr Ala Pro Gln Leu Ser
65 70 75 80

Leu Leu Pro Glu Leu Lys Glu Gly Asp Asp Gly Ser Asp Ala Ile Val
85 90 95

Thr Ile Thr Gly Gly Gly Asn Asp Met Phe Tyr Ile Gly Ser Met Phe
100 105 110

Gly Leu Thr Phe Lys Asn Thr Trp Trp Gly Arg Leu Leu Ser Tyr Phe
115 120 125

Val Leu Ser Lys Glu Glu Lys Glu His Phe Glu His Pro Thr Ile Ala
130 135 140

Ser Pro Asp Glu Ile Ser Gln Arg Phe Ala Thr Leu Ile Asp Gly Val

```
145                 150                 155                 160

Gln Lys Lys Tyr Pro Lys Ala Thr Ile Tyr Leu Val Glu Tyr His Ala
                165                 170                 175

Met Met Gly Pro Asp Thr Lys Ala Trp Arg Asp Val Cys Trp Asp Gln
            180                 185                 190

Gln Gln Val Gln Lys Tyr Ile Glu Met Ala Glu Gln Leu Gln Ser Leu
        195                 200                 205

Tyr Ala Lys Ala Ala Glu Gly Arg Asn Asn Val Tyr Val Val Pro Leu
    210                 215                 220

Ala Glu Glu Ser Lys Leu Lys His Ala Leu Gly Ser Lys Glu Pro Trp
225                 230                 235                 240

Val Ser Asp Gly Ser Phe Trp Asn Phe Lys Asn Arg Cys Ala Tyr His
                245                 250                 255

Pro Asn Gln Ala Gly Met Lys Ala Ala Ala Asp Ile Ile Tyr Asp Phe
            260                 265                 270

His Thr Gln Arg Ser Asn Ser Lys Ala Ala Ser
        275                 280
```

<210> SEQ ID NO 4
<211> LENGTH: 852
<212> TYPE: DNA
<213> ORGANISM: Pseudozyma tsukubaensis
<220> FEATURE:
<223> OTHER INFORMATION: Pseudog4085.t1

<400> SEQUENCE: 4

```
atgacaaggt tgatcgcgtt gggctcatcg ttcgccgctg ggccaggcat ccctcctcaa     60

gtagacactg acgctggtcg aagtgcaaac aactatccca actacttggc gcgtagactc    120

aatctcgacc cgaacaacac ggatgaattt ctcgaccttt cggtgtcaag tgcgacgcta    180

ctcaatttga tctccgaacc gcaagatact ggaaagaaag tctacgcccc tcaactaagt    240

cttcttcccg aacttaagga aggagatgat ggcagcgatg cgatagtcac gatcaccggt    300

gggggcaatg acatgttcta catcgggagt atgttcggtc tgacgttcaa gaacacatgg    360

tggggtagat tgttgtcgta ttttgtcttg tcgaaagaag agaaggagca ctttgaacac    420

cccaccatcg cttcgccaga cgagatctcc caaagattcg caaccttgat cgatggcgtc    480

cagaaaaagt atccaaaagc gacgatctac ctggtcgaat accacgccat gatgggaccc    540

gatacaaaag cgtggaggga cgtatgttgg gatcagcaac aagtgcaaaa gtacatcgag    600

atggccgaac agcttcaatc gctctacgcc aaggcagcgg aagggaggaa taacgtctat    660

gtcgttccgc tagcagaaga gagcaagctc aagcacgcac tcggatcaaa agagccttgg    720

gtatcagacg gctcgttctg gaacttcaaa aacagatgcg cataccaccc caaccaggcc    780

ggcatgaaag ctgccgccga tatcatttac gactttcaca cacagcgttc caactcgaaa    840

gcagcttcat ga                                                        852
```

<210> SEQ ID NO 5
<211> LENGTH: 767
<212> TYPE: PRT
<213> ORGANISM: Pseudozyma tsukubaensis
<220> FEATURE:
<223> OTHER INFORMATION: Pseudog4086.t1

<400> SEQUENCE: 5

```
Met Pro Tyr Thr Pro Pro Arg Ser Ser Gln Pro Pro Lys Gly Leu Pro
1               5                   10                  15
```

```
Phe Glu Leu Ser Leu Ser Thr His Pro Gly Ala Gln His Asn Arg Ser
            20                  25                  30

Ser Leu Thr Pro Val Ser Phe Leu Leu Arg Ala Ala Leu Ile Thr Pro
        35                  40                  45

Arg Lys Leu Ala Ile Thr His Pro Glu Lys Gly Tyr Ser Phe Thr Tyr
    50                  55                  60

Glu Gln Trp Ala Ala Arg Thr Leu Ser Leu Ala Phe Ala Leu Arg Ser
65                  70                  75                  80

Leu Pro Ala Phe Lys Ile Gly Asp Arg Val Ala Val Ile Ser Pro Asn
                85                  90                  95

Ala Pro Leu Ile Ala Asp Ala His Trp Gly Ile Pro Ala Val Gly Gly
            100                 105                 110

Ile Ile Thr Pro Ile Asn Ile Arg Asn Thr Pro Lys Glu Val Ala Tyr
        115                 120                 125

Val Leu Glu His Ser Gly Ser Thr Val Ile Leu Val Asp His Glu Phe
    130                 135                 140

Thr His Leu Val Pro Glu Asn Pro Gly Pro Gly Ile Thr Val Ile Val
145                 150                 155                 160

Ser Lys Asp Ser Gly Gly Gln Glu Ala Asp Asp Pro Tyr Glu Lys Phe
                165                 170                 175

Leu Asp Arg Gly Phe Leu Glu Trp Gln Arg Ala Glu Gln Ala Glu Leu
            180                 185                 190

Lys Ala Tyr Lys Ser Arg Thr Arg Pro Ser Ala Glu Pro Lys Thr Gly
        195                 200                 205

Trp Lys Leu Ile Glu Ala Pro Gln Asp Glu Glu Gln Pro Ile Ala Leu
    210                 215                 220

Cys Tyr Thr Ser Gly Thr Thr Gly Arg Pro Lys Gly Val Leu Thr Asn
225                 230                 235                 240

His Arg Gly Ala Tyr Leu Ser Ala Val Ala Asn Ala Phe Glu Ala His
                245                 250                 255

Leu Thr Gln Asp Ser Val Tyr Leu Trp Val Leu Pro Met Phe His Ala
            260                 265                 270

Cys Gly Trp Thr Tyr Pro Trp Ala Val Thr Ala Ser Leu Ala Thr His
        275                 280                 285

Phe Thr Ile Arg Lys Val Asp Asn Thr Val Ile Trp Asp Ala Leu Leu
    290                 295                 300

Asn His Gly Val Ser His Tyr Cys Gly Ala Pro Thr Val Gln Ile Gly
305                 310                 315                 320

Leu Val Asn His Pro Asn Ala Arg Lys Leu Asn Arg Arg Val Asn Val
                325                 330                 335

Ala Val Ala Ala Ser Ala Pro Thr Ala Asn Leu Leu Ala Lys Met Glu
            340                 345                 350

Gly Leu Asn Leu His Pro Val His Val Tyr Gly Leu Thr Glu Thr Tyr
        355                 360                 365

Gly Pro Phe Thr Arg Arg Tyr Phe Glu Pro Glu Trp Ala Lys Leu Asp
    370                 375                 380

Val Asp Ala Arg Ala Arg Met Met Ala Arg Gln Gly His Ser Tyr Leu
385                 390                 395                 400

Thr Ser Asp Glu Val Arg Val Val Arg Thr Ala Ser Ser Thr Asp Ala
                405                 410                 415

Ser Thr Pro Asp Leu Val Asp Val Glu Arg Asn Gly Gln Glu Thr Gly
            420                 425                 430

Glu Ile Val Ile Arg Gly Asn Met Val Met Val Gly Tyr Tyr Asn Asp
```

-continued

```
        435                 440                 445

Pro Ala Ala Thr Ser Lys Ala Val Met Lys Gly Trp Phe His Thr Gly
    450                 455                 460

Asp Leu Ala Val Arg His Pro Gly Gly Glu Ile Gln Ile Leu Asp Arg
465                 470                 475                 480

Gly Lys Asp Ile Ile Ile Ser Gly Gly Glu Asn Ile Ser Ser Leu Met
                485                 490                 495

Val Glu Gln Glu Leu Ala Ser His Pro Ser Val Leu Glu Cys Cys Val
            500                 505                 510

Ile Ala Arg Pro His Glu Lys Trp Gly Glu Arg Gly Gln Ser Phe Ile
        515                 520                 525

Val Leu Thr Glu Gln Ala Lys Ala Lys Leu Asn Phe Ala Glu Ile Lys
    530                 535                 540

Lys Lys Gly Ser Pro Glu Asn Lys Ala Phe Val Glu Glu Val Lys Lys
545                 550                 555                 560

His Cys Val Glu Arg Met Ser Lys Phe Ala Val Pro Glu Trp Phe Asp
                565                 570                 575

Val Val Asp Glu Leu Pro Lys Thr Ser Thr Gly Lys Val Gln Lys Asn
            580                 585                 590

Val Leu Arg Ala Arg Phe Ala Thr Ser Thr Ala Ser Ile Gly Thr Met
        595                 600                 605

Thr Ser Ile Leu Arg Asp Ile Leu Ser Thr Tyr Val Thr Gly Gly Lys
    610                 615                 620

Asp Pro Phe Arg Asn Leu Ser Tyr Ala Ala Val Pro Leu Ser Leu Leu
625                 630                 635                 640

Leu Ala Ala Leu Pro His Trp Tyr Thr Ile Tyr Leu Ala Glu Ser Asn
                645                 650                 655

Lys Val Gln Gly Gly Trp Ser Asn Val Asn Pro Arg Phe Trp Val Gln
            660                 665                 670

Thr Leu Thr Ala Lys Ala Leu Thr Lys Lys Leu Thr Pro Leu Glu Asn
        675                 680                 685

Gln Ile Leu Arg Gly Gln Ser Cys Gln Ala Asn Ala Phe Glu Asn Val
    690                 695                 700

Pro Leu Phe Ile Ala Thr Val Val Trp Ala Asn Val Ser Gly Leu Glu
705                 710                 715                 720

Arg Glu Thr Ile Asn Asn Phe Val Val Gly Tyr Leu Pro Ser Ser Asn
                725                 730                 735

His Thr Lys Val Arg Thr Phe Glu Tyr Lys Thr Ala Ile Arg Leu Cys
            740                 745                 750

Thr Thr Ala Phe Glu Leu Arg Tyr Ile Phe Leu Leu Thr Arg Asn
        755                 760                 765
```

<210> SEQ ID NO 6
<211> LENGTH: 3251
<212> TYPE: DNA
<213> ORGANISM: Pseudozyma tsukubaensis
<220> FEATURE:
<223> OTHER INFORMATION: Pseudog4086.t1

<400> SEQUENCE: 6

```
atgccctaca caccaccacg ttcgtcgcag cctcctaaag gtttaccctt tgagctttcg      60

ctctcgacgc atcccggcgc gcagcacaac cgatcttcgc tcacacccgt gtcgttcctc     120

ttgcgtgccg cgctgattac gcctcgcaaa ttggcaatca ctcatcctga aaagggctac     180

tcattcacct acgagcaatg ggcagcacgt actctctcgc tcgcctttgc acttcgcagc     240
```

-continued

```
cttcccgcct tcaagattgg tgatcgcgtc gctgttatct cgcctaacgc acctctgatc    300
gcagacgctc actggggtat tcctgctgtt ggtggtatca ttacgccgat caacattcga    360
aacacgccca aggaggtcgc ttacgtcttg gagcactcgg gtagcactgt aatcttggtc    420
gaccacgagt ttacacacct cgtccccgag aaccctggcc caggcatcac cgtcatcgtc    480
agcaaagatt cgggaggaca agaagctgac gatccatacg agaaatttct cgatcgtggc    540
ttcctcgaat ggcagcgtgc tgagcaggct gagctcaaag cctacaagtc tcgcactcga    600
ccttctgctg aaccaaagac gggatggaaa ctcatcgagg cgcctcaaga cgaagaacaa    660
cccatcgccc tctgctacac ctcgggtact actggtcgac ccaaaggtgt gctcactaac    720
caccgtggag cctacctttc tgccgtagcc aacgcttttg aagcccacct cacgcaggat    780
agcgtctatc tttgggttct tcccatgttc catgcttgtg gatggacgta cccttgggct    840
gttactgctt ctctcgctac gcatttcacc attcgcaagg tcgacaacac cgttatctgg    900
gacgcgttgc tcaatcacgg cgtatcgcac tactgcggtg cccctacagt tcagatcggc    960
ctcgtcaacc atcctaacgc acgcaagctc aaccgtcgcg tgaacgttgc cgtcgcagct   1020
tccgcaccca ccgccaacct cctcgccaag atggagggtc taaacttgca cccagtccac   1080
gtatacggct tgaccgaaac atacggtcct ttcaccagga ggtacttcga gcccgaatgg   1140
gccaaactag atgttgatgc tcgagcacga atgatggctc gccaaggaca ctcctacctc   1200
acttcagatg aggtacgtgt cgttcgtact gcttcttcca ccgacgcctc tacacctgac   1260
ctcgtcgatg ttgagcgcaa cggtcaagaa acgggcgaaa tcgtcattcg aggaaacatg   1320
gtcatggtag gctactacaa cgatcccgcc gccacttcca aagccgtcat gaaaggctgg   1380
ttccacactg gcgacctagc cgtccgtcac cctggcggcg aaatccaaat cctagaccga   1440
ggtaaagaca tcatcatctc cggaggcgaa aacatctcct cgctcatggt tgaacaggaa   1500
cttgcctccc acccttccgt cctcgaatgc tgcgtcattg cacgaccgca cgaaaagtgg   1560
ggcgaacgcg gccagtcgtt tatcgtgctc acagaacagg cgaaagcgaa actcaacttc   1620
gcagagataa aaaagaaggg ttcaccggag aacaaggcgt ttgttgaaga ggtgaaaaag   1680
cactgcgtgg aaaggatgtc caaattcgcc gtaccggaat ggttcgacgt agtggacgaa   1740
ttgccaaaga caagcacggg caaggtgcag aagaacgtgc tccgagctag gttcgctagt   1800
aagttgtaaa agtagatcgt gtcgcgtgga atgagagcaa tggaagtgtc atctattctt   1860
ggtcgatgca acggtgcgat gtgtgtctct tggatgcgtc ggtaacgtgc ttttgacaac   1920
ttcgagaaga ttcacccgac gacagagggt aatgcactga caagcgcata gcacggaggg   1980
gcaaagagct gcctcaacag cccaatcctg tacgaccata cgagcaagag tgagacacgt   2040
cttcattgtt tgacacgaag aagtttacgg caaggaggta actttttta cgccagagaa   2100
ggatggttcg tttggtggtg gagccgcgct tctccgcaca gcgagaagag gggcgtaggt   2160
gtgggggagg acagtccaag tccaagtcca aggtgtcgcg tgaaattgac cgattttggc   2220
aggttttgcg gctttgtgca gatcactttc aaaagccgcc gccgccgccg cctcctgcgc   2280
ccagaacatg tgtggagttt tcgtttttcg ctcgtgccac cttttccttc tctttgtgtc   2340
gtacattaca tccactcaac cttccttctc atccttccac ctttcgttct cttatttcta   2400
tccttctcac catcaccacc agcttccaca gcgtctatcg gaaccatgac ttccatcctg   2460
cgcgacatcc tttccaccta cgtcacaggt ggtaaagacc ccttccgcaa cctctcgtac   2520
gccgctgtac ccctctccct cctcctcgct gccctccctc actggtacac catctacctt   2580
```

-continued gccgaatcga acaaagtcca aggaggatgg agcaacgtca accccccgctt ttgggtccaa 2640 actctcaccg ccaaggctct caccaagaag ttgaccccgc ttgaaaacca gattttgagg 2700
ggtcaaagtt gccaagccaa cgcgtttgag aacgtgccgc tgttcatcgc caccgttgta 2760
tgggcgaacg taagcggctt ggagagggaa acgattaaca actttgtagt gggatatctg 2820
gtaagcaggg ctgcgtacac ggtgttgtat ttgaagacgg aggggtatgc gaacagtttt 2880
gctaggacgg cggttttcca agtgggaatc atctggatta ttaccgtttg gatgaagggg 2940
gcttttaggg gtttgccgct cgtcaagtga gcgtatgatc gaggcgagag gagagggagc 3000
taggaaagaa ggattggcaa acccatagaa gcacagagtg gagagcgaac aaggggtcca 3060
cactcaagac gtaacgcccc gcgaatcagc cccacgcttc gctctcactc tcgttcccct 3120
cctcaaatct acactgacga tagccaagca gcaatcacac aaaagttcga acgttcgagt 3180
ataagacagc tatccgtttg tgcacaacag catttgagtt gcgatacatc tttctcttga 3240
caagaaacta a 3251

<210> SEQ ID NO 7
<211> LENGTH: 510
<212> TYPE: PRT
<213> ORGANISM: Pseudozyma tsukubaensis
<220> FEATURE:
<223> OTHER INFORMATION: Pseudog4087.t1

<400> SEQUENCE: 7

Met Pro Lys Pro Gly Pro Ala Ser Arg Ser Ser Ile Ala Asn Leu Met
1 5 10 15

Arg Met Ser His Ala Gly Gly Cys Pro Cys His Gly Cys Ser Val Ala
20 25 30

Arg Gly Gly Ala Asn Leu Ala Arg Ala Gly Met Asn Met Ile Ala Lys
35 40 45

His Asn Ala Gln Pro Gly Ala Asn Ala Arg Gly Tyr Ala Thr Pro Val
50 55 60

Asp His Ala Val Glu Arg Glu Tyr Ala Phe Glu Leu Ala Ala Ser Asn
65 70 75 80

Ile Arg Tyr Gly Glu Gly Val Thr Lys Glu Val Gly Met Asp Phe Ala
85 90 95

Asn Met Lys Ala Arg Lys Val Gly Val Phe Thr Asp Pro Thr Val Arg
100 105 110

Asn Leu Thr Ala Met Lys Gln Ser Ile Asp Gly Leu Glu Lys Ala Gly
115 120 125

Val Lys Tyr Glu Ile Phe Asp Gln Val Arg Val Glu Pro Asn Glu Lys
130 135 140

Ser Trp Glu Ala Ala Ile Arg Phe Ala Arg Glu Gln Asp Phe Ser His
145 150 155 160

Phe Leu Ala Val Gly Gly Gly Ser Val Met Asp Thr Cys Lys Val Ala
165 170 175

Asn Leu Phe Ser Cys Tyr Pro Asp Ala Asp Leu Leu Glu Phe Val Asn
180 185 190

Ala Pro Ile Gly Arg Gly Thr Pro Ile Asp Lys Val Leu Lys Pro Leu
195 200 205

Leu Cys Val Pro Thr Thr Ala Gly Thr Gly Ser Glu Thr Thr Gly Thr
210 215 220

Ala Ile Phe Asp His Thr Ala Thr Glu Ser Lys Thr Gly Ile Ala Ser
225 230 235 240

-continued

```
Arg Ala Leu Arg Pro Leu Leu Gly Ile Val Asp Pro Leu Asn Thr Glu
                245                 250                 255

Thr Cys Pro Thr Ala Val His Ile Ser Ser Gly Leu Asp Val Leu Phe
            260                 265                 270

His Ala Leu Glu Ser Tyr Thr Ala Ile Pro Tyr Asn Glu Arg Met Pro
        275                 280                 285

Arg Pro Ala Asn Pro Leu Gln Arg Pro Ala Tyr Gln Gly Arg Asn Pro
    290                 295                 300

Ile Ser Asp Val Phe Ser Leu Trp Ala Leu Lys Gln Thr Val Lys Tyr
305                 310                 315                 320

Leu Pro Arg Val Ala Lys Asp Lys Thr Asp Phe Glu Ala Arg Gly Gln
                325                 330                 335

Met Leu Leu Ala Ser Thr Phe Ala Gly Ile Gly Phe Gly Asn Ala Gly
            340                 345                 350

Val His Leu Cys His Gly Met Ser Tyr Pro Ile Ser Gly Leu Asn Lys
        355                 360                 365

Lys Phe Gly Lys Tyr Gln His Pro Gly Tyr Glu Val Asp His Pro Ile
    370                 375                 380

Val Pro His Gly Ile Ser Val Ala Leu Thr Gly Pro Ala Val Phe Asp
385                 390                 395                 400

Phe Thr Ala Pro Ser Ala Pro Asp Arg His Arg Asp Val Ala Ala Ile
                405                 410                 415

Phe Ala Gly Tyr Asp Ser Gly Ala Glu Ala Thr Asp Ile Ala Arg Leu
            420                 425                 430

Pro Asp Ser Glu Val Gly Ala Leu Val Tyr Asp Arg Ile Ala Ser Phe
        435                 440                 445

Leu Ala Asp Leu Gly Val Pro Arg Gly Leu Ala Lys Ile Gly Tyr Gly
    450                 455                 460

Gln Glu His Val Glu Ala Leu Val Lys Gly Thr Ile Pro Gln Arg Arg
465                 470                 475                 480

Val Leu Asp Leu Ala Pro Gly Ile Gly Asp Val Met Gly Ser Asp Gly
                485                 490                 495

His Glu His Leu Ala Arg Ile Leu Glu Lys Ser Leu Ser Tyr
            500                 505                 510
```

<210> SEQ ID NO 8
<211> LENGTH: 1533
<212> TYPE: DNA
<213> ORGANISM: Pseudozyma tsukubaensis
<220> FEATURE:
<223> OTHER INFORMATION: Pseudog4087.t1

<400> SEQUENCE: 8

```
atgcccaaac caggcccagc ttcccgtagc tccatcgcca acctcatgcg catgtcgcat      60

gcaggtggat gcccctgtca cggatgctcg gttgctcggg gtggagccaa cctcgctcgt     120

gccggaatga acatgattgc caaacacaat gctcaacctg gtgccaacgc acgcggatac     180

gccactcccg tcgatcacgc cgttgaacgc gaatacgcct ttgaacttgc cgcttccaac     240

attaggtacg gtgaaggtgt caccaaggaa gtcggtatgg atttcgccaa tatgaaggcg     300

aggaaggtgg gtgttttcac cgatccaacg gtgaggaatc tgaccgcgat gaagcagagt     360

atcgatggac tagagaaggc tggggttaag tacgagatct ttgatcaggt cagggtggag     420

ccgaatgaga agagttggga ggcagcgatc aggttcgcac gtgaacagga cttctcccac     480

tttttggcgg tgggtggtgg atcggtaatg gatacgtgta aagtcgccaa ccttttcagc     540
```

-continued

```
tgctaccctg acgccgatct gctcgaattc gtcaacgctc ctatcggtcg tggtaccccc    600

atcgacaagg ttctcaagcc tctgctttgc gttcccacca ccgctggtac gggatccgaa    660

accaccggta cagccatctt tgatcatacc gctaccgagt ccaaaaccgg tattgcctcc    720

cgagcccttc gtcccctgtt gggtattgtt gatcctctca acaccgaaac ttgccctacc    780

gccgtccaca tcagttcggg attggatgtg ttgttccacg cactcgaatc gtacaccgcc    840

atcccgtaca acgaacgcat gcctcgcccc gcaaacccgc tccaacgtcc cgcttaccaa    900

ggacgtaacc ccatctcgga cgttttctcc ctctgggcgc tcaagcagac cgttaagtac    960

ctcccgcgcg ttgcgaagga caaaaccgac tttgaagccc gtggacagat gcttttggcc   1020

tccacgtttg ctggtattgg attcggtaat gctggcgtcc acctttgcca cggcatgagc   1080

taccctattt cggggttgaa caagaaattt ggtaaatacc agcacccggg gtacgaggtg   1140

gaccatccca tcgtacccca cggtatctcg gtcgctttga ctgggcctgc agtatttgac   1200

tttacggcgc cttcggcgcc cgaccgtcac cgtgacgtag cagctatttt tgcgggttac   1260

gacagcggtg cggaggctac ggatatcgct cgtctgcccg actccgaggt tggtgcactt   1320

gtgtacgata ggatcgcgtc cttcttggcc gacttgggcg tgccgagggg tctggctaag   1380

atcgggtacg ggcaggaaca tgtggaggcc ctcgtaaaag gaaccattcc acagaggagg   1440

gtgttggatt tggctccggg tatcggtgac gtgatgggca gcgatggcca cgaacacttg   1500

gctaggattc tggagaagag tctgtcttac taa                                1533
```

<210> SEQ ID NO 9
<211> LENGTH: 513
<212> TYPE: PRT
<213> ORGANISM: Pseudozyma tsukubaensis
<220> FEATURE:
<223> OTHER INFORMATION: Pseudog4088.t1

<400> SEQUENCE: 9

```
Met Lys Ser Glu Ala Ser Ser Ser Ala Leu Val Leu Ala Leu Thr Leu
1               5                   10                  15

Leu Ala Ser Ala Ser Thr Val Ile Ala Glu Pro Ser Ser His Ala Ser
            20                  25                  30

Tyr Arg Pro Ser Lys Leu His Asn Arg Arg Gln Ser Ser Pro Asn Pro
        35                  40                  45

Asn Gly Ser Thr Ala Ser Gln Glu Ala Ile Tyr Gln Gln Ala Phe Thr
    50                  55                  60

Asp Pro Val Ala Ala Ala Lys Ala Ala Asn Ala Leu Pro Tyr Ile Ala
65                  70                  75                  80

Gly Gln Tyr Ala Thr Gly Gly Leu Tyr Arg Tyr Asn Ile Val Pro Asp
                85                  90                  95

Asn Thr Gln Leu Pro Trp Asn Ala Asn Val Pro Phe Thr Pro Glu Ala
            100                 105                 110

Ala Val Asn Gly Ser Val Asp Gly Gly Trp Gln Ala Leu Pro Glu Ile
        115                 120                 125

Gln Gly Met Thr Leu Asn Arg Thr Phe Ala Val Ala Pro Gly Ala Val
    130                 135                 140

Met Pro Phe Tyr Gln Thr Gln Gly Phe Asp Ala Thr Lys Ile Lys Arg
145                 150                 155                 160

Ala Val Met Ile Met Pro Gly Lys Pro Arg Asp Cys Trp Lys Tyr Thr
                165                 170                 175

Ser Leu Ile Gln Asn Ala Leu Asn Val Phe Glu Thr Asn Pro Gln Ser
            180                 185                 190
```

```
Ala Gly Ser Ser Ala Asp Gly Ser Thr Thr Gly Asp Asp Ser Gly Arg
        195                 200                 205

Leu Gly Lys Asp Gln Val Leu Ile Leu Gly Pro Cys Trp Met Asn Ser
    210                 215                 220

Asp Asp Ala Lys Ala Gly Ala Ile Gln Ser Gly Glu Leu Tyr Trp His
225                 230                 235                 240

Gly Ser Gln Trp Gln Ser Gly Met Ala Ser Arg Gly Pro Gly Asn Thr
                245                 250                 255

Ala Ile Ser Ser Tyr Gln Val Met Asp Ser Phe Met Asp Ala Leu Phe
            260                 265                 270

Asp Lys Thr Thr Phe Pro Ala Leu Asn Thr Val Val Met Ala Gly His
        275                 280                 285

Ser Met Gly Ala Gln Met Val Gln Arg Tyr Ser Val Val Lys Lys Pro
    290                 295                 300

Asp Ala Tyr Asp Ser Asn Ile Ile Phe Trp Val Gly Asn Pro Gly Ser
305                 310                 315                 320

Tyr Val Trp Leu Thr Ser Ser Arg Pro Asn Asn Ser Asn Thr Ser Cys
                325                 330                 335

Ala Ser Thr Ala Asp Asp Trp Ala Tyr Gly Leu Asp Gly Ser Gly Val
            340                 345                 350

Pro Asn Tyr Ala Arg Asp Arg Val Lys Asn Asn Lys Gln Gln Leu Leu
        355                 360                 365

Thr Thr Phe Glu Ser Arg Asn Val His Tyr Asn Tyr Gly Leu Leu Asp
    370                 375                 380

Asn Gly Gln Gly Asp Thr Ala Cys Glu Ala Ser Leu Gln Gly Ala Asn
385                 390                 395                 400

His Leu Glu Arg Gly Cys His Phe Val Glu Ser Leu Ala Ser Leu Thr
                405                 410                 415

Gly Asn Gly Lys Leu Pro Val Thr Gln Thr Ala Asn Phe Met Pro Asn
            420                 425                 430

Val Ser His Glu Asp Tyr Ala Met Leu Ser Tyr Asn Ile Ser Leu Tyr
        435                 440                 445

Arg Leu Phe Gln Glu Met Pro Thr Gly Ala Ala Asn Val Thr Ala Ala
    450                 455                 460

Asn Asn Gly Ser Ser Ala Ser Ser Thr Ala Lys Lys Gly Gly Ser Gly
465                 470                 475                 480

Ser Ser Ala Gly Ser Lys Ser Ser Ala Ser Ser Met Val Thr Gly Gly
                485                 490                 495

Val Val Thr Leu Gly Ala Gly Ala Val Leu Ala Phe Ala Leu Ser Leu
            500                 505                 510

Leu


<210> SEQ ID NO 10
<211> LENGTH: 1542
<212> TYPE: DNA
<213> ORGANISM: Pseudozyma tsukubaensis
<220> FEATURE:
<223> OTHER INFORMATION: Pseudog4088.t1

<400> SEQUENCE: 10

atgaagtcgg aagcatcctc atcagccttg gtgctggctc tcaccttgct cgcctctgcc      60

tcgaccgtca tcgccgaacc ttcctctcac gcctcgtatc gaccttccaa gctccataac     120

cgcagacaat catccccaaa ccctaacggc agcaccgctt ctcaagaagc catctatcaa     180
```

-continued

```
caagctttca ccgatcctgt tgctgctgcc aaagctgcca atgcactccc ctacatcgca    240

ggccaatacg ctaccggagg tctttaccgc tacaacattg tcccggacaa tacgcagctt    300

ccttggaacg ccaatgtgcc tttcactcct gaagccgcag tcaacggaag cgtcgatgga    360

ggctggcaag cattacccga gatccaaggt atgacgctca accgcacctt tgctgttgca    420

cctggagctg tgatgccttt ctaccagacc caaggatttg acgctaccaa gatcaagaga    480

gctgttatga tcatgccagg caaaccaaga gattgctgga agtacacttc gctcatccag    540

aacgcgttga atgtgttcga gaccaacccg cagagcgctg gtagcagtgc ggacggatcg    600

actacaggcg atgacagtgg aagacttgga aaagatcaag tgctgatctt gggtccctgc    660

tggatgaatt ccgatgatgc caaagcgggc gccatccagt ctggcgaact gtactggcac    720

ggatcgcagt ggcaatcggg tatggcttcg cgaggacccg gcaacaccgc catctcgtct    780

tatcaggtta tggactcctt catggatgca ctcttcgaca aaaccacctt ccccgccctc    840

aacaccgtcg tcatggccgg tcactcgatg ggcgcccaaa tggtccaacg ctactctgtc    900

gtcaagaaac ccgacgccta cgactccaac atcatctttt gggtcggcaa ccccggcagt    960

tacgtctggc tcacctcctc tcgtcccaac aactccaaca ccagctgcgc ctccaccgca   1020

gacgactggg cgtacggcct cgatggctcc ggcgtcccca actacgctcg cgaccgtgtc   1080

aagaacaaca aacagcaact cctgaccacg ttcgaatcgc gtaacgtcca ctacaactac   1140

ggcctcctcg acaacggtca aggcgatacc gcatgcgaag cttctctgca aggcgcaaac   1200

cacctcgaaa gaggatgtca ctttgttgaa tcgctcgcca gtttgacggg gaatgggaag   1260

ctgcccgtga cgcagacggc taactttatg cccaatgttt cgcacgagga ttacgccatg   1320

ttgtcgtaca acatttcgct gtatagattg ttccaggaga tgccgacggg tgctgcgaac   1380

gtgacggcgg cgaacaatgg gagcagtgcg agcagtacgg cgaagaaggg tggtagtgga   1440

agcagtgctg ggtcgaagag ttcggcatcg tccatggtca cgggtggggt tgtgactcta   1500

ggagcaggag cggtgcttgc tttcgccttg agcttgcttt ga                      1542
```

<210> SEQ ID NO 11
<211> LENGTH: 283
<212> TYPE: PRT
<213> ORGANISM: Pseudozyma tsukubaensis
<220> FEATURE:
<223> OTHER INFORMATION: Pseudog4089.t1

<400> SEQUENCE: 11

```
Met Ser Lys Leu Thr Leu Gln Ser Thr Tyr Ser Leu Gly Asp Gly Val
1               5                   10                  15

Asp Met Pro Val Leu Gly Phe Gly Val Tyr Leu Ser Pro Ser Asp Val
            20                  25                  30

Cys Val Asn Ser Val Thr Thr Ala Leu Lys Thr Gly Tyr Arg His Ile
        35                  40                  45

Asp Ser Ala Gln Tyr Tyr Glu Asn Glu Lys Glu Val Gly Asp Ala Val
    50                  55                  60

Arg Gln Trp Cys Lys Glu Glu Gln Val Ser Arg Arg Gly Ile Phe Val
65                  70                  75                  80

Thr Thr Lys Val Ile Phe Pro Ser Lys Thr Lys Glu Glu Thr Leu Glu
                85                  90                  95

Ser Leu Arg Glu Ser Val Lys Lys Ile Asn Leu Asp Gly Tyr Val Asp
            100                 105                 110

Cys Phe Leu Ile His Thr Pro Thr Ser Gly Pro Glu Gly Arg Lys His
        115                 120                 125
```

-continued

```
Leu Trp Glu Ala Leu Lys Glu Leu Gln Ser Glu Gly Lys Val Val Thr
    130                 135                 140

Ile Gly Val Ser Asn Tyr Gly Leu Lys His Leu Gln Glu Leu Ile Asp
145                 150                 155                 160

Ala Gly Glu Thr Pro Ala Val Asn Gln Ile Glu Leu His Pro Trp Cys
                165                 170                 175

Gln Gln Arg Pro Ile Val Glu Leu Cys Lys Lys His Asn Ile Val Leu
            180                 185                 190

Gln Ala Tyr Cys Pro Ile Val Arg Gly Glu His Lys Asp Asp Glu Glu
        195                 200                 205

Leu Leu Lys Ile Ala Ala Lys His Lys Val Asp Trp Ser Gln Val Leu
    210                 215                 220

Ile Arg Trp Ser Leu Gln Lys Gly Phe Val Pro Leu Pro Lys Ser Asp
225                 230                 235                 240

Thr Pro Ser Arg Ile Ala Ser Asn Ala Asp Val Phe Asn Phe Glu Leu
                245                 250                 255

Asp Asp Glu Asp Met Ala Thr Leu Asp Ala Lys Asp Gln Gly Ala Lys
            260                 265                 270

Gly Ala Val Ala Pro Asn Pro Val Asp Cys Glu
        275                 280


<210> SEQ ID NO 12
<211> LENGTH: 1309
<212> TYPE: DNA
<213> ORGANISM: Pseudozyma tsukubaensis
<220> FEATURE:
<223> OTHER INFORMATION: Pseudog4089.t1

<400> SEQUENCE: 12

atgtcgaagc ttactctgca gtcaacttac tcgctcggcg atggcgtcga tatgcccgtt      60

ttgggtttcg gcgtctacct gagtccttcg gatgtttgcg tcaactcggt aactaccgct     120

ctcaagactg gatacaggca cattgactcg gcgcagtact atgagaatga gaaggagtga     180

gtgcggccct tcccgctttt ccagctgact tagaggaaag gaaagacgat gctgacggtt     240

ttgctcttga ctcttttcgc attggtgcta tcttagagtc ggcgacgccg ttcgacagtg     300

gtgcaaggag gagcaggtct cgcgtcgtgg tatctttgtg acgaccaagg tgatcttccc     360

ttccaagacg aaagaggaga cgctcgagtc gttgcgcgag tcggtgaaga agattaacct     420

cgatggtaag tctccctcct taacctttcc agattcgatg atagatgcaa tgctgatcaa     480

caaacgagta actctggaac cacaggctac gtcgactgct tcctcatcca cacgcctact     540

tcgggtcccg agggacgcaa gcacctctgg gaagcgctca aggagttgca gtccgaaggc     600

aaagttgtta ctatcggcgt tagcaactag tgagtagctc ccatcaattg tcattggcta     660

caaggcttag gtgatgctga ccagaatcct tcttcctttg catggatccc aacagcggtc     720

tcaagcacct ccaagaactc atcgacgccg gcgagacacc cgctgtcaac cagatcgaac     780

ttcatccttg gtgccagcag cgtccgatcg ttgagctttg caagaagcac aacattgttc     840

tccaggctta ctgcgtatgt tactctccct ctctcccact cttccctttc attgtaatct     900

gtgcgaggga agacaactga cattctgtgc atttctttga tgtgtattgc agccaatcgt     960

tcgaggcgag cacaaggacg acgaagaact cctcaagatc gctgccaagc acaaggtgga    1020

ctggtcgcaa gtgttgatcc gatggtcgtt gcagaaaggg tgagttcagc ggtgtcctgc    1080

ttcattctct caagctctct ttttatctga gtactgacct ctttgctgtg cacacatcgt    1140
```

-continued

```
ttgtcctaac agcttcgtcc ctcttcccaa gtcggacaca ccttcgcgta tcgcctccaa   1200

cgccgacgtc ttcaactttg agctcgacga cgaagacatg gctaccctcg acgctaagga   1260

tcagggcgct aaaggtgccg ttgctcctaa ccctgttgac tgcgagtga              1309


<210> SEQ ID NO 13
<211> LENGTH: 428
<212> TYPE: PRT
<213> ORGANISM: Pseudozyma tsukubaensis
<220> FEATURE:
<223> OTHER INFORMATION: Pseudog4090.t1

<400> SEQUENCE: 13

Met Pro Ser Ile Pro Lys Pro Pro Ser Leu Thr Leu Leu Phe Ala Ser
1               5                   10                  15

Leu Phe Thr Leu Leu Leu Thr Gln Asn Ala Tyr Arg Ala Gln Ala Asp
            20                  25                  30

Thr Val Val Gln Asp Pro Leu Gln Ala Gln Ala Asn Ser Phe Gly Trp
        35                  40                  45

Leu Ala Ile Arg Asn Phe Thr Tyr Cys Met Gly Asp Ser Pro Asp Pro
    50                  55                  60

Pro Thr Lys Pro Arg Gly Ile Gln Pro Lys Gly Lys Asn Thr Ile Asn
65                  70                  75                  80

Ala Asp Asp Ala Ser Lys Lys Arg Leu Thr Gly Met Gly Asp Ser Val
                85                  90                  95

Val Val Leu Tyr His Pro Glu Asn Thr Asn Lys Ala Ile Ala Trp Cys
            100                 105                 110

Asn Thr Leu Val Ala Phe Gln Ser Thr Glu His Val Gln Cys His Thr
        115                 120                 125

Ala Leu Pro Thr Cys Gln Arg Cys Asp Ala Val Arg Glu Lys Asn Gly
    130                 135                 140

Val Lys Ser Met Ser Leu Gly Gly Val His Ala Gly Lys Gly Lys Ala
145                 150                 155                 160

Pro Ser Gly Lys Leu Gly Arg Lys Lys His Lys Lys Met His Lys Lys
                165                 170                 175

Met Glu Ser Ile Gly Leu Glu Gly Glu Asp Ala Gly Leu Val Ala Leu
            180                 185                 190

Gln Lys Arg Asp Glu Ser Lys Gln Gln Glu Gly Thr Lys Thr Gly Ser
        195                 200                 205

Gly Thr Thr Thr Ala Asn Asp Ala Gly Gln Arg Gly Gly Ala Asp Pro
    210                 215                 220

Asn Asp Pro Trp Ile Pro Gly Pro Asp Ser Glu Thr Lys Pro Asp Ile
225                 230                 235                 240

Asn Pro Val Ala Ser Thr His Gly Thr Thr Pro Arg Pro Leu Gly Ser
                245                 250                 255

Thr Thr Thr Thr Thr Ala Asp Asn Pro Pro Asp Asn Thr Phe Ser Glu
            260                 265                 270

Asp Pro Glu Leu Glu Ala Ala Ile Ser Glu Phe Gln Asp Tyr Cys Glu
        275                 280                 285

Asn Lys Leu Thr Leu Ala Val Arg Ala Asp Cys Pro Leu His Leu Val
    290                 295                 300

Lys Gly Trp Leu Asp Glu Pro Pro Phe Asp Leu His Arg Phe Cys Met
305                 310                 315                 320

Ala Leu Lys Gly Ser Asp Gly Tyr Thr Leu His Thr Val Pro Ala Pro
                325                 330                 335
```

```
Asp Leu Asp Asp Gly Gly Lys Ala Gly Gly Asn Asp Gly Ala Gly Lys
            340                 345                 350

Asn Gly Ala Ala Thr Lys Gly Lys Pro Ala Ala Val Gln Gly Gly Thr
        355                 360                 365

Ser Gly Gly Ala Gln Thr Gly Gly Arg Gly Asp Gly Glu Thr Ala Thr
    370                 375                 380

Gly Gly Gly Gly Gly Gln Phe Asp Pro Asn Asp Pro Leu Val Pro Leu
385                 390                 395                 400

Pro Asp Gly Gly Leu Thr Thr Thr Pro Pro Pro Thr Gln Pro Gln Pro
                405                 410                 415

Lys Val Glu Ala Lys Pro Glu Lys Pro Lys Gln Ala
            420                 425
```

```
<210> SEQ ID NO 14
<211> LENGTH: 1287
<212> TYPE: DNA
<213> ORGANISM: Pseudozyma tsukubaensis
<220> FEATURE:
<223> OTHER INFORMATION: Pseudog4090.t1

<400> SEQUENCE: 14

atgccatcca tacccaaacc gccctcgcta accctcctct tcgcctccct tttcaccctc     60

cttctcaccc aaaacgccta tcgcgcacaa gcagacaccg tcgtccaaga ccccctccaa    120

gcgcaagcca acagtttcgg ttggctcgcc attcgcaact tcacctattg tatgggtgac    180

tcgcccgatc cacccacaaa gccacgcgga atccaaccca agggcaagaa tacgatcaat    240

gccgacgatg caagtaagaa gcgcttaacg ggtatgggag atagcgtggt tgtgctctac    300

catccggaga atacgaataa ggcgatcgct tggtgtaaca cgctggtggc gtttcagagt    360

acggagcatg tccagtgtca cacggcgcta cctacgtgtc agaggtgtga tgctgtgagg    420

gagaagaacg gggtcaaaag tatgagcttg ggaggtgtgc atgcgggtaa gggtaaggcg    480

ccaagtggga agttaggtag aaagaagcat aagaagatgc ataagaagat ggagtcgata    540

gggctcgaag gggaagatgc agggttggtg gctttacaga agcgtgacga aagtaagcaa    600

caagaaggta cgaagactgg atcaggaacg accacggcta acgacgctgg tcagagaggc    660

ggcgcggatc ccaatgatcc ttggatccct ggtcccgact ccgaaacgaa gccagacatc    720

aaccctgtcg catcgactca cggtactaca cctcgtccgt tgggctctac caccaccaca    780

actgccgata atcctcccga taacaccttt tccgaagacc ccgaactcga agctgcgatc    840

tcagaattcc aagactactg cgaaaacaag ctcactctcg cagtccgcgc cgattgcccc    900

ctacacctcg tcaaaggttg gctagacgaa cctcccttcg acttgcatcg cttctgtatg    960

gcgttgaagg gaagcgacgg gtacacgctg catacggtcc cggcccctga tctggacgac   1020

ggcggcaagg cgggagggaa cgatggcgcg ggcaagaatg gggctgcaac caagggaaag   1080

ccggcggccg tccaaggagg tactagcgga ggagcacaaa caggaggccg cggtgacggt   1140

gagacagcaa caggaggtgg tggtggacaa ttcgacccga acgatccgtt ggtaccttta   1200

cctgatggtg ggctgacaac gacgccaccg ccaacacagc cgcagcccaa ggttgaagcg   1260

aagccggaga agccaaagca ggcttga                                       1287


<210> SEQ ID NO 15
<211> LENGTH: 280
<212> TYPE: PRT
<213> ORGANISM: Pseudozyma tsukubaensis
<220> FEATURE:
<223> OTHER INFORMATION: Pseudog4091.t1
```

<400> SEQUENCE: 15

Met Ala Ser Thr Asp Val Ala Cys Glu Lys Thr Pro Ser Ser Ser Ala
1 5 10 15

Leu Gly Leu Phe Asn Leu Ser Gly Lys Thr Ala Leu Leu Thr Gly Gly
20 25 30

Thr Arg Gly Ile Gly Gln Ala Cys Ala Val Ala Leu Ala Glu Ala Gly
35 40 45

Ala Ser Val Ile Leu Ala Val Arg Pro Gly Thr Ala Pro Gly Ala Asp
50 55 60

Gly Asn His Pro Ala Leu Ser Pro Leu Leu Ala Val Ser Asp Gln Thr
65 70 75 80

Ser Ser Gln Lys His Ser Thr Val Glu Ala Asp Leu Ser Asp Leu Ser
85 90 95

Ser Val Lys Ser Leu Phe Asp Arg Ala Leu Pro Leu Ser Pro Ser Gly
100 105 110

Gly Ile Asp Ile Leu Val Asn Cys Gly Gly Ile Gln Arg Arg His Pro
115 120 125

Ser Thr Asp Phe Pro Glu Ser Asp Trp Asp Glu Val Leu Asn Val Asn
130 135 140

Leu Lys Ala Val Trp Leu Leu Ser Gln Ala Ala Gly Arg His Met Ile
145 150 155 160

Pro Arg Arg Ser Gly Lys Ile Ile Asn Phe Gly Ser Leu Leu Thr Phe
165 170 175

Gln Gly Gly Leu Thr Val Pro Ala Tyr Ala Ser Ala Lys Gly Ala Val
180 185 190

Gly Gln Leu Thr Lys Ala Leu Ser Asn Glu Trp Ala Lys His Asn Val
195 200 205

Gln Val Asn Gly Ile Ala Pro Gly Tyr Ile Ala Thr Asp Met Asn Glu
210 215 220

Lys Leu Leu Ala Asp Pro Thr Arg Leu Arg Gln Ile Ser Glu Arg Ile
225 230 235 240

Pro Ala Gly Arg Trp Gly Glu Ala Ala Asp Phe Lys Gly Pro Leu Leu
245 250 255

Phe Leu Ala Ser Gln Ala Ser Gln Tyr Val Ser Gly Glu Met Leu Val
260 265 270

Val Asp Gly Gly Trp Met Gly Arg
275 280

<210> SEQ ID NO 16
<211> LENGTH: 843
<212> TYPE: DNA
<213> ORGANISM: Pseudozyma tsukubaensis
<220> FEATURE:
<223> OTHER INFORMATION: Pseudog4091.t1

<400> SEQUENCE: 16
atggcatcca ccgacgtagc ctgcgaaaag accccctcgt cctccgcttt gggacttttc 60
aacctctctg gcaagaccgc attgttgacc ggtggtacta gaggtattgg tcaagcatgt 120
gccgttgcac ttgctgaagc tggtgcatcg gtcatcctgg ccgttagacc aggtaccgct 180
cctggcgctg atggcaacca ccctgccctc tccccttgc ttgctgtttc cgaccagact 240
tcctcgcaga agcactcgac cgtcgaagcc gacctctccg atctctcctc ggtcaagtct 300
ctcttcgacc gcgcgcttcc cctctcccct tcaggcggca tcgacatcct cgtcaactgt 360

-continued

```
ggaggcatcc aacgccgtca cccatccacc gacttccccg aatccgattg ggacgaagtt    420

ctcaacgtca acctcaaagc tgtctggctt ctctcccaag ctgctggtcg ccacatgatc    480

ccccgccgct ccggcaagat catcaacttt ggttcgctgc ttacattcca aggtggcctc    540

acggtcccag cttacgccag cgcaaaggga gccgtaggcc aactcacgaa ggcacttagc    600

aacgaatggg caaaacacaa cgttcaagtc aacggaattg ctcccggcta catcgcgacc    660

gacatgaacg aaaaattgct tgccgaccca acgaggttga ggcagatcag cgagaggatt    720

cctgcgggta ggtggggtga ggccgctgat tttaagggcc cattgctgtt tttggccagt    780

caagcgagtc agtatgtcag tggtgaaatg ttggttgttg acggtggatg gatgggtcgt    840

taa                                                                  843


<210> SEQ ID NO 17
<211> LENGTH: 247
<212> TYPE: PRT
<213> ORGANISM: Pseudozyma tsukubaensis
<220> FEATURE:
<223> OTHER INFORMATION: Pseudog4092.t1

<400> SEQUENCE: 17

Met Arg Met Leu Ile Val Gly Ser Pro Gly Ser Gly Lys Gly Thr Gln
1               5                   10                  15

Ser Thr Arg Leu Leu Lys His Tyr Ser Phe Ser Val Leu Ser Ala Gly
            20                  25                  30

Asp Val Leu Arg Ser His Ile Gln Arg Gly Thr Glu Ile Gly Gln Arg
        35                  40                  45

Ala Asp Ala Val Ile Lys Gln Gly Gly Leu Met Pro Asp Gln Val Met
    50                  55                  60

Met Asp Leu Val Gly Ala Glu Val Lys Thr Leu Ala Gly Ser Asp Trp
65                  70                  75                  80

Leu Leu Asp Gly Phe Pro Arg Thr Leu Gly Gln Ala Glu Met Leu Asp
                85                  90                  95

Glu Met Leu Glu Asp Gln Glu Lys Gly Leu Arg Leu Val Val Asn Leu
            100                 105                 110

Asp Val Pro Glu Glu Val Ile Leu Asp Arg Ile Leu Gln Arg Trp Thr
        115                 120                 125

His Leu Pro Ser Gly Arg Val Tyr Asn Leu Ser Phe Asn Pro Pro Lys
    130                 135                 140

Val Glu Gly Lys Asp Asp Ile Thr Gly Glu Pro Leu Val Lys Arg Glu
145                 150                 155                 160

Asp Asp Asn Val Glu Thr Phe Gly Lys Arg Leu Lys Thr Phe Tyr Ala
                165                 170                 175

Gln Thr Glu Pro Met Leu Asp His Tyr Arg Arg Lys Ser Gly Ser Ile
            180                 185                 190

Thr Glu Ile Asp Cys Arg Thr Glu Thr Asn Ala Asp Leu Ala Ala Ser
        195                 200                 205

Gly Lys Lys Asp Leu Phe Val Asn Leu Lys Gly Glu Thr Ser Lys Gln
    210                 215                 220

Ile Trp Pro His Leu Val Lys Ile Val His Glu Arg Phe Pro Asn Leu
225                 230                 235                 240

Lys Ala Ala Ala Ala Ala Gln
                245


<210> SEQ ID NO 18
<211> LENGTH: 944
```

```
<212> TYPE: DNA
<213> ORGANISM: Pseudozyma tsukubaensis
<220> FEATURE:
<223> OTHER INFORMATION: Pseudog4092.t1

<400> SEQUENCE: 18

atgcgaatgc tcatcgttgg ctctccagga tcaggcaaag gcactcaatc gacacgcctc      60

ctgaaacact actcttttc ggtcctctcc gcaggcgacg tactgcgatc gcacatccaa     120

cgtggaaccg aaataggcca acgcgcagat gcagtcatca agcaaggcgg attgatgccg    180

gatcaggtca tgatggatct cgtaggagct gaagtcaaaa cattagcggg gagcgactgg    240

ctgctggatg gattcccgag aacactgggg caagcagaaa tgttggatga gatgttggag    300

gaccaagaga aagggttgag gttggtggtg aatctggatg tgcctgaaga ggtgattttg    360

gataggatct tgcgtgagtc acaaacccca tcaaaccgca atcagatcga gtgcgagctt    420

atacactgac ccgacatcga tgactgtact tgttcctggc gaacaacaga acgatggacg    480

cacttaccct caggacgagt ctacaacctc tccttcaacc ctcccaaagt cgaaggcaaa    540

gacgacataa ccggagaacc actggtcaag agggaagatg acaacgtcgt acgtatcccc    600

tcctttcccc ttccccgcct gctgtttcat ttatcttaca ctctctaact cctcctcatc    660

cccgtcatca tgctacgccg ttgctactgc aggaaacctt cggcaaacgc ctcaaaacat    720

tctacgcaca aaccgaaccc atgctcgacc actaccgtcg caaaagcggc tccatcaccg    780

agatcgattg ccgtaccgaa acaaacgctg atctcgcagc atcaggcaag aaggatctat    840

ttgtcaactt gaagggcgaa acttcgaaac agatctggcc gcacttggtc aaaattgtac    900

acgagcgatt tcccaaccta aaggcagcag cggcggcgca gtga                      944


<210> SEQ ID NO 19
<211> LENGTH: 975
<212> TYPE: PRT
<213> ORGANISM: Pseudozyma tsukubaensis
<220> FEATURE:
<223> OTHER INFORMATION: Pseudog4093.t1

<400> SEQUENCE: 19

Met Ala Asp His Glu Thr Ser Val Ser Pro Ala Glu Arg Pro Ala Leu
1               5                   10                  15

Leu Pro Ala Ala Ser Ser Leu Gln Pro Thr His Ile Thr Ser His Leu
            20                  25                  30

Pro Pro Leu Lys Ser Leu Gln Ser His Asn His Ser Ala Ser Arg Asp
        35                  40                  45

Arg Ser Pro Phe Arg Arg Arg Lys Asp Ile Thr Pro Pro Ser Glu Lys
    50                  55                  60

Pro Pro Ala Gln Pro Ala Tyr Lys His Arg Gly Leu Pro Asn Thr Asn
65                  70                  75                  80

Thr Leu Gln Thr Phe Leu Thr Val Thr Asp Val Pro His Phe Gly His
                85                  90                  95

Ala Val His Tyr Asn Thr His His His Phe His Arg His Asp Ser Gly
            100                 105                 110

Asp Gly Pro Ala His Ser Ala Asp Leu Gly His Gly Trp Arg Val Arg
        115                 120                 125

Lys Thr Pro Ile Phe Ser Gly Leu Leu Ala Pro Phe Ser Ile Val Leu
    130                 135                 140

Glu Val Pro Gly Leu Thr Ser Lys Trp Tyr Ala Lys Ile Asp Ala Asp
145                 150                 155                 160
```

-continued

```
Gly Ile Val Glu Arg Tyr Ile Asp Asn Pro Pro Ile Leu Thr Val Gly
                165                 170                 175

Leu Ala Ile Ser Leu Ser Ala Ala Val Val Ala Asn Ala Ala Ile Ile
            180                 185                 190

Phe Arg Phe Leu Glu Phe Leu Lys Pro Arg Ala Ser Ile Ala Leu Ala
        195                 200                 205

Ile Ala Gly Phe Ala Leu His Asp Ile Ile Asn Val Val Ala Leu Ala
    210                 215                 220

Val Phe Gly Gly Ile Tyr Gly Pro Lys His Asp Gly Leu Ser Leu Ser
225                 230                 235                 240

Ala Ser Tyr Trp Met Val Cys Ala Ser Thr Ile Thr Ser Thr Ile Val
                245                 250                 255

Thr Ile Ser Leu Val Ala Asp Tyr Val Arg Thr Lys Asp Phe Lys His
            260                 265                 270

Ala Gly Ser Gly Leu Thr Gln Leu Gln Lys Gly Leu Val Leu Ala Gly
        275                 280                 285

Met Gly Leu Leu Leu Tyr Leu Ser Leu Gly Ser Leu Ile Phe Val Tyr
    290                 295                 300

Leu Ile Lys Ile Asp Phe Ile Thr Ala Leu Tyr Phe Ser Thr Ala Thr
305                 310                 315                 320

Val Leu Thr Val Gly Phe Gly Asp Val Val Pro Thr Ser Pro Gly Gly
                325                 330                 335

Lys Val Leu Val Ile Leu Tyr Ala Pro Ile Gly Ile Ile Leu Val Ala
            340                 345                 350

Leu Val Val Ser Ser Ala Arg Ser Thr Ile Leu Glu Thr Phe Gln Ala
        355                 360                 365

Ala Leu Ile Ala Arg Thr Lys Glu Arg Arg Arg Arg Ile Ala Glu Arg
    370                 375                 380

Lys Ala Ala Val Lys Glu His Lys Arg Gln Asp Arg Ala Ile Arg Arg
385                 390                 395                 400

Ile Met Pro Arg Thr Phe Thr Phe Gly Pro Asn Ser Asn Ala Val Ser
                405                 410                 415

Asn Ser Pro Asp Asp Asp Ser Asn Asn Asn Glu Phe Ala Glu Ala Leu
            420                 425                 430

Ala Gln Met Glu Lys Gln Ala Ala Ala Gly Gly Ala Pro Pro Ala Asp
        435                 440                 445

Asn Val Ala Ser Ser Ile Thr Thr Thr Ala Ala Ser Ser Gly Asn Ala
    450                 455                 460

Ala Ser Asn Asp Glu Pro Lys Leu Ala Glu Ala Glu Lys Pro Ala Thr
465                 470                 475                 480

Ala Thr Val Gly Asp Pro Ala Leu Gln His Gln Ile His Ala Leu Gln
                485                 490                 495

Thr Glu Leu Leu Ala Ala Lys Lys Arg Thr Glu Gln Asp Phe Leu Thr
            500                 505                 510

Tyr Glu Glu His Ala Arg His Glu Ala Ile Met Ala Ala Arg Met Lys
        515                 520                 525

Leu Val Leu Ala Ala Ser Val Thr Ala Ala Phe Trp Leu Leu Gly Ala
    530                 535                 540

Val Ala Phe Thr Tyr Ala Glu Arg Trp Ser Tyr Gly Gly Ala Met Trp
545                 550                 555                 560

Phe Cys Phe Ile Ala Met Ile Thr Ile Gly Tyr Gly Asp Tyr His Pro
                565                 570                 575

Thr Thr Gln Ile Gly Arg Ala Ile Phe Val Ile Trp Gly Leu Met Gly
```

-continued

```
            580                 585                 590

Val Ala Val Leu Thr Ile Leu Leu Ala Val Val Gln Asp Ala Phe Gly
        595                 600                 605

Gly Val Leu His Arg Met Leu Thr Gln Ser Thr Ser Arg Leu Phe Asp
    610                 615                 620

Arg Ala Glu Glu Arg Ala Arg Lys Arg Arg Leu Lys Lys Glu Gln Met
625                 630                 635                 640

Gln Arg Glu Gln Arg Gln Ala Asp Ala Glu Glu Glu Gly Glu Asp Val
                645                 650                 655

Glu Thr Arg Gly Ala Thr Ala Gly Ala Ser Ala Met Arg Lys Arg Arg
            660                 665                 670

Arg Ser Arg Thr Arg Ser His Arg Lys Ser Glu Ser Asp Val Lys Arg
        675                 680                 685

Glu Lys Phe Lys Met Val Glu Ala Gly Ser Asn Asp Thr Gly Glu Arg
    690                 695                 700

Thr Lys Val Glu Arg Lys Ser Met Glu Ala Thr Phe Ala Arg Asp Arg
705                 710                 715                 720

His Thr Ser Ser Pro Glu Pro Leu Glu Glu Leu Glu Arg Asp Leu Asp
                725                 730                 735

Thr Pro Asp Gly Val Pro Leu Ala Ile Pro Ser Phe Ile Leu Lys Asn
            740                 745                 750

Ala Ser Gly Val Thr Asp Ser Gly Leu Ile Thr Ala Glu Val Gln Leu
        755                 760                 765

Pro Val Gly Ala Ala Ala Arg Val Glu Asp Thr Leu Val Ser Ala Pro
    770                 775                 780

Gln Lys Leu Ala Leu Ala Ala Leu Leu Thr Phe Gln His Ser Val Arg
785                 790                 795                 800

Val Leu Arg Leu His Asp Thr Ala Ile Ser Ala Ala Met Thr Asp Val
                805                 810                 815

Pro Ala Leu Arg His Tyr Tyr Asn Ser Arg Gln Lys Ser Ser Ser Leu
            820                 825                 830

Ser Gly Thr Asp Leu Ala Pro Gln Asp Ser Ser Glu Gly Thr Ser Lys
        835                 840                 845

Ser Lys Asp Gly Glu Glu Thr Asp Pro Glu Thr Ala Leu Gln Asn Leu
    850                 855                 860

His Ala Ala Ile Gln Gln Ile Ala Asn Pro Glu Tyr Glu Lys Val Ala
865                 870                 875                 880

Lys Leu Val Val Ala Asn Leu Glu Phe Glu His His Leu Lys Val Phe
                885                 890                 895

Leu Glu Gln Phe Gln Gly Leu Lys Asp Arg Val Glu Gly Phe Lys Gln
            900                 905                 910

Arg Thr Thr Glu Met Arg Arg Arg Arg Gly Gln Thr Val Gly Glu Ala
        915                 920                 925

Asp Gly Glu Glu His His Pro Thr Leu Ala His Leu Phe His Pro His
    930                 935                 940

Glu His Glu His Glu His Gln Gln Gly His Glu His Glu His Gln Gln
945                 950                 955                 960

Pro Tyr Gly Arg Asn Gln Glu Pro Glu Gly Pro Ala Pro Ser Glu
                965                 970                 975
```

<210> SEQ ID NO 20
<211> LENGTH: 2928
<212> TYPE: DNA
<213> ORGANISM: Pseudozyma tsukubaensis
<220> FEATURE:
<223> OTHER INFORMATION: Pseudog4093.t1

<400> SEQUENCE: 20

```
atggccgacc acgaaacatc tgtgtcgcct gctgagcgac cggctttgtt gccagctgcc     60
tcgtcgttgc aacccacgca tatcacctcg catcttccac cactcaagtc gttgcaaagt    120
cacaatcact ctgcaagtcg tgacaggtcg ccgtttcgac gtcgaaaaga cattacacca    180
ccgtcagaga aaccacctgc acagcccgca tacaaacata gaggtctacc caacacaaac    240
actcttcaga ctttcctcac tgtcactgac gtaccacact tcggccatgc tgtccattac    300
aacactcatc atcactttca tcgacatgac agcggagatg gaccagcgca cagtgcagac    360
ctgggtcacg gatggagggt gcgcaaaaca ccgatctttt ccggtcttct cgcccctttc    420
tccatcgtac tcgaagtgcc aggtttgacg tccaaatggt acgccaagat cgatgcagac    480
ggtattgtgg aacgatacat cgataatccg cctatcctaa ccgttggact cgccatctcg    540
cttagtgcgg cagtcgtggc caacgcagcg atcatctttc gatttctcga gttcttgaaa    600
ccgagagcaa gtattgcgct tgccattgcg ggtttcgctc ttcacgacat catcaatgtc    660
gtcgccttgg ctgtctttgg tggtatctat ggacccaaac atgacggcct cagtctcagt    720
gccagttact ggatggtctg cgcttcgacc atcacgtcga cgatcgtcac catcagcttg    780
gttgccgact acgtcaggac aaaggatttc aagcacgcag gctcggggtt gacacagctg    840
caaaagggac tggtgctggc aggtatggga ctgctgctgt atctgtcgct gggaagtctg    900
atctttgtct acctcatcaa gatcgatttc atcactgcgc tgtacttttc gacggcaaca    960
gtattgacgg ttggttttgg agatgtggta ccgacaagtc cgggcggcaa agtcttggtc   1020
atcttgtatg cgccaatcgg aatcatcctc gttgcgcttg tcgtatcttc ggcgaggagc   1080
acgatcctag agactttcca agcggccctc atcgcgagga caaaggagcg acgtaggaga   1140
atagcagaac gaaaagctgc ggttaaagag cacaagaggc aggaccgtgc aatacggagg   1200
atcatgcctc gcacgttcac gtttggaccc aactccaacg ctgtcagtaa ttcgccggat   1260
gacgatagca acaacaacga attcgctgaa gctttggctc agatggagaa gcaagctgct   1320
gccggtggtg cacctccagc cgacaatgtt gcgtcttcca tcaccaccac tgctgcctcc   1380
tccggcaacg ccgcctccaa tgacgaaccc aaactcgcag aagcagaaaa gccagcaact   1440
gcaaccgtcg gcgaccccgc tctacaacac caaatccacg cccttcaaac cgaacttcta   1500
gcagcaaaaa aacgcacaga acaagacttc ctcacctacg aagaacacgc gcgacacgaa   1560
gccatcatgg ccgcacgcat gaaactcgtc ctggccgcct ccgtcaccgc tgctttctgg   1620
ctcctcggcg ccgttgcttt tacttatgca gagagatgga gttacggtgg tgcaatgtgg   1680
ttctgcttca tcgccatgat cacgattggg tatggagact atcatccgac gacgcagatc   1740
ggtagggcga tctttgtcat atggggtttg atgggtgttg ctgtgttgac gatcttgttg   1800
gcggttgttc aggatgcgtt tggtggagtg ctgcatcgaa tgctaacgca atccacgtcg   1860
aggttgttcg atcgagcaga ggagagggct aggaagaggc ggttgaagaa ggagcaaatg   1920
cagcgcgagc agcgtcaagc ggacgcggag gaggaaggtg aggatgtgga aacgagaggt   1980
gctacagcag gagcatcagc gatgcgaaag cgaagacggt cacgaacgcg atctcaccgc   2040
aaaagcgaaa gtgacgtcaa gagggagaag ttcaagatgg tcgaagccgg atccaatgac   2100
acaggagagc ggacaaaagt agagcgaaag agtatggaag ccacctttgc acgcgaccgg   2160
cacacatctt cacccgaacc tctagaggag ctcgaacgag atctcgacac gcctgacggt   2220
```

```
gtacctctcg ccatcccctc tttcatcctt aagaatgctt ctggtgttac cgactctggt   2280

ctcatcactg ctgaagtcca attgcccgtc ggagcagccg cgcgtgtgga agacaccctc   2340

gtctcagcac ctcaaaaact cgcccttgcc gccctgctca ccttccaaca ctctgttcgc   2400

gtacttcgct tacacgacac agccatctct gcagccatga ccgacgtccc cgccctgcga   2460

cactactaca actcgcgtca gaagtcttct tcgctctcag ggaccgatct tgccccacaa   2520

gactcctccg aaggaacctc aaaaagtaaa gacggggagg aaacagaccc ggaaacagcg   2580

ttgcaaaacc tccatgcggc gatccagcaa attgcgaatc cggagtatga aaaggtggcg   2640

aagttggtag ttgccaatct ggagtttgag catcatctga aggtgtttct agaacagttc   2700

caggggttga aggatagggt ggaggggttc aagcagcgga cgacggagat gaggcggagg   2760

agggggcaaa cggtgggaga ggcggatgga gaggagcatc atccgacgtt ggcgcatctg   2820

tttcatccgc acgaacacga gcatgagcat cagcaggggc acgagcatga gcatcaacaa   2880

ccatacggaa ggaaccaaga accggaagga ccggcaccgt cggaatag               2928
```

```
<210> SEQ ID NO 21
<211> LENGTH: 411
<212> TYPE: PRT
<213> ORGANISM: Pseudozyma tsukubaensis
<220> FEATURE:
<223> OTHER INFORMATION: Pseudog4094.t1

<400> SEQUENCE: 21

Met Pro Lys Leu Pro Leu Ser Ile Ala Leu Gly Thr Val Leu Ile Ala
1               5                   10                  15

Gly Cys Ile Gly Ala Pro Thr Ser Ser Ser Glu Glu Gly Asp Ser Asp
            20                  25                  30

Tyr Arg Leu Phe Ser Ser Gly Arg Pro Asp Leu Ser Ser Arg Leu Glu
        35                  40                  45

Arg Leu Lys Ile Asp Thr Thr Gln Arg Tyr Asp Pro Glu Leu Gln Tyr
    50                  55                  60

His His Ala Ala Leu Pro Pro Ser Pro Gln Pro Ile Glu Pro Leu Ala
65                  70                  75                  80

Trp Tyr Asp Ser Arg Met Arg Pro Leu Phe Ser Pro Pro Ala Val Gly
                85                  90                  95

Asn Gln Val Ala Leu Val Pro Met Tyr Pro Phe Gln Val Val Pro Gly
            100                 105                 110

Met Gln His Gly His Val Leu Gly His Ala Pro Glu Pro Ser Phe Ala
        115                 120                 125

Gln Val Leu Val Thr Ala Gln Pro Pro Pro Gln Pro Thr Tyr Ser Val
    130                 135                 140

His Pro Asp Thr Lys Leu Pro Val Ser Glu Leu Val Ala Pro Thr Pro
145                 150                 155                 160

Ser Arg Asp Gly Ala Leu Arg Tyr Thr Ile Pro Arg Phe Ala Leu Arg
                165                 170                 175

Asp Gly Arg Gln Phe Gly Pro Leu Gln Val Gly Lys Asp Lys Phe Gln
            180                 185                 190

Ile Ala Ala Tyr Pro Leu Asp Ile Pro Val Leu Arg His Leu Tyr Gln
        195                 200                 205

Tyr Asp Gln Leu Ile Phe Ala Asn Phe Glu Asp Phe Val Leu Gly Asp
    210                 215                 220

Lys Asn Lys Ala Ser Tyr Arg Asn Phe His Gly Val Tyr Arg Pro Glu
225                 230                 235                 240
```

-continued

```
Pro Lys Ile Leu Asp Asp Ile His Arg Ala Ile Arg Ala His Met Ser
                245                 250                 255

Phe Gly Gly Leu Thr Pro Gln Arg Val Ser Pro Asp His Asp Leu Met
            260                 265                 270

Glu Gly Gln Leu Leu Trp Pro Pro Ala His Ile Ile Pro Lys Gln Leu
        275                 280                 285

Gln Ser Glu Glu Val Arg Arg Leu Thr Leu Thr Arg Asn Leu Arg Asp
    290                 295                 300

Asp Leu Arg Lys Ala Val Leu Thr Gln Ile Ser Ala His Gln Arg Asp
305                 310                 315                 320

Phe Ser Lys Val Tyr His Leu Glu Ile Val Ser Asn Gln Gly Lys Arg
                325                 330                 335

His Ile Met Met Thr Thr Leu Pro Tyr Gln Thr Tyr Thr Gln Leu Ala
            340                 345                 350

Asn Gly Gln Ala Thr Asn Leu Asp Phe Trp Val Phe His Glu Gly Ile
        355                 360                 365

Gln Pro Ala Gly Glu Asn Arg Gln Pro Met Val Ala Leu Leu Gly Gly
    370                 375                 380

Ala Phe Leu Ser Lys Glu Thr Lys Glu Ala Leu Leu Ser Ser Leu Arg
385                 390                 395                 400

Met Arg Pro Ala Trp Thr Thr Thr Val Arg Phe
                405                 410


<210> SEQ ID NO 22
<211> LENGTH: 1236
<212> TYPE: DNA
<213> ORGANISM: Pseudozyma tsukubaensis
<220> FEATURE:
<223> OTHER INFORMATION: Pseudog4094.t1

<400> SEQUENCE: 22

atgccaaaac ttccgctgag catagcactc ggcacagtgc tgatagcggg ctgcatcggc     60

gccccaacca gctctagcga ggaaggagac tccgactaca gactattttc atcaggcaga    120

ccggatcttt cttcgcgtct cgagcgactc aagatcgata ccacccagcg gtacgatccg    180

gagttgcaat accaccacgc agcccttcct cccagtccgc agcctattga gccacttgct    240

tggtacgact cccgcatgcg acccttgttt tcgcctcctg ctgttggaaa ccaggttgct    300

ctcgtcccta tgtacccttt ccaagtcgtc cctgggatgc agcatgggca cgttcttggg    360

cacgctccag agccatcctt cgcccaagtc cttgtcacag ctcaacctcc accccaaccc    420

acctattcag tacaccccga cactaagctg ccagtgagtg agctggtagc ccctacgccc    480

tcgcgagatg gagctcttcg atacacgatt ccacgattcg cattgagaga cggaagacag    540

tttggtccgc ttcaagtggg aaaggacaag ttccagatag ctgcctaccc gctagacatt    600

cccgtcctcc gtcacctgta tcagtacgat cagctcattt ttgccaactt cgaagatttc    660

gtccttggcg acaagaacaa ggctagctac cgaaactttc acggagttta tcgacccgag    720

ccgaagatct tggatgacat tcatcgcgcc atccgggcgc acatgtcgtt tggcggacta    780

accccacagc gtgtcagtcc agatcacgat ctgatggaag gccagcttct gtggccacca    840

gctcatatca tacccaagca gctccaaagc gaagaggtcc gtcggctgac actcacccgc    900

aatctacgtg atgacctcag gaaggctgtc ttgacgcaga tctctgcgca tcagagggac    960

ttttcgaagg tttatcatct tgagatcgtc tcgaaccaag gaaaaaggca tatcatgatg   1020

actactctac cttatcagac atacacccag ctcgcaaatg gccaagctac caatttggac   1080
```

-continued

```
ttttgggtct ttcatgaagg catccaaccg gcaggagaga atagacagcc aatggtggct   1140

ttgctaggtg gcgccttcct gtcgaaagag accaaagagg cgctactttc gtccttgcgt   1200

atgcgacctg cctggaccac taccgttcga ttctga                             1236
```

```
<210> SEQ ID NO 23
<211> LENGTH: 313
<212> TYPE: PRT
<213> ORGANISM: Pseudozyma tsukubaensis
<220> FEATURE:
<223> OTHER INFORMATION: Pseudog4095.t1

<400> SEQUENCE: 23

Met Val Val Thr Gly Val Pro Thr Phe Asp Asn Gln Gly His Ala Ser
1               5                   10                  15

Ala Pro Asp Leu Ser Pro Thr Glu Arg Leu Gly His Arg Asp Gly Ser
            20                  25                  30

Val His Pro Pro Phe Trp Arg Arg Gln Ala Ser Ser Ser Asp Ser Trp
        35                  40                  45

Glu Pro Asp Ala Glu Glu Lys Ala Gly Arg Thr Ile Ser Gly Pro Arg
    50                  55                  60

Arg Gly Pro Glu Gly Thr Thr Arg Thr Arg Ala Ile Ile Pro Ala Phe
65                  70                  75                  80

Lys Asp Val Ser Gly Val Ile Trp Gly Pro Tyr Lys Leu Asn Ser Lys
                85                  90                  95

Lys Phe Gln Leu Ile Trp Tyr Pro Leu Glu Met Glu Arg Leu Lys His
            100                 105                 110

Leu Tyr Gln Pro Asp Gly Thr Ile Pro Ala Thr Ile Asp Glu Pro Val
        115                 120                 125

Pro Gly Gln Pro Phe Arg Leu Gln Val Arg Pro Ile Ser Phe Arg Pro
    130                 135                 140

Glu Pro Glu Val Leu Lys His Ile Arg Ser Thr Ile Trp Asn Thr Leu
145                 150                 155                 160

Thr Asp Gln Gly Ile Ser Ala Lys Pro Ile Asp Ser Lys Asn Lys Phe
                165                 170                 175

Phe Arg Glu Gly Met Tyr Leu Trp Pro Pro Leu Thr His Thr Lys Ser
            180                 185                 190

Val Leu Gln Met Pro Glu Ala Leu Leu Ser Asn Arg Ile Ser Val Ala
        195                 200                 205

Pro Gly Asn Arg Phe Arg Thr Met Arg Ala Lys Asn Ile Tyr Gln Phe
    210                 215                 220

Thr Val Pro Ser Ser Ala Gly Asp Arg His Ile Ile Met Thr Pro Ala
225                 230                 235                 240

Val Thr Glu Val Trp Thr Thr Ser Thr Gly Gly Asp Ser Asp Leu Trp
                245                 250                 255

Leu Phe Tyr Glu Gly Arg Lys Leu His Asp Gly Ile Gln Ser Tyr Arg
            260                 265                 270

Gly Lys Arg Leu Thr Ser Asn Val Ile Gly Lys Lys Thr Met Ala Phe
        275                 280                 285

Leu Gly Ala Met Phe Leu Pro Ser Ser Ala His Glu Thr Leu Leu Arg
    290                 295                 300

Ala Lys Val Ile Ser Thr Phe Ala Ala
305                 310


<210> SEQ ID NO 24
<211> LENGTH: 942
```

```
<212> TYPE: DNA
<213> ORGANISM: Pseudozyma tsukubaensis
<220> FEATURE:
<223> OTHER INFORMATION: Pseudog4095.t1

<400> SEQUENCE: 24

atggtggtca ctggtgttcc gacatttgac aaccaaggac acgcctctgc tcctgatttg     60

tcgccgactg agcgtttggg tcaccgcgac ggttctgtcc atcctccctt ctggcgacgt    120

caggcgagca gctcggactc ttgggagcct gacgccgagg agaaagccgg gagaaccatc    180

tcgggtcctc gacgaggtcc ggagggtacc actaggaccc gagctatcat tcccgctttc    240

aaagatgtct caggcgtcat ctggggaccg tataaactca actccaagaa gtttcagctg    300

atatggtacc cgttggaaat ggagcgactg aaacacctct accagcccga cggcacgatt    360

ccagcgacca tcgacgagcc tgtaccaggc cagccgttcc gactgcaggt gcggcccatt    420

agcttccgtc ccgaaccaga agttcttaag cacatccgat cgaccatttg gaacacgctt    480

acggatcaag ggatcagcgc gaagcctatc gactccaaga acaagttttt ccgcgaggga    540

atgtacctat ggccgccttt gacccacaca aagtcggttc ttcaaatgcc cgaggcactc    600

ctgtcgaatc gcatctccgt tgctcctgga aatcgctttc gtacgatgcg tgccaagaac    660

atctatcagt ttacagttcc ttcttccgct ggagacagac atatcatcat gactccagct    720

gtgaccgagg tctggacaac cagcacggga ggagactcag atctgtggct cttctacgaa    780

ggcagaaagc ttcacgatgg gatccaatcc tacagaggca agaggttgac aagcaacgtg    840

ataggcaaaa agaccatggc ctttcttggc gccatgtttt tgccgagttc agcacacgaa    900

acgctgctca gagccaaggt aatttcaact ttcgctgctt ga                       942


<210> SEQ ID NO 25
<211> LENGTH: 164
<212> TYPE: PRT
<213> ORGANISM: Pseudozyma tsukubaensis
<220> FEATURE:
<223> OTHER INFORMATION: Pseudog4096.t1

<400> SEQUENCE: 25

Met Met Leu Phe Arg Leu Leu Leu Leu Leu Leu Gly Ala Ala Leu Val
1               5                   10                  15

Ser Ala Phe Phe Glu Ser Asp Tyr Val Asn Leu Lys Gly Thr Asp Arg
            20                  25                  30

Ser Met Trp Leu Lys Met His Glu Arg Phe Asp Pro Ser Phe Lys Gln
        35                  40                  45

Gly Leu Ala Arg Glu His Ile Ser Ser Pro Arg Val Val Ala Phe Gly
    50                  55                  60

Pro Glu Trp Tyr Gln Ser Ala Leu Gln His Ala Arg Asp Lys Gly Val
65                  70                  75                  80

Leu Val Leu Gly Val His Ser Pro Leu Thr Ser Leu Thr Gly Asn Lys
                85                  90                  95

Lys Thr Tyr Phe Val Thr Leu Ile His Tyr Asp Asp Gly Val Val Ala
            100                 105                 110

Arg Gln Leu Gln Leu His Pro Gln Ser Met Val Gly Ala Val Leu Trp
        115                 120                 125

Lys His Ser Lys Gly Gln Asn Lys Ile Val Ser Ile Asp Arg Leu Ile
    130                 135                 140

Arg Lys Thr Glu Met Asn Trp Asp Pro Glu Val Leu Glu Ser Val Leu
145                 150                 155                 160
```

Gln Arg Glu His

<210> SEQ ID NO 26
<211> LENGTH: 495
<212> TYPE: DNA
<213> ORGANISM: Pseudozyma tsukubaensis
<220> FEATURE:
<223> OTHER INFORMATION: Pseudog4096.t1

<400> SEQUENCE: 26
atgatgctct tccgcttgtt gctcctgctt ctgggcgctg ccttggtttc tgccttcttt 60
gaaagcgatt acgtcaatct caaagggaca gaccgaagca tgtggctaaa gatgcacgaa 120
cgattcgacc cttccttcaa gcaaggtctt gcacgagaac atatttcttc tcctcgagtg 180
gtcgccttcg gccccgaatg gtaccagtcg gccttgcagc atgcacgcga caagggagtg 240
ttggttcttg gcgttcacag tcctctcaca tcattgacgg ggaacaagaa gacgtatttt 300
gtcacgctga tccattatga cgatggagtt gttgcacgtc agctccaatt gcatcctcaa 360
agcatggtgg gtgcagtctt gtggaagcac agtaaaggtc aaaacaagat tgtttcgatt 420
gacaggttaa ttaggaagac ggagatgaac tgggatccag aggtactgga aagtgtccta 480
caacgcgagc attga 495

<210> SEQ ID NO 27
<211> LENGTH: 185
<212> TYPE: PRT
<213> ORGANISM: Pseudozyma tsukubaensis
<220> FEATURE:
<223> OTHER INFORMATION: Pseudog4097.t1

<400> SEQUENCE: 27

Met Gln Val Leu Ser Asn Arg Phe Leu Gly Leu Leu Ala Leu Leu Phe
1 5 10 15

Ser Leu Val Ile Leu Gly Val Ala Ala Thr Arg Leu Ser Asp Lys Glu
20 25 30

Glu Asp Met Leu Asn Gln Ala Arg Ser Pro Tyr Gln Ser Pro Ile Tyr
35 40 45

Glu Asn Ala Gly His Ala Trp Gln Thr Trp Thr Leu Tyr Pro Lys Leu
50 55 60

Gln Asp Tyr Ser His Ile Pro Asp Phe Glu Arg Asp Ala Leu Glu Met
65 70 75 80

Ala Tyr Arg Lys Gly Ala Met His Ile Ser Asp Thr Met Asp Asp Asn
85 90 95

Asp Ile Arg Asn Arg Ala Trp Arg Ser Gly Ser His Ser Gly Ser Lys
100 105 110

Leu Ala Arg Asp Gly His Ile Tyr Phe Tyr Ser Ile Val Pro Pro Arg
115 120 125

Ser Tyr Met Gly Leu Gln Met Gly Leu Pro Glu Lys Asn Arg Val Ala
130 135 140

Ser Leu Leu Trp Lys His Asp Pro Gly Thr Gly Gln Thr Lys Leu Ile
145 150 155 160

His Val Asp Glu Leu Gln His Tyr Lys Asn Leu Gln Trp Asp Met Asp
165 170 175

Lys Leu Glu Asp Ile Leu Arg His His
180 185

<210> SEQ ID NO 28
<211> LENGTH: 558

<212> TYPE: DNA
<213> ORGANISM: Pseudozyma tsukubaensis
<220> FEATURE:
<223> OTHER INFORMATION: Pseudog4097.t1

<400> SEQUENCE: 28

```
atgcaggttc tctctaaccg cttcctcggc cttttggccc tcctcttctc acttgtcatc      60

ctgggtgtcg ctgccacccg gcttagtgat aaagaggaag acatgctcaa tcaggcacga     120

agtccttacc agtctcccat ctacgaaaat gctggtcatg catggcagac ctggacactt     180

tatcctaaac ttcaggatta ctcgcacatc cctgactttg agcgtgatgc tcttgaaatg     240

gcttatagga aaggtgccat gcacatcagc gacaccatgg acgacaacga catccgaaac     300

agggcatggc gttctggtag ccacagtggt agcaagttgg ccagagatgg acatatctac     360

ttttacagta ttgttcctcc tcgatcttac atgggactcc agatgggact tcccgagaaa     420

aaccgggtcg ctagtctgct ttggaagcat gatccgggaa cggggcagac caagttgatt     480

catgttgacg aacttcagca ctataagaac ctacagtggg acatggataa gttggaagac     540

attctcaggc atcactga                                                   558
```

<210> SEQ ID NO 29
<211> LENGTH: 167
<212> TYPE: PRT
<213> ORGANISM: Pseudozyma tsukubaensis
<220> FEATURE:
<223> OTHER INFORMATION: Pseudog4098.t1

<400> SEQUENCE: 29

```
Met Val Ala Ile His Arg Arg Leu Phe Leu Leu Leu Leu Leu Gly Val
1               5                   10                  15

Ile Phe Ala Met Thr Ala Thr Ala Ala Pro Pro Tyr Ile Asn Pro Asp
            20                  25                  30

Glu Glu Met Ile Gln His Ser Ile Gly Lys Leu Gly Thr Val Tyr Ala
        35                  40                  45

Asp Ser Gly Val Thr Tyr Ala Pro Val Asn Ala Ala Gly Lys Tyr Arg
    50                  55                  60

Val Tyr Asn Phe Glu Glu Lys Ala Trp Asp Met Ala His Gly Gly Ala
65                  70                  75                  80

Thr Tyr Val Gly Thr Arg Gln His Phe Arg Gly Gly Gln Lys Tyr Gly
                85                  90                  95

Gln Pro Trp Lys Tyr Phe Tyr Ser Ile Ile Pro Pro Asp Thr Pro Leu
            100                 105                 110

Gly Arg Glu Met Gly Leu Pro Asp His Lys Leu Ala Thr Val Leu Trp
        115                 120                 125

Arg Tyr Gly Asn Gly Arg Lys Ser Met Val Glu Leu Gln Glu Ala Asp
    130                 135                 140

Asn Tyr Met His His Ser Gly Phe Asn Trp Asn Gly Met Gln Glu Leu
145                 150                 155                 160

Lys Asp Val Ile Gly His His
                165
```

<210> SEQ ID NO 30
<211> LENGTH: 504
<212> TYPE: DNA
<213> ORGANISM: Pseudozyma tsukubaensis
<220> FEATURE:
<223> OTHER INFORMATION: Pseudog4098.t1

<400> SEQUENCE: 30

```
atggttgcca ttcaccgccg tctcttcctt ctcctgctcc ttggcgtcat ctttgcaatg     60

accgccaccg ccgccccacc ctacatcaat ccggacgaag agatgatcca acactctatc    120

ggcaaacttg gcactgtcta cgccgattcg ggtgtcacat atgcaccggt caacgccgcg    180

ggcaaatatc gcgtctacaa ctttgaagaa aaggcgtggg acatggctca cggtggcgca    240

acctatgtcg gtacgcgtca acacttccga ggaggtcaaa agtatggtca accttggaag    300

tatttctatt ccatcattcc tcctgacaca ccgttgggac gggagatggg cttgcctgac    360

cacaaactcg cgacggtgct gtggaggtac gggaacggtc gaaagtcgat ggtggaactt    420

caggaggcgg ataactatat gcatcattct gggttcaatt ggaacgggat gcaggagctg    480

aaggatgtaa ttggacatca ctga                                           504
```

```
<210> SEQ ID NO 31
<211> LENGTH: 485
<212> TYPE: PRT
<213> ORGANISM: Pseudozyma tsukubaensis
<220> FEATURE:
<223> OTHER INFORMATION: Pseudog6271.t1

<400> SEQUENCE: 31

Met Ala Pro Ser Leu Asn Ala Asn Ser Thr Ala Asp Arg Arg Asn Ala
1               5                   10                  15

Thr Ala Ala Pro Asp Leu Leu Ser Gly Asn Lys Ala Gly Gly Gly Leu
            20                  25                  30

Lys Leu Ser Gly Leu Pro Asp Leu Ser Asp Ser Ala Gly Thr Leu Ser
        35                  40                  45

Asp Val Phe Gly Thr Pro Ala Met Arg Leu Ile Trp Ser Asp Gln Asn
    50                  55                  60

Arg Val Ala Cys Tyr Leu Glu Ile Glu Ala Ala Leu Ala Val Val Gln
65                  70                  75                  80

Ala Glu Leu Gly Ile Ile Pro Lys His Ala Ala Gln Glu Ile Val Lys
                85                  90                  95

His Cys Arg Val Asp Glu Ile Asp Trp Ala Leu Tyr Lys Gln Lys Thr
            100                 105                 110

Glu Leu Ile Gly Tyr Pro Val Leu Gly Ile Val Gln Gln Leu Val Ala
        115                 120                 125

Asn Cys Lys Asp Gly Leu Gly Glu Tyr Cys His Trp Gly Ala Thr Thr
    130                 135                 140

Gln Asp Ile Thr Asp Thr Ala Thr Ile Met Gln Ile Arg Gln Ser Leu
145                 150                 155                 160

Ala Leu Val Lys Glu Lys Leu Cys Ser Ile Val Ala Ser Leu Arg Tyr
                165                 170                 175

Leu Ala Glu Lys His Arg Asn Leu Pro Met Ala Ala Arg Ser Asn Leu
            180                 185                 190

Lys Gln Ala Val Pro Ile Thr Phe Gly Phe Lys Met Ala Arg Phe Leu
        195                 200                 205

Ala Thr Phe Arg Arg His Gln Glu Arg Leu Ala Glu Leu Glu Lys Arg
    210                 215                 220

Thr Tyr Thr Leu Glu Phe Gly Gly Ala Ala Gly Asn Leu Ser Ser Leu
225                 230                 235                 240

Gly Glu Lys Gly Ile Ala Thr His Asp Ala Leu Ala Lys Met Leu Asp
                245                 250                 255

Leu Ser Pro Ala Asp Ile Ala Trp His Thr Glu His Asp Arg Phe Ala
            260                 265                 270
```

```
Glu Val Gly Ala Phe Leu Gly Leu Leu Thr Gly Thr Leu Ala Lys Leu
        275                 280                 285

Ala Thr Asp Ile Lys Leu Met Ser Gln Thr Glu Val Gly Glu Val Gly
    290                 295                 300

Glu Pro Phe Ile Ser Asn Arg Gly Ser Ser Ser Thr Met Pro Gln Lys
305                 310                 315                 320

Asn Asn Pro Ile Ser Cys Val Tyr Ile His Ala Cys Ala Ala Asn Val
                325                 330                 335

Arg Gln Gly Thr Ala Ala Leu Leu Asp Ala Met Gln Ser Asp His Glu
            340                 345                 350

Arg Gly Thr Gly Pro Trp Glu Ile Ile Trp Val Gln Leu Pro Leu Met
        355                 360                 365

Met Asn Trp Ser Ala Ala Ala Leu Ala Asn Ala Asp Phe Ile Leu Lys
    370                 375                 380

Gly Leu Gln Val Phe Pro Asp Ala Met Val Arg Asn Leu Ala Leu Ser
385                 390                 395                 400

Lys Gly Leu Ile Val Ser Glu Ala Val Met Met Ala Leu Gly Asp Thr
                405                 410                 415

Leu Gly Arg Gln Tyr Ala His Asp Ala Val Tyr Glu Cys Cys Arg Ala
            420                 425                 430

Ala Phe Glu His Asn Arg Pro Leu Leu Asp Val Leu Leu Glu Asn Gln
        435                 440                 445

Glu Ile Ala Ser Lys Leu Lys Arg Ala Glu Leu Glu Arg Leu Cys Glu
    450                 455                 460

Pro Ala Asn Tyr Leu Gly Gln Cys Ser Gln Trp Ile Asp Arg Val Leu
465                 470                 475                 480

Leu Pro Pro Ser Thr
                485
```

<210> SEQ ID NO 32
<211> LENGTH: 478
<212> TYPE: PRT
<213> ORGANISM: Pseudozyma tsukubaensis
<220> FEATURE:
<223> OTHER INFORMATION: Pseudog6268.t1

<400> SEQUENCE: 32

```
Met Ser Asn Pro Leu Ala Gly Arg Val Lys Trp Phe Arg Arg Ile Pro
1               5                   10                  15

Ser Ile Leu Leu Ala Phe Val Val Ser His Thr Asp Ser Phe Thr Met
            20                  25                  30

Leu Arg Gly Ile Glu Thr Thr Ile Tyr Arg Ala Gly Thr Ser Arg Gly
        35                  40                  45

Leu Tyr Leu Leu Ala Ser Asp Leu Pro Ser Glu Pro Ser Ala Arg Asp
    50                  55                  60

Ala Ala Leu Leu Ser Ile Met Gly Ser Gly His Pro Leu Gln Ile Asp
65                  70                  75                  80

Gly Met Gly Gly Gly Asn Ser Leu Thr Ser Lys Val Ala Ile Val Ser
                85                  90                  95

Pro Ser Ala Gln Ser Asp His Ser Asp Val Asp Tyr Leu Phe Cys Gln
            100                 105                 110

Val Gly Ile Asn Glu Arg Ile Val Asp Thr Ala Pro Asn Cys Gly Asn
        115                 120                 125

Leu Met Ser Gly Val Ala Ala Phe Ala Ile Glu Arg Gly Leu Val Lys
    130                 135                 140
```

-continued

Pro His Pro Ser Asp Thr Thr Cys Leu Val Arg Ile Phe Asn Leu Asn
145 150 155 160

Ser Asn Gln Ala Ser Glu Leu Leu Ile Pro Val Gln Asp Gly Arg Val
165 170 175

His Tyr Lys Asp Val Asp Asp Thr Gly Leu Gln Arg Pro Ser Ala Arg
180 185 190

Val Ser Leu Arg Phe Leu Asn Thr Val Gly Ala Cys Thr Gly Lys Leu
195 200 205

Leu Pro Thr Gly Asn Ala Thr Asp Ser Ile Glu Gly Leu Glu Val Ser
210 215 220

Val Ile Asp Ser Ala Ile Pro Val Val Phe Val Arg Gln Ala Asp Val
225 230 235 240

Gly Ile Thr Gly Phe Glu Thr Pro Ala Thr Leu Asn Ala Asp Thr Ala
245 250 255

Leu Leu Ser Arg Leu Glu Arg Val Arg Leu Glu Ala Gly Arg Arg Met
260 265 270

Gly Trp Gly Asp Val Ser Ser Ser Val Val Pro Lys Leu Ser Leu Ile
275 280 285

Gly Pro Gly Ser Asn Cys Thr Thr Phe Thr Ala Arg Tyr Phe Thr Pro
290 295 300

Lys Thr Cys His Asn Ala His Ala Val Thr Gly Ala Ile Cys Thr Ala
305 310 315 320

Gly Ala Ala Tyr Val Pro Gly Thr Val Val Ser Asp Ile Phe Ser Ser
325 330 335

Arg Thr Pro Ser Leu Ser Ser Ser Pro Gly Asp Thr Thr Pro Pro Tyr
340 345 350

Thr Pro Gln Arg Arg Ile Ser Ile Glu His Pro Ser Gly Val Leu Glu
355 360 365

Ile Gly Leu Thr Ala Ala Glu Ser Asp Ser Pro Arg Ser Leu Asp Ile
370 375 380

Ala His Val Glu Arg Ser Val Ala Leu Ile Ala His Ala Arg Val Tyr
385 390 395 400

Tyr Thr Met Pro Asp Arg His Pro Ser Val Glu Ile Pro Ile Ile Ser
405 410 415

Pro Val Thr Pro Thr Ser Ala Glu Met Leu Asp Arg Ala Tyr Gln Ser
420 425 430

Leu Ala Leu Ala Leu Gly Arg Gly Lys Asp Arg Ser His Ile Ile Pro
435 440 445

Leu Gly Ser Glu Gly Lys Glu Ser Glu Leu Tyr Tyr Asn Met Pro Asp
450 455 460

Ser Thr Val Ser Ser Tyr Arg Gly Thr His Ser Thr Ala Leu
465 470 475

<210> SEQ ID NO 33
<211> LENGTH: 532
<212> TYPE: PRT
<213> ORGANISM: Pseudozyma tsukubaensis
<220> FEATURE:
<223> OTHER INFORMATION: Pseudog6270.t1

<400> SEQUENCE: 33

Met Leu Pro Gln Thr Pro Val Pro Asp Tyr Arg Leu Ser Met Arg Tyr
1 5 10 15

Ser Thr Asp Ser Val Ala Ala Ser Gln Ala Leu Thr Thr Pro Glu Ala
20 25 30

-continued

```
Ala Pro Ser Ile Ser His His Ala Asp Thr Gly Glu Val Gln Gln Ala
        35                  40                  45

His Ser Gly Asp Asp Gly Ala Leu Glu Glu Gly Ala Ile Ala His Ser
    50                  55                  60

Ser Lys Glu Gly Ser Gln Arg Asp Gln Gln Thr Glu Leu Tyr Cys Ala
65                  70                  75                  80

Phe Thr Lys Gly Thr Lys Leu Phe Val Val Leu Ser Val Ser Ile Ala
                85                  90                  95

Gly Phe Phe Ser Pro Phe Ser Ile Asn Ile Tyr Ile Pro Ala Leu Pro
            100                 105                 110

Gln Ile Ser Lys Leu Leu His Thr Ser Glu Ala Ala Thr Asn Val Thr
        115                 120                 125

Val Thr Val Tyr Met Ile Ala Gln Gly Leu Ser Pro Val Ile Trp Ala
    130                 135                 140

Pro Leu Ser Asp Val Phe Gly Arg Arg Pro Ile Tyr Ile Ala Thr Phe
145                 150                 155                 160

Leu Val Phe Phe Val Ala Asn Leu Gly Leu Ser Phe Thr Asn Val Tyr
                165                 170                 175

Trp Leu Leu Val Val Leu Arg Met Val Gln Ala Ala Gly Ala Cys Ser
            180                 185                 190

Ala Ile Ala Ile Gly Ala Gly Thr Ile Gly Asp Val Thr Glu Arg Lys
        195                 200                 205

Glu Arg Gly Ser Tyr Met Gly Tyr Tyr Ala Leu Ala Gln Tyr Thr Gly
    210                 215                 220

Pro Ala Ile Gly Pro Val Ile Gly Gly Ala Leu Ser Gln Arg Trp Asp
225                 230                 235                 240

Tyr His Ser Thr Phe Phe Phe Leu Ser Ala Val Ser Gly Val Phe Leu
                245                 250                 255

Ile Phe Met Ala Phe Phe Leu Leu Glu Thr Leu Arg Val Leu Val Gly
            260                 265                 270

Asn Gly Ser Ala Arg Thr Phe Gly Ile Tyr Arg Thr Leu Val Gly Pro
        275                 280                 285

Arg Leu Val Lys Ser Thr Ala Asn Ser Met Arg Pro Arg Met Lys Ser
    290                 295                 300

Pro Leu Glu Gly Arg Leu Glu Phe Gly Phe His Arg Pro Phe Leu Val
305                 310                 315                 320

Phe Ala Arg Pro Glu Thr Ser Leu Ala Ile Leu Ala Phe Ser Met Val
                325                 330                 335

Tyr Ala Thr Tyr Tyr Leu Ser Ser Ala Ser Leu Pro Tyr Leu Phe Lys
            340                 345                 350

Gln Val Tyr Gly Leu His Glu Leu Leu Ile Gly Val Cys Phe Val Pro
        355                 360                 365

Ser Gly Val Gly Cys Ala Leu Gly Thr Val Leu Ala Gly Lys Ile Leu
    370                 375                 380

Asp Ser Asp Tyr Arg Arg Ala Leu Asp Lys Asn Lys Ser Gly Val Lys
385                 390                 395                 400

Val Thr Arg Ala Arg Leu Gln Ser Ala Trp Ile Tyr Leu Pro Gly Tyr
                405                 410                 415

Ala Ser Ser Leu Leu Ala Tyr Gly Trp Cys Val Arg Ala His Thr His
            420                 425                 430

Ile Ala Ala Pro Ile Leu Phe Gln Phe Thr Leu Gly Met Phe Ser Thr
        435                 440                 445
```

-continued

Met Tyr Phe Thr Asn Ile Asn Thr Leu Val Val Asp Leu Tyr Pro Gly
    450                 455                 460

Lys Ala Ala Thr Ala Thr Ala Ala Val Asn Val Gly Arg Cys Leu Leu
465                 470                 475                 480

Gly Ala Val Ala Val Ala Ile Val Gln Pro Met Thr Asp Ala Met Gly
                485                 490                 495

Ala Gly Trp Thr Phe Thr Val Gly Ala Leu Leu Ala Leu Phe Ile Gly
            500                 505                 510

Leu Ile Cys Gln Thr Leu Ile His Phe His Gly Glu Lys Trp Ala Ala
        515                 520                 525

Arg Lys His Ser
    530

<210> SEQ ID NO 34
<211> LENGTH: 191
<212> TYPE: PRT
<213> ORGANISM: Pseudozyma tsukubaensis
<220> FEATURE:
<223> OTHER INFORMATION: Pseudog6267.t1

<400> SEQUENCE: 34

Met Pro Ser Val Gln Arg Asn Ile Ser Pro Ser Val Ser Val Leu Ala
1               5                   10                  15

Gly Ala Thr Ala Gly Ala Val Glu Gly Glu Thr Lys Leu Ile Asp Asp
            20                  25                  30

Gly Lys Arg Ala Lys Pro Arg Tyr Glu Gln Gly Leu Phe Arg Gly Thr
        35                  40                  45

Ala Ser Ile Ile Arg Gln Glu Gly Phe Gly Gly Ile Tyr Lys Gly Val
    50                  55                  60

Phe Pro Val Ile Leu Arg Gln Gly Ser Ala Ser Ala Ile Arg Leu Gly
65                  70                  75                  80

Thr Tyr Ser Ala Met Arg Asp Phe Ile Pro Lys Ala Gln Gly Lys Gly
                85                  90                  95

Ser Ser Phe Val Asn Trp Leu Thr Thr Phe Ser Ile Gly Ala Thr Ser
            100                 105                 110

Gly Val Val Ala Val Tyr Gly Thr Met Pro Phe Asp Val Leu Lys Thr
        115                 120                 125

Arg Met Gln Ala Ile Asp Ala Ser Arg Tyr Arg Ser Thr Trp His Cys
    130                 135                 140

Leu Thr Asp Thr Ile Gly Thr Glu Gly Ile Ala Ala Leu Trp Arg Gly
145                 150                 155                 160

Ser Val Ser Arg Ser Met Arg Leu Ile Val Ser Gly Gly Val Ile Phe
                165                 170                 175

Ser Val Tyr Glu Gln Val Val Trp Leu Leu Ala Gly Pro Glu Phe
            180                 185                 190

<210> SEQ ID NO 35
<211> LENGTH: 348
<212> TYPE: PRT
<213> ORGANISM: artificial
<220> FEATURE:
<223> OTHER INFORMATION: synthetic RIA1 sequence

<400> SEQUENCE: 35

Met Lys Met Ser Gly Ser Asn Ile Asp Asp Asp Asp Cys Ala Asn Met
1               5                   10                  15

Phe Asp Leu Met Ala Pro Pro Leu Ala Ser Ser Ser Cys Gly Pro Tyr
            20                  25                  30

Phe Ser Thr Pro Asp Leu Ala Leu Pro Ser Ile Ser Pro Val Ser Thr
35 40 45

Asp Ala Asp Thr Thr Leu Pro Ser Pro Leu Gly Val Ala Pro Cys Thr
50 55 60

Tyr Ser Thr Cys Pro Ile Arg Asp Glu Gly Glu Thr Ser Thr Ser Val
65 70 75 80

Ser Gly Lys Arg Lys His Ser Glu Val Glu Lys Asp Arg Arg Arg Ser
85 90 95

Ile Ser Asn Gly Phe Ala Val Cys Leu Gln Asn Val Leu His Asn Asp
100 105 110

Ser Asn Cys Ala Lys Pro Ile Ser Lys Ser Val Leu Leu Gln Gln Ala
115 120 125

Cys Asp Glu Ile Arg Glu Leu Arg Lys Lys Leu Asp Ala Ser Thr Thr
130 135 140

Ile Ile Ser Arg Phe Gly Leu Glu Asn Leu Phe Pro Thr Pro Asn Ser
145 150 155 160

Ser His Ala Ser Pro Pro Asn Gly Ser Ser Arg Thr Tyr Pro Pro Tyr
165 170 175

Asn Asn Gly Pro Asp Phe Asp Thr Arg Arg Ala Ser Ser Thr Ser Thr
180 185 190

Pro Tyr Asn Asn Glu Lys Arg Glu Ala Asn Val Lys Arg Arg His Ser
195 200 205

Tyr His Asn Ser Trp Asn Ala Ser Asp Arg Ser Ser Asp Asp Asp Thr
210 215 220

Asn Ala Ser Cys Ser Ser Thr Ser His His Asp Asp Asp Thr Asp Ser
225 230 235 240

Ser Glu Ser Asp Ser Asp Phe Pro Asp Glu Thr Lys Asn Arg Thr Lys
245 250 255

Arg His Lys Ala Arg Ala Lys Lys Asp Arg Asp Arg Ala Lys Pro Arg
260 265 270

Tyr Lys Pro Lys Pro His Thr Asn Arg Pro Pro Pro Ser Ser Cys Ser
275 280 285

Asp Ser Ser Pro Ser Ser Pro Cys Pro Ser Pro Asn Arg Asn Ala Asp
290 295 300

Glu Leu Gln Gln Ala Ile Leu Ser Leu Leu Leu Glu Leu Pro His His
305 310 315 320

Leu Glu Asp Val His Asn Asp Lys Arg Ala Ser Gln Gln Pro Thr Asp
325 330 335

Pro Thr Gly Lys Thr Arg Asn Lys Lys Arg His Arg
340 345

<210> SEQ ID NO 36
<211> LENGTH: 393
<212> TYPE: PRT
<213> ORGANISM: Pseudozyma tsukubaensis
<220> FEATURE:
<223> OTHER INFORMATION: Pseudog6266.t1

<400> SEQUENCE: 36

Met Ser Leu Ser Asn Ser Asn His Asn Glu Arg His Asn Asp Asp Asn
1 5 10 15

Asn Ile Asn Asp Asp Asp Cys Ala Asn Phe Phe Glu Leu Met Val Gln
20 25 30

Pro Ala Ser Ser Ser Ser Tyr Gly Pro Tyr Phe Pro Asp Pro Gly Leu
35 40 45

-continued

```
Ala Leu Pro Ala Ile Ser Asp Val Ser Ser Thr Thr Asp Thr Arg Leu
    50                  55                  60

Pro Ser Gln Leu Gly Val Thr Pro Phe Ser His Gln Thr Ser Pro Ile
65                  70                  75                  80

Arg Ser Ala Asp Glu Gly Glu Lys Thr Thr Thr Thr Ala Ser Tyr Lys
                85                  90                  95

Arg Lys His Ser Glu Val Glu Lys Asp Arg Arg Arg Ile Ile Ser Asn
            100                 105                 110

Gly Phe Ala Asn Val Leu His Asn Asp Ser Thr Ser Lys Pro Ile Ser
        115                 120                 125

Lys Ala Thr Leu Leu Gln Gln Ala Cys Asp Glu Ile Arg Glu Leu Arg
    130                 135                 140

Lys Lys Leu Asp Thr Ser Ile Thr Ile Ile Ser Arg Tyr Gly Leu Glu
145                 150                 155                 160

Asn Leu Phe Gln Val Ala Pro Thr Pro Asn Ser Leu Ser Asn Ala Ser
                165                 170                 175

Pro Pro Asn Gly Thr Ser Arg Ala Tyr Pro Thr Tyr Ser Asn Asp Leu
            180                 185                 190

Gly Pro Asp Arg Phe Gln Asp Ser Arg Arg Ser Ser Thr Ser Ala Thr
        195                 200                 205

Ser Val Ser Gly Ser Gln Tyr Asn Asn Gly Ala Ala Ala Lys Glu Asp
    210                 215                 220

Gly Asn Glu Arg Arg Asn Ser Asn Val Lys Arg Arg Ser Ser Tyr Thr
225                 230                 235                 240

Asn Ser Ile Asn Ser Ser Phe Glu Ser Ser Glu Glu Asp Thr Leu Asn
                245                 250                 255

Ser Ser Cys Asp Asn Thr Ser Asp Phe Asp Glu Ser Val Gly Ser Ser
            260                 265                 270

Glu Ser Glu Ser Glu Thr Asn Asn Arg Thr Arg Asn Arg Asn Arg Thr
        275                 280                 285

Lys Arg Ala Met Ala Thr Ala Lys Leu Lys Asp Arg Asp Arg Ala Lys
    290                 295                 300

Ala Arg Thr Ala Pro Lys Pro His Ser Asn Arg Leu Ser Pro Ala Ser
305                 310                 315                 320

Thr Ile Thr Pro Ser Glu Met Ser Ser Ser Leu Ala Ser Pro Asn Thr
                325                 330                 335

Ser Ser Gln Glu His Ile Gln Gln Ala Ile Leu Ser Leu Leu Leu Glu
            340                 345                 350

Leu Pro Lys His Leu Glu Asn Val His Lys Ser Lys Arg Pro Ser Ser
        355                 360                 365

Gln Gln Pro Ser Thr Gln Ile Asp Gln Thr Gly Asn Arg Thr Thr Thr
    370                 375                 380

Val Thr Lys Thr Arg Arg Arg His Arg
385                 390
```

<210> SEQ ID NO 37
<211> LENGTH: 288
<212> TYPE: PRT
<213> ORGANISM: artificial
<220> FEATURE:
<223> OTHER INFORMATION: synthetic shortened RIA1 sequence

<400> SEQUENCE: 37

```
Met Ser Leu Ser Asn Ser Asn Ile Asn Asp Asp Asp Cys Ala Asn Phe
1               5                   10                  15
```

```
Phe Glu Leu Met Val Gln Pro Ala Ser Ser Ser Ser Tyr Tyr Phe Pro
            20                  25                  30

Asp Pro Gly Leu Ala Leu Pro Ala Ile Ser Asp Val Ser Ser Thr Thr
        35                  40                  45

Asp Thr Arg Leu Pro Ser Gln Leu Gly Val Thr Pro Phe His Gln Thr
    50                  55                  60

Ser Pro Ile Lys Thr Thr Thr Thr Ala Ser Tyr Lys Arg Lys His Ser
65                  70                  75                  80

Glu Val Glu Lys Asp Arg Arg Arg Ile Ile Ser Asn Gly Phe Ala Asn
                85                  90                  95

Val Leu His Asn Asp Ser Thr Ser Lys Pro Ile Ser Lys Ala Thr Leu
            100                 105                 110

Leu Gln Gln Ala Cys Asp Glu Ile Arg Glu Leu Arg Lys Lys Leu Asp
        115                 120                 125

Thr Ser Ile Thr Ile Ile Ser Arg Tyr Gly Leu Glu Asn Leu Phe Pro
    130                 135                 140

Asn Ser Ser Asn Ala Ser Pro Pro Asn Gly Thr Ser Arg Ala Tyr Pro
145                 150                 155                 160

Arg Arg Asn Ser Asn Val Lys Arg Arg Ser Ser Tyr Thr Asn Ser Asn
                165                 170                 175

Ser Ser Phe Glu Ser Ser Glu Glu Asp Ser Cys Asp Asn Thr Ser Asp
            180                 185                 190

Phe Asp Glu Ser Val Gly Ser Ser Glu Ser Glu Ser Glu Thr Asn Asn
        195                 200                 205

Asn Arg Thr Lys Arg Ala Met Ala Thr Ala Lys Lys Asp Arg Asp Arg
    210                 215                 220

Ala Lys Ala Arg Thr Ala Pro Lys Pro Ala Ser Thr Ile Thr Pro Ser
225                 230                 235                 240

Glu Met Ser Ser Ser Leu Ala Ser Pro Asn Thr Ser Ser Gln Ile Gln
                245                 250                 255

Gln Ala Ile Leu Ser Leu Leu Leu Glu Leu Pro Lys His Leu Glu Asn
            260                 265                 270

Val His Lys Ser Lys Arg Pro Ser Thr Lys Thr Arg Arg Arg His Arg
        275                 280                 285


<210> SEQ ID NO 38
<211> LENGTH: 7
<212> TYPE: PRT
<213> ORGANISM: artificial
<220> FEATURE:
<223> OTHER INFORMATION: 1st RIA1 motif

<400> SEQUENCE: 38

Ser Gly Lys Arg Lys His Ser
1               5


<210> SEQ ID NO 39
<211> LENGTH: 8
<212> TYPE: PRT
<213> ORGANISM: artificial
<220> FEATURE:
<223> OTHER INFORMATION: 2nd RIA1 motif

<400> SEQUENCE: 39

Lys Arg Lys His Ser Glu Val Glu
1               5
```

<210> SEQ ID NO 40
<211> LENGTH: 8
<212> TYPE: PRT
<213> ORGANISM: artificial
<220> FEATURE:
<223> OTHER INFORMATION: 3rd RIA1 motif

<400> SEQUENCE: 40

Lys Asp Arg Arg Arg Ser Ile Ser
1 5

<210> SEQ ID NO 41
<211> LENGTH: 6
<212> TYPE: PRT
<213> ORGANISM: artificial
<220> FEATURE:
<223> OTHER INFORMATION: 4th RIA1 motif

<400> SEQUENCE: 41

Ile Ser Asn Gly Phe Ala
1 5

<210> SEQ ID NO 42
<211> LENGTH: 5
<212> TYPE: PRT
<213> ORGANISM: artificial
<220> FEATURE:
<223> OTHER INFORMATION: 5th RIA1 motif

<400> SEQUENCE: 42

Asn Val Leu His Asn
1 5

<210> SEQ ID NO 43
<211> LENGTH: 6
<212> TYPE: PRT
<213> ORGANISM: artificial
<220> FEATURE:
<223> OTHER INFORMATION: 6th RIA1 motif

<400> SEQUENCE: 43

Ser Lys Pro Ile Ser Lys
1 5

<210> SEQ ID NO 44
<211> LENGTH: 13
<212> TYPE: PRT
<213> ORGANISM: artificial
<220> FEATURE:
<223> OTHER INFORMATION: 7th RIA1 motif

<400> SEQUENCE: 44

Leu Leu Gln Gln Ala Cys Asp Glu Ile Arg Glu Leu Arg
1 5 10

<210> SEQ ID NO 45
<211> LENGTH: 14
<212> TYPE: PRT
<213> ORGANISM: artificial
<220> FEATURE:
<223> OTHER INFORMATION: 8th RIA1 motif

<400> SEQUENCE: 45

Gln Ala Cys Asp Glu Ile Arg Glu Leu Arg Lys Lys Leu Asp
1 5 10

<210> SEQ ID NO 46

<211> LENGTH: 12
<212> TYPE: PRT
<213> ORGANISM: artificial
<220> FEATURE:
<223> OTHER INFORMATION: 9th RIA1 motif

<400> SEQUENCE: 46

Gln Gln Ala Ile Leu Ser Leu Leu Leu Glu Leu Pro
1 5 10

<210> SEQ ID NO 47
<211> LENGTH: 7
<212> TYPE: PRT
<213> ORGANISM: Pseudozyma tsukubaensis
<220> FEATURE:
<223> OTHER INFORMATION: 1st RIA motif as found in P. tsukubaensis

<400> SEQUENCE: 47

Ser Tyr Lys Arg Lys His Ser
1 5

<210> SEQ ID NO 48
<211> LENGTH: 295
<212> TYPE: PRT
<213> ORGANISM: Pseudozyma tsukubaensis
<220> FEATURE:
<223> OTHER INFORMATION: Pseudog4640.t1

<400> SEQUENCE: 48

Met Ser Leu Phe Asn Val Ser Asn Gly Leu Arg Ala Ala Leu Arg Pro
1 5 10 15

Ser Ile Ala Ser Ser Ser Arg Val Thr Ala Ala Phe Ser Thr Ser Ala
20 25 30

Ala Ala Arg Leu Ala Thr Pro Thr Asn Asp Ala Pro Gly Ser Gly Lys
35 40 45

Pro Gln His Leu Lys Gln Phe Lys Ile Tyr Arg Trp Asn Pro Asp Lys
50 55 60

Pro Ser Glu Lys Pro Arg Leu Gln Ser Tyr Thr Leu Asp Leu Asn Gln
65 70 75 80

Thr Gly Pro Met Val Leu Asp Ala Leu Ile Lys Ile Lys Asn Glu Ile
85 90 95

Asp Pro Thr Leu Thr Phe Arg Arg Ser Cys Arg Glu Gly Ile Cys Gly
100 105 110

Ser Cys Ala Met Asn Ile Asp Gly Val Asn Thr Leu Ala Cys Leu Cys
115 120 125

Arg Ile Asp Lys Ala Asn Asp Thr Lys Ile Tyr Pro Leu Pro His Met
130 135 140

Tyr Val Val Lys Asp Leu Val Pro Asp Leu Thr Gln Phe Tyr Lys Gln
145 150 155 160

Tyr Arg Ser Ile Glu Pro Phe Leu Lys Ser Asn Asn Thr Pro Ala Glu
165 170 175

Gly Glu His Leu Gln Ser Pro Glu Glu Arg Arg Arg Leu Asp Gly Leu
180 185 190

Tyr Glu Cys Ile Leu Cys Ala Cys Cys Ser Thr Ser Cys Pro Ser Tyr
195 200 205

Trp Trp Asn Gln Asp Glu Tyr Leu Gly Pro Ala Val Leu Met Gln Ala
210 215 220

Tyr Arg Trp Met Ala Asp Ser Arg Asp Asp Phe Gly Glu Glu Arg Arg
225 230 235 240

-continued

```
Gln Lys Leu Glu Asn Thr Phe Ser Leu Tyr Arg Cys His Thr Ile Met
                245                 250                 255

Asn Cys Ser Arg Thr Cys Pro Lys Asn Leu Asn Pro Gly Lys Ala Ile
            260                 265                 270

Ser Gln Ile Lys Lys Asp Met Ala Val Gly Ala Pro Lys Ala Ala Asp
        275                 280                 285

Arg Pro Ile Met Ala Ser Ser
    290                 295
```

<210> SEQ ID NO 49
<211> LENGTH: 1974
<212> TYPE: DNA
<213> ORGANISM: Pseudozyma tsukubaensis
<220> FEATURE:
<223> OTHER INFORMATION: Pseudog4640.t1

<400> SEQUENCE: 49

```
cgtgttgcat gaggttgctg gggaggcttc acggtctttc acaccgagac ttttgggagc     60

tgggaggcgc aaagaggacc ctgagcagga tgcgtagaaa cgcagtgtgg agcttggccg    120

agttccgcaa aaatgtcaaa atgttacatc ttcaaataag acatcgactg cacagcggga    180

gcttacggat gcgccgggtc tcttccggtc taacacgatg gtaaattgta caaaatcggc    240

aggaaacggc gttccgccaa atgcgatgag gcaaaggcgc gctgttgtca attatgtcag    300

cgacgagcga gacttggcgg gaaaaagatt ctaatttcgc acactcacac tgctgcctgg    360

caggcgcgcg taggcatgcc caatcagact cgatttgatt tcaaagccaa aagctcaaat    420

tgcagcagtc agccactgca cactgtgact gcgaaattca gctgaaaagc cgatacaggc    480

cgagttttag aggcagcaca ctgcgaagct gagaaaatga gctacgaacg tgttttggta    540

atcagccggc gtaacccaca ctgcactgca cgcttgagag ggtcagggtg tgtgtggcta    600

cagcagcagc agcggcagac ttcgagttcc aactctcccc gcacaagcga ccgcgagttc    660

cattcggtca gagttggcaa gtctctcgcg cgcacacctt gagttgattg aaagattgta    720

gccaacgcca tcttcattgc tgaacaccat caccaatacc tacattcgta ctcgcatcac    780

acattggtcg tcatgtcgct tttcaacgtc agcaacggtc ttcgtgccgc cctccgaccc    840

tccatcgcga gctcgtcccg cgttactgct gctttctcga catccgcagc tgcccgtctt    900

gccacgccca ccaacgatgc tcctggctct ggcaagcctc agcacttgaa gcagttcaag    960

atctaccgct ggaaccccga caagccttcc gagaagcctc gtctccagtc ctacactctt   1020

gaccttaacc agaccggccc aatggtgctc gatgccttga ttaagatcaa gaacgagatc   1080

gaccccactc ttactttccg tcgctcgtgc cgtgaaggta tctgcggttc ttgcgccatg   1140

aacatcgacg gtgtcaacac ccttgcttgt ctttgccgaa ttgacaaggc caacgacacc   1200

aagatctacc ccctccctca catgtacgtc gtcaaggacc ttgttcctga cttgacccag   1260

ttctacaagc agtaccgttc catcgagcct ttcctcaagt ccaacaacac ccctgctgag   1320

ggagagcacc ttcagtcgcc cgaggagcgt cgtcgtctcg acggtcttta cgagtgcatt   1380

ctctgcgctt gctgctccac gtcctgcccc tcctactggt ggaaccagga cgagtacctt   1440

ggtcccgccg tcctcatgca ggcttaccga tggatggccg actcccgtga tgactttggt   1500

gaggagcgaa gacagaagct cgagaacacc ttctcgctct accgttgcca caccatcatg   1560

aactgctcca ggacttgccc caagaacctt aacccaggca aggccatctc ccagatcaag   1620

aaggacatgg ctgtcggtgc cccaaggct gccgaccgtc ccatcatggc ctcgtcttaa   1680

gaaaagtaaa aggcttcggt agttcggttt gtattcgacc cttgtttcat tctttcaatc   1740
```

tagtcatttc gcattgcaat tcgttgttgc tcgtgtgtgt tactcgtccg tcaatttcag 1800
gttggttctt cgcaattttt cactgtagga gagagatcga agcaatgtct cacagcaaga 1860
cgttcgacta ccatgctctg aagtcatgtg gatcccaggt gttaaatgat agaggtaacc 1920
aacaatatat tcacaacgaa aaggtgacaa tcttaggcat acaggttgaa gcgt 1974

<210> SEQ ID NO 50
<211> LENGTH: 888
<212> TYPE: DNA
<213> ORGANISM: Ustilago maydis
<220> FEATURE:
<223> OTHER INFORMATION: coding region of Embl entry Z11738.1 (entry
Z11738 is SEQ ID NO. 52)

<400> SEQUENCE: 50
atgtcgctat tcaacgtcag caacggtctt cgtaccgctc tccgaccttc tgttgccagc 60
tcttcgcgcg ttgctgcctt ttccacaacc gccgctgccc gtctcgccac acccacctct 120
gacaacgttg gcagttcggg caagcctcag cacttgaagc agttcaagat ctaccgatgg 180
aaccctgaca agccctcgga gaagcctcgt ctgcagtcgt acacactgga cctcaaccag 240
accggtccaa tggttctcga cgcgctcatc aaaatcaaga acgaaattga ccctacgctc 300
accttccgtc gctcgtgccg tgagggtatc tgcggttcgt gcgctatgaa tattgacggt 360
gtcaacaccc tcgcctgcct ctgccggatc gacaagcaga atgacaccaa gatctacccc 420
ttgccgcaca tgtacattgt caaggacctc gtgccagact tgacccagtt ctacaagcag 480
taccgatcca tcgagccttt cctcaagtcc aacaacaccc cttctgaggg tgaacatctt 540
cagtcgcccg aggagcgtcg tcgactcgac ggtctgtacg agtgcattct gtgcgcgtgc 600
tgctccacat cctgcccctc ttactggtgg aatcaggacg agtaccttgg ccccgccgtg 660
ctcatgcagg cgtaccgatg gatggccgac tcgcgtgacg actttggtga ggagcgaaga 720
cagaagctcg agaacacctt ttcgctctac cgatgccaca ccatcatgaa ctgctccagg 780
acctgcccca agaacctcaa ccctggtaag gcaattgcac agatcaagaa ggacatggcc 840
gtcggcgcac ccaaggcttc cgagcgccct atcatggctt cgtcgtaa 888

<210> SEQ ID NO 51
<211> LENGTH: 1145
<212> TYPE: DNA
<213> ORGANISM: Pseudozyma tsukubaensis
<220> FEATURE:
<223> OTHER INFORMATION: Pseudozyma tsukubaensis genomic sequence
corresponding to Embl entry Z11738 (entry Z11738 is SEQ ID NO. 52)

<400> SEQUENCE: 51
cagcggcaga cttcgagttc caactctccc cgcacaagcg accgcgagtt ccattcggtc 60
agagttggca agtctctcgc gcgcacacct tgagttgatt gaaagattgt agccaacgcc 120
atcttcattg ctgaacacca tcaccaatac ctacattcgt actcgcatca cacattggtc 180
gtcatgtcgc ttttcaacgt cagcaacggt cttcgtgccg ccctccgacc ctccatcgcg 240
agctcgtccc gcgttactgc tgctttctcg acatccgcag ctgcccgtct tgccacgccc 300
accaacgatg ctcctggctc tggcaagcct cagcacttga agcagttcaa gatctaccgc 360
tggaaccccg acaagccttc cgagaagcct cgtctccagt cctacactct tgaccttaac 420
cagaccggcc caatggtgct cgatgccttg attaagatca agaacgagat cgaccccact 480
cttactttcc gtcgctcgtg ccgtgaaggt atctgcggtt cttgcgccat gaacatcgac 540

-continued

```
ggtgtcaaca cccttgcttg tctttgccga attgacaagg ccaacgacac caagatctac    600

cccctccctc acatgtacgt cgtcaaggac cttgttcctg acttgaccca gttctacaag    660

cagtaccgtt ccatcgagcc tttcctcaag tccaacaaca cccctgctga gggagagcac    720

cttcagtcgc ccgaggagcg tcgtcgtctc gacggtcttt acgagtgcat tctctgcgct    780

tgctgctcca cgtcctgccc ctcctactgg tggaaccagg acgagtacct tggtcccgcc    840

gtcctcatgc aggcttaccg atggatggcc gactcccgtg atgactttgg tgaggagcga    900

agacagaagc tcgagaacac cttctcgctc taccgttgcc acaccatcat gaactgctcc    960

aggacttgcc ccaagaacct taacccaggc aaggccatct cccagatcaa gaaggacatg   1020

gctgtcggtg cccccaaggc tgccgaccgt cccatcatgg cctcgtctta agaaaagtaa   1080

aaggcttcgg tagttcggtt tgtattcgac ccttgtttca ttctttcaat ctagtcattt   1140

cgcat                                                               1145
```

<210> SEQ ID NO 52
<211> LENGTH: 1145
<212> TYPE: DNA
<213> ORGANISM: Ustilago maydis
<220> FEATURE:
<223> OTHER INFORMATION: Embl Z11738.1 (genomic sequence from U. maydis)

<400> SEQUENCE: 52

```
atcgtgctct acgactttgc acaccacaaa gtgtgcgggg agcaaaggac ccgatcttgg     60

tcgcgcgcaa agcagtcttg aacctgagag tgtgcgtgtc ttctgacgct tgcccttctg    120

tactttgctg tgacactacc accacatctg tcttggcttt ttgttcatac atccacaccg    180

accatgtcgc tattcaacgt cagcaacggt cttcgtaccg ctctccgacc ttctgttgcc    240

agctcttcgc gcgttgctgc cttttccaca accgccgctg cccgtctcgc cacacccacc    300

tctgacaacg ttggcagttc gggcaagcct cagcacttga agcagttcaa gatctaccga    360

tggaaccctg acaagccctc ggagaagcct cgtctgcagt cgtacacact ggacctcaac    420

cagaccggtc caatggttct cgacgcgctc atcaaaatca agaacgaaat tgaccctacg    480

ctcaccttcc gtcgctcgtg ccgtgagggt atctgcggtt cgtgcgctat gaatattgac    540

ggtgtcaaca ccctcgcctg cctctgccgg atcgacaagc agaatgacac caagatctac    600

cccttgccgc acatgtacat tgtcaaggac ctcgtgccag acttgaccca gttctacaag    660

cagtaccgat ccatcgagcc tttcctcaag tccaacaaca ccccttctga gggtgaacat    720

cttcagtcgc ccgaggagcg tcgtcgactc gacggtctgt acgagtgcat tctgtgcgcg    780

tgctgctcca catcctgccc ctcttactgg tggaatcagg acgagtacct tggccccgcc    840

gtgctcatgc aggcgtaccg atggatggcc gactcgcgtg acgactttgg tgaggagcga    900

agacagaagc tcgagaacac cttttcgctc taccgatgcc acaccatcat gaactgctcc    960

aggacctgcc ccaagaacct caaccctggt aaggcaattg cacagatcaa gaaggacatg   1020

gccgtcggcg cacccaaggc ttccgagcgc cctatcatgg cttcgtcgta atcttgatat   1080

atcatatcgt tctttcctca gcacttcttt tgtcaatttc aaaagtatct aattgcattc   1140

aactc                                                               1145
```

<210> SEQ ID NO 53
<211> LENGTH: 1974
<212> TYPE: DNA
<213> ORGANISM: Pseudozyma tsukubaensis
<220> FEATURE:
<223> OTHER INFORMATION: extended ip locus

<400> SEQUENCE: 53
cgtgttgcat gaggttgctg gggaggcttc acggtctttc acaccgagac ttttgggagc 60
tgggaggcgc aaagaggacc ctgagcagga tgcgtagaaa cgcagtgtgg agcttggccg 120
agttccgcaa aaatgtcaaa atgttacatc ttcaaataag acatcgactg cacagcggga 180
gcttacggat gcgccgggtc tcttccggtc taacacgatg gtaaattgta caaaatcggc 240
aggaaacggc gttccgccaa atgcgatgag gcaaaggcgc gctgttgtca attatgtcag 300
cgacgagcga gacttggcgg gaaaaagatt ctaatttcgc acactcacac tgctgcctgg 360
caggcgcgcg taggcatgcc caatcagact cgatttgatt tcaaagccaa aagctcaaat 420
tgcagcagtc agccactgca cactgtgact gcgaaattca gctgaaaagc cgatacaggc 480
cgagttttag aggcagcaca ctgcgaagct gagaaaatga gctacgaacg tgttttggta 540
atcagccggc gtaacccaca ctgcactgca cgcttgagag ggtcagggtg tgtgtggcta 600
cagcagcagc agcggcagac ttcgagttcc aactctcccc gcacaagcga ccgcgagttc 660
cattcggtca gagttggcaa gtctctcgcg cgcacacctt gagttgattg aaagattgta 720
gccaacgcca tcttcattgc tgaacaccat caccaatacc tacattcgta ctcgcatcac 780
acattggtcg tcatgtcgct tttcaacgtc agcaacggtc ttcgtgccgc cctccgaccc 840
tccatcgcga gctcgtcccg cgttactgct gctttctcga catccgcagc tgcccgtctt 900
gccacgccca ccaacgatgc tcctggctct ggcaagcctc agcacttgaa gcagttcaag 960
atctaccgct ggaaccccga caagccttcc gagaagcctc gtctccagtc ctacactctt 1020
gaccttaacc agaccggccc aatggtgctc gatgccttga ttaagatcaa gaacgagatc 1080
gaccccactc ttactttccg tcgctcgtgc cgtgaaggta tctgcggttc ttgcgccatg 1140
aacatcgacg gtgtcaacac ccttgcttgt ctttgccgaa ttgacaaggc caacgacacc 1200
aagatctacc ccctccctca catgtacgtc gtcaaggacc ttgttcctga cttgacccag 1260
ttctacaagc agtaccgttc catcgagcct ttcctcaagt ccaacaacac ccctgctgag 1320
ggagagcacc ttcagtcgcc cgaggagcgt cgtcgtctcg acggtcttta cgagtgcatt 1380
ctctgcgctt gctgctccac gtcctgcccc tcctactggt ggaaccagga cgagtacctt 1440
ggtcccgccg tcctcatgca ggcttaccga tggatggccg actcccgtga tgactttggt 1500
gaggagcgaa gacagaagct cgagaacacc ttctcgctct accgttgcca caccatcatg 1560
aactgctcca ggacttgccc caagaacctt aacccaggca aggccatctc ccagatcaag 1620
aaggacatgg ctgtcggtgc ccccaaggct gccgaccgtc ccatcatggc ctcgtcttaa 1680
gaaaagtaaa aggcttcggt agttcggttt gtattcgacc cttgtttcat tctttcaatc 1740
tagtcatttc gcattgcaat tcgttgttgc tcgtgtgtgt tactcgtccg tcaatttcag 1800
gttggttctt cgcaattttt cactgtagga gagagatcga agcaatgtct cacagcaaga 1860
cgttcgacta ccatgctctg aagtcatgtg gatcccaggt gttaaatgat agaggtaacc 1920
aacaatatat tcacaacgaa aaggtgacaa tcttaggcat acaggttgaa gcgt 1974

<210> SEQ ID NO 54
<211> LENGTH: 2001
<212> TYPE: DNA
<213> ORGANISM: Pseudozyma tsukubaensis
<220> FEATURE:
<223> OTHER INFORMATION: upstream of SEQ ID NO 53

<400> SEQUENCE: 54

-continued

```
gcaaagtgga gtaagctgtg tttctcggat gccgggattc agaaagtggc gagaagaaca      60
ctcgtgctca aagcacatgg taacgttcgc tacgacgtcc tcactgtact tcgcaccctg     120
cactcctcat acccaagtcc tttgagcttc aagatgttag gcaccgtcac tagactggca     180
cgcgccgacc tgaagtcaag tcagctcacg ctagagcatt tcctcatgcg agctcgcact     240
ctttcgctct accgcaaata cctcagagct accagagaca ttccaaatcc gctcgctcga     300
tgggagacaa tccatttctt ccgggacgat gtccaccgct ttcgtcacga aacagatctg     360
gagaagatca aggacttgct tgtacagggc aaccgcttct tgaagcaaat gcaaggacag     420
atgactttgg cgggagcagc ttcggatggc aacgccaata agcttcgtgg cacacggcaa     480
ttgtgattgc tcaaaagctc aatcacaggc acagctttga ctcatcatgg cttagcccca     540
caccgcagct acgcaacgca cttgcgtcct acagctatat acctgaacgc cgcatcacag     600
caacacacaa gagcgacaca gagcagctag ccttaggcga ccagccttcg attcgttctc     660
tcgtcgaaag actgcaccag tctgctacat ttcatagatt ttcgcatgac ggcatcagcc     720
ccgggtcaca agcacggcga acgagcaaag gatcgaccat gctctcccgc tcaatacaat     780
atgccccgta cacttggctt cttggcagca gccagagccg aggcgtccat cagcacgatc     840
aaaggtcaat cagtctcagg accagcgaaa tattgcaaca ggaagcttca atttatgcct     900
ttacatcgtc tacatggtaa taccaaccca tcaaacagac tcgtcgagca gaacgtactc     960
tcgcgtgcta gccccaaatg tgagcgtgtc acccgatctg agctggtagt atctcgaagt    1020
aggaatctcc ttgtcgttga cgtaggagcc attactcgat tcgagatcga tcaagaaagg    1080
ctgtatacgc ttctttcggt ctccgaattc gttggttgtg atggtttggc ggtactgaag    1140
cacagcgtgc tgtttcgaac acgattcgtg atccagagga atgtcgacca ctgtacgatc    1200
tcgaccaaga aggaaacaag attgtgaagc gagatggagc acttgctgct ctttgccgtc    1260
tttgaaacag tagagacgcc atggcgtttt gggtttgcga gcttcaggtg gttcgtgata    1320
cttgagagcg acgccattga cggtatttga ttcggcggcg aggagtccag atggagcaaa    1380
gtttggagca tcttcgtcga atccttcctc gagagcgtga gaagcaggtg caggagggga    1440
tgcaggacgt ggcgagcgtg aagctacagg tcttgaagag gtggaagcgg ctggaattgg    1500
tgagcgtgag cgtgagcggc gagatggctc tttgtctttg cgagaggagc tctctcgagc    1560
ctctcgagcc tctcgatcat gtcgatcatg tcggcgatga cggtttgatg atgagtagtg    1620
gcgatgtgag cgatcatcgt ctcgcttccg attggagctg gagcgacggt cttcgtcgcg    1680
atgtcgtcga tgcctatcct catccctgtc atctcgatgc cttttggagc ttgagctcgc    1740
tcggtggctg tcgtctggat cctccttatg cctccttgat cctgaagaat gttctttgtc    1800
acccttattg tggctcgatc cgtgcctgtg cctgtcacgc tctgcgtctg catgttctcg    1860
atgtgagtgt gatctccttt cgcggtgttg atctcggtca tatctggagc tgcctgagcg    1920
attggaggat gatggcggga tgtctgcctt ctcagcaaca atgcgtcttg aggagccgga    1980
atcagctgct gagtccgaca t                                              2001
```

<210> SEQ ID NO 55
<211> LENGTH: 2000
<212> TYPE: DNA
<213> ORGANISM: Pseudozyma tsukubaensis
<220> FEATURE:
<223> OTHER INFORMATION: downstream of SEQ ID NO 53

<400> SEQUENCE: 55

```
ttaccaagtg aagcagtcct caagcagatc gacatgtacg cctttcttca acatgtgcac      60
```

cgtctccacc ctgacgtcgt cgcataggct tggcggcccg caaagaccaa cagtcaagcc 120
tttgctctcc tgcaacattt gctcgttcaa gtgtccaaac atagcgccct tcaaactctc 180
cggtcggcct ccgaactggg acactgcgat cttggctccg ttggcgccgt ccgagaacaa 240
gtctgctcgg gcgtcaatat gctcgttgcg ctgctcttgc tgctgctttg gaatcatggc 300
aagctcgacg acttcgctcg taagctcgga cgaaggtgtg gagggttcgc cagcctgcga 360
ttcggattgc tggacgggca gcttctcctt gatcgaggcg gatgacgagg atcgagagta 420
aggcgtgctg gagatcgact tgtcagagtc agcttcgaca gcgcgcttcc ccccatcgac 480
ccgtccgtgc gaggtgacat agagatcgag agagaattgg cagcccttcc agctctcctg 540
tccctccatc tctttgatca gctctgcaaa cgcttcggca atcacagtca gcgtatctgt 600
aagtagatca aaacgacgtg ggtttttacg gagcgtcagc aagatgttcc cttgggataa 660
tttgagaacg gagcgagtct gagctacgga tacttacttt gttctcgaac gatccagata 720
agcttgcaag atttgagctt tttgttcgca gcactgccct tcactgcagc cacgaagagc 780
ggccagcagt aagtgatagc aatgccacca gcaaccagaa ctagatccgt agcatggtcg 840
atgttgggga tcacgccgaa aggtccttcg accagaacag ctacctttcc gttgtcatcc 900
gcgttcctgc cggccagctc aacatctttc tccgcaacct ctccgtgagt gtgagcattg 960
atgtggtggg cgagctttcg cgtaagacca gcctcggttt tgatgaccag atcgatgaag 1020
ccttgggtgg ggtttctgg ctgaacaccg acagagaaga cggtgaaagg atgctcgccg 1080
acccattgca agcgagggat tgtgatgcgg atgtcgtcgc cgccagcgat acctccgatc 1140
aagcgcggct ggttggcaag tcgcagcttc gatgcaggaa cagagataca caagcgagtg 1200
tactggctgt tcgagccata ggtgcggata tcgccagtgg cgcaagtgat gagcgaagat 1260
ccgcgaccgt tcattcgtgg ggacgagaac gagaggtaga tccggcttgc gagtcgagct 1320
acgcggtcga aagcccacac agcggccgcg atctctgtga gcacgacgaa catttggaac 1380
tgacatccga aagcattgag gagaggtgat ggtcagcatg tgtcgtcgta tcaaatcttt 1440
cagtgtacga gatgcatgtc gacatctgtc gaggtgtagt aaaagactta ccctgctcga 1500
tttgatcaag gagatgtgca ggtatgttcc cagaatagca aagaaagcca tagcgatgtg 1560
tagcatcaca aagatctgca aagaattgtc gttagcgtgt aaacatcaaa aagcaaaatg 1620
ccatggtcag cgtctactca aagatataca cgagtccaag acggatcact cacttcgtaa 1680
aagcgttgtc gcagagctcg aaccgaaaag aagaccagtc cgaacatcat actcaacgcc 1740
acaatacccc acgtaacata atcgtcctcg agcatctctg caactcctcc aggccgccta 1800
acgtaaatcg cagtccaagc cgaagcatga acaacaatgt gaagccagaa ccacctcgca 1860
atccacctgt gccacagcat aagactgttc atgttcaaac cggacatgat ggccaaagga 1920
gtccttttgc tcgccatcaa gatcaagagc ggaagttggg ccgttcccag aattgcagtt 1980
cgatcggcta agtgtcgagc 2000

<210> SEQ ID NO 56
<211> LENGTH: 5975
<212> TYPE: DNA
<213> ORGANISM: Pseudozyma tsukubaensis
<220> FEATURE:
<223> OTHER INFORMATION: most extended ip locus

<400> SEQUENCE: 56
gcaaagtgga gtaagctgtg tttctcggat gccgggattc agaaagtggc gagaagaaca 60

-continued

```
ctcgtgctca aagcacatgg taacgttcgc tacgacgtcc tcactgtact tcgcaccctg    120
cactcctcat acccaagtcc tttgagcttc aagatgttag gcaccgtcac tagactggca    180
cgcgccgacc tgaagtcaag tcagctcacg ctagagcatt tcctcatgcg agctcgcact    240
ctttcgctct accgcaaata cctcagagct accagagaca ttccaaatcc gctcgctcga    300
tgggagacaa tccatttctt ccgggacgat gtccaccgct ttcgtcacga aacagatctg    360
gagaagatca aggacttgct tgtacagggc aaccgcttct tgaagcaaat gcaaggacag    420
atgactttgg cgggagcagc ttcggatggc aacgccaata agcttcgtgg cacacggcaa    480
ttgtgattgc tcaaaagctc aatcacaggc acagctttga ctcatcatgg cttagcccca    540
caccgcagct acgcaacgca cttgcgtcct acagctatat acctgaacgc cgcatcacag    600
caacacacaa gagcgacaca gagcagctag ccttaggcga ccagccttcg attcgttctc    660
tcgtcgaaag actgcaccag tctgctacat ttcatagatt ttcgcatgac ggcatcagcc    720
ccgggtcaca agcacggcga acgagcaaag gatcgaccat gctctcccgc tcaatacaat    780
atgccccgta cacttggctt cttggcagca gccagagccg aggcgtccat cagcacgatc    840
aaaggtcaat cagtctcagg accagcgaaa tattgcaaca ggaagcttca atttatgcct    900
ttacatcgtc tacatggtaa taccaaccca tcaaacagac tcgtcgagca gaacgtactc    960
tcgcgtgcta gccccaaatg tgagcgtgtc acccgatctg agctggtagt atctcgaagt   1020
aggaatctcc ttgtcgttga cgtaggagcc attactcgat tcgagatcga tcaagaaagg   1080
ctgtatacgc ttctttcggt ctccgaattc gttggttgtg atggtttggc ggtactgaag   1140
cacagcgtgc tgtttcgaac acgattcgtg atccagagga atgtcgacca ctgtacgatc   1200
tcgaccaaga aggaaacaag attgtgaagc gagatggagc acttgctgct ctttgccgtc   1260
tttgaaacag tagagacgcc atggcgtttt gggtttgcga gcttcaggtg gttcgtgata   1320
cttgagagcg acgccattga cggtatttga ttcggcggcg aggagtccag atggagcaaa   1380
gtttggagca tcttcgtcga atccttcctc gagagcgtga gaagcaggtg caggagggga   1440
tgcaggacgt ggcgagcgtg aagctacagg tcttgaagag gtggaagcgg ctggaattgg   1500
tgagcgtgag cgtgagcggc gagatggctc tttgtctttg cgagaggagc tctctcgagc   1560
ctctcgagcc tctcgatcat gtcgatcatg tcggcgatga cggtttgatg atgagtagtg   1620
gcgatgtgag cgatcatcgt ctcgcttccg attggagctg gagcgacggt cttcgtcgcg   1680
atgtcgtcga tgcctatcct catccctgtc atctcgatgc cttttggagc ttgagctcgc   1740
tcggtggctg tcgtctggat cctccttatg cctccttgat cctgaagaat gttctttgtc   1800
acccttattg tggctcgatc cgtgcctgtg cctgtcacgc tctgcgtctg catgttctcg   1860
atgtgagtgt gatctccttt cgcggtgttg atctcggtca tatctggagc tgcctgagcg   1920
attggaggat gatggcggga tgtctgcctt ctcagcaaca atgcgtcttg aggagccgga   1980
atcagctgct gagtccgaca tcgtgttgca tgaggttgct ggggaggctt cacggtcttt   2040
cacaccgaga cttttgggag ctgggaggcg caaagaggac cctgagcagg atgcgtagaa   2100
acgcagtgtg gagcttggcc gagttccgca aaaatgtcaa aatgttacat cttcaaataa   2160
gacatcgact gcacagcggg agcttacgga tgcgccgggt ctcttccggt ctaacacgat   2220
ggtaaattgt acaaaatcgg caggaaacgg cgttccgcca aatgcgatga ggcaaaggcg   2280
cgctgttgtc aattatgtca gcgacgagcg agacttggcg ggaaaaagat tctaatttcg   2340
cacactcaca ctgctgcctg gcaggcgcgc gtaggcatgc ccaatcagac tcgatttgat   2400
ttcaaagcca aaagctcaaa ttgcagcagt cagccactgc acactgtgac tgcgaaattc   2460
```

-continued

```
agctgaaaag ccgatacagg ccgagtttta gaggcagcac actgcgaagc tgagaaaatg   2520
agctacgaac gtgttttggt aatcagccgg cgtaacccac actgcactgc acgcttgaga   2580
gggtcagggt gtgtgtggct acagcagcag cagcggcaga cttcgagttc caactctccc   2640
cgcacaagcg accgcgagtt ccattcggtc agagttggca agtctctcgc gcgcacacct   2700
tgagttgatt gaaagattgt agccaacgcc atcttcattg ctgaacacca tcaccaatac   2760
ctacattcgt actcgcatca cacattggtc gtcatgtcgc ttttcaacgt cagcaacggt   2820
cttcgtgccg ccctccgacc ctccatcgcg agctcgtccc gcgttactgc tgctttctcg   2880
acatccgcag ctgcccgtct tgccacgccc accaacgatg ctcctggctc tggcaagcct   2940
cagcacttga agcagttcaa gatctaccgc tggaaccccg acaagccttc cgagaagcct   3000
cgtctccagt cctacactct tgaccttaac cagaccggcc caatggtgct cgatgccttg   3060
attaagatca agaacgagat cgaccccact cttactttcc gtcgctcgtg ccgtgaaggt   3120
atctgcggtt cttgcgccat gaacatcgac ggtgtcaaca cccttgcttg tctttgccga   3180
attgacaagg ccaacgacac caagatctac cccctccctc acatgtacgt cgtcaaggac   3240
cttgttcctg acttgaccca gttctacaag cagtaccgtt ccatcgagcc tttcctcaag   3300
tccaacaaca cccctgctga gggagagcac cttcagtcgc ccgaggagcg tcgtcgtctc   3360
gacggtcttt acgagtgcat tctctgcgct tgctgctcca cgtcctgccc ctcctactgg   3420
tggaaccagg acgagtacct tggtcccgcc gtcctcatgc aggcttaccg atggatggcc   3480
gactcccgtg atgactttgg tgaggagcga agacagaagc tcgagaacac cttctcgctc   3540
taccgttgcc acaccatcat gaactgctcc aggacttgcc ccaagaacct taacccaggc   3600
aaggccatct cccagatcaa gaaggacatg gctgtcggtg cccccaaggc tgccgaccgt   3660
cccatcatgg cctcgtctta agaaaagtaa aaggcttcgg tagttcggtt tgtattcgac   3720
ccttgtttca ttctttcaat ctagtcattt cgcattgcaa ttcgttgttg ctcgtgtgtg   3780
ttactcgtcc gtcaatttca ggttggttct tcgcaatttt tcactgtagg agagagatcg   3840
aagcaatgtc tcacagcaag acgttcgact accatgctct gaagtcatgt ggatcccagg   3900
tgttaaatga tagaggtaac caacaatata ttcacaacga aaaggtgaca atcttaggca   3960
tacaggttga agcgtttacc aagtgaagca gtcctcaagc agatcgacat gtacgccttt   4020
cttcaacatg tgcaccgtct ccaccctgac gtcgtcgcat aggcttggcg gcccgcaaag   4080
accaacagtc aagcctttgc tctcctgcaa catttgctcg ttcaagtgtc caaacatagc   4140
gcccttcaaa ctctccggtc ggcctccgaa ctgggacact gcgatcttgg ctccgttggc   4200
gccgtccgag aacaagtctg ctcgggcgtc aatatgctcg ttgcgctgct cttgctgctg   4260
ctttggaatc atggcaagct cgacgacttc gctcgtaagc tcggacgaag gtgtggaggg   4320
ttcgccagcc tgcgattcgg attgctggac gggcagcttc tccttgatcg aggcggatga   4380
cgaggatcga gagtaaggcg tgctggagat cgacttgtca gagtcagctt cgacagcgcg   4440
cttcccccca tcgacccgtc cgtgcgaggt gacatagaga tcgagagaga attggcagcc   4500
cttccagctc tcctgtccct ccatctcttt gatcagctct gcaaacgctt cggcaatcac   4560
agtcagcgta tctgtaagta gatcaaaacg acgtgggttt ttacggagcg tcagcaagat   4620
gttcccttgg gataatttga gaacggagcg agtctgagct acggatactt actttgttct   4680
cgaacgatcc agataagctt gcaagatttg agctttttgt tcgcagcact gcccttcact   4740
gcagccacga agagcggcca gcagtaagtg atagcaatgc caccagcaac cagaactaga   4800
```

tccgtagcat ggtcgatgtt ggggatcacg ccgaaaggtc cttcgaccag aacagctacc 4860
tttccgttgt catccgcgtt cctgccggcc agctcaacat ctttctccgc aacctctccg 4920
tgagtgtgag cattgatgtg gtgggcgagc tttcgcgtaa gaccagcctc ggttttgatg 4980
accagatcga tgaagccttg ggtggggttt tctggctgaa caccgacaga gaagacggtg 5040
aaaggatgct cgccgaccca ttgcaagcga gggattgtga tgcggatgtc gtcgccgcca 5100
gcgatacctc cgatcaagcg cggctggttg gcaagtcgca gcttcgatgc aggaacagag 5160
atacacaagc gagtgtactg gctgttcgag ccataggtgc ggatatcgcc agtggcgcaa 5220
gtgatgagcg aagatccgcg accgttcatt cgtggggacg agaacgagag gtagatccgg 5280
cttgcgagtc gagctacgcg gtcgaaagcc cacacagcgg ccgcgatctc tgtgagcacg 5340
acgaacattt ggaactgaca tccgaaagca ttgaggagag gtgatggtca gcatgtgtcg 5400
tcgtatcaaa tctttcagtg tacgagatgc atgtcgacat ctgtcgaggt gtagtaaaag 5460
acttaccctg ctcgatttga tcaaggagat gtgcaggtat gttcccagaa tagcaaagaa 5520
agccatagcg atgtgtagca tcacaaagat ctgcaaagaa ttgtcgttag cgtgtaaaca 5580
tcaaaaagca aaatgccatg gtcagcgtct actcaaagat atacacgagt ccaagacgga 5640
tcactcactt cgtaaaagcg ttgtcgcaga gctcgaaccg aaaagaagac cagtccgaac 5700
atcatactca acgccacaat accccacgta acataatcgt cctcgagcat ctctgcaact 5760
cctccaggcc gcctaacgta aatcgcagtc caagccgaag catgaacaac aatgtgaagc 5820
cagaaccacc tcgcaatcca cctgtgccac agcataagac tgttcatgtt caaaccggac 5880
atgatggcca aaggagtcct tttgctcgcc atcaagatca agagcggaag ttgggccgtt 5940
cccagaattg cagttcgatc ggctaagtgt cgagc 5975

<210> SEQ ID NO 57
<211> LENGTH: 1126
<212> TYPE: DNA
<213> ORGANISM: artificial
<220> FEATURE:
<223> OTHER INFORMATION: (BsrGI)-pActin-olapAC01

<400> SEQUENCE: 57
atatatgtac aggcccgttc aacacaatgc gcctgcaatt tctatccccg ctttccacct 60
ctgtctccct cttcaaagtc acagagtctg ccatttgtat tcgagcatga aaaatgatga 120
cctcctttct tctcgttcaa tacagcggac atgaacaaga aaggggtggc ctgagccacc 180
aagttctaca cttgcagcca gacgtattca aaaatcgacg tggacgagtt gcgactcaac 240
atcctctgtg aattgcaatc gagtgagtga ttacgacctg tattcacgtc aaaatgcagg 300
tgtgacattt gaattttgaa atacatgagg caggctcgat ttgctccact caagtcgagt 360
ttgccaaatt caagaagcgc taatcggagc caaccgaccg accacaacca gccaaatcag 420
ccagccaagg cagagaagca gaagcaaagg cggtgcattg agaggtgagc cgtgtgctgt 480
gctgtgctct gctgtgctgt ctgtcaatgc ttgctgcgtg tgtttgtctc gcctctacag 540
cctgcccctc aagatgtgac cgattggaag gaaaggaagg tcacacgcag ttctggcatg 600
ccacgcacgc acagcccgaa attgcgatct caagagactg ccgacgccgc cgtccgccgt 660
tgagcgctct gcttgggtca aagcgtaagc gcttctcgaa ttcaaactca cagagttcca 720
agtctgcaca ggtcatctgt tcgtcctttt gagactgcct gactggctgg ctggaacgca 780
cgcacgcaca cttccgattc gacaccgccc gctgctgctg tcttctgcgc tcttgtgccc 840
ttcttctgta cttggccttt gcgtcgactt ctttgcttgc tcggcagtgc cgtctcatct 900

```
gccccaagtc aagctcagca gcacagcaca cacgcatcac cctctcggct tgggtttgcc    960

cctgttgcct gtctgtccac actcacacac atccctatcg cttgctcgac atcatcgctt   1020

acctcttccc caccacctcg tctttgacac ctttactttc tcaacccctc ttccaccacc   1080

aaccccccca ccacttactt tcaacatgct tccccttcgc gcactc                 1126
```

<210> SEQ ID NO 58
<211> LENGTH: 3507
<212> TYPE: DNA
<213> ORGANISM: artificial
<220> FEATURE:
<223> OTHER INFORMATION: (BsrGI)_pActin_ACO1_(NsiI)

<400> SEQUENCE: 58

```
atatatgtac aggcccgttc aacacaatgc gcctgcaatt tctatccccg ctttccacct     60

ctgtctccct cttcaaagtc acagagtctg ccatttgtat tcgagcatga aaaatgatga    120

cctcctttct tctcgttcaa tacagcggac atgaacaaga aaggggtggc ctgagccacc    180

aagttctaca cttgcagcca gacgtattca aaaatcgacg tggacgagtt gcgactcaac    240

atcctctgtg aattgcaatc gagtgagtga ttacgacctg tattcacgtc aaaatgcagg    300

tgtgacattt gaattttgaa atacatgagg caggctcgat ttgctccact caagtcgagt    360

ttgccaaatt caagaagcgc taatcggagc caaccgaccg accacaacca gccaaatcag    420

ccagccaagg cagagaagca gaagcaaagg cggtgcattg agaggtgagc cgtgtgctgt    480

gctgtgctct gctgtgctgt ctgtcaatgc ttgctgcgtg tgtttgtctc gcctctacag    540

cctgcccctc aagatgtgac cgattggaag gaaaggaagg tcacacgcag ttctggcatg    600

ccacgcacgc acagcccgaa attgcgatct caagagactg ccgacgccgc cgtccgccgt    660

tgagcgctct gcttgggtca aagcgtaagc gcttctcgaa ttcaaactca cagagttcca    720

agtctgcaca ggtcatctgt tcgtcctttt gagactgcct gactggctgg ctggaacgca    780

cgcacgcaca cttccgattc gacaccgccc gctgctgctg tcttctgcgc tcttgtgccc    840

ttcttctgta cttggccttt gcgtcgactt ctttgcttgc tcggcagtgc cgtctcatct    900

gccccaagtc aagctcagca gcacagcaca cacgcatcac cctctcggct tgggtttgcc    960

cctgttgcct gtctgtccac actcacacac atccctatcg cttgctcgac atcatcgctt   1020

acctcttccc caccacctcg tctttgacac ctttactttc tcaacccctc ttccaccacc   1080

aaccccccca ccacttactt tcaacatgct tccccttcgc gcactccgtt cttcctccct   1140

ccgggctgcc gccaaggctc ccctcgccag gggctatgcc accaccgtcg ccgaggaggc   1200

tgccgaaatc tcgccttccc tcttcgacaa gaaggttgag atgtccgttg tcgagtccgg   1260

caagggttac tacatcaact acaagcgtat cgaggacaac ctcaaggtcg ttcgatcccg   1320

cctcaaccga cctctttcgc tcgccgagaa gatcgtttac ggtcacttgg acaaccccca   1380

cgagcaggaa atcaccccgtg gccagtccta cctcaagctc cgccctgacc gtgttgcttg   1440

ccaggatgcc accgcccaga tggccctcct ccaattcatg tcggctggtc ttcccaccgt   1500

cgccgtcccc tccaccgtcc actgtgatca ccttatcgag gctcaggtcg gcggtgccaa   1560

ggacttggcc cgtgctatcg agatcaacaa ggaggtttac gacttccttg ccactgccac   1620

tgccaagtac ggtcttggtt tctggaagcc cggatctggt atcatccacc agatcatcct   1680

tgagaactac gccttccccg gtggtctcat gatcggtacc gactcgcaca cccccaacgc   1740

cggtggtctc ggtatgatcg cctgtggtgt cggaggtgcc gacgctgtcg acgtcatggc   1800
```

-continued tgacatcccc tgggagctca aggcccccaa ggtgatcggt gtcgagctca agggtaagct 1860
ctcgggctgg accaccccta aggatgttat cctcaaggtc gctggtgagc tcaccgttaa 1920
gggtggtacc ggtgccatca tcgagtacaa gggtgctggt gtcgactcgc tctcgtgcac 1980
tggtatggcc accatctgca acatgggtgc cgagattggt gctaccacct ccgtcttccc 2040
ttacaacgag cgcatgggtg actacctccg tgccaccaac cgttccgaca ttgctgacct 2100
cgccaagggc ttccagcgca accttcttcc cgactcgggt gccgagtacg actcgcacat 2160
cgagatcaac ctcgacaccc tcgagcccca catcaacggt cccttcaccc ccgatcttgc 2220
cacccccctc tccaagttcg ccgaggccgt caagaagaac gactggcccg aggagctcaa 2280
ggtttcgctc atcggttcgt gcaccaactc ctcgtacgag gacatgagcc gatccgcctc 2340
catcgctgag gaggctgccg cccacggcct caaggtcaag tcggccttca ccatcacccc 2400
cggttccgag cagattcgtg ctaccatcga gcgtgacggt cagatggccg ccctcgagaa 2460
cgctggtggt atggttcttg ccaacgcctg tggcccttgc attggtcagt gggaccgaaa 2520
ggacatcaag aagggtgaca agaactcgat catcacttct tacaaccgta acttcactgg 2580
tcgtaacgac gccaaccctg ctacccacgc tttcgtcgcc tcgcccgatc tcgttaccgc 2640
catggctttc gccggtaagc tcaccttcaa ccccatgacc gacagcctca agggtgctga 2700
cggcaaggag ttcaagttca ccgcccccag cggtaaggag ctccctcccc gcggctacga 2760
ccccggtaac aacacctacc aagacccccc caaggaccgc tcttcggttc aggtcgccat 2820
tgaccccaag tcggaccgtc tccagaggct cgagcccttc aagccctgga acggcaagaa 2880
ccccaccgac tgccccgtcc tcattaaggc tcagggcaag tgcaccactg accacatctc 2940
ggccggtggt ccttggctca agtaccgtgg tcaccttgag aacatctcga acaactgttt 3000
gattggtgcc atcaacgctg ccaacggcaa ggccaacgag gtccagaacg tcttctccgg 3060
cgagtggggc cccgttcccg ccactgccat ctcgtaccgt gagcagggca agccctgggt 3120
tgtcattggt gacgagaact acggtgaggg ttcgtcgcgt gagcacgccg ctcttgagcc 3180
ccgtttcctc ggtggttgcg ccgtcattgc ccgttcgttc gctcgtatcc accagaccaa 3240
cttgcgcaag cagggtatgc tcgccttcga gttcgccaac cccgctgact acgacaaggt 3300
tcgccccgat gaccttgttg acattctcgg tgttaccgag ctcgctgagg gctccaaggt 3360
ttcgctcctt gccaagcaca aggacggctc caaggatgag atccccctta cccacaccat 3420
gaacgacaat cagatctcgt ggttcaagca cggttcggcc ctcaacagga tggctgctgc 3480
cgccaagtcc gcctaaatgc attatat 3507

<210> SEQ ID NO 59
<211> LENGTH: 2702
<212> TYPE: DNA
<213> ORGANISM: artificial
<220> FEATURE:
<223> OTHER INFORMATION: (KpnI)-pActin-ADI1-(NsiI)

<400> SEQUENCE: 59
atataggtac cggcccgttc aacacaatgc gcctgcaatt tctatccccg ctttccacct 60
ctgtctccct cttcaaagtc acagagtctg ccatttgtat tcgagcatga aaaatgatga 120
cctcctttct tctcgttcaa tacagcggac atgaacaaga aaggggtggc ctgagccacc 180
aagttctaca cttgcagcca gacgtattca aaaatcgacg tggacgagtt gcgactcaac 240
atcctctgtg aattgcaatc gagtgagtga ttacgacctg tattcacgtc aaaatgcagg 300
tgtgacattt gaattttgaa atacatgagg caggctcgat ttgctccact caagtcgagt 360

-continued

```
ttgccaaatt caagaagcgc taatcggagc caaccgaccg accacaacca gccaaatcag    420
ccagccaagg cagagaagca gaagcaaagg cggtgcattg agaggtgagc cgtgtgctgt    480
gctgtgctct gctgtgctgt ctgtcaatgc ttgctgcgtg tgtttgtctc gcctctacag    540
cctgcccctc aagatgtgac cgattggaag gaaaggaagg tcacacgcag ttctggcatg    600
ccacgcacgc acagcccgaa attgcgatct caagagactg ccgacgccgc cgtccgccgt    660
tgagcgctct gcttgggtca aagcgtaagc gcttctcgaa ttcaaactca cagagttcca    720
agtctgcaca ggtcatctgt tcgtcctttt gagactgcct gactggctgg ctggaacgca    780
cgcacgcaca cttccgattc gacaccgccc gctgctgctg tcttctgcgc tcttgtgccc    840
ttcttctgta cttggccttt gcgtcgactt ctttgcttgc tcggcagtgc cgtctcatct    900
gccccaagtc aagctcagca gcacagcaca cacgcatcac cctctcggct tgggtttgcc    960
cctgttgcct gtctgtccac actcacacac atccctatcg cttgctcgac atcatcgctt   1020
acctcttccc caccacctcg tctttgacac ctttactttc tcaacccctc ttccaccacc   1080
aaccccccca ccacttactt tcaacatgtc gaatcctctt gcgggacgtg tcaagtggtt   1140
cagaaggata gtaggtactt ccatggcctc gaccgaagaa ctcaggcgaa gaaagatcat   1200
ataacgacgt tttggttagc cgtccatctt attggctttt gtcgttagtc acactgacag   1260
cttcacgatg ctgcgaggca ttgagaccac aatttaccgc gctggcacca gtcgtggctt   1320
atacctcttg gcaagtgacc tgccatccga gccaagcgct cgtgatgcgg cgctgctgtc   1380
catcatgggt tccggacatc cactgcagat cgacggtatg gggggtggca attctctgac   1440
ttcaaaagtg gccatagtct cgccaagtgc acagagcgat cactccgatg ttgactacct   1500
cttttgccaa gttggcatca atgagcgcat cgtcgacaca gcacccaact gcggcaattt   1560
gatgagcggg gtggctgcct tcgcgatcga gcgaggtcta gtcaagcctc atccatccga   1620
caccacctgc cttgtgcgca tctttaatct caactccaac caggcatccg agctcctcat   1680
tccggttcaa gatggtcgag tccactacaa agatgtggac gatacgggct tgcagcgtcc   1740
ttcggctcgc gtcagcttac gcttccttaa taccgtgggt gcatgcacag gcaagcttct   1800
tccaactggc aatgccactg actcaatcga gggactcgag gtatccgtca tcgattcggc   1860
catccctgtt gtttttgttc gtcaagccga tgttggtatc acaggtttcg agaccccagc   1920
gacgctcaat gcggacactg ccttgctatc tcgactggaa cgtgtacgcc tggaggcagg   1980
tcgacgaatg ggctggggtg atgtttcttc tagcgtggtg cccaaattgt ctctcatcgg   2040
accaggttcc aattgcacca cttttacggc acggtgtaag ttctcaacgc tgaattgacc   2100
gtaccttgtt gaatgattga cggctgctga ttctcagttc ctttttgtcc aacagacttc   2160
actcccaaaa cttgccacaa cgcacacgcc gtcaccggtg ccatctgcac cgccggagcc   2220
gcctatgtac ctggaacggt ggtctcggac atcttttcgt cacgcactcc ttcgctctct   2280
tcatcgcctg gcgataccac ccctccctac acgcctcagc gtcgcatctc tatcgaacat   2340
cctagtggcg ttctcgagat tggacttaca gccgccgaaa gcgactcacc ccgttcgcta   2400
gatattgccc acgttgagcg ttccgtagcc ctgattgcac acgcccgcgt ctattatact   2460
atgcctgatc ggcacccttc ggttgaaata ccgatcatct cacccgtcac tccaaccagc   2520
gcggagatgc tcgatagggc atatcagtcg ctggcgctcg cattgggaag aggtaaagat   2580
agatctcaca tcattccact tggttcggaa gggaaggaaa gtgagctata ttacaatatg   2640
ccggacagca ctgtgtctag ctaccgcggc acgcattcca cagccctatg aatgcattat   2700
```

at 2702

<210> SEQ ID NO 60
<211> LENGTH: 2589
<212> TYPE: DNA
<213> ORGANISM: artificial
<220> FEATURE:
<223> OTHER INFORMATION: (KpnI)-pActin-AtCAD1-(NsiI)

<400> SEQUENCE: 60
atataggtac cggcccgttc aacacaatgc gcctgcaatt tctatccccg ctttccacct 60
ctgtctccct cttcaaagtc acagagtctg ccatttgtat tcgagcatga aaaatgatga 120
cctcctttct tctcgttcaa tacagcggac atgaacaaga aaggggtggc ctgagccacc 180
aagttctaca cttgcagcca gacgtattca aaaatcgacg tggacgagtt gcgactcaac 240
atcctctgtg aattgcaatc gagtgagtga ttacgacctg tattcacgtc aaaatgcagg 300
tgtgacattt gaattttgaa atacatgagg caggctcgat ttgctccact caagtcgagt 360
ttgccaaatt caagaagcgc taatcggagc caaccgaccg accacaacca gccaaatcag 420
ccagccaagg cagagaagca gaagcaaagg cggtgcattg agaggtgagc cgtgtgctgt 480
gctgtgctct gctgtgctgt ctgtcaatgc ttgctgcgtg tgtttgtctc gcctctacag 540
cctgcccctc aagatgtgac cgattggaag gaaaggaagg tcacacgcag ttctggcatg 600
ccacgcacgc acagcccgaa attgcgatct caagagactg ccgacgccgc cgtccgccgt 660
tgagcgctct gcttgggtca aagcgtaagc gcttctcgaa ttcaaactca cagagttcca 720
agtctgcaca ggtcatctgt tcgtcctttt gagactgcct gactggctgg ctggaacgca 780
cgcacgcaca cttccgattc gacaccgccc gctgctgctg tcttctgcgc tcttgtgccc 840
ttcttctgta cttggccttt gcgtcgactt ctttgcttgc tcggcagtgc cgtctcatct 900
gccccaagtc aagctcagca gcacagcaca cacgcatcac cctctcggct tgggtttgcc 960
cctgttgcct gtctgtccac actcacacac atccctatcg cttgctcgac atcatcgctt 1020
acctcttccc caccacctcg tctttgacac ctttactttc tcaacccctc ttccaccacc 1080 aacccccccca ccacttactt tcaacatgac caagcaatct gcggacagca acgcaaagtc 1140
aggagttacg tccgaaatat gtcattgggc atccaacctg gccactgacg acatcccttc 1200
ggacgtatta gaaagagcaa aatacettat tctcgacggt attgcatgtg cctgggttgg 1260
tgcaagagtg ccttggtcag agaagtatgt tcaggcaacg atgagctttg agccgccggg 1320
ggcctgcagg gtgattggat atgggcagaa actggggcct gttgcagcag ccatgaccaa 1380
ttccgctttc atacaggcta cggagcttga cgactaccac agcgaagccc ccctacactc 1440
tgcaagcatt gtccttcctg cggtctttgc agcaagtgag gtcttagccg agcagggcaa 1500
aacaatttcc ggtatagatg ttattctagc cgccattgtg gggtttgaat ctggcccacg 1560
gatcggcaaa gcaatctacg gatcggacct cttgaacaac ggctggcatt gtggagctgt 1620
gtatggcgct ccagccggtg cgctggccac aggaaagctc ctcggtctaa ctccagactc 1680
catggaagat gctctcggaa ttgcgtgcac gcaagcctgt ggtttaatgt cggcgcaata 1740
cggaggcatg gtaaagcgtg tgcaacacgg attcgcagcg cgtaatggtc ttcttggggg 1800
actgttggcc catggtgggt acgaggcaat gaaaggtgtc ctggagagat cttacggcgg 1860
tttcctcaag atgttcacca agggcaacgg cagagagcct ccctacaaag aggaggaagt 1920
ggtggctggt ctcggttcat tctggcatac ctttactatt cgcatcaagc tctatgcctg 1980
ctgcggactt gtccatggtc cagtcgaggc tatcgaaaac cttcagggga gataccccga 2040
gctcttgaat agagccaacc tcagcaacat tcgccatgtt catgtacagc tttcaacggc 2100
ctcgaacagt cactgtggat ggataccaga ggagagaccc atcagttcaa tcgcagggca 2160
gatgagtgtc gcatacattc tcgccgtcca gctggtcgac cagcaatgtc ttttgtccca 2220
gttttctgag tttgatgaca acctggagag gccagaagtt tgggatctgg ccaggaaggt 2280
tacttcatct caaagcgaag agtttgatca agacggcaac tgtctcagtg cgggtcgcgt 2340
gaggattgag ttcaacgatg gttcttctat tacggaaagt gtcgagaagc ctcttggtgt 2400
caaagagccc atgccaaacg aacggattct ccacaaatac cgaacccttg ctggtagcgt 2460
gacggacgaa tcccgggtga aagagattga ggatcttgtc ctcggcctgg acaggctcac 2520
cgacattagc ccattgctgg agctgctgaa ttgccccgtg aaatcgccac tggtataaat 2580
gcattatat 2589

<210> SEQ ID NO 61
<211> LENGTH: 2971
<212> TYPE: DNA
<213> ORGANISM: artificial
<220> FEATURE:
<223> OTHER INFORMATION: (KpnI)-pActin-ITP1-(NsiI)

<400> SEQUENCE: 61
atataggtac cggcccgttc aacacaatgc gcctgcaatt tctatccccg ctttccacct 60
ctgtctccct cttcaaagtc acagagtctg ccatttgtat tcgagcatga aaaatgatga 120
cctcctttct tctcgttcaa tacagcggac atgaacaaga aaggggtggc ctgagccacc 180
aagttctaca cttgcagcca gacgtattca aaaatcgacg tggacgagtt gcgactcaac 240
atcctctgtg aattgcaatc gagtgagtga ttacgacctg tattcacgtc aaaatgcagg 300
tgtgacattt gaattttgaa atacatgagg caggctcgat ttgctccact caagtcgagt 360
ttgccaaatt caagaagcgc taatcggagc caaccgaccg accacaacca gccaaatcag 420
ccagccaagg cagagaagca gaagcaaagg cggtgcattg agaggtgagc cgtgtgctgt 480
gctgtgctct gctgtgctgt ctgtcaatgc ttgctgcgtg tgtttgtctc gcctctacag 540
cctgcccctc aagatgtgac cgattggaag gaaaggaagg tcacacgcag ttctggcatg 600
ccacgcacgc acagcccgaa attgcgatct caagagactg ccgacgccgc cgtccgccgt 660
tgagcgctct gcttgggtca aagcgtaagc gcttctcgaa ttcaaactca cagagttcca 720
agtctgcaca ggtcatctgt tcgtcctttt gagactgcct gactggctgg ctggaacgca 780
cgcacgcaca cttccgattc gacaccgccc gctgctgctg tcttctgcgc tcttgtgccc 840
ttcttctgta cttggccttt gcgtcgactt ctttgcttgc tcggcagtgc cgtctcatct 900
gccccaagtc aagctcagca gcacagcaca cacgcatcac cctctcggct tgggtttgcc 960
cctgttgcct gtctgtccac actcacacac atccctatcg cttgctcgac atcatcgctt 1020
acctcttccc caccacctcg tctttgacac ctttactttc tcaacccctc ttccaccacc 1080 aacccccccca ccacttactt tcaacatgct tccacagaca cctgttccag attaccgtct 1140
cagcatgaga tattcgacag acagcgtcgc agcatcgcaa gcgttaacaa cgcctgaagc 1200
agctccaagt atttcccatc acgcagacac gggcgaggtt caacaggcgc atagcggcga 1260
tgacggcgcg ctcgaagagg gcgcaattgc tcactcaagt aaggaagggt cacaacgaga 1320
tcagcaaacg gagctttact gtgctttcac aaagggcacc aagctcttcg tcgtcttgtc 1380
cgtgtctatc gcgggctttt tctcgccatt ctccatcaat atatatatcc ctgcgttgcc 1440

-continued tcagatctcg aagctactac atacatcgga aggtgagtga gacgatttct cgtagagaca 1500
gtttcccaga agcagctcct catcatcata ttttgtctta ttgtagcggc tactaatgta 1560
acggtaaccg tctacatgat cgcacaaggc ctctcgccgg tcatctgggc acctctttca 1620
gatgtaagtc cccattttat gtgacgcctg tctctgttgt aagatgtttc cacaggatca 1680
atctctgaaa tttctcgcct gtcaaatcgg cacgtacagg tttttggccg cagacccatc 1740
tacattgcaa ctttcctcgt ttttttcgtc gccaatcttg ggctttcgtt caccaatgtc 1800
tactggctct tggtcgtctt gcgtatggtt caagccgcag gagcatgcag cgccatcgct 1860
attggcgcag gaacgattgg cgatgttacc gagcgcaagg aacgaggaag ttatatgggc 1920
tattatgcgc ttgcccaata tactggtcca gccatcgggc ccgtaattgg aggtgcgctt 1980
tcgcaaagat gggattacca ttctaccttc ttcttcctca gtgccgtttc tggtgtcttt 2040
ctgatcttca tggccttctt cttacttgaa acgcttcgtg ttctagtggg gaacggaagt 2100
gcacgcacat tcggcatcta tcgcacttta gtgggaccca gactggtcaa gtcgacggca 2160
aattcgatgc gtccaaggat gaagagtccg cttgaaggtc gactcgaatt tggattccat 2220
cgtccatttt tggtgtttgc acgccccgag actagcctgg caatcctggc tttttcgatg 2280
gtgtatgcaa catactatct atcgtctgcc tctttgcctt atctcttcaa gcaagtatat 2340
ggtctacacg agctactcat tggggtatgc ttcgtgccta gtggtgttgg ttgtgccttg 2400
ggcacggtgc tcgctggcaa gatcctcgat tcggactatc gacgcgcgtt agacaagaac 2460
aagtcgggtg tcaaggttac gcgcgcacgg ctgcagtcgg cctggatcta cttgccaggc 2520
tatgcctcct cgcttctagc gtacggatgg tgtgttcggg cgcataccca catcgccgct 2580
cccatccttt ttcagtttac acgtaagtga gaattcaatc ttccgaatcg tggatcctgt 2640
tcgtgtacag cagtgctgac tctgcctttc aattaatcta cgaaacagtc ggcatgtttt 2700
caacaatgta cttcaccaac atcaacacac tcgttgtgga tctgtacccg ggcaaggcag 2760
ctactgccac agctgctgtt aacgtagggc gttgcttact cggcgctgtg gctgtggcca 2820
tcgtacaacc aatgaccgat gctatgggcg ctggatggac attcacagtc ggcgcgctcc 2880
ttgctctgtt catcggtctg atttgccaga cactcattca ctttcatggc gagaagtggg 2940
cagctcgcaa gcactcttga atgcattata t 2971

<210> SEQ ID NO 62
<211> LENGTH: 2234
<212> TYPE: DNA
<213> ORGANISM: artificial
<220> FEATURE:
<223> OTHER INFORMATION: (KpnI)-pActin-MTT1-(SdaI)

<400> SEQUENCE: 62
atataggtac cggcccgttc aacacaatgc gcctgcaatt tctatccccg ctttccacct 60
ctgtctccct cttcaaagtc acagagtctg ccatttgtat tcgagcatga aaaatgatga 120
cctcctttct tctcgttcaa tacagcggac atgaacaaga aaggggtggc ctgagccacc 180
aagttctaca cttgcagcca gacgtattca aaaatcgacg tggacgagtt gcgactcaac 240
atcctctgtg aattgcaatc gagtgagtga ttacgacctg tattcacgtc aaaatgcagg 300
tgtgacattt gaattttgaa atacatgagg caggctcgat ttgctccact caagtcgagt 360
ttgccaaatt caagaagcgc taatcggagc caaccgaccg accacaacca gccaaatcag 420
ccagccaagg cagagaagca gaagcaaagg cggtgcattg agaggtgagc cgtgtgctgt 480
gctgtgctct gctgtgctgt ctgtcaatgc ttgctgcgtg tgtttgtctc gcctctacag 540
cctgcccctc aagatgtgac cgattggaag gaaaggaagg tcacacgcag ttctggcatg 600
ccacgcacgc acagcccgaa attgcgatct caagagactg ccgacgccgc cgtccgccgt 660
tgagcgctct gcttgggtca aagcgtaagc gcttctcgaa ttcaaactca cagagttcca 720
agtctgcaca ggtcatctgt tcgtcctttt gagactgcct gactggctgg ctggaacgca 780
cgcacgcaca cttccgattc gacaccgccc gctgctgctg tcttctgcgc tcttgtgccc 840
ttcttctgta cttggccttt gcgtcgactt ctttgcttgc tcggcagtgc cgtctcatct 900
gccccaagtc aagctcagca gcacagcaca cacgcatcac cctctcggct tgggtttgcc 960
cctgttgcct gtctgtccac actcacacac atccctatcg cttgctcgac atcatcgctt 1020
acctcttccc caccacctcg tctttgacac ctttactttc tcaacccctc ttccaccacc 1080
aaccccccca ccacttactt tcaacatgcc gtccgttcaa cgcaacatct ctccttcagt 1140
ctcggtgctg gccggtgcga ctgcaggcgc tgttgaagga ggtgagttct atcgctttcg 1200
cctcgtccat tttgctagta attttacctt acaatcttct tgtcttcctt agtggccact 1260
ttccccatcg agtatctcaa gacagttaca cagttcgcac agcgagatac tcacggcaat 1320
cgtgaacgtc tttcaccatt ggatgttttc cgatcaacac ttgaaaaaga agggcctaga 1380
gggctctttc gtggttgttc ggctgtagtt gtcggcaacg cttccaaggc tggtgttcgc 1440
tttttggctt ttgagaattt tcgaaatatg ctcaagaaca aatcaacagt gagtgttttc 1500
ccctagcatg gatgcattag gaaatagact gacactgaaa tctttcgcag gggaaattat 1560
cgagcggtag caactacatt gcaggaatgg gcgctggcac gctggaagcc atattcgctg 1620
tgacaccgag tgaaacgatc agtgagtgcc cacgcaaact cgcagaacag aaccaaagaa 1680
gggcgagaca gactgacctt gcgctgtatt gctttcacca gaaacaaaac tcatcgacga 1740
cggcaagcgt gccaaaccac gctacgaaca gggtctcttc cgtggaaccg cctcgatcat 1800
ccgacaagaa gggtttggcg gtatctacaa aggtgtattt ccagtcattc tacgccaagg 1860
ctcggcctca gcgatccgac taggtacata ctctgctatg cgagatttca ttcccaaagc 1920
ccaaggcaag ggttcatcct tcgtcaattg gttgaccact ttctccatcg gtgctacatc 1980
tggcgttgtc gccgtgtatg ggaccatgcc atttgacgtt ctcaaaacga ggatgcaggc 2040
catcgacgct tcgcgctacc gatccacgtg gcactgcttg accgacacca tcggtacaga 2100
gggcatagca gctctgtggc gtggttccgt atcacgtagt atgcgcctca tcgttagtgg 2160
aggagtcatt tttagcgtgt atgaacaggt agtttggctt ctcgccggtc ccgagttttg 2220
acctgcaggt atat 2234

<210> SEQ ID NO 63
<211> LENGTH: 1125
<212> TYPE: DNA
<213> ORGANISM: artificial
<220> FEATURE:
<223> OTHER INFORMATION: (KpnI)-pActin-olapADI1

<400> SEQUENCE: 63
atataggtac cggcccgttc aacacaatgc gcctgcaatt tctatccccg ctttccacct 60
ctgtctccct cttcaaagtc acagagtctg ccatttgtat tcgagcatga aaaatgatga 120
cctcctttct tctcgttcaa tacagcggac atgaacaaga aaggggtggc ctgagccacc 180
aagttctaca cttgcagcca gacgtattca aaaatcgacg tggacgagtt gcgactcaac 240
atcctctgtg aattgcaatc gagtgagtga ttacgacctg tattcacgtc aaaatgcagg 300

-continued

```
tgtgacattt gaattttgaa atacatgagg caggctcgat ttgctccact caagtcgagt    360

ttgccaaatt caagaagcgc taatcggagc caaccgaccg accacaacca gccaaatcag    420

ccagccaagg cagagaagca gaagcaaagg cggtgcattg agaggtgagc cgtgtgctgt    480

gctgtgctct gctgtgctgt ctgtcaatgc ttgctgcgtg tgtttgtctc gcctctacag    540

cctgcccctc aagatgtgac cgattggaag gaaaggaagg tcacacgcag ttctggcatg    600

ccacgcacgc acagcccgaa attgcgatct caagagactg ccgacgccgc cgtccgccgt    660

tgagcgctct gcttgggtca aagcgtaagc gcttctcgaa ttcaaactca cagagttcca    720

agtctgcaca ggtcatctgt tcgtcctttt gagactgcct gactggctgg ctggaacgca    780

cgcacgcaca cttccgattc gacaccgccc gctgctgctg tcttctgcgc tcttgtgccc    840

ttcttctgta cttggccttt gcgtcgactt ctttgcttgc tcggcagtgc cgtctcatct    900

gccccaagtc aagctcagca gcacagcaca cacgcatcac cctctcggct tgggtttgcc    960

cctgttgcct gtctgtccac actcacacac atccctatcg cttgctcgac atcatcgctt   1020

acctcttccc caccacctcg tctttgacac ctttactttc tcaacccctc ttccaccacc   1080

aacccccccca ccacttactt tcaacatgtc gaatcctctt gcggg                  1125
```

<210> SEQ ID NO 64
<211> LENGTH: 1125
<212> TYPE: DNA
<213> ORGANISM: artificial
<220> FEATURE:
<223> OTHER INFORMATION: (KpnI)-pActin-olapAtCAD1

<400> SEQUENCE: 64

```
atataggtac cggcccgttc aacacaatgc gcctgcaatt tctatccccg ctttccacct     60

ctgtctccct cttcaaagtc acagagtctg ccatttgtat tcgagcatga aaaatgatga    120

cctcctttct tctcgttcaa tacagcggac atgaacaaga aaggggtggc ctgagccacc    180

aagttctaca cttgcagcca gacgtattca aaaatcgacg tggacgagtt gcgactcaac    240

atcctctgtg aattgcaatc gagtgagtga ttacgacctg tattcacgtc aaaatgcagg    300

tgtgacattt gaattttgaa atacatgagg caggctcgat ttgctccact caagtcgagt    360

ttgccaaatt caagaagcgc taatcggagc caaccgaccg accacaacca gccaaatcag    420

ccagccaagg cagagaagca gaagcaaagg cggtgcattg agaggtgagc cgtgtgctgt    480

gctgtgctct gctgtgctgt ctgtcaatgc ttgctgcgtg tgtttgtctc gcctctacag    540

cctgcccctc aagatgtgac cgattggaag gaaaggaagg tcacacgcag ttctggcatg    600

ccacgcacgc acagcccgaa attgcgatct caagagactg ccgacgccgc cgtccgccgt    660

tgagcgctct gcttgggtca aagcgtaagc gcttctcgaa ttcaaactca cagagttcca    720

agtctgcaca ggtcatctgt tcgtcctttt gagactgcct gactggctgg ctggaacgca    780

cgcacgcaca cttccgattc gacaccgccc gctgctgctg tcttctgcgc tcttgtgccc    840

ttcttctgta cttggccttt gcgtcgactt ctttgcttgc tcggcagtgc cgtctcatct    900

gccccaagtc aagctcagca gcacagcaca cacgcatcac cctctcggct tgggtttgcc    960

cctgttgcct gtctgtccac actcacacac atccctatcg cttgctcgac atcatcgctt   1020

acctcttccc caccacctcg tctttgacac ctttactttc tcaacccctc ttccaccacc   1080

aacccccccca ccacttactt tcaacatgac caagcaatct gcgga                  1125
```

<210> SEQ ID NO 65
<211> LENGTH: 1125

<212> TYPE: DNA
<213> ORGANISM: artificial
<220> FEATURE:
<223> OTHER INFORMATION: (KpnI)-pActin-olapITP1

<400> SEQUENCE: 65
atataggtac cggcccgttc aacacaatgc gcctgcaatt tctatccccg ctttccacct 60
ctgtctccct cttcaaagtc acagagtctg ccatttgtat tcgagcatga aaaatgatga 120
cctcctttct tctcgttcaa tacagcggac atgaacaaga aaggggtggc ctgagccacc 180
aagttctaca cttgcagcca gacgtattca aaaatcgacg tggacgagtt gcgactcaac 240
atcctctgtg aattgcaatc gagtgagtga ttacgacctg tattcacgtc aaaatgcagg 300
tgtgacattt gaattttgaa atacatgagg caggctcgat ttgctccact caagtcgagt 360
ttgccaaatt caagaagcgc taatcggagc caaccgaccg accacaacca gccaaatcag 420
ccagccaagg cagagaagca gaagcaaagg cggtgcattg agaggtgagc cgtgtgctgt 480
gctgtgctct gctgtgctgt ctgtcaatgc ttgctgcgtg tgtttgtctc gcctctacag 540
cctgcccctc aagatgtgac cgattggaag gaaaggaagg tcacacgcag ttctggcatg 600
ccacgcacgc acagcccgaa attgcgatct caagagactg ccgacgccgc cgtccgccgt 660
tgagcgctct gcttgggtca aagcgtaagc gcttctcgaa ttcaaactca cagagttcca 720
agtctgcaca ggtcatctgt tcgtcctttt gagactgcct gactggctgg ctggaacgca 780
cgcacgcaca cttccgattc gacaccgccc gctgctgctg tcttctgcgc tcttgtgccc 840
ttcttctgta cttggccttt gcgtcgactt ctttgcttgc tcggcagtgc cgtctcatct 900
gccccaagtc aagctcagca gcacagcaca cacgcatcac cctctcggct tgggtttgcc 960
cctgttgcct gtctgtccac actcacacac atccctatcg cttgctcgac atcatcgctt 1020
acctcttccc caccacctcg tctttgacac ctttacttc tcaacccctc ttccaccacc 1080 aacccccca ccacttactt tcaacatgct tccacagaca cctgt 1125

<210> SEQ ID NO 66
<211> LENGTH: 1125
<212> TYPE: DNA
<213> ORGANISM: artificial
<220> FEATURE:
<223> OTHER INFORMATION: (KpnI)-pActin-olapMTT1

<400> SEQUENCE: 66
atataggtac cggcccgttc aacacaatgc gcctgcaatt tctatccccg ctttccacct 60
ctgtctccct cttcaaagtc acagagtctg ccatttgtat tcgagcatga aaaatgatga 120
cctcctttct tctcgttcaa tacagcggac atgaacaaga aaggggtggc ctgagccacc 180
aagttctaca cttgcagcca gacgtattca aaaatcgacg tggacgagtt gcgactcaac 240
atcctctgtg aattgcaatc gagtgagtga ttacgacctg tattcacgtc aaaatgcagg 300
tgtgacattt gaattttgaa atacatgagg caggctcgat ttgctccact caagtcgagt 360
ttgccaaatt caagaagcgc taatcggagc caaccgaccg accacaacca gccaaatcag 420
ccagccaagg cagagaagca gaagcaaagg cggtgcattg agaggtgagc cgtgtgctgt 480
gctgtgctct gctgtgctgt ctgtcaatgc ttgctgcgtg tgtttgtctc gcctctacag 540
cctgcccctc aagatgtgac cgattggaag gaaaggaagg tcacacgcag ttctggcatg 600
ccacgcacgc acagcccgaa attgcgatct caagagactg ccgacgccgc cgtccgccgt 660
tgagcgctct gcttgggtca aagcgtaagc gcttctcgaa ttcaaactca cagagttcca 720

-continued

```
agtctgcaca ggtcatctgt tcgtcctttt gagactgcct gactggctgg ctggaacgca     780

cgcacgcaca cttccgattc gacaccgccc gctgctgctg tcttctgcgc tcttgtgccc     840

ttcttctgta cttggccttt gcgtcgactt ctttgcttgc tcggcagtgc cgtctcatct     900

gccccaagtc aagctcagca gcacagcaca cacgcatcac cctctcggct tgggtttgcc     960

cctgttgcct gtctgtccac actcacacac atccctatcg cttgctcgac atcatcgctt    1020

acctcttccc caccacctcg tctttgacac ctttactttc tcaacccctc ttccaccacc    1080

aacccccca ccacttactt tcaacatgcc gtccgttcaa cgcaa                     1125
```

<210> SEQ ID NO 67
<211> LENGTH: 1125
<212> TYPE: DNA
<213> ORGANISM: artificial
<220> FEATURE:
<223> OTHER INFORMATION: (KpnI)-pActin-olapRIA1

<400> SEQUENCE: 67

```
atataggtac cggcccgttc aacacaatgc gcctgcaatt tctatccccg ctttccacct      60

ctgtctccct cttcaaagtc acagagtctg ccatttgtat tcgagcatga aaaatgatga     120

cctcctttct tctcgttcaa tacagcggac atgaacaaga aaggggtggc ctgagccacc     180

aagttctaca cttgcagcca gacgtattca aaaatcgacg tggacgagtt gcgactcaac     240

atcctctgtg aattgcaatc gagtgagtga ttacgacctg tattcacgtc aaaatgcagg     300

tgtgacattt gaattttgaa atacatgagg caggctcgat ttgctccact caagtcgagt     360

ttgccaaatt caagaagcgc taatcggagc caaccgaccg accacaacca gccaaatcag     420

ccagccaagg cagagaagca gaagcaaagg cggtgcattg agaggtgagc cgtgtgctgt     480

gctgtgctct gctgtgctgt ctgtcaatgc ttgctgcgtg tgtttgtctc gcctctacag     540

cctgcccctc aagatgtgac cgattggaag gaaaggaagg tcacacgcag ttctggcatg     600

ccacgcacgc acagcccgaa attgcgatct caagagactg ccgacgccgc cgtccgccgt     660

tgagcgctct gcttgggtca aagcgtaagc gcttctcgaa ttcaaactca cagagttcca     720

agtctgcaca ggtcatctgt tcgtcctttt gagactgcct gactggctgg ctggaacgca     780

cgcacgcaca cttccgattc gacaccgccc gctgctgctg tcttctgcgc tcttgtgccc     840

ttcttctgta cttggccttt gcgtcgactt ctttgcttgc tcggcagtgc cgtctcatct     900

gccccaagtc aagctcagca gcacagcaca cacgcatcac cctctcggct tgggtttgcc     960

cctgttgcct gtctgtccac actcacacac atccctatcg cttgctcgac atcatcgctt    1020

acctcttccc caccacctcg tctttgacac ctttactttc tcaacccctc ttccaccacc    1080

aacccccca ccacttactt tcaacatgag cctctcgaac agcaa                     1125
```

<210> SEQ ID NO 68
<211> LENGTH: 1125
<212> TYPE: DNA
<213> ORGANISM: artificial
<220> FEATURE:
<223> OTHER INFORMATION: (KpnI)-pActin-olapTAD1

<400> SEQUENCE: 68

```
atataggtac cggcccgttc aacacaatgc gcctgcaatt tctatccccg ctttccacct      60

ctgtctccct cttcaaagtc acagagtctg ccatttgtat tcgagcatga aaaatgatga     120

cctcctttct tctcgttcaa tacagcggac atgaacaaga aaggggtggc ctgagccacc     180

aagttctaca cttgcagcca gacgtattca aaaatcgacg tggacgagtt gcgactcaac     240
```

```
atcctctgtg aattgcaatc gagtgagtga ttacgacctg tattcacgtc aaaatgcagg    300
tgtgacattt gaattttgaa atacatgagg caggctcgat ttgctccact caagtcgagt    360
ttgccaaatt caagaagcgc taatcggagc caaccgaccg accacaacca gccaaatcag    420
ccagccaagg cagagaagca gaagcaaagg cggtgcattg agaggtgagc cgtgtgctgt    480
gctgtgctct gctgtgctgt ctgtcaatgc ttgctgcgtg tgtttgtctc gcctctacag    540
cctgcccctc aagatgtgac cgattggaag gaaaggaagg tcacacgcag ttctggcatg    600
ccacgcacgc acagcccgaa attgcgatct caagagactg ccgacgccgc cgtccgccgt    660
tgagcgctct gcttgggtca aagcgtaagc gcttctcgaa ttcaaactca cagagttcca    720
agtctgcaca ggtcatctgt tcgtcctttt gagactgcct gactggctgg ctggaacgca    780
cgcacgcaca cttccgattc gacaccgccc gctgctgctg tcttctgcgc tcttgtgccc    840
ttcttctgta cttggccttt gcgtcgactt ctttgcttgc tcggcagtgc cgtctcatct    900
gccccaagtc aagctcagca gcacagcaca cacgcatcac cctctcggct tgggtttgcc    960
cctgttgcct gtctgtccac actcacacac atccctatcg cttgctcgac atcatcgctt   1020
acctcttccc caccacctcg tctttgacac ctttactttc tcaacccctc ttccaccacc   1080
aaccccccca ccacttactt tcaacatggc accttctctc aacgc                   1125
```

<210> SEQ ID NO 69
<211> LENGTH: 2382
<212> TYPE: DNA
<213> ORGANISM: artificial
<220> FEATURE:
<223> OTHER INFORMATION: (KpnI)-pActin-RIA1-(NsiI)

<400> SEQUENCE: 69

```
atataggtac cggcccgttc aacacaatgc gcctgcaatt tctatccccg ctttccacct     60
ctgtctccct cttcaaagtc acagagtctg ccatttgtat tcgagcatga aaaatgatga    120
cctcctttct tctcgttcaa tacagcggac atgaacaaga aaggggtggc ctgagccacc    180
aagttctaca cttgcagcca gacgtattca aaaatcgacg tggacgagtt gcgactcaac    240
atcctctgtg aattgcaatc gagtgagtga ttacgacctg tattcacgtc aaaatgcagg    300
tgtgacattt gaattttgaa atacatgagg caggctcgat ttgctccact caagtcgagt    360
ttgccaaatt caagaagcgc taatcggagc caaccgaccg accacaacca gccaaatcag    420
ccagccaagg cagagaagca gaagcaaagg cggtgcattg agaggtgagc cgtgtgctgt    480
gctgtgctct gctgtgctgt ctgtcaatgc ttgctgcgtg tgtttgtctc gcctctacag    540
cctgcccctc aagatgtgac cgattggaag gaaaggaagg tcacacgcag ttctggcatg    600
ccacgcacgc acagcccgaa attgcgatct caagagactg ccgacgccgc cgtccgccgt    660
tgagcgctct gcttgggtca aagcgtaagc gcttctcgaa ttcaaactca cagagttcca    720
agtctgcaca ggtcatctgt tcgtcctttt gagactgcct gactggctgg ctggaacgca    780
cgcacgcaca cttccgattc gacaccgccc gctgctgctg tcttctgcgc tcttgtgccc    840
ttcttctgta cttggccttt gcgtcgactt ctttgcttgc tcggcagtgc cgtctcatct    900
gccccaagtc aagctcagca gcacagcaca cacgcatcac cctctcggct tgggtttgcc    960
cctgttgcct gtctgtccac actcacacac atccctatcg cttgctcgac atcatcgctt   1020
acctcttccc caccacctcg tctttgacac ctttactttc tcaacccctc ttccaccacc   1080
aaccccccca ccacttactt tcaacatgag cctctcgaac agcaatcaca acgagcgcca   1140
```

-continued

```
caacgacgac aacaacatca atgacgatga ttgtgctaac ttctttgagc tgatggttca   1200
gcctgcctct tcttcttctt acggcccta ctttcccgac ccaggactgg cgcttccagc   1260
aatttccgat gtctcatcaa caacagatac gcgactaccg tcacagctcg gagtgacccc   1320
attcagtcat cagacatcgc ccatccgatc cgcagatgaa ggagagaaga cgacaacaac   1380
cgcatcatac aaaagaaagc attccgaggt ggagaaagac cgtcgaagaa tcatctcaaa   1440
cggatttgca gtgagtttcc ctcttcttct accataaagt tcaggctggt tgagctgaag   1500
tcgacgtttg gcaatatttg tgtagatctt gcagaacgtc ctccataacg actcaacttc   1560
caaacccatc tcgaaagcga ccctacttca acaagcgtgc gacgaaatcc gtgaactgcg   1620
caaaaaactt gatacgagca ttaccatcat ctcccgctat ggtctcgaaa atttgtttca   1680
ggtggctcca acccccaatt ctttgagcaa tgcttctcct cccaatggta cgagtagggc   1740
ttaccctacc tattcgaacg acctcggccc ggatcgtttc caagactcgc ggcgtagttc   1800
cacttcggcg acgagtgtgt ctggatctca atataacaat ggcgctgccg ctaaggagga   1860
tggaaacgag aggcgtaatt ccaacgtgaa gaggagaagt tcttacacca acagcatcaa   1920
cagcagcttc gagtcatccg aggaggacac tctgaatagc agttgcgaca acacaagtga   1980
cttcgacgaa agcgttggca gcagcgaaag cgaaagtgaa acaaacaaca ggacaagaaa   2040
cagaaacaga accaagaggg caatggcaac agcaaagctc aaagaccgag accgcgccaa   2100
agctcgaacc gcacccaagc cacacagcaa tcgcttatcg cctgcatcca ctataacgcc   2160
aagtgagatg agcagcagct tagccagccc aaacacctct tcacaagagc atatccagca   2220
agccatcttg tcattgctcc tcgaattgcc gaaacatctg gagaatgtgc acaagtcgaa   2280
gcgtccttcc tctcagcagc caagcacaca gattgatcaa accggaaacc ggactacgac   2340
ggtaacgaag accaggagac ggcaccgatg aatgcattat at                      2382
```

<210> SEQ ID NO 70
<211> LENGTH: 2574
<212> TYPE: DNA
<213> ORGANISM: artificial
<220> FEATURE:
<223> OTHER INFORMATION: (KpnI)-pActin-TAD1-(NsiI)

<400> SEQUENCE: 70

```
atataggtac cggcccgttc aacacaatgc gcctgcaatt tctatccccg ctttccacct     60
ctgtctccct cttcaaagtc acagagtctg ccatttgtat tcgagcatga aaaatgatga    120
cctcctttct tctcgttcaa tacagcggac atgaacaaga aaggggtggc ctgagccacc    180
aagttctaca cttgcagcca gacgtattca aaaatcgacg tggacgagtt gcgactcaac    240
atcctctgtg aattgcaatc gagtgagtga ttacgacctg tattcacgtc aaaatgcagg    300
tgtgacattt gaattttgaa atacatgagg caggctcgat ttgctccact caagtcgagt    360
ttgccaaatt caagaagcgc taatcggagc caaccgaccg accacaacca gccaaatcag    420
ccagccaagg cagagaagca gaagcaaagg cggtgcattg agaggtgagc cgtgtgctgt    480
gctgtgctct gctgtgctgt ctgtcaatgc ttgctgcgtg tgtttgtctc gcctctacag    540
cctgcccctc aagatgtgac cgattggaag gaaaggaagg tcacacgcag ttctggcatg    600
ccacgcacgc acagcccgaa attgcgatct caagagactg ccgacgccgc cgtccgccgt    660
tgagcgctct gcttgggtca aagcgtaagc gcttctcgaa ttcaaactca cagagttcca    720
agtctgcaca ggtcatctgt tcgtcctttt gagactgcct gactggctgg ctggaacgca    780
cgcacgcaca cttccgattc gacaccgccc gctgctgctg tcttctgcgc tcttgtgccc    840
```

```
ttcttctgta cttggccttt gcgtcgactt ctttgcttgc tcggcagtgc cgtctcatct    900

gccccaagtc aagctcagca gcacagcaca cacgcatcac cctctcggct tgggtttgcc    960

cctgttgcct gtctgtccac actcacacac atccctatcg cttgctcgac atcatcgctt   1020

acctcttccc caccacctcg tctttgacac ctttactttc tcaacccctc ttccaccacc   1080

aacccccccca ccacttactt tcaacatggc accttctctc aacgcgaact caacagccga   1140

tcggcggaac gccactgctg cccctgacct tctatccggc aataaagccg gtggtggcct   1200

caagctttcc ggattaccag acctctccga ctcggcaggc accttgagcg acgtatttgg   1260

aacgccggcc atgcgcctca tctggtctga ccaaaatcga gttgcttgct acctcgagat   1320

cgaggcagcg ctcgccgttg tccaagctga actcggtatc atcccaaagc acgccgctca   1380

ggagatcgtc aaacactgcc gtgtagatga gatcgattgg gctctgtaca agcaaaagac   1440

cgaattgatc ggctatcctg tcttgggaat cgtccagcag ctggttgcca actgcaaaga   1500

tggcttggga gagtactgtc attggggcgc tacgacacaa gatatcaccg acacagctac   1560

cattatgcag attcgtcagt cgctcgccct cgttaaggag aagctgtgca gcatcgttgc   1620

gagccttcgg tacttggcgg aaaagcaccg caaccttccc atggctgcgc gttcgaatct   1680

caagcaagcc gtgccaataa cttttggttt caagatggcg cgcttcttgg ccactttccg   1740

ccgacatcag gagcgtctgg ccgagctcga gaagagaaca tacacactag aattcggcgg   1800

tgcggcgggc aacttgtcct cgttaggcga aaagggtatt gcgacgcacg atgcactcgc   1860

caagatgctt gacctttcac ccgctgacat cgcctggcat accgaacacg atcgctttgc   1920

agaggtaggt gccttcctgg gtcttctgac gggaacgcta gccaaactcg ccacagacat   1980

caaactcatg tcgcagaccg aggtgggtga ggtcggggag ccattcatct caaaccgtgg   2040

ctcatcgtcc accatgccgc agaagaacaa cccgatttcg tgcgtgtata ttcatgcctg   2100

tgccgccaat gtccgtcagg gaactgctgc gctgttggat gccatgcagt cggatcacga   2160

gcgtggcact ggaccttggg agatcatctg ggttcaactc ccgctcatga tgaactggtc   2220

ggcagcggct ctggccaatg ccgacttcat tttgaaggga ttgcaggtct tccccgatgc   2280

catggtccga aacctggcct tgtccaaggg cttgatcgtc tccgaagcag tcatgatggc   2340

gctcggcgac actctcggcc gccagtacgc ccatgacgcc gtctacgagt gctgtcgagc   2400

ggcctttgag cataacagac cgttgcttga tgttcttctc gagaaccaag aaatagctag   2460

caagctgaag cgtgccgagc tagagaggct ttgcgagcca gccaattatc ttggacaatg   2520

ctcccaatgg atcgatcgtg tcttgctacc tccttccacg tgaatgcatt atat         2574
```

<210> SEQ ID NO 71
<211> LENGTH: 1123
<212> TYPE: DNA
<213> ORGANISM: artificial
<220> FEATURE:
<223> OTHER INFORMATION: (Pfl23II)-pActin-olapACO2

<400> SEQUENCE: 71

```
atatacgtac gggcccgttc aacacaatgc gcctgcaatt tctatccccg ctttccacct     60

ctgtctccct cttcaaagtc acagagtctg ccatttgtat tcgagcatga aaaatgatga    120

cctcctttct tctcgttcaa tacagcggac atgaacaaga aaggggtggc ctgagccacc    180

aagttctaca cttgcagcca gacgtattca aaaatcgacg tggacgagtt gcgactcaac    240

atcctctgtg aattgcaatc gagtgagtga ttacgacctg tattcacgtc aaaatgcagg    300
```

```
tgtgacattt gaattttgaa atacatgagg caggctcgat ttgctccact caagtcgagt    360
ttgccaaatt caagaagcgc taatcggagc caaccgaccg accacaacca gccaaatcag    420
ccagccaagg cagagaagca gaagcaaagg cggtgcattg agaggtgagc cgtgtgctgt    480
gctgtgctct gctgtgctgt ctgtcaatgc ttgctgcgtg tgtttgtctc gcctctacag    540
cctgcccctc aagatgtgac cgattggaag gaaaggaagg tcacacgcag ttctggcatg    600
ccacgcacgc acagcccgaa attgcgatct caagagactg ccgacgccgc cgtccgccgt    660
tgagcgctct gcttgggtca aagcgtaagc gcttctcgaa ttcaaactca cagagttcca    720
agtctgcaca ggtcatctgt tcgtcctttt gagactgcct gactggctgg ctggaacgca    780
cgcacgcaca cttccgattc gacaccgccc gctgctgctg tcttctgcgc tcttgtgccc    840
ttcttctgta cttggccttt gcgtcgactt ctttgcttgc tcggcagtgc cgtctcatct    900
gccccaagtc aagctcagca gcacagcaca cacgcatcac cctctcggct tgggtttgcc    960
cctgttgcct gtctgtccac actcacacac atccctatcg cttgctcgac atcatcgctt   1020
acctcttccc caccacctcg tctttgacac ctttactttc tcaacccctc ttccaccacc   1080
aacccccca ccacttactt tcaacatgat tgcctcgctc gct                      1123
```

<210> SEQ ID NO 72
<211> LENGTH: 4269
<212> TYPE: DNA
<213> ORGANISM: artificial
<220> FEATURE:
<223> OTHER INFORMATION: (Pfl23II)_pActin_ACO2_(NsiI)

<400> SEQUENCE: 72

```
atatacgtac gggcccgttc aacacaatgc gcctgcaatt tctatccccg ctttccacct     60
ctgtctccct cttcaaagtc acagagtctg ccatttgtat tcgagcatga aaaatgatga    120
cctcctttct tctcgttcaa tacagcggac atgaacaaga aaggggtggc ctgagccacc    180
aagttctaca cttgcagcca gacgtattca aaaatcgacg tggacgagtt gcgactcaac    240
atcctctgtg aattgcaatc gagtgagtga ttacgacctg tattcacgtc aaaatgcagg    300
tgtgacattt gaattttgaa atacatgagg caggctcgat ttgctccact caagtcgagt    360
ttgccaaatt caagaagcgc taatcggagc caaccgaccg accacaacca gccaaatcag    420
ccagccaagg cagagaagca gaagcaaagg cggtgcattg agaggtgagc cgtgtgctgt    480
gctgtgctct gctgtgctgt ctgtcaatgc ttgctgcgtg tgtttgtctc gcctctacag    540
cctgcccctc aagatgtgac cgattggaag gaaaggaagg tcacacgcag ttctggcatg    600
ccacgcacgc acagcccgaa attgcgatct caagagactg ccgacgccgc cgtccgccgt    660
tgagcgctct gcttgggtca aagcgtaagc gcttctcgaa ttcaaactca cagagttcca    720
agtctgcaca ggtcatctgt tcgtcctttt gagactgcct gactggctgg ctggaacgca    780
cgcacgcaca cttccgattc gacaccgccc gctgctgctg tcttctgcgc tcttgtgccc    840
ttcttctgta cttggccttt gcgtcgactt ctttgcttgc tcggcagtgc cgtctcatct    900
gccccaagtc aagctcagca gcacagcaca cacgcatcac cctctcggct tgggtttgcc    960
cctgttgcct gtctgtccac actcacacac atccctatcg cttgctcgac atcatcgctt   1020
acctcttccc caccacctcg tctttgacac ctttactttc tcaacccctc ttccaccacc   1080
aacccccca ccacttactt tcaacatgat tgcctcgctc gctcgcgttc agaggggccg   1140
caatggcttc tctgccgctc acaaggccat cggtgccaag cgcaccctcg ccaccccccgc   1200
tgctgatggt cgcgtcccta cattccaccc gtcgcgcgtt ccaccataca cagagttgct   1260
```

```
cgccaccctc gagaccgttc gtcaacagct caaccgtcct ctcacactct ccgaaaagat   1320
tctctactcg catcttcgca accccgagca ggacctcgct ggtgtcggtg ctgatgtttc   1380
ggctattcga ggcaaaaagt acctcaagct caagatcgac cgtttggcca tgcaggatgc   1440
ttccgcccag atggctttgc ttcagttcat gacttgcggt ttgccacgta ccgccattcc   1500
ttccagtgtt cactgcgacc atctcattca ggcgttcgag ggtgctgagg ccgatcttaa   1560
gcgttccatc gcttccaacc aggaggtctt tgctttcctc gaatcggctt ccaagaagta   1620
cggtatcgag ttctggggtc caggctccgg tatcattcac cagattgttc tcgagaacta   1680
cgcagcaccc ggtcttctca tgctcggtac cgactcgcac actcccaacg cttccggtct   1740
cggttgtctt gctatcggtg tcggaggtgc tgatgccgtc gatgctatga ccaacactcc   1800
ttgggagctc atggcaccca aggtgctcgg tgttcacctc aagggagagc tcagcccttg   1860
gtgcacgccc aaggatgtca ttcttcacct tgccggcaag ctgaccgttc gtggtggtac   1920
cggaaagatc gtcgaatact cgggtcccgg tctccagact cttcccgcca ctggtcttgc   1980
taccatgtcc aacatgggtg ctgaggttgg tgccactact tccgctttcc ccttcactcc   2040
tgccatggga tcctacctcg aggctactgg ccgtgctgaa gtcgctcgcg ctgccgagaa   2100
ggctgctggc caaggtttcc ttgctgctga cgaaggcgca gagtacgatg agcgtatcga   2160
gatcaacctt tccgacctcg agccttgcct caacggtccc ttcactcccg atctcagcac   2220
tcccctttcc gaattcgtca acaaggccaa gtccgacgct cgtgaccacc ccgtcgagct   2280
cagcgccgct ctcatcggct catgcaccaa ttcttcttac gccgacatgg ctcgttgcgc   2340
ttcgctcgcc cagcaggcca gggaccgcgg catgaaggtc aagtccagct tcgatgtcac   2400
tcccggttcc gagcaggttc gtgccactgt tgagcgcgat ggtattcagc aagtcttgac   2460
cgatgtcggc ggacgtgttc ttgccaacgc ttgcggtcct tgcatcggac aatggaaccg   2520
aaaggagctc cagggcgagg acaacgtcat cttgacctcg ttcaaccgaa acttccgtgg   2580
ccgtaacgat ggcaactcca agacttggaa cttgctcgca tcccccgaga ttgtcaccgc   2640
catggccttt gctggtcgtc tcgacttcaa ccctatgacc gacagcctca ctgctcccga   2700
tggcaagcct ttcaagttcg agcctcctca gtctgatgtt ttgcccgcca gcggttttgc   2760
tcagggtgac attgactacc ttcccgcccc catgcctgag cctcaacctg acactgaggt   2820
tctcatcagc cccacctccg cgcgtctcga gcacttggca cctttcgaca gccccttcgc   2880
cgctactgcc gctcagggca agtacgagct ccccaccatg cgttgtctcc tccgtatcaa   2940
gggcaagtgc acaaccgacc acatcagtgc cgctggtcct tggctcaagt acaagggtca   3000
cctttccaac ttggccgaga acaccctcat cggtgccacc aatgacgagt tcgacgctgt   3060
caacgtcgct caagactacg agactggcaa gaaagacacc atccccggcg tcgccaagat   3120
ctacaagtcg cgtcaacagc catggatgat ggtcgccgac cacaactacg gagaaggatc   3180
cgctcgtgag cacgccgcct tgcagcctcg attctacggt tgcaacctca tcgttgcccg   3240
cagcatcgct cgtattgctg agactaactt gcgcaagcag ggtgtcttga cgttgctctt   3300
cgagaacgag gacgactacc tcaggatcag ctcgggtgac cttgtcgaga cggtcaacct   3360
gacggatttg atcaagcccg gaggagattt ggctacccag gtcaagttga aggtgaccaa   3420
gttcgaggag gatggaaaga cggtgaagga gactttcgag ttgcccacca agcactcgtt   3480
gagtgccgct catttggact ggatcagggc tggttccgcg ctcaacctca tccgtgagca   3540
ggctgcttcc tctgctgctg ctggcggtat cgctggtggt gtctctggtg ccttcgccgc   3600
```

```
tgctgctggc gctgccaagt ctgccgcgtc taaggttgcc tcccttggtg gtgtccgtgg   3660

atacgctact gccgctaagc ctgccaccgg tggatcgcgc aaccccaacg atcccaacta   3720

cgtcccgccc gcagctgatc cccgtaccga atccattcgc aagatcgttt acccccccttc  3780

ccccgtctca gccaaggaca aagccgcgca ctcggccacc tccgcctctg ccgtcctccc   3840

cttcggctct gcctcagaag agatccacag caccattacc cgcgcatggc tcctctacca   3900

acgcacacaa cgcgaatccc tcgctgcctc cctcaacgcc aaacaagctc gcctccgcga   3960

agcgctccaa gacctcaaag aaacagacga acgcctgtac gcagcagcaa cgtacaaagt   4020

tgcccccaac aaacgttccc ctaaggaaca ccgtaaactt gttgaacttg ggttggtaac   4080

gctgccaggt gcaacaccca agccggacgc tccgagcggt gctgaggcga ggaggctggt   4140

gaaggcggtt gcgggaggtg ctaggttgga ggggttgttc cctagggagt tgagggttcc   4200

gactatgacg cccggtagga aggtttggaa ctcgaacttt gagcctagtc agatttgaat   4260

gcattatat                                                           4269


<210> SEQ ID NO 73
<211> LENGTH: 21820
<212> TYPE: DNA
<213> ORGANISM: artificial
<220> FEATURE:
<223> OTHER INFORMATION: Vector_surroundings

<400> SEQUENCE: 73

tgtgtgaaag tcgtaaatga tatcggcggc agctttcatg ccggcctggt tggggtggta     60

tgcgcatctg tttttgaagt tccagaacga gccgtctgat acccaaggct cttttgatcc    120

gagtgcgtgc ttgagcttgc tctcttctgc tagcggaacg acatagacgt tattcctccc    180

ttccgctgcc ttggcgtaga gcgattgaag ctgttcggcc atctcgatgt acttttgcac    240

ttgttgctga tcccaacata cgtccctcca cgcttttgta tcgggtccca tcatggcgtg    300

gtattcgacc aggtagatcg tcgcttttgg atactttttc tggacgccat cgatcaaggt    360

tgcgaatctt tgggagatct cgtctggcga agcgatggtg gggtgttcaa agtgctcctt    420

ctcttctttc gacaagacaa aatacgacaa caatctaccc caccatgtgt tcttgaacgt    480

cagaccgaac atactcccga tgtagaacat gtcattgccc ccaccggtga tcgtgactat    540

cgcatcgctg ccatcatctc cttccttaag ttcgggaaga agacttagtt gaggggcgta    600

gactttcttt ccagtatctt gcggttcgga gatcaaattg agtagcgtcg cacttgacac    660

cgaaaggtcg agaaattcat ccgtgttgtt cgggtcgaga ttgagtctac gcgccaagta    720

gttgggatag ttgtttgcac ttcgaccagc gtcagtgtct acttgaggag ggatgcctgg    780

cccagcggcg aacgatgagc ccaacgcgat caaccttgtc atttggactt gttatggcac    840

agtgttgata ttgccaagat cgacgtcgaa gatgcaatga tgaagcaaaa cggagcgaag    900

tgcaaacagg gtctcgataa gatgaattga cgagttcaaa ggaagggttc ccgatatgaa    960

gactaacgac ttcatcggca ggcttctagc ggaaaccgga ctggataagg cgggcagcgt   1020

gtaggtgggt ctgtgcgttt gcgtcaaccc cgcatttcct cggcaaagaa aaagcaagaa   1080

atttgagaaa aaggcgggaa aattgtaaca caggctaagg accggttgtc ggaggtcaaa   1140

ttgaagcgtt gagccggtac gacctagaga atggggaaac tcatcaccag ccgtgtcatt   1200

ctcttttgct gaggttgtga tcagattctc atctacatag cttgtcgttc gaagcaaccg   1260

ggcacttatt ctacctctat gcgtccatca tgatgaatct tcgcgaggct gtgtacccat   1320

gggtacattt gggcgaagaa aggacgtcgc acgaccgaca gcctaagaag catagcgcac   1380
```

caaagtaacg gttgaatgac tgcaaatgta gagccgtgtc aagttcgcga tcatagccga 1440
agcgagtgag ggatgtctcg agctatgtgg ccggcatgtt ctcagtgccc cgcaattttt 1500
tgtgtgtgtt cttgtggcac gagcaatcgg ctcaaccgag tctgcagcaa aactgagcca 1560
tttacccgtc gtggccgact tgaccgtgtg cgagccaaga gcaagccgaa aacgtgagtc 1620
ttcgccgagt ctcttccttc ctttgcttca ctaacatcag tagccgtcac tatagatccc 1680
ttatgagcag ctagccggca gattttggct gcgtttcctc cccaccatca tcgcattcct 1740
gcatcacctt gcctactccg tcacgatgcc ctacacacca ccacgttcgt cgcagcctcc 1800
taaaggttta ccctttgagc tttcgctctc gacgcatccc ggcgcgcagc acaaccgatc 1860
ttcgctcaca cccgtgtcgt tcctcttgcg tgccgcgctg attacgcctc gcaaattggc 1920
aatcactcat cctgaaaagg gctactcatt cacctacgag caatgggcag cacgtactct 1980
ctcgctcgcc tttgcacttc gcagccttcc cgccttcaag attggtgatc gcgtcgctgt 2040
tatctcgcct aacgcacctc tgatcgcaga cgctcactgg ggtattcctg ctgttggtgg 2100
tatcattacg ccgatcaaca ttcgaaacac gcccaaggag gtcgcttacg tcttggagca 2160
ctcgggtagc actgtaatct tggtcgacca cgagtttaca cacctcgtcc ccgagaaccc 2220
tggcccaggc atcaccgtca tcgtcagcaa agattcggga ggacaagaag ctgacgatcc 2280
atacgagaaa tttctcgatc gtggcttcct cgaatggcag cgtgctgagc aggctgagct 2340
caaagcctac aagtctcgca ctcgaccttc tgctgaacca aagacgggat ggaaactcat 2400
cgaggcgcct caagacgaag aacaacccat cgccctctgc tacacctcgg gtactactgg 2460
tcgacccaaa ggtgtgctca ctaaccaccg tggagcctac ctttctgccg tagccaacgc 2520
ttttgaagcc cacctcacgc aggatagcgt ctatctttgg gttcttccca tgttccatgc 2580
ttgtggatgg acgtaccctt gggctgttac tgcttctctc gctacgcatt tcaccattcg 2640
caaggtcgac aacaccgtta tctgggacgc gttgctcaat cacggcgtat cgcactactg 2700
cggtgcccct acagttcaga tcggcctcgt caaccatcct aacgcacgca agctcaaccg 2760
tcgcgtgaac gttgccgtcg cagcttccgc acccaccgcc aacctcctcg ccaagatgga 2820
gggtctaaac ttgcacccag tccacgtata cggcttgacc gaaacatacg gtcctttcac 2880
caggaggtac ttcgagcccg aatgggccaa actagatgtt gatgctcgag cacgaatgat 2940
ggctcgccaa ggacactcct acctcacttc agatgaggta cgtgtcgttc gtactgcttc 3000
ttccaccgac gcctctacac ctgacctcgt cgatgttgag cgcaacggtc aagaaacggg 3060
cgaaatcgtc attcgaggaa acatggtcat ggtaggctac tacaacgatc ccgccgccac 3120
ttccaaagcc gtcatgaaag gctggttcca cactggcgac ctagccgtcc gtcaccctgg 3180
cggcgaaatc caaatcctag accgaggtaa agacatcatc atctccggag gcgaaaacat 3240
ctcctcgctc atggttgaac aggaacttgc ctcccaccct tccgtcctcg aatgctgcgt 3300
cattgcacga ccgcacgaaa agtggggcga acgcggccag tcgtttatcg tgctcacaga 3360
acaggcgaaa gcgaaactca acttcgcaga gataaaaaag aagggttcac cggagaacaa 3420
ggcgtttgtt gaagaggtga aaaagcactg cgtggaaagg atgtccaaat tcgccgtacc 3480
ggaatggttc gacgtagtgg acgaattgcc aaagacaagc acgggcaagg tgcagaagaa 3540
gggcgcaggg tcgatgcgac gcaatcgtcc gatccggagc cgggactgtc gggcgtacac 3600
aaatcgcccg cagaagcgcg gccgtctgga ccgatggctg tgtagaagta ctcgccgata 3660
gtggaaaccg acgccccagc actcgtccga gggcaaagga atagagtaga tgccgaccgg 3720

-continued

```
gatctgggca gcaccaagac acggaacttt caacagtcgt gagtaggtgg tgatctgcat   3780
gtccaaatcg tgaaacgtga atcacgaacc acgaatcgtg aatagccact ttgcgcgaaa   3840
atcactgaat gccgccaaac cgacgcgacg cgagttgcgt gaagtattcg tgattcacat   3900
tcacgattga cgattgtgag ttggtcgacg acattcgcta gccagaccaa cactcacgac   3960
tttttgaaga gcgttgcagg ttgagccaac tttctccctc actctttgct ttcttctcca   4020
tcacgctcat tccttttaag tgttcatccg gtatcattag cactatatca tagtgaaact   4080
cgcaacaacc cggtcttcgt cgcgaaagca accctccatc gctgctgcct cttgcagtga   4140
agaccgccac catgcagtct acgcagtcga agaccctaca cgtccagttc gtccattctg   4200
gtcctacaca ttgtatccac gcacccaagt ctgccaacgt ggagtaagtg aacctttttt   4260
tgtcctgtcg aggctcaacg tagatcacag gctgatcatc cacactcttc taccttttga   4320
cattacgcag tcgacttttt acaggaggag atgactacct cgtccgaatc ttacccaccc   4380
tgcctctctc cgacgtagag ccgcagctta tcgaagacgc cactgaagcg gtgacctcgc   4440
tcgatgctga cggccgcttc ctcgtcaccg cttccgaaga tggctctgta cgcctctacc   4500
gacaccaccc aatcgacgcg gaaggcaacc cagcatcacc aactgtgctt caatcgctgc   4560
tgcgccgcga agcttggctg caggtcgacg gatcccgggt accggcccgt tcaacacaat   4620
gcgcctgcaa tttctatccc cgctttccac ctctgtctcc ctcttcaaag tcacagagtc   4680
tgccatttgt attcgagcat gaaaaatgat gacctccttt cttctcgttc aatacagcgg   4740
acatgaacaa gaaaggggtg gcctgagcca ccaagttcta cacttgcagc cagacgtatt   4800
caaaaatcga cgtggacgag ttgcgactca acatcctctg tgaattgcaa tcgagtgagt   4860
gattacgacc tgtattcacg tcaaaatgca ggtgtgacat ttgaattttg aaatacatga   4920
ggcaggctcg atttgctcca ctcaagtcga gtttgccaaa ttcaagaagc gctaatcgga   4980
gccaaccgac cgaccacaac cagccaaatc agccagccaa ggcagagaag cagaagcaaa   5040
ggcggtgcat tgagaggtga gccgtgtgct gtgctgtgct ctgctgtgct gtctgtcaat   5100
gcttgctgcg tgtgtttgtc tcgcctctac agcctgcccc tcaagatgtg accgattgga   5160
aggaaaggaa ggtcacacgc agttctggca tgccacgcac gcacagcccg aaattgcgat   5220
ctcaagagac tgccgacgcc gccgtccgcc gttgagcgct ctgcttgggt caaagcgtaa   5280
gcgcttctcg aattcaaact cacagagttc caagtctgca caggtcatct gttcgtcctt   5340
ttgagactgc ctgactggct ggctggaacg cacgcacgca cacttccgat tcgacaccgc   5400
ccgctgctgc tgtcttctgc gctcttgtgc ccttcttctg tacttggcct ttgcgtcgac   5460
ttctttgctt gctcggcagt gccgtctcat ctgccccaag tcaagctcag cagcacagca   5520
cacacgcatc accctctcgg cttgggtttg cccctgttgc ctgtctgtcc acactcacac   5580
acatccctat cgcttgctcg acatcatcgc ttacctcttc cccaccacct cgtctttgac   5640
acctttactt tctcaacccc tcttccacca ccaacccccc caccacttac tttcaacatg   5700
agcctctcga acagcaatca caacgagcgc cacaacgacg acaacaacat caatgacgat   5760
gattgtgcta acttctttga gctgatggtt cagcctgcct cttcttcttc ttacggcccc   5820
tactttcccg acccaggact ggcgcttcca gcaatttccg atgtctcatc aacaacagat   5880
acgcgactac cgtcacagct cggagtgacc ccattcagtc atcagacatc gcccatccga   5940
tccgcagatg aaggagagaa gacgacaaca accgcatcat acaaaagaaa gcattccgag   6000
gtggagaaag accgtcgaag aatcatctca aacggatttg cagtgagttt ccctcttctt   6060
ctaccataaa gttcaggctg gttgagctga agtcgacgtt tggcaatatt tgtgtagatc   6120
```

-continued

```
ttgcagaacg tcctccataa cgactcaact tccaaaccca tctcgaaagc gaccctactt   6180
caacaagcgt gcgacgaaat ccgtgaactg cgcaaaaaac ttgatacgag cattaccatc   6240
atctcccgct atggtctcga aaatttgttt caggtggctc caacccccaa ttctttgagc   6300
aatgcttctc ctcccaatgg tacgagtagg gcttacccta cctattcgaa cgacctcggc   6360
ccggatcgtt tccaagactc gcggcgtagt tccacttcgg cgacgagtgt gtctggatct   6420
caatataaca atggcgctgc cgctaaggag gatggaaacg agaggcgtaa ttccaacgtg   6480
aagaggagaa gttcttacac caacagcatc aacagcagct tcgagtcatc cgaggaggac   6540
actctgaata gcagttgcga caacacaagt gacttcgacg aaagcgttgg cagcagcgaa   6600
agcgaaagtg aaacaaacaa caggacaaga aacagaaaca gaaccaagag ggcaatggca   6660
acagcaaagc tcaaagaccg agaccgcgcc aaagctcgaa ccgcacccaa gccacacagc   6720
aatcgcttat cgcctgcatc cactataacg ccaagtgaga tgagcagcag cttagccagc   6780
ccaaacacct cttcacaaga gcatatccag caagccatct tgtcattgct cctcgaattg   6840
ccgaaacatc tggagaatgt gcacaagtcg aagcgtcctt cctctcagca gccaagcaca   6900
cagattgatc aaaccggaaa ccggactacg acggtaacga agaccaggag acggcaccga   6960
tgaatgcata gtagatgccg accgggatct gggcagcacc aagacacgga acttcaacag   7020
tcgtgagtag gtggtgatct gcatgtccaa atcgtgaaac gtgaatcacg aaccacgaat   7080
cgtgaatagc cactttgcgc gaaaatcact gaatgccgcc aaaccgacgc gacgcgagtt   7140
gcgtgaagta ttcgtgattc acattcacga ttgacgattg tgagttggtc gacgacattc   7200
gctagccaga ccaacactca cgactttttg aagagcgttg caggctgagc caactttctc   7260
cctcactctt tgctttcttc tccatcacgc tcattccttt taagtgttca tccggtatca   7320
ttagcactat atcatagtga aactcgcaac aacccggtct tcgtcgcgaa agcaaccctc   7380
catcgctgct gcctcttgca gtgaagaccg ccaccatgca gtctacgcag tcgaagaccc   7440
tacacgtcca gttcgtccat tctggtccta cacattgtat ccacgcaccc aagtctgcca   7500
acgtggagta agtgaacctt tttttgtcct gtcgaggctc aacgtagatc acaggctgat   7560
catccacact cttctacctt ttgacattac gcagtcgact ttttacagga ggagatgact   7620
acctcgtccg aatcttaccc accctgcctc tctccgacgt agagccgcag cttatcgaag   7680
acgccactga agcggtgacc tcgctcgatg ctgacggccg cttcctcgtc accgcttccg   7740
aagatggctc tgtacgcctc taccgacacc acccaatcga cgcggaaggc aacccagcat   7800
caccaactgt gcttcaatcg ctgctgcgcc gcgaagcttg gctgcaggtc gacggatccc   7860
ggttatcgag ctcgaattcg ccctatagtg agtcgtatta caattcactg gccgtcgttt   7920
tacaacgtcg tgactgggaa aaccctggcg ttacccaact taatcgcctt gcagcacatc   7980
cccctttcgc cagctggcgt aatagcgaag aggcccgcac cgatcgccct tcccaacagt   8040
tgcgcagcct gaatggcgaa tggacgcgcc ctgtagcggc gcattaagcg cggcgggtgt   8100
ggtggttacg cgcagcgtga ccgctacact tgccagcgcc ctagcgcccg ctcctttcgc   8160
tttcttccct tcctttctcg ccacgttcgc cggctttccc cgtcaagctc taaatcgggg   8220
gctcccttta gggttccgat ttagtgcttt acggcacctc gaccccaaaa aacttgatta   8280
gggtgatggt tcacgtagtg ggccatcgcc ctgatagacg gtttttcgcc ctttgacgtt   8340
ggagtccacg ttctttaata gtggactctt gttccaaact ggaacaacac tcaaccctat   8400
ctcggtctat tcttttgatt tataagggat tttgccgatt tcggcctatt ggttaaaaaa   8460
```

```
tgagctgatt taacaaaaat ttaacgcgaa ttttaacaaa atattaacgc ttacaatttc   8520
ctgatgcggt attttctcct tacgcatctg tgcggtattt cacaccgcat atggtgcact   8580
ctcagtacaa tctgctctga tgccgcatag ttaagccagc cccgacaccc gccaacaccc   8640
gctgacgcgc cctgacgggc ttgtctgctc ccggcatccg cttacagaca agctgtgacc   8700
gtctccggga gctgcatgtg tcagaggttt tcaccgtcat caccgaaacg cgcgagacga   8760
aagggcctcg tgatacgcct atttttatag gttaatgtca tgataataat ggtttcttag   8820
acgtcaggtg gcacttttcg gggaaatgtg cgcggaaccc ctatttgttt atttttctaa   8880
atacattcaa atatgtatcc gctcatgaga caataaccct gataaatgct tcaataatat   8940
tgaaaaagga agagtatgag tattcaacat ttccgtgtcg cccttattcc cttttttgcg   9000
gcattttgcc ttcctgtttt tgctcaccca gaaacgctgg tgaaagtaaa agatgctgaa   9060
gatcagttgg gtgcacgagt gggttacatc gaactggatc tcaacagcgg taagatcctt   9120
gagagttttc gccccgaaga acgttttcca atgatgagca cttttaaagt tctgctatgt   9180
ggcgcggtat tatcccgtat tgacgccggg caagagcaac tcggtcgccg catacactat   9240
tctcagaatg acttggttga gtactcacca gtcacagaaa agcatcttac ggatggcatg   9300
acagtaagag aattatgcag tgctgccata accatgagtg ataacactgc ggccaactta   9360
cttctgacaa cgatcggagg accgaaggag ctaaccgctt ttttgcacaa catgggggat   9420
catgtaactc gccttgatcg ttgggaaccg gagctgaatg aagccatacc aaacgacgag   9480
cgtgacacca cgatgcctgt agcaatggca acaacgttgc gcaaactatt aactggcgaa   9540
ctacttactc tagcttcccg gcaacaatta atagactgga tggaggcgga taaagttgca   9600
ggaccacttc tgcgctcggc ccttccggct ggctggttta ttgctgataa atctggagcc   9660
ggtgagcgtg ggtctcgcgg tatcattgca gcactggggc cagatggtaa gccctcccgt   9720
atcgtagtta tctacacgac ggggagtcag gcaactatgg atgaacgaaa tagacagatc   9780
gctgagatag gtgcctcact gattaagcat tggtaactgt cagaccaagt ttactcatat   9840
atactttaga ttgatttaaa acttcatttt taatttaaaa ggatctaggt gaagatcctt   9900
tttgataatc tcatgaccaa aatcccttaa cgtgagtttt cgttccactg agcgtcagac   9960
cccgtagaaa agatcaaagg atcttcttga gatccttttt ttctgcgcgt aatctgctgc  10020
ttgcaaacaa aaaaaccacc gctaccagcg gtggtttgtt tgccggatca agagctacca  10080
actctttttc cgaaggtaac tggcttcagc agagcgcaga taccaaatac tgttcttcta  10140
gtgtagccgt agttaggcca ccacttcaag aactctgtag caccgcctac atacctcgct  10200
ctgctaatcc tgttaccagt ggctgctgcc agtggcgata agtcgtgtct taccgggttg  10260
gactcaagac gatagttacc ggataaggcg cagcggtcgg gctgaacggg gggttcgtgc  10320
acacagccca gcttggagcg aacgacctac accgaactga gatacctaca gcgtgagcta  10380
tgagaaagcg ccacgcttcc cgaagggaga aaggcggaca ggtatccggt aagcggcagg  10440
gtcggaacag gagagcgcac gagggagctt ccagggggaa acgcctggta tctttatagt  10500
cctgtcgggt ttcgccacct ctgacttgag cgtcgatttt tgtgatgctc gtcagggggg  10560
cggagcctat ggaaaaacgc cagcaacgcg gcctttttac ggttcctggc cttttgctgg  10620
ccttttgctc acatgttctt tcctgcgtta tcccctgatt ctgtggataa ccgtattacc  10680
gcctttgagt gagctgatac cgctcgccgc agccgaacga ccgagcgcag cgagtcagtg  10740
agcgaggaag cggaagagcg cccaatacgc aaaccgcctc tccccgcgcg ttggccgatt  10800
cattaatgca gctggcacga caggtttccc gactggaaag cgggcagtga gcgcaacgca  10860
```

-continued

```
attaatgtga gttagctcac tcattaggca ccccaggctt tacactttat gcttccggct  10920
cgtatgttgt gtggaattgt gagcggataa caatttcaca caggaaacca cagctatgac  10980
ctgattacgc caagctattt aggtgacact atagaatact caagcttgca tgcctgcagg  11040
tcgactctag aggatcctag ggataacagg gtaatctcga gtggcggcag atgtgagtcg  11100
tgtgctacaa aacgtgaatc gacacgcgca gggcggaacc aaaaaaaacc cccaccccgc  11160
tgtcaagttg acaaatcaac acatttgttc caagttcaaa tcgggaaatc aaaaattagg  11220
gccagatcag cgatcaggaa tggtaatcgg gtaacagagg tcgcaaaatc gtctagaaaa  11280
tggaagaaga acgtggtaac taccagcgag ttctgcaaac ttcaaaaaaa aaatctgggc  11340
acgatgaaag ttgagctaac gctgacgctc acaaatggcg tggctaaagg aagcgagaca  11400
atcggaaaat tgttctctcg ggcaccacaa agctgttgtt agtcgctgaa gaacaattcc  11460
aactgattcc gccgccttcc tattgcgtca gccttgtacc taagctgccg agtaacgtca  11520
ctcaacctct cttttcagac tgctttgctc cgcgaatact tttcttctat gcgctcaaga  11580
aaatgacaca gcacaccaag ctctgcaaac tttcttcgct aatctgacgc gaaatgtgag  11640
ccatttcttc tcgcctgcaa tggcaatgcg tctgtgcggc gatgagaatc acgatgccgg  11700
aatgggtggc tggaagttca tagagatgct gaattgttgg agcgacatgg tacataagca  11760
tgaatctgtc ctgatttcca ccctccgtct ttcatcaact ttctcgtctg acccttccgt  11820
tgccagatcc cgggggcaat gagatatgaa aaagcctgaa ctcaccgcga cgtctgtcga  11880
gaagtttctg atcgaaaagt tcgacagcgt ctccgacctg atgcagctct cggagggcga  11940
agaatctcgt gctttcagct tcgatgtagg agggcgtgga tatgtcctgc gggtaaatag  12000
ctgcgccgat ggtttctaca aagatcgtta tgtttatcgg cactttgcat cggccgcgct  12060
cccgattccg gaagtgcttg acattgggga attcagcgag agcctgacct attgcatctc  12120
ccgccgtgca cagggtgtca cgttgcaaga cctgcctgaa accgaactgc ccgctgttct  12180
gcagccggtc gcggaggcca tggatgcgat cgctgcggcc gatcttagcc agacgagcgg  12240
gttcggccca ttcggaccgc aaggaatcgg tcaatacact acatggcgtg atttcatatg  12300
cgcgattgct gatccccatg tgtatcactg gcaaactgtg atggacgaca ccgtcagtgc  12360
gtccgtcgcg caggctctcg atgagctgat gctttgggcc gaggactgcc ccgaagtccg  12420
gcacctcgtg cacgcggatt tcggctccaa caatgtcctg acggacaatg gccgcataac  12480
agcggtcatt gactggagcg aggcgatgtt cggggattcc caatacgagg tcgccaacat  12540
cttcttctgg aggccgtggt tggcttgtat ggagcagcag acgcgctact tcgagcggag  12600
gcatccggag cttgcaggat cgccgcggct ccgggcgtat atgctccgca ttggtcttga  12660
ccaactctat cagagcttgg ttgacggcaa tttcgatgat gcagcttggg cgcagggtcg  12720
atgcgacgca atcgtccgat ccggagccgg gactgtcggg cgtacacaaa tcgcccgcag  12780
aagcgcggcc gtctggaccg atggctgtgt agaagtactc gccgatagtg gaaaccgacg  12840
ccccagcact cgtccgaggg caaaggaata gagtagatgc cgaccgggat ctgggcagca  12900
ccaagacacg gaactttcaa cagtcgtgag taggtggtga tctgcatgtc caaatcgtga  12960
aacgtgaatc acgaaccacg aatcgtgaat agccactttg cgcgaaaatc actgaatgcc  13020
gccaaaccga cgcgacgcga gttgcgtgaa gtattcgtga ttcacattca cgattgacga  13080
ttgtgagttg gtcgacgaca ttcgctagcc agaccaacac tcacgacttt ttgaagagcg  13140
ttgcaggttg agccaacttt ctccctcact ctttgctttc ttctccatca cgctcattcc  13200
```

-continued

```
ttttaagtgt tcatccggta tcattagcac tatatcatag tgaaactcgc aacaacccgg  13260
tcttcgtcgc gaaagcaacc ctccatcgct gctgcctctt gcagtgaaga ccgccaccat  13320
gcagtctacg cagtcgaaga ccctacacgt ccagttcgtc cattctggtc ctacacattg  13380
tatccacgca cccaagtctg ccaacgtgga gtaagtgaac ctttttttgt cctgtcgagg  13440
ctcaacgtag atcacaggct gatcatccac actcttctac cttttgacat tacgcagtcg  13500
actttttaca ggaggagatg actacctcgt ccgaatctta cccaccctgc ctctctccga  13560
cgtagagccg cagcttatcg aagacgccac tgaagcggtg acctcgctcg atgctgacgg  13620
ccgcttcctc gtcaccgctt ccgaagatgg ctctgtacgc ctctaccgac accacccaat  13680
cgacgcggaa ggcaacccag catcaccaac tgtgcttcaa tcgctgctgc gccgcgaagc  13740
ttggctgcag gtcgacggat cccgggtacc ggcccgttca acacaatgcg cctgcaattt  13800
ctatccccgc tttccacctc tgtctccctc ttcaaagtca cagagtctgc catttgtatt  13860
cgagcatgaa aaatgatgac ctcctttctt ctcgttcaat acagcggaca tgaacaagaa  13920
aggggtggcc tgagccacca agttctacac ttgcagccag acgtattcaa aaatcgacgt  13980
ggacgagttg cgactcaaca tcctctgtga attgcaatcg agtgagtgat tacgacctgt  14040
attcacgtca aaatgcaggt gtgacatttg aattttgaaa tacatgaggc aggctcgatt  14100
tgctccactc aagtcgagtt tgccaaattc aagaagcgct aatcggagcc aaccgaccga  14160
ccacaaccag ccaaatcagc cagccaaggc agagaagcag aagcaaaggc ggtgcattga  14220
gaggtgagcc gtgtgctgtg ctgtgctctg ctgtgctgtc tgtcaatgct tgctgcgtgt  14280
gtttgtctcg cctctacagc ctgcccctca agatgtgacc gattggaagg aaaggaaggt  14340
cacacgcagt tctggcatgc cacgcacgca cagcccgaaa ttgcgatctc aagagactgc  14400
cgacgccgcc gtccgccgtt gagcgctctg cttgggtcaa agcgtaagcg cttctcgaat  14460
tcaaactcac agagttccaa gtctgcacag gtcatctgtt cgtccttttg agactgcctg  14520
actggctggc tggaacgcac gcacgcacac ttccgattcg acaccgcccg ctgctgctgt  14580
cttctgcgct cttgtgccct tcttctgtac ttggcctttg cgtcgacttc tttgcttgct  14640
cggcagtgcc gtctcatctg ccccaagtca agctcagcag cacagcacac acgcatcacc  14700
ctctcggctt gggtttgccc ctgttgcctg tctgtccaca ctcacacaca tccctatcgc  14760
ttgctcgaca tcatcgctta cctcttcccc accacctcgt ctttgacacc tttactttct  14820
caacccctct tccaccacca acccccccac cacttacttt caacatgagc ctctcgaaca  14880
gcaatcacaa cgagcgccac aacgacgaca acaacatcaa tgacgatgat tgtgctaact  14940
tctttgagct gatggttcag cctgcctctt cttcttctta cggcccctac tttcccgacc  15000
caggactggc gcttccagca atttccgatg tctcatcaac aacagatacg cgactaccgt  15060
cacagctcgg agtgacccca ttcagtcatc agacatcgcc catccgatcc gcagatgaag  15120
gagagaagac gacaacaacc gcatcataca aaagaaagca ttccgaggtg gagaaagacc  15180
gtcgaagaat catctcaaac ggatttgcag tgagtttccc tcttcttcta ccataaagtt  15240
caggctggtt gagctgaagt cgacgtttgg caatatttgt gtagatcttg cagaacgtcc  15300
tccataacga ctcaacttcc aaacccatct cgaaagcgac cctacttcaa caagcgtgcg  15360
acgaaatccg tgaactgcgc aaaaaacttg atacgagcat taccatcatc tcccgctatg  15420
gtctcgaaaa tttgtttcag gtggctccaa cccccaattc tttgagcaat gcttctcctc  15480
ccaatggtac gagtagggct taccctacct attcgaacga cctcggcccg gatcgtttcc  15540
aagactcgcg gcgtagttcc acttcggcga cgagtgtgtc tggatctcaa tataacaatg  15600
```

gcgctgccgc taaggaggat ggaaacgaga ggcgtaattc caacgtgaag aggagaagtt 15660
cttacaccaa cagcatcaac agcagcttcg agtcatccga ggaggacact ctgaatagca 15720
gttgcgacaa cacaagtgac ttcgacgaaa gcgttggcag cagcgaaagc gaaagtgaaa 15780
caaacaacag gacaagaaac agaaacagaa ccaagagggc aatggcaaca gcaaagctca 15840
aagaccgaga ccgcgccaaa gctcgaaccg cacccaagcc acacagcaat cgcttatcgc 15900
ctgcatccac tataacgcca agtgagatga gcagcagctt agccagccca aacacctctt 15960
cacaagagca tatccagcaa gccatcttgt cattgctcct cgaattgccg aaacatctgg 16020
agaatgtgca caagtcgaag cgtccttcct ctcagcagcc aagcacacag attgatcaaa 16080
ccggaaaccg gactacgacg gtaacgaaga ccaggagacg gcaccgatga atgcatagta 16140
gatgccgacc gggatctggg cagcaccaag acacggaact tcaacagtcg tgagtaggtg 16200
gtgatctgca tgtccaaatc gtgaaacgtg aatcacgaac cacgaatcgt gaatagccac 16260
tttgcgcgaa aatcactgaa tgccgccaaa ccgacgcgac gcgagttgcg tgaagtattc 16320
gtgattcaca ttcacgattg acgattgtga gttggtcgac gacattcgct agccagacca 16380
acactcacga ctttttgaag agcgttgcag gctgagccaa ctttctccct cactctttgc 16440
tttcttctcc atcacgctca ttccttttaa gtgttcatcc ggtatcatta gcactatatc 16500
atagtgaaac tcgcaacaac ccggtcttcg tcgcgaaagc aaccctccat cgctgctgcc 16560
tcttgcagtg aagaccgcca ccatgcagtc tacgcagtcg aagaccctac acgtccagtt 16620
cgtccattct ggtcctacac attgtatcca cgcacccaag tctgccaacg tggagtaagt 16680
gaaccttttt ttgtcctgtc gaggctcaac gtagatcaca ggctgatcat ccacactctt 16740
ctaccttttg acattacgca gtcgactttt tacaggagga gatgactacc tcgtccgaat 16800
cttacccacc ctgcctctct ccgacgtaga gccgcagctt atcgaagacg ccactgaagc 16860
ggtgacctcg ctcgatgctg acggccgctt cctcgtcacc gcttccgaag atggctctgt 16920
acgcctctac cgacaccacc caatcgacgc ggaaggcaac ccagcatcac caactgtgct 16980
tcaatcgctg ctgcgccgcg aagcttggct gcaggtcgac ggatcccggt tatcgagctc 17040
gaattcgccc tatagtgagt cgtattacaa ttcactggcc gtcgttttac aacgtcgtga 17100
ctgggaaaac cctggcgtta cccaacttaa tcgccttgca gcacatcccc ctttcgccag 17160
ctggcgtaat agcgaagagg cccgcaccga tcgcccttcc caacagttgc gcagcctgaa 17220
tggcgaatgg acgcgccctg tagcggcgca ttaagcgcgg cgggtgtggt ggttacgcgc 17280
agcgtgaccg ctacacttgc cagcgcccta gcgcccgctc ctttcgcttt cttcccttcc 17340
tttctcgcca cgttcgccgg ctttccccgt caagctctaa atcgggggct ccctttaggg 17400
ttccgattta gtgctttacg gcacctcgac cccaaaaaac ttgattaggg tgatggttca 17460
cgtagtgggc catcgccctg atagacggtt tttcgccctt tgacgttgga gtccacgttc 17520
tttaatagtg gactcttgtt ccaaactgga acaacactca accctatctc ggtctattct 17580
tttgatttat aagggatttt gccgatttcg gcctattggt taaaaaatga gctgatttaa 17640
caaaaattta acgcgaattt taacaaaata ttaacgctta caatttcctg atgcggtatt 17700
ttctccttac gcatctgtgc ggtatttcac accgcatatg gtgcactctc agtacaatct 17760
gctctgatgc cgcatagtta agccagcccc gacacccgcc aacacccgct gacgcgccct 17820
gacgggcttg tctgctcccg gcatccgctt acagacaagc tgtgaccgtc tccgggagct 17880
gcatgtgtca gaggttttca ccgtcatcac cgaaacgcgc gagacgaaag ggcctcgtga 17940

```
tacgcctatt tttataggtt aatgtcatga taataatggt ttcttagacg tcaggtggca  18000
cttttcgggg aaatgtgcgc ggaaccccta tttgtttatt tttctaaata cattcaaata  18060
tgtatccgct catgagacaa taaccctgat aaatgcttca ataatattga aaaaggaaga  18120
gtatgagtat tcaacatttc cgtgtcgccc ttattccctt ttttgcggca ttttgccttc  18180
ctgtttttgc tcacccagaa acgctggtga aagtaaaaga tgctgaagat cagttgggtg  18240
cacgagtggg ttacatcgaa ctggatctca acagcggtaa gatccttgag agttttcgcc  18300
ccgaagaacg ttttccaatg atgagcactt ttaaagttct gctatgtggc gcggtattat  18360
cccgtattga cgccgggcaa gagcaactcg gtcgccgcat acactattct cagaatgact  18420
tggttgagta ctcaccagtc acagaaaagc atcttacgga tggcatgaca gtaagagaat  18480
tatgcagtgc tgccataacc atgagtgata acactgcggc caacttactt ctgacaacga  18540
tcggaggacc gaaggagcta accgcttttt tgcacaacat gggggatcat gtaactcgcc  18600
ttgatcgttg ggaaccggag ctgaatgaag ccataccaaa cgacgagcgt gacaccacga  18660
tgcctgtagc aatggcaaca acgttgcgca aactattaac tggcgaacta cttactctag  18720
cttcccggca acaattaata gactggatgg aggcggataa agttgcagga ccacttctgc  18780
gctcggccct tccggctggc tggtttattg ctgataaatc tggagccggt gagcgtgggt  18840
ctcgcggtat cattgcagca ctggggccag atggtaagcc cgcccaggtc gcaatcgtgt  18900
gatatcggac aacaccggta acaatagcgc ttaacagtcg tgctaacgtg ggcaactatg  18960
cagctcgctg tgctctttgc acagtcacag aagctcgaaa ggggcagcta cagttcgtaa  19020
acgtgtgcta agactcgcgc cgagccagca ttgaacacaa gcgcaacgat gccggattgc  19080
atatgagctt gtttcatata tcgttgttgt ttgtgagcag acaacacgat ttcatacatt  19140
cgttgcaatg taagagcaca ttatttctct attgtcacca gggccacatc aatgcgaagc  19200
aactttgtgg ctttcaattc actgcaaggt gctcagtgag cccactttgc atgcgttgac  19260
gtgggtaccg aagggtcgag acaagaccat cgtgggagag agccgttcaa tcctgagtca  19320
gtgtgaagaa ggatgagtac aaagctgatc agccagaaag acaatcgaca cgtacaacgg  19380
cgcctgaaga tcaagatggg aatacgtacg aaagctccga tcggggtcgc tcccttcttg  19440
agatgttggt gtcaatgctc gcgttgtagg acactttcca gtacctctgg atcccagttc  19500
atctccgtct tcctaattaa cctgtcaatc gaaacaatct tgttttgacc tttactgtgc  19560
ttccacaaga ctgcacccac catgctttga ggatgcaatt ggagctgacg tgcaacaact  19620
ccatcgtcat aatggatcag cgtgacaaaa tacgtcttct tgttccccgt caatgatgtg  19680
agaggactgt gaacgccaag aaccaacact cccttgtcgc gtgcatgctg caaggccgac  19740
tggtaccatt cggggccgaa ggcgaccact cgaggagaag aaatatgttc tcgtgcaaga  19800
ccttgcttga aggaagggtc gaatcgttcg tgcatcttta gccacatgct tcggtctgtc  19860
cctttgagat tgacgtaatc gctttcaaag aaggcagaaa ccaaggcagc gcccagaagc  19920
aggagcaaca agcggaagag catcatcttg gtgtagtagg cggtgtgatt gcccgtgctt  19980
gccggtcgac actggaatcg cagatcgcaa gctgcttata ttgtagctcg atgcatctca  20040
cttggcgttt tggggctcgt ccttccatgc cgactgggtg cccagcaacc cctgaattcg  20100
gctcttcgcg gcttctcggc attatttggt tcttagcact gccgttgcca cgttctgtgt  20160
ggcggtaggc gggacggtac tttgtggcgt tgacaccgcc cacatgaatc ggtctaccgt  20220
cggttgactg taacatattg gcaacatgcc ataatactgg ttcacagcga tttcttgctc  20280
tccttcggcc ttcggcgtct accactatct aagtgcaagg aacagacttc tctcagttat  20340
```

ctcatcgacc ttgtgtagat ctgggagcaa taccagatcc cattctgcta tctgtcacgt 20400
gtttgaagct gccggacgtt cagaccctca ataagccgat gttgtcctcg ctttatgaaa 20460
tgtcctgcca ctggcctcgt ggcgtcctgt cagaaccaaa ctgtcggctc aacgaatatg 20520
tttgcgtgaa aacagtcatc attctacaca gagtttgtcg cacacgcctg gaatatcgct 20580
tctgtttgat tttgggttga gatcaaagag ctgtgttact gactcggata gcagcatgtt 20640
gcttagaaag cggttgacat acgttacaaa gacgctcaga agcaaaaatc tgacgggagc 20700
tacggttatt gtcgacagga tcagcgagga tttgtagggt acaaagaagt ggtggtactg 20760
cggcaaggca gggaagctaa gatcggcgct gtaaagcccg catgactcct tcgacttgtt 20820
cccaagaaag ggcagggtga gcctgctgac gggctggcca ggcatccagt cgcagcaaaa 20880
ctggacgatg ccctataggc ttgtgccaga aagcatagat gtctttgtgc tcttcattgc 20940
ctgcgccgtc attcaaacgt acattcatac cccacttatg gccaacatca gaattgaacg 21000
gaatcttggt ggtcgcgtat gcattttcat gcttgcggtc gtaggtgacg tggatgggtc 21060
cgtttcctag cgactttgaa tggtcgtacg cttgacccgg agccagcggt tttccagata 21120
cgagatggga gtagtattca acacggctct ctgggtcgat gaccgctggc aataggctgt 21180
ccctgatata cgtgatatgg tgttgcttgt agtgcttctt ggcatcgctt gtcagacttg 21240
gttggctcac agcgaaagtc gcagtcgtaa ggacggaaat ggatagtaat agatggatga 21300
taatgcgagt cgagagaacc atcggagcaa cttgactggg cgatgagctg ggaaaacgat 21360
tggggtgccg tgaaggaagt gagtcggact tttcacttaa ttgactctat ttatggcttc 21420
aatccagaca gcaatctaat gctacatcgt ctcaaaagct cgaaagacag atcagaggcg 21480
gttcaggaaa gggctttgca gcttgcaagc aggcgacaac agtccaaagc ggctaaagag 21540
gcacccttga gacggttgtt tctatgatgg cgctcgtcgc attgtttcgg ctggttgtct 21600
tcctacatat caacaccgat cgtgcaagct tgacaacacc gatgctttgc ttatcaccat 21660
gccagcagca gttgcaggag gtacatctca cataaagaag aacgcggcct tgaggccaac 21720
ccagaagatt gtgacagcat ttgagtgggc tcgatgctag acaataagaa gcgtggttgc 21780
tcgttgtatc cttctgtcaa gccacgcaca ggtgagatgt 21820

<210> SEQ ID NO 74
<211> LENGTH: 1097
<212> TYPE: DNA
<213> ORGANISM: artificial
<220> FEATURE:
<223> OTHER INFORMATION: Actin promoter of P.tsukubaensis: last 4 nucleotides are start codon + G of genomic DNA coding for Pseudog6713.t1

<400> SEQUENCE: 74
gcccgttcaa cacaatgcgc ctgcaatttc tatccccgct ttccacctct gtctccctct 60
tcaaagtcac agagtctgcc atttgtattc gagcatgaaa aatgatgacc tcctttcttc 120
tcgttcaata cagcggacat gaacaagaaa ggggtggcct gagccaccaa gttctacact 180
tgcagccaga cgtattcaaa aatcgacgtg gacgagttgc gactcaacat cctctgtgaa 240
ttgcaatcga gtgagtgatt acgacctgta ttcacgtcaa aatgcaggtg tgacatttga 300
attttgaaat acatgaggca ggctcgattt gctccactca agtcgagttt gccaaattca 360
agaagcgcta atcggagcca accgaccgac cacaaccagc caaatcagcc agccaaggca 420
gagaagcaga agcaaaggcg gtgcattgag aggtgagccg tgtgctgtgc tgtgctctgc 480

-continued

```
tgtgctgtct gtcaatgctt gctgcgtgtg tttgtctcgc ctctacagcc tgcccctcaa    540

gatgtgaccg attggaagga aaggaaggtc acacgcagtt ctggcatgcc acgcacgcac    600

agcccgaaat tgcgatctca agagactgcc gacgccgccg tccgccgttg agcgctctgc    660

ttgggtcaaa gcgtaagcgc ttctcgaatt caaactcaca gagttccaag tctgcacagg    720

tcatctgttc gtccttttga gactgcctga ctggctggct ggaacgcacg cacgcacact    780

tccgattcga caccgcccgc tgctgctgtc ttctgcgctc ttgtgccctt cttctgtact    840

tggcctttgc gtcgacttct ttgcttgctc ggcagtgccg tctcatctgc cccaagtcaa    900

gctcagcagc acagcacaca cgcatcaccc tctcggcttg ggtttgcccc tgttgcctgt    960

ctgtccacac tcacacacat ccctatcgct tgctcgacat catcgcttac ctcttcccca   1020

ccacctcgtc tttgacacct ttactttctc aacccctctt ccaccaccaa ccccccccacc   1080

acttactttc aacatgg                                                  1097
```

<210> SEQ ID NO 75
<211> LENGTH: 2042
<212> TYPE: DNA
<213> ORGANISM: Pseudozyma tsukubaensis
<220> FEATURE:
<223> OTHER INFORMATION: Pseudog6713.t1 genomic DNA

<400> SEQUENCE: 75

```
atggagggtg agtactttac ttgatcagct tctcttcgcc atcccgtcat tcgccatccg     60

ccagccaaag tgtgggaaga cagccacacc gcaattcgcc cctcagccgg ccattgcttt    120

gatagcgacg aacccttgca atctttgatc gagtgcaaag cttaaagcgc cacttggcgg    180

atggatcaaa gcatcttcag acagtcttcg cgaccatgct cggcgtcgtc gcgaccaggt    240

tgcacacctt caactgacga acggctgacc taccatcgtc ggatcagctt ccgatcatgg    300

atacaagtta ggtgggaaag gcctcacgca tccgactgca tgagctattc gctccgtcat    360

tttttggcaa ttggatgcaa actcggcgat gcgcttgggc caactagaat gcgtcatcgg    420

aagatttgct tgtcaaccat gtgcacacgg cttgactgtt tcggcgaatg actacggatg    480

gctggatggc ttcgacggac ttgtgactga ccttcccata ccttgttgcg ctcctttctc    540

gcctcaaatc caattctgca atccacagac gaagtcgctg ctgtaagtag ctcattcgag    600

cttccacctc gcacggaacc aaaggcccta atgcgctcta atttcgcgag ggggatgcac    660

acacaggtag tattgtaaca gagcaacgag gctgacttct gaatgctgct ttgtcttgaa    720

tcacacaaat ttgcacggac gcttgctttc ttcgaacgct tttccgcttc gccctctgac    780

agctcgttat cgacaatggt tcgggaatgt gcaaaggtaa gtttctacaa atttgcttcc    840

caaaaggagc ttcaatagct ttgcagccgt tctttgaccg gcactgcgca gcaattcacc    900

ccaagcaccg tttctgacgc tttcttccat gcacttttct gctacatttc actttgtctc    960

gcacaacagc cggtttcgcc ggtgatgacg ctccccgagc tgtcttccct tccgttgtcg   1020

gtcgtccccg tcaccagggt gtcatggtcg gcatgggcca gaaggactcg tacgtcggtg   1080

acgaggctca gtccaagcgt ggtatcttga ccctcaagta ccccatcgag cacggtatcg   1140

ttaccaattg ggacgacatg gagaagatct ggcaccacac cttctacaac gagcttcgtg   1200

tcgcccctga ggagcacccc gttctcctta ccgaggctcc cctcaacccc aaggctaacc   1260

gtgagaagat gacccagatc cttttcgaga ccttcaacgc tcccgccttc tacgttgcta   1320

tccaggccgt tctctcgctc tacgcctccg gtcgtaccac cggtatcgtt ctcgactcgg   1380

gtgatggtgt tacccacacc gtgcccatct acgaaggtta ctcgcttccc cactcgatcc   1440
```

```
tccgtctcga ccttgccggt cgtgacttga ccgagtacct cgcccgtatc ttgaccgagc   1500

gtggttaccc cttcaccacc actgccgagc gcgaaatcgt tcgtgacatc aaggagaagc   1560

tctgctacgt cgccctcgac tttgagcagg agatgcttac cgctacccag tcttcggccc   1620

tcgagaagtc atacgagctt cctgacggac aggtgatcac cattggtaac gagcgattcc   1680

gtacccccga agttctcttc cagcccgcct tcctcggtct tgaggctgcc ggtatccacg   1740

agaccactta caactcgatc atgaagtgtg acttggacat ccgaaaggac ctctacggta   1800

acattgtcat gtcgggtggt accacgatgt acgccggtat ctcggaccgt atgcagaagg   1860

agatcaccgc tcttgccccc agctcgatga aggtcaagat tgttgctccc cctgagcgca   1920

agtactcggt ctggattggt ggatcgattc tcgcctcgct ctctaccttc cagcagatgt   1980

ggatctcgaa gcaggagtac gacgagtctg gaccttcgat cgtccaccgc aagtgcttct   2040

aa                                                                  2042
```

```
<210> SEQ ID NO 76
<211> LENGTH: 375
<212> TYPE: PRT
<213> ORGANISM: Pseudozyma tsukubaensis
<220> FEATURE:
<223> OTHER INFORMATION: Pseudog6713.t1

<400> SEQUENCE: 76

Met Glu Asp Glu Val Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
            20                  25                  30

Ser Val Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Leu Phe Glu Thr Phe Asn
        115                 120                 125

Ala Pro Ala Phe Tyr Val Ala Ile Gln Ala Val Leu Ser Leu Tyr Ala
    130                 135                 140

Ser Gly Arg Thr Thr Gly Ile Val Leu Asp Ser Gly Asp Gly Val Thr
145                 150                 155                 160

His Thr Val Pro Ile Tyr Glu Gly Tyr Ser Leu Pro His Ser Ile Leu
                165                 170                 175

Arg Leu Asp Leu Ala Gly Arg Asp Leu Thr Glu Tyr Leu Ala Arg Ile
            180                 185                 190

Leu Thr Glu Arg Gly Tyr Pro Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Leu Thr Ala Thr Gln Ser Ser Ala Leu Glu Lys Ser Tyr
225                 230                 235                 240

Glu Leu Pro Asp Gly Gln Val Ile Thr Ile Gly Asn Glu Arg Phe Arg
```

```
                245                 250                 255

Thr Pro Glu Val Leu Phe Gln Pro Ala Phe Leu Gly Leu Glu Ala Ala
            260                 265                 270

Gly Ile His Glu Thr Thr Tyr Asn Ser Ile Met Lys Cys Asp Leu Asp
        275                 280                 285

Ile Arg Lys Asp Leu Tyr Gly Asn Ile Val Met Ser Gly Gly Thr Thr
    290                 295                 300

Met Tyr Ala Gly Ile Ser Asp Arg Met Gln Lys Glu Ile Thr Ala Leu
305                 310                 315                 320

Ala Pro Ser Ser Met Lys Val Lys Ile Val Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375
```

```
<210> SEQ ID NO 77
<211> LENGTH: 6327
<212> TYPE: DNA
<213> ORGANISM: Pseudozyma tsukubaensis
<220> FEATURE:
<223> OTHER INFORMATION: P. tsukubaensis genomic region of Actin
      promoter and gene

<400> SEQUENCE: 77

atctccccaa tacaaatatt cataatcgtc atcatcacgg tcttgatcat gtatctgaaa      60

gctgcgaggg tggccgtaca aagaattggt gtccgtgggg atcatagtga gcaagcgaag     120

caacggactg aagttgttag accgtttcaa attctggacc ttagctcggt gatcggcaat     180

ccatattaga cacagcccga catcttctca aagccgtgcc ggtaccttgg ctgctcgatt     240

ggctgtttgt cgacattctt tccctccgcg gatagcattg ctttcgagtg acagaggtga     300

taccatacac tatcgcatcc cggccaattc ctcatactag gtgccgtgac ggtgccgtct     360

cggtgaaagt gaaatcaatc tcgctacgat gagtcggggt aagggttcaa gagatcgaac     420

accaggtcaa ctctcgcgaa ctgcgaactg caagtgtcag accctgatcc atccatccat     480

ccgtcgattc aaccgtccga ccacaagctg tcgtcatcag aacggagcaa tgcaagccgg     540

tttcccaccc tgcgttccct accagagata tagactggac acctcgtggc agctactgac     600

caacagcaac cacggcagta caagttcgat tcttgcttgg ttcaggcgga gagggcgcac     660

aggccagggt ttagaagaaa cgctgctgtc tcttgacgct tgacggagaa ggggcccgtt     720

caacacaatg cgcctgcaat ttctatcccc gctttccacc tctgtctccc tcttcaaagt     780

cacagagtct gccatttgta ttcgagcatg aaaaatgatg acctcctttc ttctcgttca     840

atacagcgga catgaacaag aaaggggtgg cctgagccac caagttctac acttgcagcc     900

agacgtattc aaaaatcgac gtggacgagt tgcgactcaa catcctctgt gaattgcaat     960

cgagtgagtg attacgacct gtattcacgt caaaatgcag gtgtgacatt tgaattttga    1020

aatacatgag gcaggctcga tttgctccac tcaagtcgag tttgccaaat tcaagaagcg    1080

ctaatcggag ccaaccgacc gaccacaacc agccaaatca gccagccaag gcagagaagc    1140

agaagcaaag gcggtgcatt gagaggtgag ccgtgtgctg tgctgtgctc tgctgtgctg    1200

tctgtcaatg cttgctgcgt gtgtttgtct cgcctctaca gcctgcccct caagatgtga    1260
```

-continued

```
ccgattggaa ggaaaggaag gtcacacgca gttctggcat gccacgcacg cacagcccga   1320

aattgcgatc tcaagagact gccgacgccg ccgtccgccg ttgagcgctc tgcttgggtc   1380

aaagcgtaag cgcttctcga attcaaactc acagagttcc aagtctgcac aggtcatctg   1440

ttcgtccttt tgagactgcc tgactggctg gctggaacgc acgcacgcac acttccgatt   1500

cgacaccgcc cgctgctgct gtcttctgcg ctcttgtgcc cttcttctgt acttggcctt   1560

tgcgtcgact tctttgcttg ctcggcagtg ccgtctcatc tgccccaagt caagctcagc   1620

agcacagcac acacgcatca ccctctcggc ttgggtttgc ccctgttgcc tgtctgtcca   1680

cactcacaca catccctatc gcttgctcga catcatcgct tacctcttcc ccaccacctc   1740

gtctttgaca cctttacttt ctcaacccct cttccaccac caaccccccc accacttact   1800

ttcaacatgg agggtgagta ctttacttga tcagcttctc ttcgccatcc cgtcattcgc   1860

catccgccag ccaaagtgtg ggaagacagc cacaccgcaa ttcgcccctc agccggccat   1920

tgctttgata gcgacgaacc cttgcaatct ttgatcgagt gcaaagctta aagcgccact   1980

tggcggatgg atcaaagcat cttcagacag tcttcgcgac catgctcggc gtcgtcgcga   2040

ccaggttgca caccttcaac tgacgaacgg ctgacctacc atcgtcggat cagcttccga   2100

tcatggatac aagttaggtg ggaaaggcct cacgcatccg actgcatgag ctattcgctc   2160

cgtcattttt tggcaattgg atgcaaactc ggcgatgcgc ttgggccaac tagaatgcgt   2220

catcggaaga tttgcttgtc aaccatgtgc acacggcttg actgtttcgg cgaatgacta   2280

cggatggctg gatggcttcg acggacttgt gactgacctt cccatacctt gttgcgctcc   2340

tttctcgcct caaatccaat tctgcaatcc acagacgaag tcgctgctgt aagtagctca   2400

ttcgagcttc cacctcgcac ggaaccaaag gccctaatgc gctctaattt cgcgaggggg   2460

atgcacacac aggtagtatt gtaacagagc aacgaggctg acttctgaat gctgctttgt   2520

cttgaatcac acaaatttgc acggacgctt gctttcttcg aacgcttttc cgcttcgccc   2580

tctgacagct cgttatcgac aatggttcgg gaatgtgcaa aggtaagttt ctacaaattt   2640

gcttcccaaa aggagcttca atagctttgc agccgttctt tgaccggcac tgcgcagcaa   2700

ttcaccccaa gcaccgtttc tgacgctttc ttccatgcac ttttctgcta catttcactt   2760

tgtctcgcac aacagccggt ttcgccggtg atgacgctcc ccgagctgtc ttcccttccg   2820

ttgtcggtcg tccccgtcac cagggtgtca tggtcggcat gggccagaag gactcgtacg   2880

tcggtgacga ggctcagtcc aagcgtggta tcttgaccct caagtacccc atcgagcacg   2940

gtatcgttac caattgggac gacatggaga agatctggca ccacaccttc tacaacgagc   3000

ttcgtgtcgc ccctgaggag caccccgttc tccttaccga ggctcccctc aaccccaagg   3060

ctaaccgtga gaagatgacc cagatccttt tcgagacctt caacgctccc gccttctacg   3120

ttgctatcca ggccgttctc tcgctctacg cctccggtcg taccaccggt atcgttctcg   3180

actcgggtga tggtgttacc cacaccgtgc ccatctacga aggttactcg cttccccact   3240

cgatcctccg tctcgacctt gccggtcgtg acttgaccga gtacctcgcc cgtatcttga   3300

ccgagcgtgg ttaccccttc accaccactg ccgagcgcga aatcgttcgt gacatcaagg   3360

agaagctctg ctacgtcgcc ctcgactttg agcaggagat gcttaccgct acccagtctt   3420

cggccctcga gaagtcatac gagcttcctg acggacaggt gatcaccatt ggtaacgagc   3480

gattccgtac cccccgaagtt ctcttccagc ccgccttcct cggtcttgag gctgccggta   3540

tccacgagac cacttacaac tcgatcatga agtgtgactt ggacatccga aaggacctct   3600

acggtaacat tgtcatgtcg ggtggtacca cgatgtacgc cggtatctcg gaccgtatgc   3660
```

agaaggagat caccgctctt gcccccagct cgatgaaggt caagattgtt gctccccctg 3720
agcgcaagta ctcggtctgg attggtggat cgattctcgc ctcgctctct accttccagc 3780
agatgtggat ctcgaagcag gagtacgacg agtctggacc ttcgatcgtc caccgcaagt 3840
gcttctaagc gagttgcatt tcgaaggcgc tctggttgtg ttactagcgg ccagcgggcc 3900
cgaatctgac tcgcatttga caacaacgac aacatcatca tcactgtact tcaaggcagt 3960
atgtagacgg gcctttgacg agcgcagtgg caccagcggg agagcgagta gaaggagacg 4020
gcagcagact tgttgtactt cttggaatcg tctctggctg gtgtgacacg cgagcggcag 4080
ggaaccattt ccatttcgcg tcttctatgt aggcttttgg ccaaaccttt tcctcctcac 4140
aaatgaaaga tatgataacg acctcacaga atcttggtgc atggaacgaa agctcgtgat 4200
tagcgctgac tgaacctgga tttggacctt gggtgtgaag actttcccgg gaaaccatgc 4260
gaagagcgtt tgagagactt gcgaatggct tcagtgatgc aagacgctat caatgcaaat 4320
cgaaccctgc tcatctgcga acgagaagag cacttaacct tgcctcacag agagtaggag 4380
aagcaggcac gacgaggaga aaggttgcat ctagccgtcg gacctgtcaa agatcggaat 4440
ccatcggggc aaaagcaacg ttgacatatt gagattcatt attttagatc ggctgtactg 4500
taaatcttgg ccttttggta ttcagctccg atcctctagc tctgcgtcgc tcgctggcaa 4560
cctcctgcgt gctccttcct tcttgtaatc cctcggctat gcctttccta gcgtctgcgc 4620
tgttgcaggc tagcatcgca cttgagattc cttgcatgga tttagcttgt cattgctttt 4680
tggcgcacgg atcgctacat tgctcatctg catcccgagg cgaatcggaa aaagaagcat 4740
ctgcaacggt ctagcgacga cgaaagaaga cggaaagagc gcttgcgagc tgaggttctg 4800
cctagacagt agcgagcgct acagacaatg aaaggagcgg aacgctgcaa ggcaagatca 4860
gaggtctgtg cgtgtgatgc tgcgggtcct gtgctaaatt cggcatgcta agttactact 4920
ttgtctcttt tgcctctcac gacatgaaag ggaaacccga aaacgaaaga ggaaagagag 4980
agacgacctg tcaacctacc tcttgctttc cccggtcttg gcagcgtgtt ggcatggatg 5040
acggtctgcg atcgaaatcg acgccgaggc cttctttcct ttctgtgcgt tcgaaagggc 5100
caaaagaggt atcgaattcg accgacacac cgaggcggag agcggataaa gggcgcattc 5160
cgaagaaaaa gttgctggca catgtgcaca ctcgcttggc gtttctcaaa gagtgctgca 5220
tcgaaatgca catgcattcc tgcatgactg cgttgctctg tctggtcttt gtgcgccttt 5280
ttgctaaaat cacattttac tcgcttgcac agacatccaa gaaaagacag gcatgtgtct 5340
gcgtccatat cggtggtcgc ttggcacatt tgctagacca ctttcctcgg ctgcttgtgt 5400
tgttactgcg cacacacagg cggcagatgg tatcaaaacg agcgcttcga atggcatcaa 5460
aagtgagaga aaaagcacag acagccacag agtgtaaaaa agaacgaact cgacccaagc 5520
tgcggggttg gcgagacatt ttggtctttt tgacaggcgc agcacgaggc tagtcaagtc 5580
cgttcaagtc aaaaagtgtt ggtgtcagac gcgagtgcca gccagccagc aagcaagcaa 5640
aagcgcgaat ttggacagcc acgctagaac aaagaaaggg cagcacaccg cgacactgca 5700
acaaagagag agagagagag agagaaaggc gtcggaaagc cccattcctg cgctgcgtgt 5760
gtgactgcgc ttggcgttct gtctcttgcg ctgctgctgc tcctcgtcct cattgacctc 5820
ttcgctagtg tattcctttg ttcatcttac tctccaaccc cttccttccc ttccttccct 5880
tccatcactt ccctcatcct cattctcaat acggccccct atctctctct tcctcaaaca 5940
aagcagcacg gttcttcctt tcaacccctc tcttttctga cattcagttc cctttctttg 6000

-continued

```
gctggtccat acaaaggtct ctcaggtacc cgacacatac acaaacgcac gcataccact   6060

tcgtttgctt tcccatctcc gtctcacaaa acgcatcctg caaatcccat atcaactgcc   6120

ttgcatcgtc atccaaactc tctttcgctc ccactcgatc aataatctct atctctccac   6180

tctcccttac cttcccaacc ctttggtccc tataccacct ccccacccac ttactgctgc   6240

tgcttcgtca atcacgttct ttgacagaac tctcaatcgc atacatctca ttgatcccca   6300

gcaacatttc aactctagac aacaaca                                       6327
```